(12) United States Patent
Spangenberg et al.

(10) Patent No.: US 10,881,060 B2
(45) Date of Patent: Jan. 5, 2021

(54) ENDOPHYTES AND RELATED METHODS

(71) Applicant: Agriculture Victoria Services PTY LTD, Attwood (AU)

(72) Inventors: German Spangenberg, Bundoora (AU); Kathryn Michaela Guthridge, Hadfield (AU); John White Forster, Diamond Creek (AU); Timothy Ivor Sawbridge, Coburg (AU); Emma Jane Isobel Ludlow, Viewbank (AU); Jatinder Kaur, Taylors Hill (AU); Simone Jane Rochfort, Reservoir (AU); Maia Andrea Rabinovich, Buenos Aires (AR); Piyumi Ekanayake, Bundoora (AU)

(73) Assignee: Agriculture Victoria Services PTY LTD, Bundoora (AU)

( * ) Notice: Subject to any disclaimer, the term of this patent is extended or adjusted under 35 U.S.C. 154(b) by 170 days.

(21) Appl. No.: 14/692,094

(22) Filed: Apr. 21, 2015

(65) Prior Publication Data

US 2016/0046901 A1    Feb. 18, 2016

Related U.S. Application Data

(63) Continuation of application No. 13/543,200, filed on Jul. 6, 2012, now abandoned, which is a continuation-in-part of application No. PCT/AU2011/000020, filed on Jan. 7, 2011.

(30) Foreign Application Priority Data

| Jan. 7, 2010 | (AU) | 2010900054 |
| Jun. 25, 2010 | (AU) | 2010902821 |
| Jun. 1, 2012 | (AU) | 2012902275 |
| Jun. 1, 2012 | (AU) | 2012902276 |

(51) Int. Cl.
| *A01H 5/12* | (2018.01) |
| *C12N 1/14* | (2006.01) |
| *C12Q 1/6895* | (2018.01) |
| *A01H 17/00* | (2006.01) |
| *A01H 5/10* | (2018.01) |

(52) U.S. Cl.
CPC .......... *A01H 5/12* (2013.01); *A01H 5/10* (2013.01); *A01H 17/00* (2013.01); *C12N 1/14* (2013.01); *C12Q 1/6895* (2013.01); *C12Q 2600/156* (2013.01)

(58) Field of Classification Search
None
See application file for complete search history.

(56) References Cited

U.S. PATENT DOCUMENTS

| 6,072,107 A | 6/2000 | Latch et al. |
| 6,111,170 A | 8/2000 | Latch et al. |
| 6,548,745 B2 | 4/2003 | Hiruma et al. |
| 6,815,591 B1 | 11/2004 | Hignight et al. |
| 2008/0022420 A1 | 1/2008 | Van Hanja et al. |
| 2008/0299144 A1 | 12/2008 | Rolston et al. |
| 2009/0255015 A1 | 10/2009 | West et al. |
| 2016/0262335 A1* | 9/2016 | Hume ............... C12R 1/645 |

FOREIGN PATENT DOCUMENTS

| AU | 9173853 | 10/1991 |
| AU | 2011204749 B2 | 7/2011 |
| EP | 1191103 A1 | 3/2002 |
| NZ | 233083 | 12/1991 |
| WO | 2004029227 A1 | 4/2004 |
| WO | 2004106487 A2 | 12/2004 |
| WO | 2008100892 A2 | 8/2008 |

OTHER PUBLICATIONS

Fouda et al., Ann. Argicult. Sci., 60(1):95-104 (2015).*
Kew, <https://www.kew.org/data/grasses-db/sppindex.htm> 2016, Accessed Feb. 8, 2018).*
Notice of Opposition dated Mar. 21, 2017 from corresponding European Patent No. 2521442 (Application No. 11731629.9.
Ball, O. J-P, et al., Importance of Host Plant Species, *Neotyphodium endophyte* Isolate, and Alkaloids on Feeding by *Spodoptera frugiperda* (*Lepidoptera: noctuidae*) Larvae, J. Econ. Entomol, 2006, pp. 1462-1473, vol. 99.
Bush, L. P. et al., Bioprotective Alkaloids of Grass-Fungal Endophyte Symbioses, Plant Physiol, 1997, pp. 1-7, vol. 114.
Easton, H.S. et al., Differential expression of loline alkaloids in perennial ryegrass infected with endophyte isolated from tall fescue, New Zealand Grassland Association: Endophyte Symposium, 2007, pp. 163-165.

(Continued)

*Primary Examiner* — Thomas J. Visone
(74) *Attorney, Agent, or Firm* — Larson & Anderson, LLC

(57) ABSTRACT

The present invention relates to a method for identifying and/or characterising an endophyte strain, said method including providing a plurality of samples of endophytes, subjecting said endophytes to genetic analysis; subjecting said endophytes to metabolic analysis and selecting endophytes having a desired genetic and metabolic profile. The present invention also relates to novel endophytes having a desired toxin profile wherein the endophyte produces significantly less toxic alkaloids compared with a control endophyte such as standard toxic (ST) endophyte; and/or significantly more alkaloids conferring beneficial properties compared with a control endophyte such as ST endophyte. The present invention also relates to endophyte variants having a desired genetic and metabolic profile, wherein said endophyte variants possess genetic and/or metabolic characteristics that result in a beneficial phenotype in a plant harbouring or otherwise associated with the endophyte variant. Preferably said endophyte variants are generated by polyploidisation or induced chromosome doubling.

11 Claims, 114 Drawing Sheets

Specification includes a Sequence Listing.

(56) References Cited

OTHER PUBLICATIONS

Siegel, M.R. et al., Fungal Endophyte-Infected Grasses: Alkaloid Accumulation and Aphid Response, Journal of Chemical Ecology, 1990, pp. 3301-3315, vol. 16.
Examination Report dated Oct. 17, 2017 for corresponding Australian Patent Application No. 2016259448.
Examination Report dated Oct. 18, 2017 for corresponding Australian Patent Application No. 2016259449.
Extended European Search Report dated Mar. 4, 2016 from related European Application No. 15190449.7.
Christensen, M.J. et al., Taxonomy of Acremonium endophytes of tall fescue (*Festuca arundinacea*), meadow fescue (*F. pratensis*) and perennial rye-grass (*Lolium perenne*), Mycol. Res., 1993, pp. 1083-1092, vol. 97, No. 9.
De Jong, E. Van Zijll et al, Global Genetic Diversity of the Perennial Ryegrass Fungal Endophyte *Neotyphodium lolii*, Crop Science, 2008, pp. 1487-1501, vol. 48, No. 4, XP009188759.
Young, C. A. et al., A complex gene cluster for indole-diterpene biosynthesis in the grass endophyte *Neotyphodium lolii*, Fungal Genetics and Biology, 2006, pp. 679-693.
Tapper, B. A. et al., Selection against toxin production in endophyte-infected perennial ryegrass, Grassland Research and Practice Series No. 7, 1999, pp. 107-111.
Notice of Opposition served on Feb. 27, 2015, in corresponding New Zealand Patent Application No. 601073.
Notice of Opposition served on Feb. 27, 2015, in corresponding New Zealand Patent Application No. 628160.
Statement of Case dated Apr. 24, 2015 from corresponding New Zealand application No. 628160.
Statement of Case dated Apr. 24, 2015 from corresponding New Zealand application No. 601073.
Summons to attend Oral Proceedings dated Mar. 16, 2015 from corresponding European application No. 11731629.9.
First Examination Report dated Nov. 19, 2014 from corresponding New Zealand Patent Application No. 601073.
First Examination Report dated Nov. 20, 2014 from corresponding New Zealand Patent Application No. 628160.
Groppe, K. et al., PCR Assay Based on a Microsatellite-Containing Locus for Detection and Quantification of Epichloe Endophytes in Grass Tissue, Applied and Environmental Microbiology, 1997, pp. 1543-1550, vol. 63, No. 4.
Marcelino, J. A. P. et al., Host plant associations of an entomopathogenic variety of the fungus, *Colletotrichum acutatum*, recovered from the elongate hemlock scale, *Fiorinia externa*, Journal of Insect Science, 2009, pp. 1-11, vol. 9, No. 25.
Wallace, M. M. et al., Molecular Mating Type Assay for Fusarium circinatum, Applied and Environmental Microbiology, 2000, pp. 5506-5508, vol. 66, No. 12.
Addy, H. D. et al., Distribution and molecular characterization of the root endophyte *Phialocephala fortinii* along an environmental gradient in the boreal forest of Alberta, Mycological Research, 2000, pp. 1213-1221, vol. 104, No. 10, Publisher: Elsevier, GB.
Araya, H. et al., Identification of two 5[alpha],8[alpha]-epidioxyergosta-3[beta]-ols from the endophyte, *Neotyphodium lolii*, Biochemical Systematics and Ecology, 2003, pp. 1337-1339, vol. 31, No. 11.
Felitti, S. et al., Transcriptome analysis of Neotyphodium and Epichloe grass endophytes, Fungal Genetics and Biology, 2006, pp. 465-475, vol. 43, No. 7.
Kuldau, G. et al., Clavicipitaceous endophytes: Their ability to enhance resistance of grasses to multiple stresses, Biological Control, 2008, pp. 57-71, vol. 46, No. 1.
Vega, F. E. et al., Fungal endophyte diversity in coffee plants from Colombia, Hawaii, Mexico and Puerto Rico, Fungal Ecology J, 2010, pp. 122-138, vol. 3, No. 3, Publisher: Elsevier, Amsterdam, NL.
Li, et al., Deleteagene: a fast neutron deletion mutagenesis-based gene knockout system for plants, Comparative and Functional Genomics, 2002, pp. 158-160, vol. 3.
Bouton, J. H. et al., Reinfection of Tall Fescue Cultivars with Non-Ergot Alkaloid-Producing Endophytes, Agronomy Journal, 2002, pp. 567-574, vol. 94.
Van Zijll De Jong, E. et al. Development and characterization of EST-derived simple sequence repeat (SSR) markers for pasture grass endophytes, Genome, 2003, pp. 277-290, vol. 46, No. 2.
Young, C. A. et al., Molecular cloning and genetic analysis of a symbiosis-expressed gene cluster for lolitrem biosynthesis from a mutualistic endophyte of perennial ryegrass, Mol. Gen. Genomics, 2005, pp. 13-29, vol. 274.
Schardl, C. L. et al., Symbioses of Grasses with Seedborne Fungal Endophytes, Annu. Rev. Plant Biol., 2004, pp. 315-340, vol. 55.
Rasmussen, S. et al., High nitrogen supply and carbohydrate content reduce fungal endophyte and alkaloid concentration in Lolium perenne, New Phytologist, 2007, pp. 787-797, vol. 173.
Panaccione, D. G. et al., Elimination of ergovaline from a grass-Neotyphodium endophyte symbiosis by genetic modification of the endophyte, Proceedings of the National Academy of Science USA, 2001, pp. 12820-12825, vol. 98, No. 22.
Steenkamp, E. T. et al., PCR based identification of MAT-1 and MAT-2 in the *Gibberella fujikuroi* species complex, Applied and Environmental Microbiology, 2000, pp. 4378-4382, vol. 66, No. 10.
Rodriguez et al., Tansley review—Fungal endophytes: diversity and functional roles, New Phytolotist, 2009, pp. 314-330, vol. 182.
Popay et al., Black beetle damage to perennial ryegrass infected with AR1 endophyte, Proc. NZ Grassland Assoc., 2001, pp. 267-271, vol. 63.
PRECEDENT, The Law Dictionary, <http://thelawdictionary.org/precedent>, accessed Oct. 14, 2014.
Easton, H S., Grasses and Neotyphodium endophytes: co-adaptation and adaptive breeding, Euphytica, 2007, pp. 295-306, vol. 154.
CRT Seed Buyer's Guide, New Endophyte Technologies, 2006, pp. 13-15, Third Edition.
Simpson, W. R., A high frequency change, which is both inducible and reversible, results in altered colony morphology of a fungal symbiont (*Neotyphodium lolii*) and dwarfing of its grass host (*Lolium perenne*), 2009, pp. 1-193, Msc thesis, Massey University.
Simpson, W. R. et al., An Appraisal of the Use of Axillary Buds of Grasses as Clonal Material for Inoculation with Neotyphodium Endophytes, Neotyphodium/Grass Interactions, 1997, pp. 275-277, C W Bacon and N S Hill (eds), Plenum Press, New York.
Ravel, C. et al., Enhancement of yield and persistence of perennial ryegrass inoculated with one endophyte isolate in France, Agronomie, 1999, pp. 635-644, vol. 19, No. 7.
Australian Examination Report dated Aug. 30, 2018 from corresponding Australian Patent Application No. 2016259448.
Christensen, M.J. et al., Regulation switching of Epichloë typhina within elongating perennial ryegrass leaves, Mycol Res., 2008, pp. 1056-1062, vol. 112, Pt 9.
New Zealand Examination Report dated May 18, 2016 from related New Zealand Patent Application No. 701614.
Kuldau, G. A. et al., Molecular systematics of Clavicipitaceae supporting monophyly of genus *Epichloe* and for genus *Ephelis*, Mycologia, 1997, pp. 431-441, vol. 89, No. 3.
Schardl, C. L. et al., Coevolution by Common Descent of Fungal Symbionts (*Epichloe* spp.) and Grass Hosts, Mol. Biol. Evol., 1997, pp. 133-143, vol. 14, No. 2.
Schardl, C. L. et al., Three New Species of Epichloe Symbiotic with North American Grasses, Mycologia, 1999, pp. 95-107, vol. 91, No. 1.
Schardl, C. L. et al., Molecular phylogenetic relationships of nonpathogenic grass mycosymbionts and clavicipitaceous plant pathogens, Plant Systematics and Evolution, 1991, pp. 27-41, vol. 178, Issue 1.
Tsai, H-F. et al., Evolutionary diversification of fungal endophytes of tall fescue grass by hybridization with *Epicloe* species, Proc. Natl. Acad. Sci. USA, 1994, pp. 2542-2546, vol. 91, No. 7.
Yokoyama, E. et al., Phylogenetic and structural analyses of the mating-type loci in Clavicipitaceae, FEMS Microbiology Letters, 2006, pp. 182-191, vol. 264, Issue 2.
NCBI Accession AB258373.1, Neotyphodium uncinatum gene for MAT1-1-3, partial cds, strain: NBRC 32642, Mar. 3, 2007.

(56) References Cited

OTHER PUBLICATIONS

NCBI Accession L06951.1, Neotyphodium coenophialum beta-tubulin (tub2-2) gene, exons, 2 through 4 and partial cds, Aug. 11, 2008.
NCBI Accession L06957.1, Epichloe festucae beta-tubulin (tub1) gene, exons 1, 2, 3, and 4, and partial cds, Aug. 11, 2008.
NCBI Accession L06962.1, Epichloe elymi beta-tubulin (tub2) gene, exons 1, 2, 3, and 4, and partial cds, Aug. 11, 2008.
NCBI Accessionn L06964.1, Neotyphodium coenophialum beta-tubulin (tub2-3) gene, exons 1, 2, 3, and 4, and partial cds, Aug. 11, 2008.
NCBI Accession L07131.1, Epichloe elymi 18S ribosomal RNA gene, partial sequence; internal transcribed spacer 1, 5.8S ribosomal RNA gene and internal transcribed spacer 2, complete sequence; and 28S ribosomal RNA gene, partial sequence, Aug. 11, 2008.
NCBI Accession L07132.1, Epichloe typhina 18S ribosomal RNA gene, partial sequence; internal transcribed spacer 1, 5.8S ribosomal RNA gene and internal transcribed spacer 2, complete sequence; and 28S ribosomal RNA gene, partial sequence, Aug. 11, 2008.
NCBI Accession L20306.1, Epichloe typhina 18S ribosomal RNA gene, partial sequence; internal transcribed spacer 1, 5.8S ribosomal RNA gene and internal transcribed spacer 2, complete sequence; and 28S ribosomal RNA gene, partial sequence, Aug. 11, 2008.
Amended Notice of Opposition To Grant of Patent (Section 21) dated Jan. 26, 2016, filed in opposition against corresponding New Zealand patent application No. 611308.
Statement of Case dated Jan. 26, 2016, filed in Opposition against corresponding New Zealand Patent Application No. 611308.
Statement of Grounds and Particulars dated Feb. 29, 2015,filed in Opposition against corresponding Australian Patent Application No. 2011204749.
Second Amended Statement of Case dated Mar. 29, 2016, filed in Opposition against corresponding New Zealand Patent Application 628160.
Cao, M. et al., Advanced Data-Mining Strategies for the Analysis of Direct-Infusion Ion Trap Mass Spectrometry Data from the Association of Perennial Ryegrass with Its Endophytic Fungus, *Neotyphodium lolii*, Plant Physiology, 2008, pp. 1501-1514, vol. 146.
Gurney, K.A. et al., Loss of Toxic Metabolites from *Acremonium lolii*, the Endophyte of Ryegrass, Following Mutagenesis, Naturwissenschaften, 1994, pp. 362-365, vol. 81, Springer-Verlag.
Le, T. et al, De Novo Generation of Genetic Diversity in Neotyphodium Grass Fungal Endophytes Based on Colchicine Treatment, Proceedings of the 5th Australasian Dairy Science Symposium, Nov. 2012, p. 90 (Abstract and poster).
Le, T. et al, De Novo Generation of Genetic Diversity in Neotyphodium Grass Fungal Endophytes Based on Xray Mutagenesis, Proceedings of the 7th International Symposium on the Molecular Breeding of Forage and Turf, Jun. 2012, p. 111 (Abstract and poster).
Koulman, A. et al., Petramine and other fungal alkaloids are exuded in the guttation fluid of endophyte-infected grasses, Phytochemistry, 2007, pp. 355-360, vol. 68.
Rabinovich, M. et al., Genome survey sequencing of novel pasture grass fungal endophytes, Mycologia, 2010, p. 69, vol. 61, No. 4.
Saari, S. et al., Hybridization of Neotyphodium endophytes enhances competitive ability of the host grass, New Phytologist, 2012, pp. 231-236, vol. 195.
Hanh, V. et al., Improvement of Fungal Strain by Repeated and Sequential Mutagenesis and Optimization of Solid-State Fermentation for the Hyper-Production of Raw-Starch-Digesting Enzyme, Journal of Microbiology and Biotechnology, 2010, pp. 718-726, vol. 20, No. 4.
Zhang, X., Functional Analysis of a Thiamine Biosynthetic Gene in the Interaction of Epichloë Typhina with Perennial Ryegrass, PhD Thesis, 2004, Massey University, Palmerston North, New Zealand.
Clay, K. et al, Evolutionary Origins and Ecological Consequences of Endophyte Symbiosis with Grasses, The American Naturalist, 2002, pp. S99-S127, vol. 160.
Watson, R. H. et al., Productivity of cow-calf pairs grazing tall fescue pastures infected with either the wild-type endophyte or a nonergot alkaloid-producing endophyte strain, AR542, 2004, pp. 3388-3393, vol. 82, Issue 11.

\* cited by examiner

Figure 1

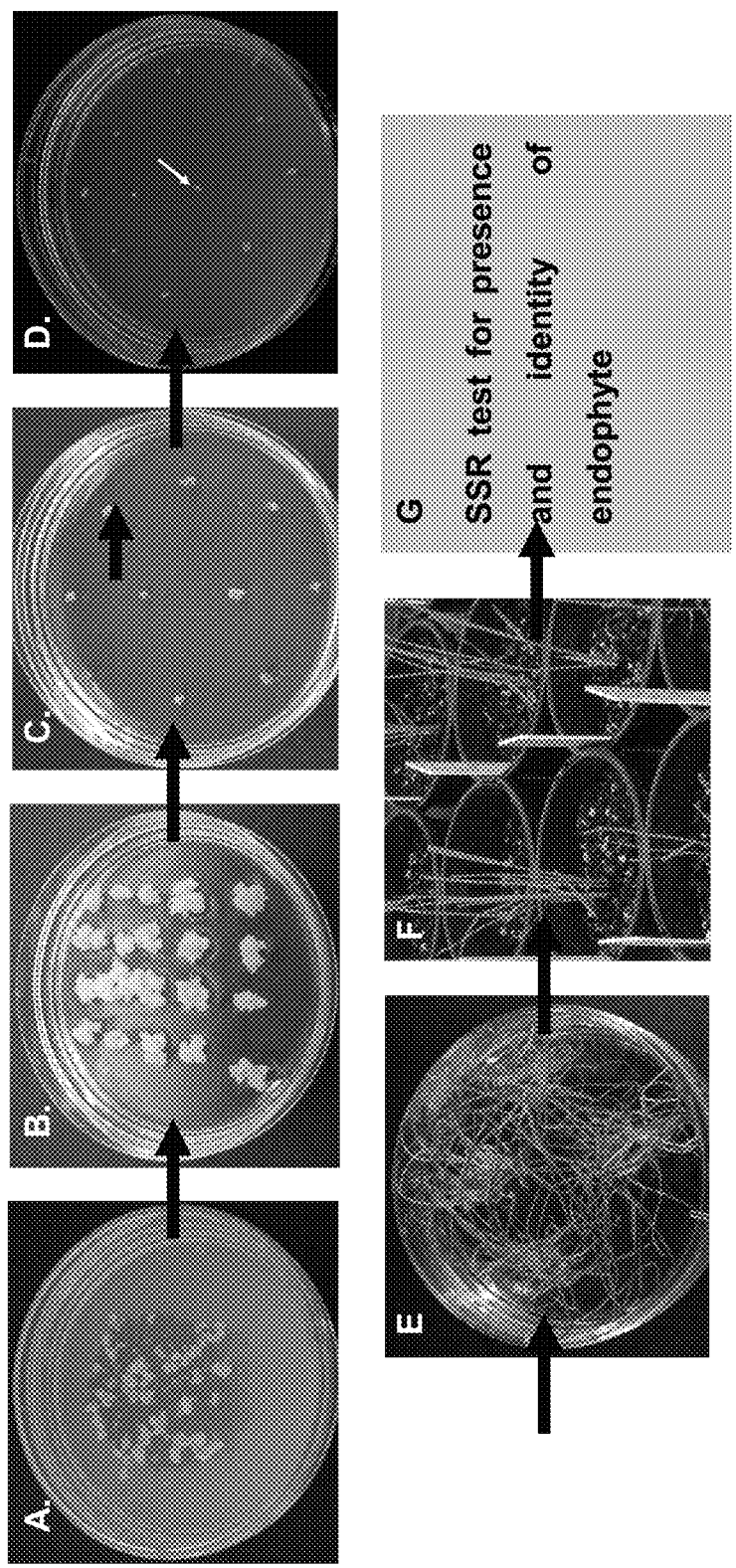

Figure 23
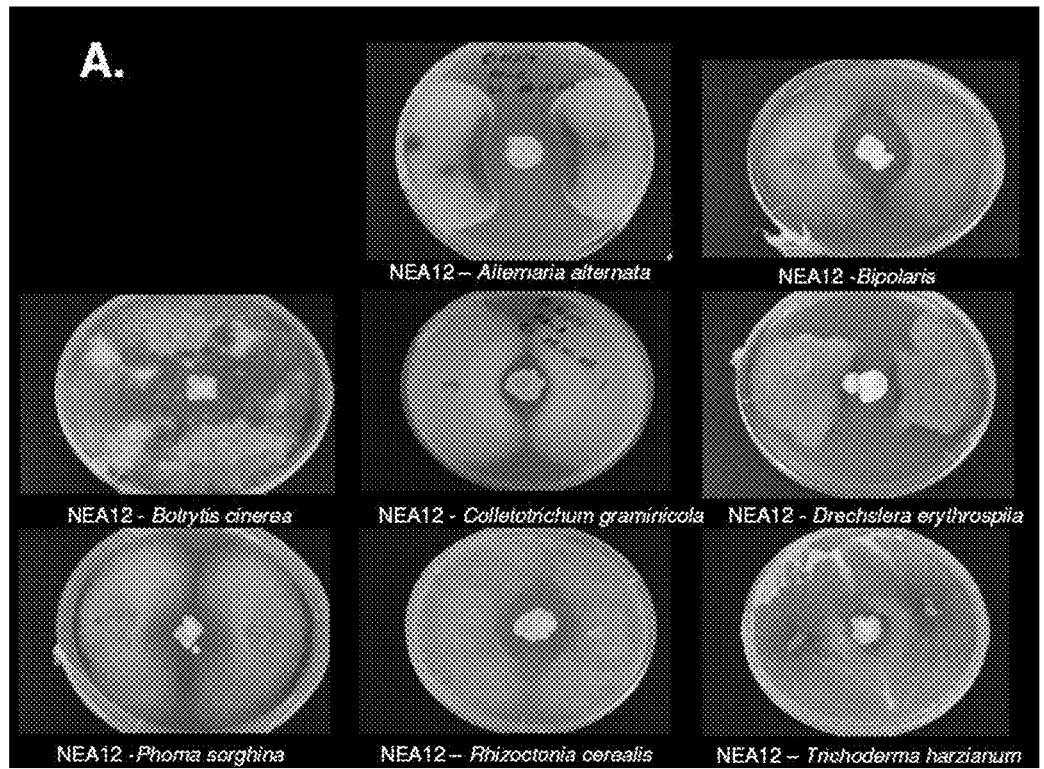
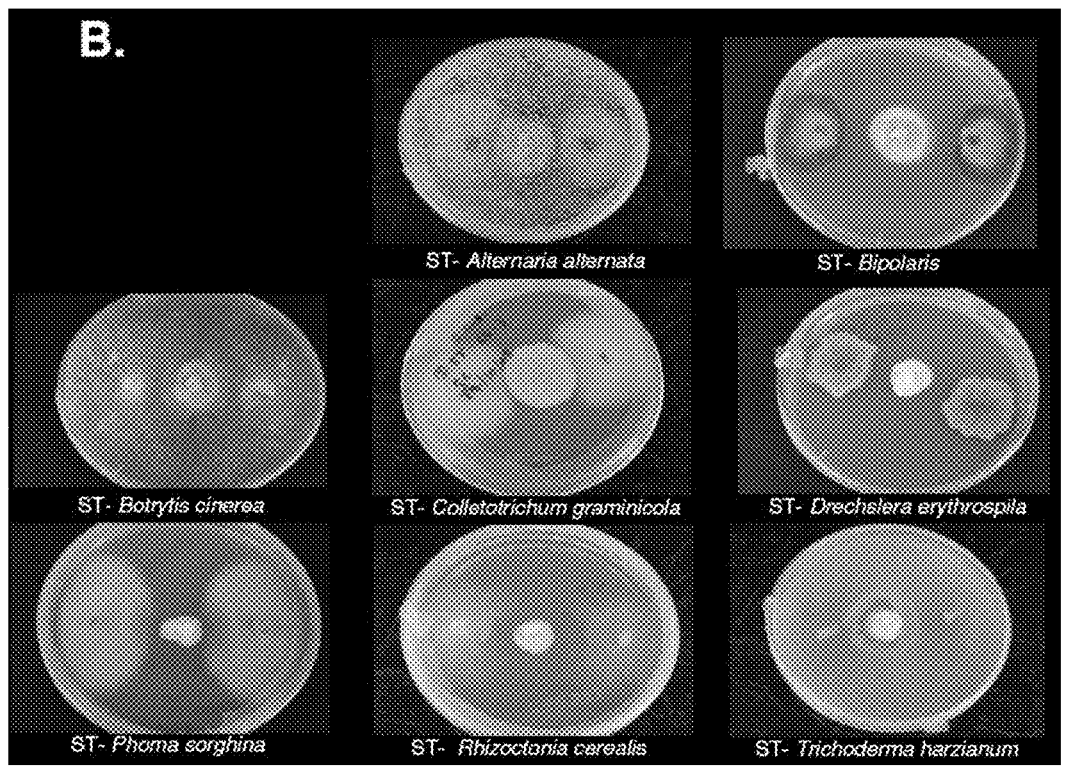

Figure 27
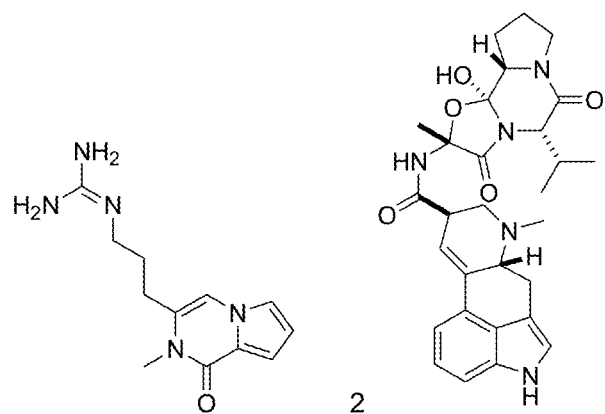
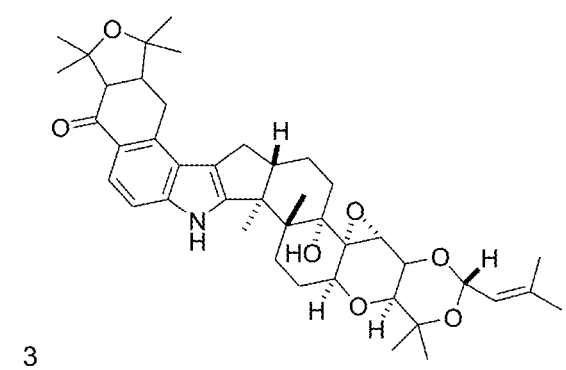
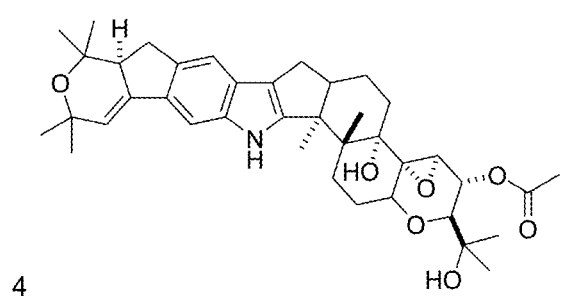
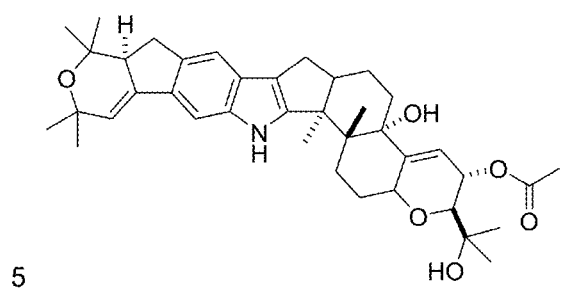

6

Figure 80
*Colletotrichum graminicola*
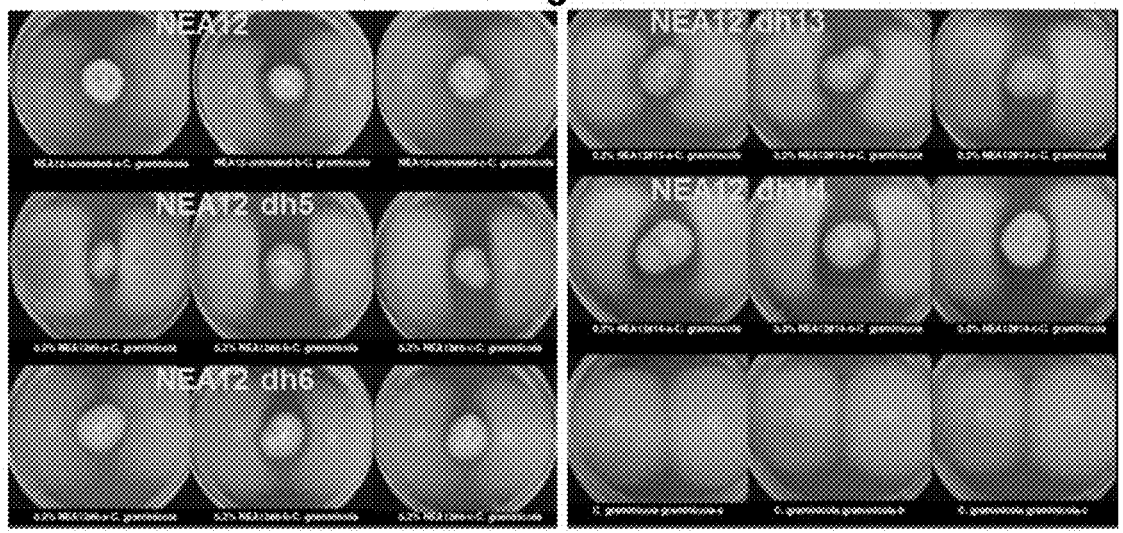
*Bipolaris portulaceae*
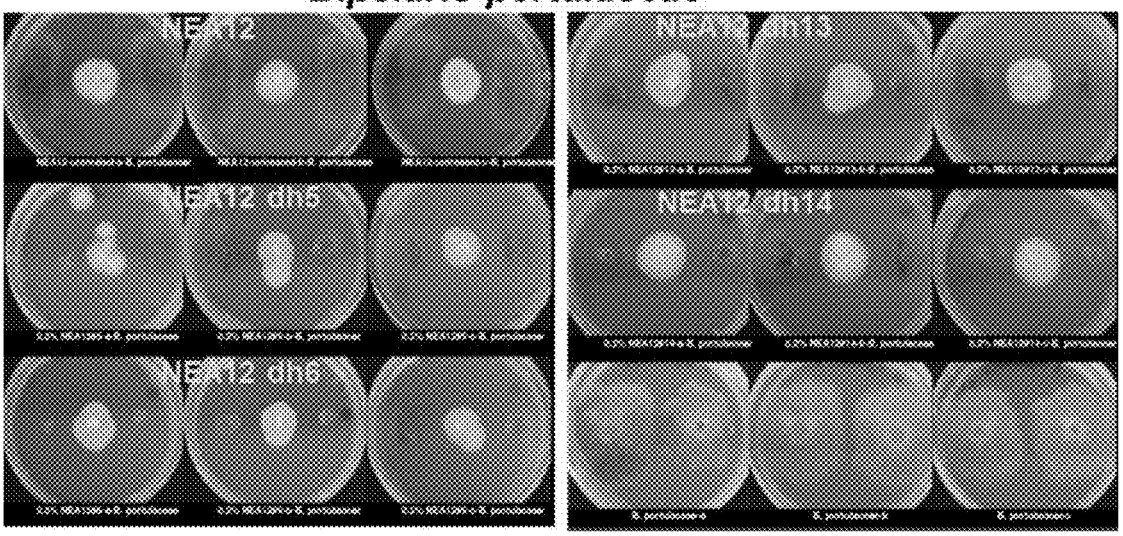

Figure 91
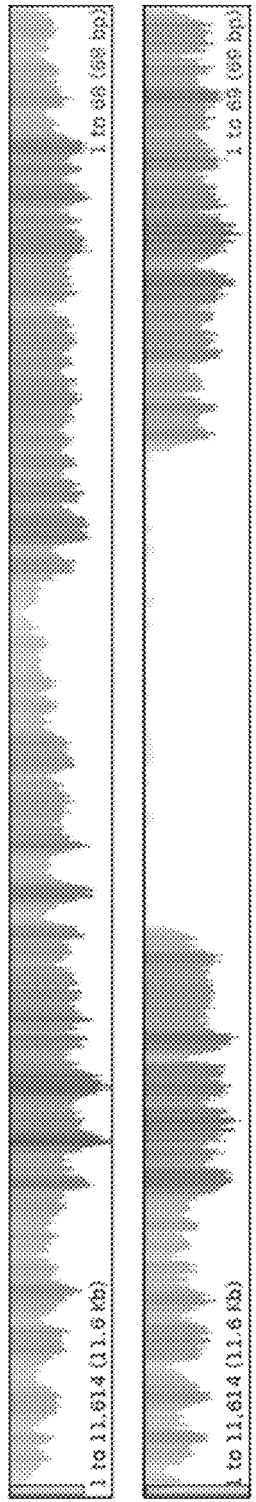
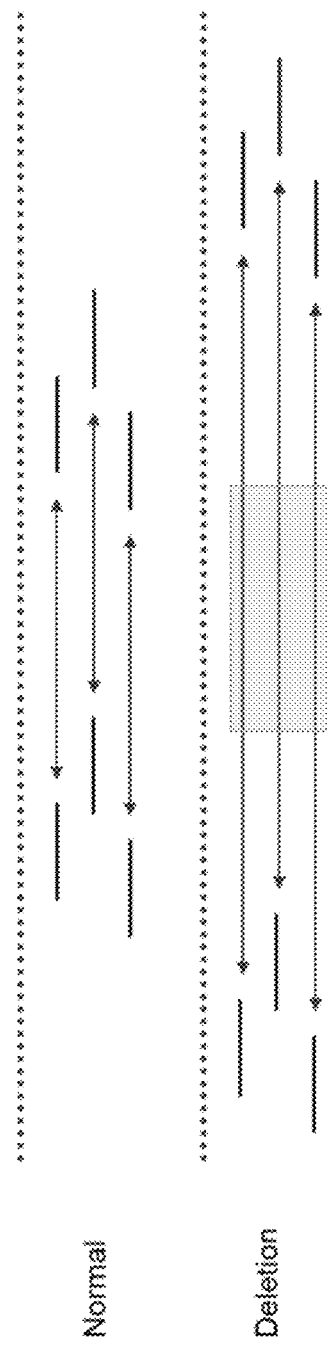
1. Differences in read depth
2. Differences in pair insert size
Normal
Deletion

```
                       SEQUENCE LISTING

<160> NUMBER OF SEQ ID NOS: 85

<210> SEQ ID NO 1
<211> LENGTH: 124
<212> TYPE: DNA
<213> ORGANISM: Epichloe festucae E2368

<400> SEQUENCE: 1 gcagggggaat gaggcgttcg gctgtgatga cggtggctgt tgaaaccgcc gcatgtttgc      60
tactgcgtac gtactttgg tgtttctcca acatagtaac tgtttcaata ttagaatgga     120
tgta                                                                  124

<210> SEQ ID NO 2
<211> LENGTH: 104
<212> TYPE: DNA
<213> ORGANISM: Endophyte E1

<400> SEQUENCE: 2
tgtgatgacg gtggctgttg aatccgccgc atgtttgcta ctgcgtacgt acttttggtg      60
tttctccaac atagtaactg tttcaatatt agaatggata tgta                     104

<210> SEQ ID NO 3
<211> LENGTH: 63
<212> TYPE: DNA
<213> ORGANISM: Endophyte NEA12

<400> SEQUENCE: 3 gcaggggggaa tgaggcgttc ggctgtgatg atggtggctg ttgaaaccgc cgcatgtttg      60
cta                                                                   63

<210> SEQ ID NO 4
<211> LENGTH: 62
<212> TYPE: DNA
<213> ORGANISM: Neotyphodium lolii

<400> SEQUENCE: 4 gcagggggaat gaggcgttcg gctgtgatga cggtggctgt tgaaaccgcc gcatgtttgc      60
ta                                                                    62

<210> SEQ ID NO 5
<211> LENGTH: 125
<212> TYPE: DNA
<213> ORGANISM: Epichloe festucae E2368

<400> SEQUENCE: 5
gccatgaaag catttaatgg tcgcttagct ttttcgcaaa tctgaacttt tgatttcaga      60
tgagagttca ttgtcgtttg gttgaatgtc ggcgtcatag tgggctgaaa tgtagtgtcg     120
aaata                                                                 125

<210> SEQ ID NO 6
```

```
<211> LENGTH: 125
<212> TYPE: DNA
<213> ORGANISM: Endophyte E1

<400> SEQUENCE: 6
gccatgaaag catttaatgg tcgcttagct ttttgcgaag tctgaacttt tgatttcaga      60
tgagagttca ttgtcgtttg gttgaatgtc ggcgtcatag tgggctgaaa tgtagtgtcg     120
aaata                                                                 125

<210> SEQ ID NO 7
<211> LENGTH: 106
<212> TYPE: DNA
<213> ORGANISM: Endophyte NEA12

<400> SEQUENCE: 7
ttatggccaa taccgatttg ctgtgcaaga ctctcacgca aatttggagg ctggtctcaa      60
atattttaaa tgttcaaatt gatgtttcag ctatgtagcg taaact                    106

<210> SEQ ID NO 8
<211> LENGTH: 105
<212> TYPE: DNA
<213> ORGANISM: Neotyphodium lolii

<400> SEQUENCE: 8
tatggccaat accgatttgc tgtgcaagac tctcacgcaa atttggaggc tggtctcaaa      60
tattttaaat gttcaaattg atgtttcagc tatgtagcgt aaact                     105

<210> SEQ ID NO 9
<211> LENGTH: 125
<212> TYPE: DNA
<213> ORGANISM: Epichloe festucae E2368

<400> SEQUENCE: 9
gcggagaaaa ccaaataggt cccgaatacc agagcaacta tggctcctga ctcgaagttg      60
atgaattgga gggcgaaact cacagggttt cagttgctgc atgtctctga attagattct     120
ctatt                                                                 125

<210> SEQ ID NO 10
<211> LENGTH: 125
<212> TYPE: DNA
<213> ORGANISM: Endophyte E1

<400> SEQUENCE: 10
gcggagaaaa ccaaataggt cccgaatacc agagcaacta tggctcctga ctcgaagttg      60
atgaattgga gggcgaaact cacagggttt cagttgctgc atgtctctga attagattct     120
ctatt                                                                 125

<210> SEQ ID NO 11
<211> LENGTH: 30
<212> TYPE: DNA
<213> ORGANISM: Endophyte NEA12

<400> SEQUENCE: 11
gagaattttc tttcaattgt acaaagcgcg                                       30

<210> SEQ ID NO 12
<211> LENGTH: 125
<212> TYPE: DNA
<213> ORGANISM: Neotyphodium lolii
```

-continued

<400> SEQUENCE: 12

```
gagaattttc tttcaattgt acaaagcgcg gaaacgtagc gacgaccgcc gcggggatca      60
atggagttat gggcgcatta cataggctct cacaagttgc atgtctctga attagattct     120
ctatt                                                                 125
```

<210> SEQ ID NO 13
<211> LENGTH: 539
<212> TYPE: DNA
<213> ORGANISM: Epichloe festucae

<400> SEQUENCE: 13

```
accagacgat acaatctcga tagtaaccgc ctgccccata gcgggattga ttacacccag      60
gcagctcatg acagtggtat caatctccaa tataagaccc tacgaacgga ctctgatata     120
acgccatcgt ccccgactca tgatgcccat gtgaaacctt taccagttgc caacgccgtg     180
tcctcgttag aggtcctgaa caatctgtgt gaacagagta gttggaaatg ggtggaaggt     240
atgttaattg gaggctgtct tcaatacggc ctagagcgat acgatgatgc gttcaagtcc     300
ttctcaagga ttgtcgcagt tgattccagg taagttgctc gccacaatac cctcactcct     360
ctgcttgatc tcacaatcac cggcttccca gccatgttga agctatcagt catatgggcg     420
cagccttgta ttgcctcgga cgtcaagatg aagcagagaa aattggctcc gggtgataaa     480
gctacgacca aattatctcg atgccacgga acacttggtg ggccatcttt ataaaaatc     539
```

<210> SEQ ID NO 14
<211> LENGTH: 540
<212> TYPE: DNA
<213> ORGANISM: Endophyte NEA11

<400> SEQUENCE: 14

```
accagacgat acaatctcga tagtaaccgc ctgccccata gcgggattga ttacacccag      60
gcagctcatg acagtggtat caatctccaa tataagaccc tacgaacgga ctctgatata     120
acgccatcgt ccccgactca tgatgcccat gtgaaacctt taccagttgc caacgccgtg     180
tcctcgttag aggtcctgaa caatctgtgt gaacagagta gttggaaatg ggtggaaggt     240
atgttaattg gaggctgtct tcaatacggc ctagagcgat acgatgatgc gttcaagtcc     300
ttctcaagga ttgtcgcagt tgattccagg taagttgctc gccacaatac cctcactcct     360
ctgcttgatc tcacaatcac cggcttccca gccatgttga agctatcagt catatgggcg     420
cagccttgta ttgcctcgga cgtcaagatg aagcagaga aaaattggct ccgggtgataa     480 agctacgac caaattatct cgatgccacg gaacacttgg tgggccatct ttataaaaatc    540
```

<210> SEQ ID NO 15
<211> LENGTH: 473
<212> TYPE: DNA
<213> ORGANISM: Endophyte NEA11

<400> SEQUENCE: 15

```
atagcggaat tgattacagc caggcagttc attacagtgg tatcaatctc caatataaga      60
ccacacgaac ggactctgat gtaacgccat cgtccccgac tcatgatgcc catgtgaagc     120
ctttacccgt cgccaacgcc gtgtcttcgc tagaggtcct gaacaacctg tgtgaacaga     180
gtggttggaa atgggtggaa ggtatgttag ttggaggctg tcttcagtac ggtctagagc     240
agtacgaaga tgccgttcaag tccttctcaa ggattgtcgc agttgattca aggtaagctg    300
```

```
cccgccacaa tactcccatt ccgttgcttg atctcacgat ccctggcttc ctagccatgt    360
tgaagctatc agtcatatgg gcgcagcctt gtattgcctc ggacgccaag acgaagcaga    420
gcaaaattgg ctccgggtgg taaagctacg accaaactat ctcgatgcca cgg           473

<210> SEQ ID NO 16
<211> LENGTH: 300
<212> TYPE: DNA
<213> ORGANISM: Neotyphodium lolii

<400> SEQUENCE: 16
gcgcgtcacg atttcccatt taacaccctc agtcacgcgg ctgatagacc cagattcaca     60
accttttcta aagacgatgg tgtttaccgg cgagcctctg tctgtggacg atgctacccg    120
atggtgggga aagtcgacg tcgtcaacga atatgggcct gacgagtgca ccatcaacac    180
tgtcaacagc cgacctatca gtcctgaagc tgctacgaac atagggctgc cggttggagt    240
ggccgcttgg attaccgacc cggaaaacca tcaagtactc gttccgatcg gctgtgttgg    300

<210> SEQ ID NO 17
<211> LENGTH: 266
<212> TYPE: DNA
<213> ORGANISM: Endophyte NEA11

<400> SEQUENCE: 17
gcgcgtcacg attgcccatt taacaccctc agtcacgcga ctgatagacc cagattcaca     60
acccgtcctc aagacgatgg tgtttaccgg cgagcctctg tctgtggacg atgctacccg    120
atggtgggga aagtcgacg tcgtcaacga atatgggctg cagagtgcac catcaacact    180
gtcaacagcc gacctatcag tcctgaagcc gctgcgaaca tagggctgcc ggttggagtg    240
gccgcttgga ttacagaccc ggaaaa                                         266

<210> SEQ ID NO 18
<211> LENGTH: 255
<212> TYPE: DNA
<213> ORGANISM: Endophyte NEA11

<400> SEQUENCE: 18
gcgcgtcacg attgcccatt taacaccctc agtcacgcga ctgatagacc cagattcaca     60
acccgtcctc aagacgatgg tgtttaccgg cgagcctctg tctgtggacg atgctacccg    120
atggtgggga aagttcgacg tcgtcaacga atatgggcct gcagagtgca ccatcaacac    180
tgtcaacagc cgacctatca gtcctgaagc cgctgcgaac atagggctgc cggttggagt    240
ggccgcttgg attac                                                     255

<210> SEQ ID NO 19
<211> LENGTH: 53
<212> TYPE: DNA
<213> ORGANISM: Endophyte NEA11

<400> SEQUENCE: 19
gcgcgtcacg attgcccatt taacaccctc agtcacgcga ctgatagacc cag            53

<210> SEQ ID NO 20
<211> LENGTH: 85
<212> TYPE: DNA
<213> ORGANISM: Endophyte NEA11

<400> SEQUENCE: 20
gcgcgtcacg attgcccatt taacaccctc agtcacgcga ctgatagacc cagattcaca     60
```
acccgtcctc aagacgatgg tgttt    85

<210> SEQ ID NO 21
<211> LENGTH: 44
<212> TYPE: DNA
<213> ORGANISM: Endophyte NEA11

<400> SEQUENCE: 21
gacccggaaa atgatcaagt actcgttcca atcggctgtg ttgg    44

<210> SEQ ID NO 22
<211> LENGTH: 107
<212> TYPE: DNA
<213> ORGANISM: Neotyphodium lolii

<400> SEQUENCE: 22
gtacggtgtc cttatcttct tgccattat ttgcggaagc gtcgcgggca cattttggac    60
caccattgga ccagtgacgg cggaagtcgt gggcctcaga aatgtac    107

<210> SEQ ID NO 23
<211> LENGTH: 107
<212> TYPE: DNA
<213> ORGANISM: Neotyphodium lolii

<400> SEQUENCE: 23
gtacggtgtc cttatcttct tgccattat ttgcggaagc gtcgcgggca cattctggac    60
caccattgga ccagtgacgg cggaagtcgt gggcctcaga aatgtac    107

<210> SEQ ID NO 24
<211> LENGTH: 104
<212> TYPE: DNA
<213> ORGANISM: Neotyphodium lolii

<400> SEQUENCE: 24
gtacggtgtc cttatcttct tgccattat ttgcggaagc gtcgcgggca cattctggac    60
caccattgga ccagtgacgg cggaagtggg cctcagaaat gtac    104

<210> SEQ ID NO 25
<211> LENGTH: 103
<212> TYPE: DNA
<213> ORGANISM: Neotyphodium lolii

<400> SEQUENCE: 25
gtacggtgtc cttatcttct tgccattat ttgcggaagc gtcgcgggca cattctggac    60
caccattgga ccagtgacgg cgtcgtgggc ctcagaaatg tac    103

<210> SEQ ID NO 26
<211> LENGTH: 101
<212> TYPE: DNA
<213> ORGANISM: Neotyphodium lolii

<400> SEQUENCE: 26
ttacggtgtc cttatcttct tgccattat ttgcggaagc gtcgcgggca cattctggac    60
ctccattgga ccagtggaag tcgtgggcct cagaaatgta c    101

<210> SEQ ID NO 27
<211> LENGTH: 99
<212> TYPE: DNA
<213> ORGANISM: Neotyphodium lolii

<400> SEQUENCE: 27
gtacggtgtc cttatcttct tgccattat ttgcggaagc gtcgcgggca cattctggac    60
caccattgga ccagtgacgc gtgggcctca gaaatgtac                          99

<210> SEQ ID NO 28
<211> LENGTH: 104
<212> TYPE: DNA
<213> ORGANISM: Neotyphodium lolii

<400> SEQUENCE: 28
gtacggtgtc cttatcttct tgccattat ttgcggaagc gtcgcgggca cattctggac    60
caccattgga ccagtgacgg cggaagtcgg cctcagaaat gtac                   104

<210> SEQ ID NO 29
<211> LENGTH: 100
<212> TYPE: DNA
<213> ORGANISM: Neotyphodium lolii

<400> SEQUENCE: 29
gtacggtgac cttatcttct tgccattat ttgcggaagc gtcgcgggca cattctggac    60
caccattgga ccagtgacgg cggaagtcgt gggcctcagc                        100

<210> SEQ ID NO 30
<211> LENGTH: 104
<212> TYPE: DNA
<213> ORGANISM: Neotyphodium lolii

<400> SEQUENCE: 30
gtacggtgtc cttatcttct tgccattat ttgcggaagc gtcgcgggca cattctggac    60
caccattgga ccagtgacgg cggaagtcgt gggcctaaat gtac                   104

<210> SEQ ID NO 31
<211> LENGTH: 101
<212> TYPE: DNA
<213> ORGANISM: Neotyphodium lolii

<400> SEQUENCE: 31
tacggtgtcc ttatcttctt tgccattatt tgcggaagcg tcgcgggcac attctggacc    60
accattggac cagtgacggc ggaagtcgtg ggcctcagaa a                       101

<210> SEQ ID NO 32
<211> LENGTH: 101
<212> TYPE: DNA
<213> ORGANISM: Neotyphodium lolii

<400> SEQUENCE: 32
ggtgtcctta tcttctttgc cattatttgc ggaagcgtcg cgggcacatt ctggaccacc    60
atttgaccag tgacggcgga agtcgtgggc tcagaaatg t                        101

<210> SEQ ID NO 33
<211> LENGTH: 101
<212> TYPE: DNA
<213> ORGANISM: Neotyphodium lolii

<400> SEQUENCE: 33
tgtccttatc ttctttgcca ttatttgcgg aagcgtcgcg ggcacattct ggaccaccat    60
tggaccagtg acggcggaag tcgtgggcct cagaaatgta c                       101

```
<210> SEQ ID NO 34
<211> LENGTH: 102
<212> TYPE: DNA
<213> ORGANISM: Neotyphodium lolii

<400> SEQUENCE: 34
gtgtccttat cttctttgcc attatttgcg gaagcgtcgc gggcacattc tggaccacca    60
ttggaccagt gacggcggaa gtcgtgggcc tcagaaatgt ac                      102

<210> SEQ ID NO 35
<211> LENGTH: 96
<212> TYPE: DNA
<213> ORGANISM: Neotyphodium lolii

<400> SEQUENCE: 35
ttatcttctt tgccattatt tgcggaagcg tcgcgggcac attctggacc accattggac    60
cagtgacggc ggaagtcgtg ggcctcagaa atgtac                              96

<210> SEQ ID NO 36
<211> LENGTH: 95
<212> TYPE: DNA
<213> ORGANISM: Neotyphodium lolii

<400> SEQUENCE: 36
tatcttcttt gccattattt gcggaagcgt cgcgggcaca ttctggacca ccattggacc    60
agtgacggcg gaagtcgtgg gcctcagaaa tgtac                               95

<210> SEQ ID NO 37
<211> LENGTH: 97
<212> TYPE: DNA
<213> ORGANISM: Neotyphodium lolii

<400> SEQUENCE: 37
gtactcttct tgccattat ttgcggaagc ggcgcgggca cattctggac caccattgga     60
ccagtgacgg cggaagtcgt gggcctcaga aatgtac                             97

<210> SEQ ID NO 38
<211> LENGTH: 100
<212> TYPE: DNA
<213> ORGANISM: Neotyphodium lolii

<400> SEQUENCE: 38
gtacggttct tctttgccat tatttgcgga agcgtcgcgg gcacattctg gaccaccatt    60
ggaccagtga cggcggaagt cgtgggcctc agaaatgtac                         100

<210> SEQ ID NO 39
<211> LENGTH: 97
<212> TYPE: DNA
<213> ORGANISM: Neotyphodium lolii

<400> SEQUENCE: 39
gtacgcttct tgccattat ttgcggaagc gtcgcgggca cattctggac caccattgga     60
ccagtgacgg cggaagtcgt gggcctcaga aatgtac                             97

<210> SEQ ID NO 40
<211> LENGTH: 89
<212> TYPE: DNA
<213> ORGANISM: Neotyphodium lolii

<400> SEQUENCE: 40
```

```
ctttgccatt atttgcggaa gcgtcgcggg cacattctgg accaccattg gaccagtgac    60
ggcggaagtc gtgggcctca gaaatgtac                                      89
```

<210> SEQ ID NO 41
<211> LENGTH: 95
<212> TYPE: DNA
<213> ORGANISM: Neotyphodium lolii

<400> SEQUENCE: 41

```
gtacggtgtc gccattattt gcggaagcgt cgcgggcaca ttctggacca ccattggacc    60
agtgacggcg gaagtcgtgg gcctcagaaa tgtac                               95
```

<210> SEQ ID NO 42
<211> LENGTH: 94
<212> TYPE: DNA
<213> ORGANISM: Neotyphodium lolii

<400> SEQUENCE: 42

```
gtacggtgtc ccattatttg cggaagcgtc gcgggcacat tctggaccac cattggacca    60
gtgacggcgg aagtcgtggg ccccagaaat gtac                                94
```

<210> SEQ ID NO 43
<211> LENGTH: 84
<212> TYPE: DNA
<213> ORGANISM: Neotyphodium lolii

<400> SEQUENCE: 43

```
ccattatttg cggaagcgtc gcgggcacat tctggaccac cattggacca gtgacggcgg    60
aagtcgtggg cctcagaaat gtac                                           84
```

<210> SEQ ID NO 44
<211> LENGTH: 98
<212> TYPE: DNA
<213> ORGANISM: Neotyphodium lolii

<400> SEQUENCE: 44

```
gtacggtgtc cttatcatta tttgcggaag cgtcgcgggc acattctgga ccaccattgg    60
accagtgacg gcggaagtcg tgggcctcag aaatgtac                            98
```

<210> SEQ ID NO 45
<211> LENGTH: 102
<212> TYPE: DNA
<213> ORGANISM: Neotyphodium lolii

<400> SEQUENCE: 45

```
gtacggtgtc cttatcttct attatttgcg gaagcgtcgc gggcacattc tggaccacca    60
ttggaccagt gacggcggaa gtcgtgggcc tcagaaatgt ac                      102
```

<210> SEQ ID NO 46
<211> LENGTH: 93
<212> TYPE: DNA
<213> ORGANISM: Neotyphodium lolii

<400> SEQUENCE: 46

```
gtacggtgtc cttatcttct ttcattattt gcggaagcgt cgcgggcaca ttctggacca    60
ccattggacc agtgacgggc ctcagaaatg tac                                 93
```

<210> SEQ ID NO 47
<211> LENGTH: 103

```
<212> TYPE: DNA
<213> ORGANISM: Neotyphodium lolii

<400> SEQUENCE: 47
gtacggtgtc cttatcttct ttgcatttgc ggaagcgtcg cgggcacatt ctggaccacc    60
attggaccag tgacggcgga agtcgtgggc tcagaaatg tac                      103

<210> SEQ ID NO 48
<211> LENGTH: 157
<212> TYPE: DNA
<213> ORGANISM: Neotyphodium lolii

<400> SEQUENCE: 48
tgccgccgaa attgttatcc cagttgccca cttgactcca cgaccagatt tccaaacaag    60
catctctccc aacaaaaaaa agagcaaaaa acagttcgcg cgacgacaac aaactagctc   120
ggaaaccccc ggcatgccgc atacataatg gccgaag                            157

<210> SEQ ID NO 49
<211> LENGTH: 156
<212> TYPE: DNA
<213> ORGANISM: Neotyphodium lolii

<400> SEQUENCE: 49
tgccgccgaa attgttatcc cagttgccca cttgactcca cgaccagatt tccaaacaag    60
catctctccc aacaaaaaaa agagcaaaaa acagttcgcg cgacgacaac aaactagctc   120
ggaaaccccg gcatgccgca tacataatgg ccgaag                             156

<210> SEQ ID NO 50
<211> LENGTH: 150
<212> TYPE: DNA
<213> ORGANISM: Neotyphodium lolii

<400> SEQUENCE: 50
tgccgccgaa cttgttatcc cagttgcccc acttgactcc acgaccagat tccaaacaa     60 gcatctctcc caacaaaaaa aagagcaaaa acagttgac aacaaactag ctcggaaacc    120
cccggcatgc cgcatacata atggccgaag                                    150

<210> SEQ ID NO 51
<211> LENGTH: 153
<212> TYPE: DNA
<213> ORGANISM: Neotyphodium lolii

<400> SEQUENCE: 51
cgccgaaatt gttatcccag ttgccccact tgactccacg accagatttc caaacaagca    60
tctctcccaa caaaaaaaag agcaaaaaac agttcgcgcg acgaacaaac tagctcggaa   120 accccggca tgccgcatac ataatggccg aag                                 153

<210> SEQ ID NO 52
<211> LENGTH: 153
<212> TYPE: DNA
<213> ORGANISM: Neotyphodium lolii

<400> SEQUENCE: 52
tggccgaaat tgttatccca gttgccccac ttgactccac gaccagattt ccaaacaagc    60
atctctccca acaaaaaaaa gagcaaaaaa cagttcgcgc gacaacaaac tagctcggaa   120 accccggca tgccgcatac ataatggccg aag                                 153
```

<210> SEQ ID NO 53
<211> LENGTH: 151
<212> TYPE: DNA
<213> ORGANISM: Neotyphodium lolii

<400> SEQUENCE: 53

```
tcgaaattgt tatcccagtt gccccacttg actccacgac cagatttcca aacaagcatc      60
tctcccaaca aaaaaagag caaaaaacag ttcgcgcgac gacaaaacta gctcggaaac      120
ccccggcatg ccgcatacat aatggccgaa g                                    151
```

<210> SEQ ID NO 54
<211> LENGTH: 138
<212> TYPE: DNA
<213> ORGANISM: Neotyphodium lolii

<400> SEQUENCE: 54

```
tgccggaaat tgttatccca gttgccccac ttgactccac gaccagattt ccaaacaagc      60
atctctccca acaaaaaaaa gagcaaaaaa cagttcgcgc gacgacaacc cggcatgccg      120
catacataat ggccgaag                                                   138
```

<210> SEQ ID NO 55
<211> LENGTH: 150
<212> TYPE: DNA
<213> ORGANISM: Neotyphodium lolii

<400> SEQUENCE: 55

```
taaattgtta tcccagttgc cccacttgac tccacgacca gatttccaaa caagcatctc      60
tcccaacaaa aaagagcaa aaaacagttc gcgcgacgac aacaaactag ctcggaaacc      120
cccggcatgc cgcatacata atggccgaag                                      150
```

<210> SEQ ID NO 56
<211> LENGTH: 142
<212> TYPE: DNA
<213> ORGANISM: Neotyphodium lolii

<400> SEQUENCE: 56

```
tgccgccgaa atttatccca gttgccccac ttgactccac gaccagattt ccaaacaagc      60
atctctccca acaaaaaaaa gagcaaaaaa cagttcgcgc gacgacaaca aacccggcat      120
gccgcataca taatggccga ag                                              142
```

<210> SEQ ID NO 57
<211> LENGTH: 149
<212> TYPE: DNA
<213> ORGANISM: Neotyphodium lolii

<400> SEQUENCE: 57

```
tgccgccgaa attgttatcc cagttcccac tgggctccac gaccagattt ccaaacaagc      60
atctctccca acaaaaaaaa gagcaaaaaa cagttcgcgc gacgacaaca aactagctcg      120
gcggcatgcc gcatacataa tggccgaag                                       149
```

<210> SEQ ID NO 58
<211> LENGTH: 150
<212> TYPE: DNA
<213> ORGANISM: Neotyphodium lolii

<400> SEQUENCE: 58

```
tgccgccgaa attgttatcc cagttgctga ctccacgacc agatttccaa acaagcatct      60
```
ctcccaacaa aaaaaagagc aaaaaacagt tcgcgcgacg acaacaaact agctcggaaa    120
cccggcatgc cgcatacata atggccgaag                                    150

<210> SEQ ID NO 59
<211> LENGTH: 148
<212> TYPE: DNA
<213> ORGANISM: Neotyphodium lolii

<400> SEQUENCE: 59
tgccgccgaa attgttatcc cagttgcgac tccacgacca gatttccaaa caagcatctc    60
tcccaacaaa aaaagagca aaaaacagtt cgcgcgacga caacaaacta gctcggaaac   120
ccccatgccg catacataat ggccgaag                                     148

<210> SEQ ID NO 60
<211> LENGTH: 131
<212> TYPE: DNA
<213> ORGANISM: Neotyphodium lolii

<400> SEQUENCE: 60
ttatcccagt tgccccactt gactccacga ccagatttcc aaacaagcat ctctcccaac    60 aaaaaaaga gcaaaaaaca gttcgcgcga cgacaacaaa ctacggcatg ccgcatacat   120
aatggccgaa g                                                       131

<210> SEQ ID NO 61
<211> LENGTH: 157
<212> TYPE: DNA
<213> ORGANISM: Neotyphodium lolii

<400> SEQUENCE: 61
tgccgcctaa attgttatcc cagttgcccc acttgactcc acgaccagat ttccaaacaa    60
gcatctctcc caacaaaaaa agagcaaaaa acagttcgcg cgacgacaac aaactagctc   120 ggaaacccccc ggcatgccgc atacataatg gccgaag                          157

<210> SEQ ID NO 62
<211> LENGTH: 153
<212> TYPE: DNA
<213> ORGANISM: Neotyphodium lolii

<400> SEQUENCE: 62
tgccgccgaa attgttatcc cagttgcccc actactccac gaccagattt ccaaacaagc    60
atctctccca caaaaaaaa gagcaaaaaa cagttcgcgc gacgacaaca aactagctcg   120 gaaaccccccg gcatgcatac ataatggccg aag                              153

<210> SEQ ID NO 63
<211> LENGTH: 150
<212> TYPE: DNA
<213> ORGANISM: Neotyphodium lolii

<400> SEQUENCE: 63
tgccgccgaa attgttatcc cagttgcccc acttgactga ccagatttcc aaacaagcat    60
ctctcccaac aaaaaaaga gcaaaaaaca gttcgcgcga cgacaacaaa ctagctcgga   120 aaccccggc atgccgcata catgccgaag                                    150

<210> SEQ ID NO 64
<211> LENGTH: 146
<212> TYPE: DNA

<213> ORGANISM: Neotyphodium lolii

<400> SEQUENCE: 64

| tgccgccgaa attgttatcc cagttgcccc acttgaccag atttccaaac aagcatctct | 60 |
| cccaacaaaa aaaagagcaa aaaacagttc gcgcgacgac aacaaactag ctcggaaacc | 120 |
| cccggcatgc cgcatacata ccgaag | 146 |

<210> SEQ ID NO 65
<211> LENGTH: 143
<212> TYPE: DNA
<213> ORGANISM: Neotyphodium lolii

<400> SEQUENCE: 65

| tgccgccgaa attgttatcc cagttccac gaccagattt ccaaacaagc atctctccca | 60 |
| acaaaaaaaa gagcaaaaaa cagttcgcgc gacgacaaca aactagctcg gaaaccccg | 120 |
| gcatgccgcc ataatggccg aag | 143 |

<210> SEQ ID NO 66
<211> LENGTH: 151
<212> TYPE: DNA
<213> ORGANISM: Neotyphodium lolii

<400> SEQUENCE: 66

| tgccgccgaa attgttatcc cagttgcccc acttgactcc acgaccagat caaacaagca | 60 |
| tctctcccaa caaaaaaaag agcaaaaaac agttcgcgcg acgacaacaa actagctcgg | 120 |
| aaaccccgg catgccgcat acataacgaa g | 151 |

<210> SEQ ID NO 67
<211> LENGTH: 137
<212> TYPE: DNA
<213> ORGANISM: Neotyphodium lolii

<400> SEQUENCE: 67

| tgccgccgaa attgttatcc cagttgcccc actccagatt tccaaacaag catctctccc | 60 |
| aacaaaaaaa agagcaaaaa acagttcgcg cgacgacaac aaactagctc ggaaaccccc | 120 |
| ggcatgccgc atacatg | 137 |

<210> SEQ ID NO 68
<211> LENGTH: 154
<212> TYPE: DNA
<213> ORGANISM: Neotyphodium lolii

<400> SEQUENCE: 68

| tgccgccgaa attgttatcc cagttgcccc acttgactcc acgaccagat taacaagcat | 60 |
| ctctcccaac aaaaaaaaga gcaaaaaaca gttcgcgcga cgacaacaaa ctagctcgga | 120 |
| aaccccggc atgccgcata cataatggcc gaag | 154 |

<210> SEQ ID NO 69
<211> LENGTH: 155
<212> TYPE: DNA
<213> ORGANISM: Neotyphodium lolii

<400> SEQUENCE: 69

| tgccgccgaa attgttatcc cagttgcccc acttgactcc acgaccagat ttccaaaaag | 60 |
| catctctccc aacaaaaaaa agagcaaaaa acagttcgcg cgacgacaac aaactagctc | 120 |
| ggaaaccccc ggcatgccgc atacataatg gccga | 155 |

```
<210> SEQ ID NO 70
<211> LENGTH: 153
<212> TYPE: DNA
<213> ORGANISM: Neotyphodium lolii

<400> SEQUENCE: 70
tgccgccgaa attgttatcc cagttgcccc acttgactcc acgaccagat tacaagcatc    60
tctcccaaca aaaaaagag caaaaaacag ttcgcgcgac gacaacaaac tagctcggaa    120 accccccggca tgccgcatac ataatggccg aag                                153

<210> SEQ ID NO 71
<211> LENGTH: 157
<212> TYPE: DNA
<213> ORGANISM: Neotyphodium lolii

<400> SEQUENCE: 71
tgccgccgaa attgttatcc cagttgcccc acttgactcc acgaccagat ttccaaacaa    60
gctctctccc aacaaaaaaa agagcaaaaa acagttcgcg cgacgacaac aaactagctc    120
ggaaaccccc ggcatgccgc atacataatg gccgaag                             157

<210> SEQ ID NO 72
<211> LENGTH: 152
<212> TYPE: DNA
<213> ORGANISM: Neotyphodium lolii

<400> SEQUENCE: 72
tgccgccgaa attgttatcc cagttgcccc acttgactcc acgaccagat ttccaaacaa    60
gcatctccca acaaaaaaaa gagcaaaaaa cagttcgcgc gacgacaaca aactagctgg    120
gaaacggcat gccgcataca taatggccga ag                                  152

<210> SEQ ID NO 73
<211> LENGTH: 157
<212> TYPE: DNA
<213> ORGANISM: Neotyphodium lolii

<400> SEQUENCE: 73
tgccgccgaa attgttatcc cagttgcccc acttgactcc acgaccagat ttccaaacaa    60
gcatctcccc aacaaaaaaa agagcaaaaa acagttcgcg cgacgacaac aaactagctc    120
ggaaaccccc ggcatgccgc atacataatg gccgaag                             157

<210> SEQ ID NO 74
<211> LENGTH: 157
<212> TYPE: DNA
<213> ORGANISM: Neotyphodium lolii

<400> SEQUENCE: 74
tgccgccgaa attgttatcc cagttgcccc acttgactcc acgaccagat ttccaaacaa    60
gcatctctcc aacaaaaaaa agagcaaaaa acagttcgcg cgacgacaac aaactagctc    120
ggaaaccccc ggcatgccgc atacataatg gccgaag                             157

<210> SEQ ID NO 75
<211> LENGTH: 154
<212> TYPE: DNA
<213> ORGANISM: Neotyphodium lolii

<400> SEQUENCE: 75
```

```
tgccgccgaa attgttatcc cagttgcccc acttgactcc acgaccagat ttccaaacaa    60
gcatctctcc caaaaaaaga gcaaaaaaca gttcgcgcga cgacaacaaa ctagctcgga   120 aaccccggc atgccgcata cataatggcc gaag                                154
```

<210> SEQ ID NO 76
<211> LENGTH: 158
<212> TYPE: DNA
<213> ORGANISM: Neotyphodium lolii

<400> SEQUENCE: 76

```
tgccgccgaa attgttatcc cagttgcccc acttgactcc acgaccagat ttccaaacaa    60
gcatctctcc caacaaaaaa aagagcaaaa aacagttcgc gcgacgacaa caaactagct   120
cggaaacccc cggcatgccg catacataat ggccgaag                           158
```

<210> SEQ ID NO 77
<211> LENGTH: 151
<212> TYPE: DNA
<213> ORGANISM: Neotyphodium lolii

<400> SEQUENCE: 77

```
tgccgccgaa attgttatcc cagttgcccc acttgactcc acgaccagat ttccaaacaa    60
gcatctctcc caaaaaaaga gcaaaaaaca gttcgcgcta cgacaacaaa ctagctcgga   120 aaccccggc atgccgcata cataatggcc g                                   151
```

<210> SEQ ID NO 78
<211> LENGTH: 156
<212> TYPE: DNA
<213> ORGANISM: Neotyphodium lolii

<400> SEQUENCE: 78

```
tgccgccgaa attgttatcc cagttgcccc acttgactcc acgaccagat ttccaaacaa    60
gcatctctcc caacaaaaaa gagcaaaaaa cagttcgcgc gacgacaaca aactagctcg   120 gaaaccccg gcatgccgca tacataatgg ccgaag                              156
```

<210> SEQ ID NO 79
<211> LENGTH: 157
<212> TYPE: DNA
<213> ORGANISM: Neotyphodium lolii

<400> SEQUENCE: 79

```
tgccgccgaa attgttatcc cagttgcccc acttgactcc acgaccagat ttccaaacaa    60
gcatctctcc caacaaaaaa agagcaaaaa acagttcgcg cgacgacaac aaactagctc   120 ggaaacccccc ggcatgccgc atacataatg gccgaag                           157
```

<210> SEQ ID NO 80
<211> LENGTH: 148
<212> TYPE: DNA
<213> ORGANISM: Neotyphodium lolii

<400> SEQUENCE: 80

```
tgccgccgaa attgttatcc cagttgcccc acttgactcc acgaccagat ttccaaacaa    60
gcatctctcc caacaaaaaa aacagttcgc gcgacgacaa caaactagct cggaaacccc   120
cggcatgccg catacataat ggccgaag                                      148
```

<210> SEQ ID NO 81
<211> LENGTH: 154

```
<212> TYPE: DNA
<213> ORGANISM: Neotyphodium lolii

<400> SEQUENCE: 81
tgccgccgaa attgttatcc cagttgcccc acttgactcc acgaccagat ttccaaacaa     60
gcatctctcc caacaaaaaa aagagcaaaa gttcgcgcga cgacaacaaa ctagctcgga    120 aaccccggc atgccgcata cataatggcc gaag                                 154

<210> SEQ ID NO 82
<211> LENGTH: 153
<212> TYPE: DNA
<213> ORGANISM: Neotyphodium lolii

<400> SEQUENCE: 82
tgccgccgaa attgttatcc cagttgcccc acttgactcc acgaccagat ttccaaacaa     60
gcatctctcc caacaaaaaa aagagcaaaa atcgcgcgac gacaacaaac tagctcggaa    120 accccggca tgccgcatac ataatggccg aag                                  153

<210> SEQ ID NO 83
<211> LENGTH: 138
<212> TYPE: DNA
<213> ORGANISM: Neotyphodium lolii

<400> SEQUENCE: 83
tgccgccgaa attgttatcc cagttgcccc acttgactcc acgaccagat ttccaaacaa     60
gcatctctcc caacaaaaaa aagagcaaaa aaaactagct cggaaacccc cggcatgccg    120
catacataat ggccgaag                                                  138

<210> SEQ ID NO 84
<211> LENGTH: 120
<212> TYPE: DNA
<213> ORGANISM: Neotyphodium lolii

<400> SEQUENCE: 84
tgccgccgaa attgttatcc cagttgcccc acttgactcc acgaccagat ttccaaacaa     60
gcatctctcc caacaaaaaa aagagcaaaa aacagcatgc cgcatacata atggccgaag    120

<210> SEQ ID NO 85
<211> LENGTH: 117
<212> TYPE: DNA
<213> ORGANISM: Neotyphodium lolii

<400> SEQUENCE: 85
tgccgccgaa attgttatcc cagttgcccc acttgactcc acgaccagat ttccaaacaa     60
gcatctctcc caacaaaaaa aagagcaaaa aacagttcgc atacataatg gccgaag       117
```

ENDOPHYTES AND RELATED METHODS

This application is a continuation of U.S. application Ser. No. 13/543,200, filed Jul. 6, 2012, which is a continuation in part of PCT/AU2011/000020, filed Jan. 7, 2011, which claims priority from Australian Patent Application filed Jan. 7, 2010, and Australian Patent Application 2010902821, filed Jun. 25, 2010, and also claims priority from Australian Patent Application Nos. 2012902275 and 2012902276, filed Jun. 1, 2012. All of these applications are incorporated herein by reference in their entirety.

FIELD OF THE INVENTION

The present invention relates to endophytic fungi (endophytes), including modified variants thereof, and to nucleic acids thereof. The present invention also relates to plants infected with endophytes and to related methods, including methods of selecting, breeding, characterising and/or modifying endophytes.

BACKGROUND OF THE INVENTION

Important forage grasses perennial ryegrass and tall fescue are commonly found in association with fungal endophytes.

Both beneficial and detrimental agronomic properties result from the association, including improved tolerance to water and nutrient stress and resistance to insect pests.

Insect resistance is provided by specific metabolites produced by the endophyte, in particular loline alkaloids and peramine. Other metabolites produced by the endophyte, lolitrems and ergot alkaloids, are toxic to grazing animals and reduce herbivore feeding.

Considerable variation is known to exist in the metabolite profile of endophytes. Endophyte strains that lack either or both of the animal toxins have been introduced into commercial cultivars.

Molecular genetic markers such as simple sequence repeat (SSR) markers have been developed as diagnostic tests to distinguish between endophyte taxa and detect genetic variation within taxa. The markers may be used to discriminate endophyte strains with different toxin profiles.

However, there remains a need for methods of identifying, isolating, characterising and/or modifying endophytes and a need for new endophyte strains having desired properties.

In the fungal kingdom, there is no differentiation of individuals into sexes generating different gametes, but instead mating-type identity is determined by inheritance of alleles at specific mating-type loci.

The mating-type (MAT) genes constitute master regulators of sexual reproduction in filamentous fungi. Although mating-type loci consist of one to a few linked genes, and are thus limited to a small genomic region, alternate sequences at MAT, denoted idiomorphs, lack significant sequence similarity and encode different transcriptional regulators.

Fusion events are required during sexual reproduction in filamentous ascomycete species. Although cell fusion processes associated with vegetative growth as opposed to sexual development serve different developmental functions, both require extracellular communication and chemotropic interactions, followed by cell wall breakdown, membrane-merger and pore formation.

A number of genes have been characterised that are required for both sexual reproduction and vegetative hyphal fusion, including components of the MAPK pathway which is activated in response to pheromone perception during mating. The expression of pheromone precursors and pheromone receptor genes is directly controlled by transcription factors encoded by the mating-type genes.

Hyphal fusion occurs readily within an individual colony during vegetative growth, maintaining the physiological continuity of the organism. Hyphal fusion between different endophyte strains of opposite mating-type may be promoted by treating the mycelia with a combination of cell wall-degrading enzymes and fusion agents such as PEG4000.

However, there remains a need for methods of molecular breeding of endophytes and for new endophyte strains having desired properties.

*Neotyphodium* endophytes are not only of interest in agriculture, as they are a potential source for bioactive molecules such as insecticides, fungicides, other biocides and bioprotectants, allelochemicals, medicines and nutraceuticals.

Difficulties in artificially breeding of these endophytes limit their usefulness. For example, many of the novel endophytes known to be beneficial to pasture-based agriculture exhibit low inoculation frequencies and are less stable in elite germplasm. Thus, there remains a need for methods of generating novel, highly compatible endophytes.

There also remains a need for more endophyte strains with desirable properties and for more detailed characterisation of their toxin and metabolic profiles, antifungal activity, stable host associations and their genomes.

It is an object of the present invention to overcome, or at least alleviate, one or more of the difficulties or deficiencies associated with the prior art.

SUMMARY OF THE INVENTION

In a first aspect, the present invention provides a method for selecting and/or characterising an endophyte strain, said method including:
  providing a plurality of samples of endophytes;
  subjecting said endophytes to genetic analysis;
  subjecting said endophytes to metabolic analysis; and
  selecting endophytes having a desired genetic and metabolic profile.

In a preferred embodiment, this aspect of the invention may include the further step of assessing geographic origin of the endophytes and selecting endophytes having a desired genetic and metabolic profile and a desired geographic origin.

In a preferred embodiment, the plurality of samples of endophytes may be provided by a method including:
  providing a plurality of plant samples; and
  isolating endophytes from said plant samples.

In a preferred embodiment, the method may be performed using an electronic device, such as a computer.

BRIEF DESCRIPTION OF THE DRAWINGS

Figure 1:
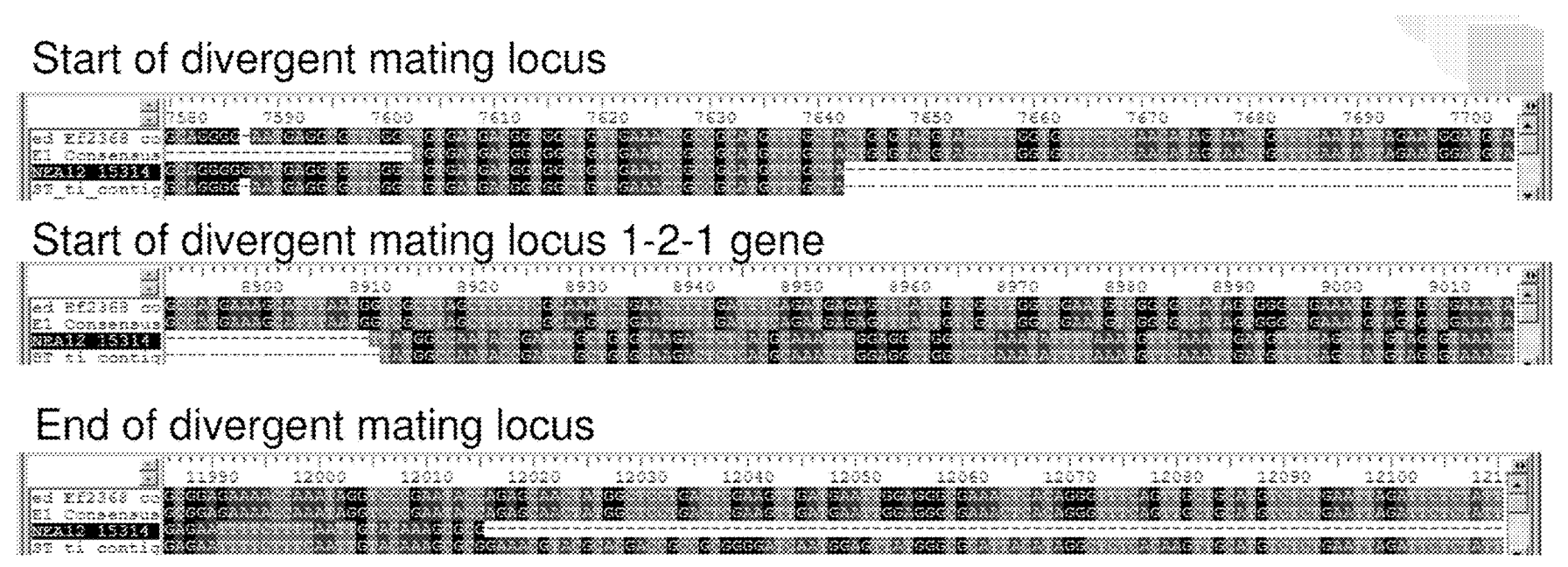

FIG. 1 shows sequence alignment analysis of mating-type loci of endophyte strains *E. festucae* strain E2368, E1, NEA12 and ST (SEQ ID NOs: 1-12).

FIG. 3 shows isogenic inoculation methodology for endophyte inoculation. A. Meristem callus induction (4 weeks); B. Embryogenic callus proliferation (4 weeks); C. Shoot (and root) regeneration (5 days, 16 hours light); D. Endophyte inoculation; E. Plantlet growth (4 weeks, 16 hours light); F. Growth in soil (3 months); G. SSR-based analysis.

FIGS. 58 A-D show presence of eas gene cluster for ergovaline biosynthesis.

FIGS. 61 A-D show presence of Lolitrem B biosynthetic gene cluster 1 (ItmG, ItmM and ItmK) in endophyte strains.

62B non-*Epichloe* out-group NEA18 (FEtc6-75)

FIGS. 63 A-D show presence of Lolitrem B biosynthetic gene cluster 3 (ItmE and ItmJ) in endophyte strains.

FIGS. 66 A-D show presence of Loline biosynthetic gene cluster in endophyte strains.

FIGS. 67 A-F show alkaloid biosynthetic gene analysis for endophyte strain NEA23 (269850).

FIG. 80 shows antifungal bioassays of NEA12$^{dh}$ *Neotyphodium* endophyte strains.

FIG. 91 shows deletions in genome sequences of X-ray irradiated *Neotyphodium* endophyte strains.

DETAILED DESCRIPTION OF THE INVENTION

Figure 2A:
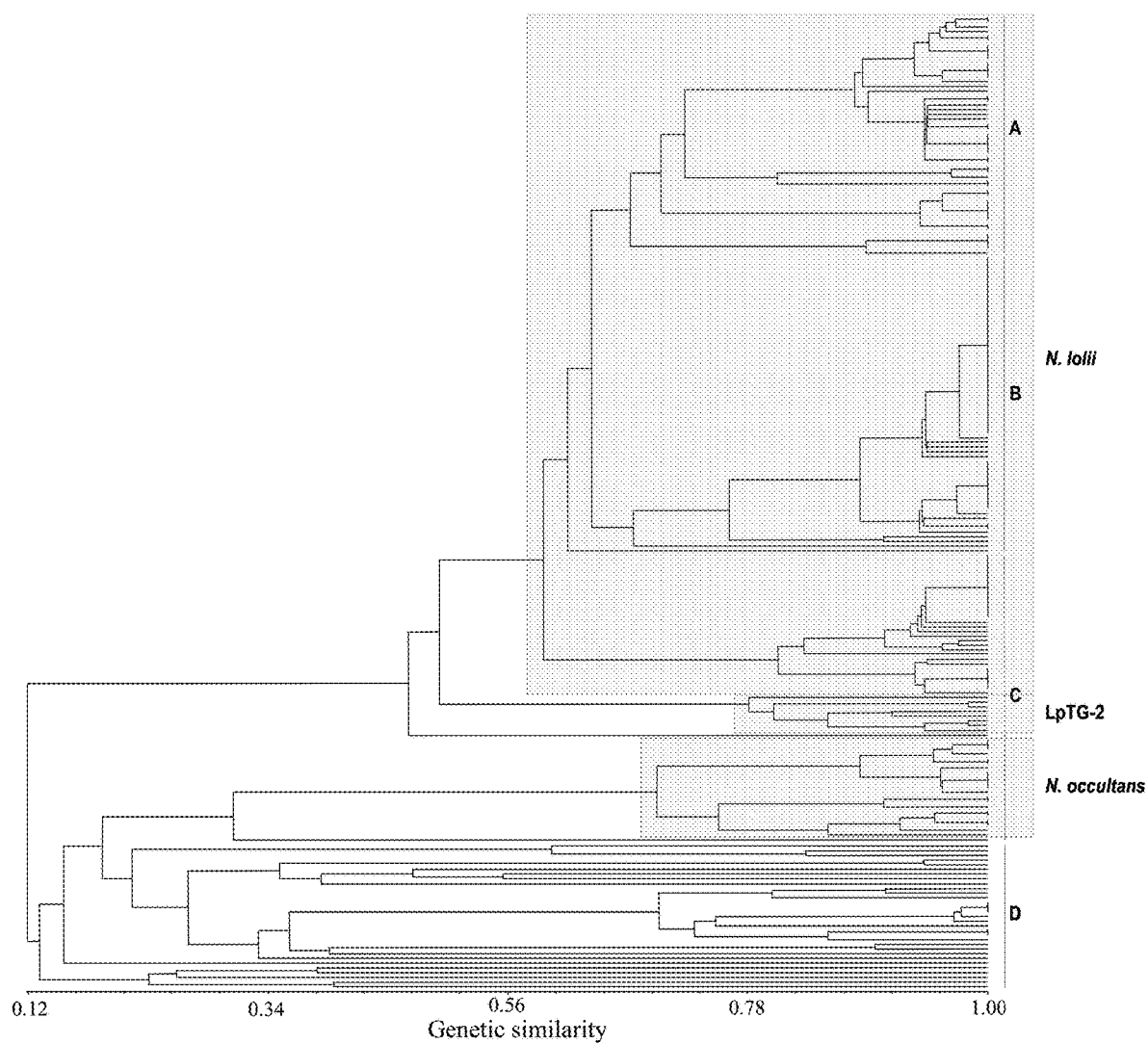
FIG. 2A shows a UPGMA phenogram of genetic relationships among endophytes in ryegrass accessions of diverse origins and reference *Neotyphodium* and *Epichloë* species. Genetic identity was measured across 18 SSR loci using the Dice coefficient. Detailed annotations for sections A-D are shown in FIGS. 2B to 2E, respectively. Specifically, accessions analysed in this study are shaded in grey, the number of genotypes host to that endophyte strain from the total number of genotypes analysed are indicated in the round brackets and a representative host genotype is given in the square brackets. Endophyte isolates from the reference collection are specified in the square brackets following the species name. *N. lolii* Group 1 comprises of isolates Aries 1, Banks 5847, Ellett 5837, Fitzroy 2, Fitzroy 3, KT1-2, North African 6, Vedette 6645 and Victorian 2.
Figure 2B:
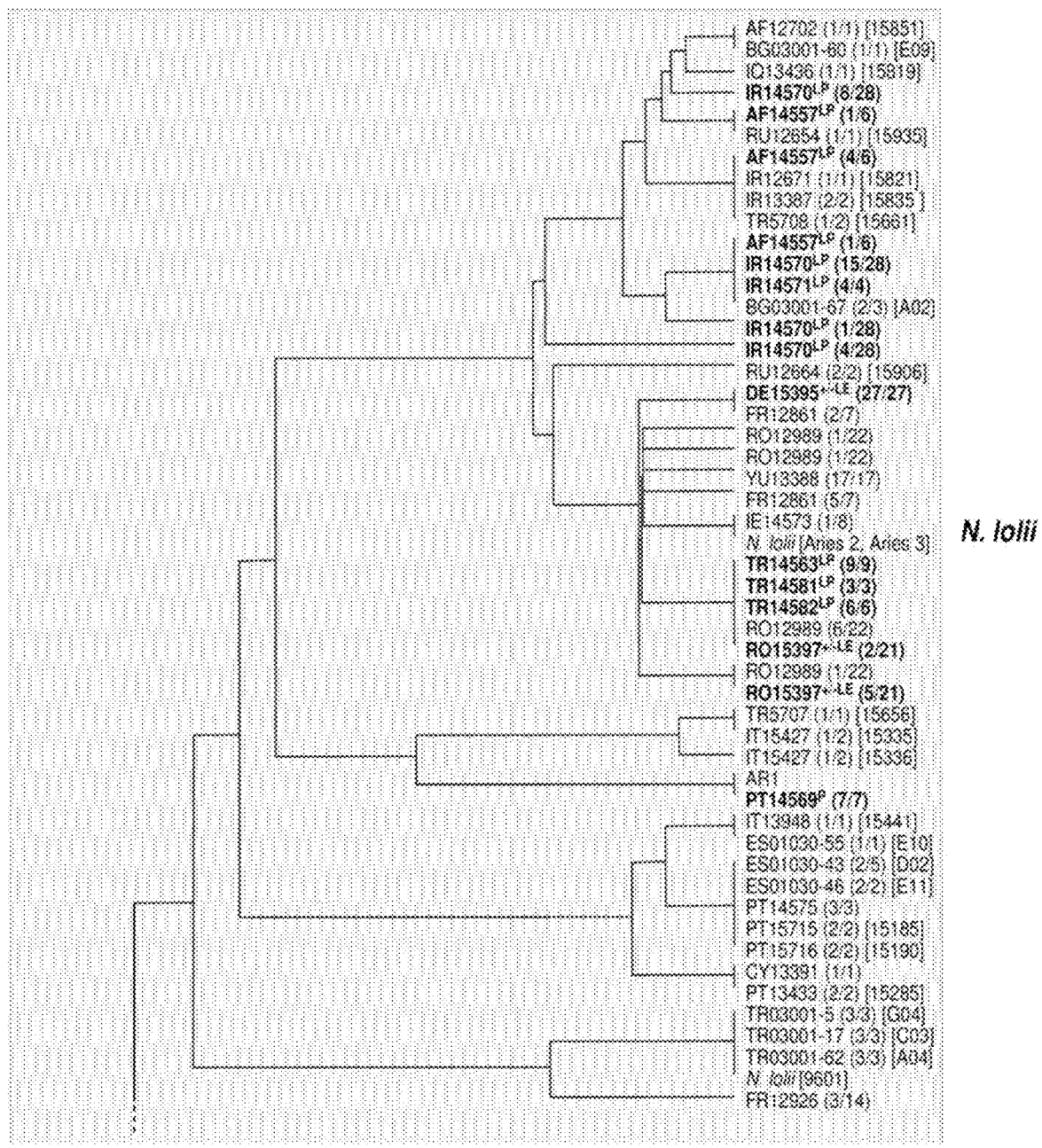
Figure 2C:
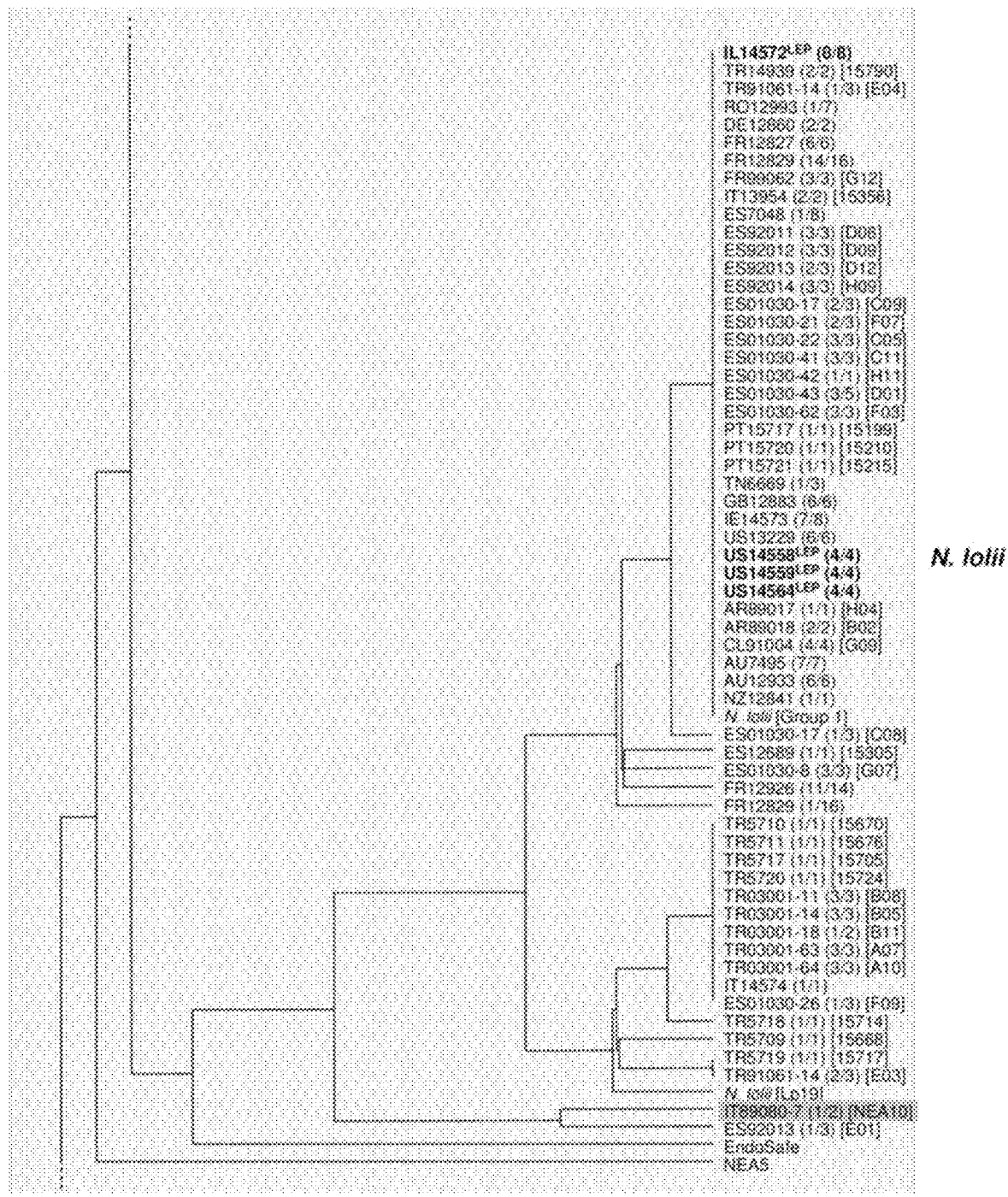
Figure 2D:
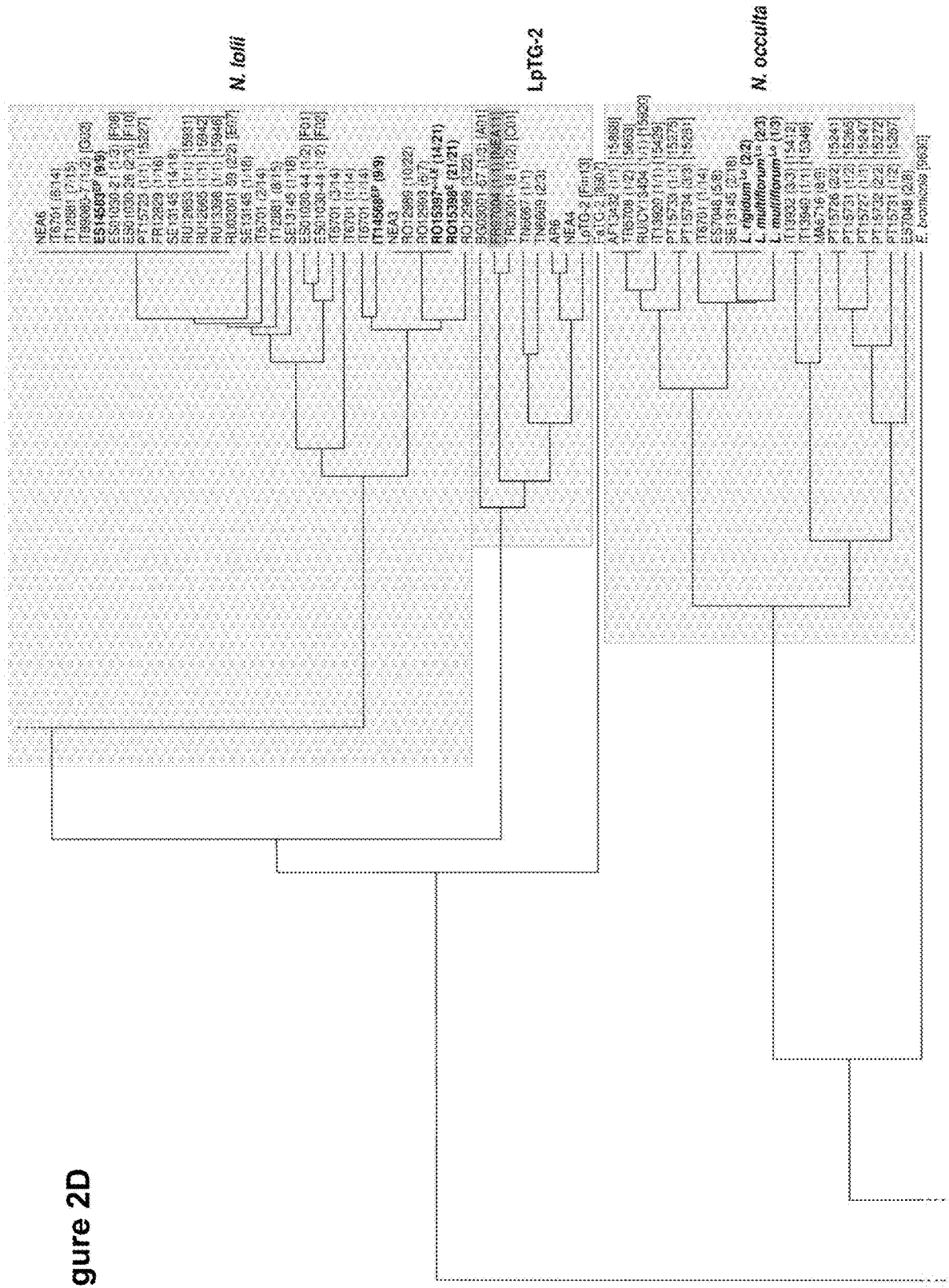
Figure 2E:
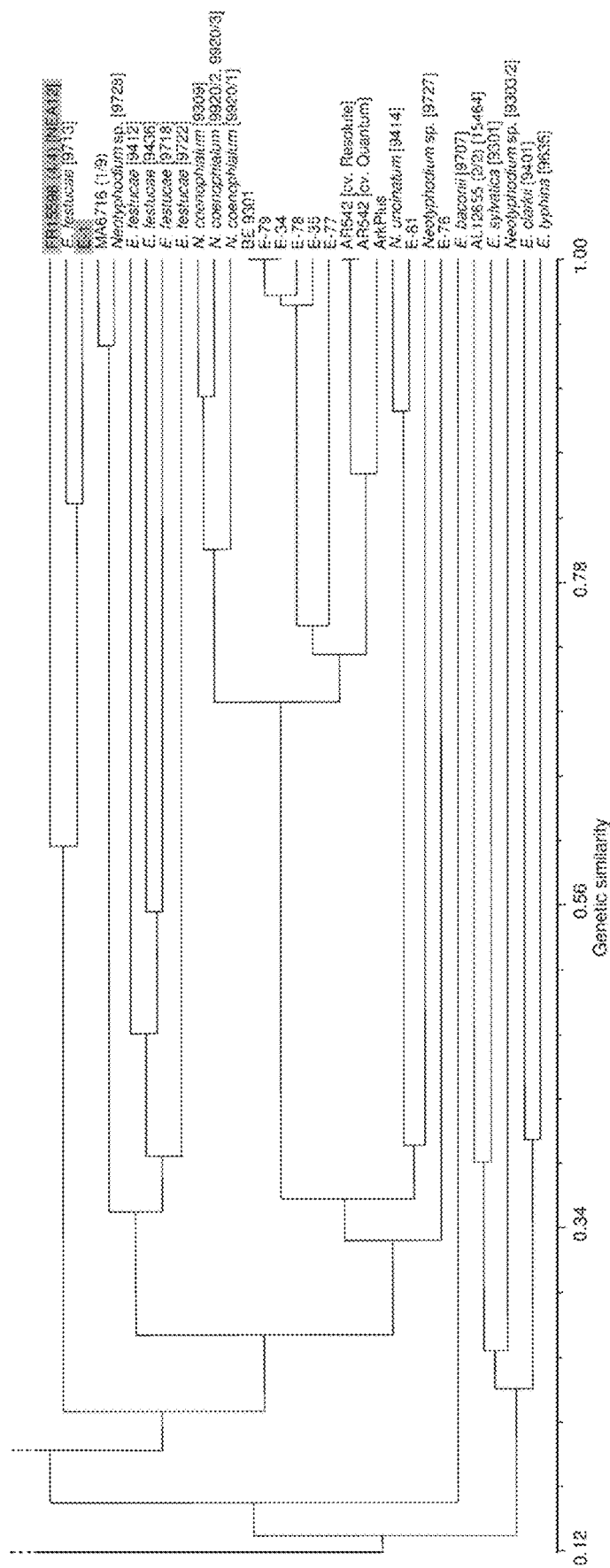

Applicant has surprisingly found that specific detection of endophytes in planta with markers such as SSR markers has provided the tools for efficient assessment of endophyte genetic diversity in diverse grass populations and the potential discovery of novel endophyte strains.

A large scale endophyte discovery program was undertaken to establish a 'library' of novel endophyte strains. A collection of perennial ryegrass and tall fescue accessions was established.

Genetic analysis of endophytes in these accessions has lead to the identification of a number of novel endophyte strains. These novel endophyte strains are genetically distinct from known endophyte strains.

Metabolic profiling was undertaken to determine the toxin profile of these strains grown in vitro and/or following inoculation in planta.

Specific detection of endophytes in planta with SSR markers may be used to confirm the presence and identity of endophyte strains artificially inoculated into, for example, grass plants, varieties and cultivars.

The endophytes have been genetically characterised to demonstrate genetic distinction from known endophyte strains and to confirm the identity of endophyte strains artificially inoculated into, for example, grass plants, varieties and cultivars.

By a 'plurality' of samples of endophytes or plant samples is meant a number sufficient to enable a comparison of genetic and metabolic profiles of individual endophytes. Preferably, between approximately 10 and 1,000,000 endophytes are provided, more preferably between approximately 100 and 1,000 endophytes.

Phenotypic screens were established to select for novel 'designer' grass-endophyte associations. These screens were for desirable characteristics such as enhanced biotic stress tolerance, enhance drought tolerance and enhanced water use efficiency, and enhanced plant vigour.

Novel 'designer' endophytes were generated by targeted methods including polyploidisation and X-ray mutagenesis.

These endophytes may be characterised, for example using antifungal bioassays, in vitro growth rate assays and/or genome survey sequencing (GSS).

Metabolic profiling may also be undertaken to determine the toxin profile of these strains grown in vitro and/or following inoculation in planta.

These endophytes may be delivered into plant germplasm to breed 'designer' grass endophyte associations.

Specific detection of endophytes in planta with SSR markers may be used to confirm the presence and identity of endophyte strains artificially inoculated into, for example, grass plants, varieties and cultivars.

The endophytes may be subject to genetic analysis (genetically characterized) to demonstrate genetic distinction from known endophyte strains and to confirm the identity of endophyte strains artificially inoculated into, for example, grass plants, varieties and cultivars.

By 'genetic analysis' is meant analysing the nuclear and/or mitochondrial DNA of the endophyte.

This analysis may involve detecting the presence or absence of polymorphic markers, such as simple sequence repeats (SSRs) or mating-type markers. SSRs, also called microsatellites, are based on a 1-7 nucleotide core element, more typically a 1-4 nucleotide core element, that is tandemly repeated. The SSR array is embedded in complex flanking DNA sequences. Microsatellites are thought to arise due to the property of replication slippage, in which the DNA polymerase enzyme pauses and briefly slips in terms of its template, so that short adjacent sequences are repeated. Some sequence motifs are more slip-prone than others, giving rise to variations in the relative numbers of SSR loci based on different motif types. Once duplicated, the SSR array may further expand (or contract) due to further slippage and/or unequal sister chromatid exchange. The total number of SSR sites is high, such that in principle such loci are capable of providing tags for any linked gene.

SSRs are highly polymorphic due to variation in repeat number and are co-dominantly inherited. Their detection is based on the polymerase chain reaction (PCR), requiring only small amounts of DNA and suitable for automation. They are ubiquitous in eukaryotic genomes, including fungal and plant genomes, and have been found to occur every 21 to 65 kb in plant genomes. Consequently, SSRs are ideal markers for a broad range of applications such as genetic diversity analysis, genotypic identification, genome mapping, trait mapping and marker-assisted selection.

Known SSR markers which may be used to investigate endophyte diversity in perennial ryegrass are described in van Zijll de Jong et al (2003).

Alternatively, or in addition, the genetic analysis may involve sequencing genomic and/or mitochondrial DNA and performing sequence comparisons to assess genetic variation between endophytes.

The endophytes may be subject to metabolic analysis to identify the presence of desired metabolic traits.

By 'metabolic analysis' is meant analysing metabolites, in particular toxins, produced by the endophytes. Preferably, this is done by generation of inoculated plants for each of the endophytes and measurement of toxin levels in planta. More preferably, this is done by generation of isogenically inoculated plants for each of the endophytes and measurement of toxin levels in planta.

By a 'desired genetic and metabolic profile' is meant that the endophyte includes genetic and metabolic characteristics that result in a beneficial phenotype in a plant harbouring, or otherwise associated with, the endophyte.

Such beneficial properties include improved tolerance to water and/or nutrient stress, improved resistance to pests and/or diseases, enhanced biotic stress tolerance, enhanced drought tolerance, enhanced water use efficiency, reduced toxicity and enhanced vigour in the plant with which the endophyte is associated, relative to a control endophyte such as standard toxic (ST) endophyte or to a no endophyte control plant.

For example, tolerance to water and/or nutrient stress may be increased by at least approximately 5%, more preferably at least approximately 10%, more preferably at least approximately 25%, more preferably at least approximately 50%, more preferably at least approximately 100%, relative to a control endophyte such as standard toxic (ST) endophyte or to no endophyte control plant. Preferably, tolerance to water and/or nutrient stress may be increased by between approximately 5% and approximately 50%, more preferably between approximately 10% and approximately 25%, relative to a control endophyte such as ST or to a no endophyte control plant.

Such beneficial properties also include reduced toxicity of the associated plant to grazing animals.

For example, toxicity may be reduced by at least approximately 5%, more preferably at least approximately 10%, more preferably at least approximately 25%, more preferably at least approximately 50%, more preferably at least approximately 100%, relative to a control endophyte such as ST endophyte. Preferably, toxicity may be reduced by between approximately 5% and approximately 100%, more preferably between approximately 50% and approximately 100% relative to a control endophyte such as ST endophyte.

In a preferred embodiment toxicity may be reduced to a negligible amount or substantially zero toxicity.

For example, water use efficiency and/or plant vigour may be increased by at least approximately 5%, more preferably at least approximately 10%, more preferably at least approximately 25%, more preferably at least approximately 50%, more preferably at least approximately 100%, relative to a control endophyte such as ST or to a no endophyte control plant. Preferably, tolerance to water and/or nutrient stress may be increased by between approximately 5% and approximately 50%, more preferably between approximately 10% and approximately 25%, relative to a control endophyte such as ST or to a no endophyte control plant.

The methods of the present invention may be applied to a variety of plants. In a preferred embodiment, the methods may be applied to grasses, preferably forage, turf or bioenergy grasses such as those of the genera *Lolium* and *Festuca*, including *L. perenne* (perennial ryegrass) and *L. arundinaceum* (tall fescue).

The methods of the present invention may be applied to a variety of endophytes. In a preferred embodiment, the methods may be applied to fungi of the genus *Neotyphodium*, including *N. lolii* and *N. coenophialum*. In another preferred embodiment, the methods may be applied to fungi of the genus *Epichloë*, including *E. festucae* and *E. typhina*. However, the methods may also be used to identify endophytes of previously undescribed taxa.

Applicants have surprisingly found that endophyte E1 is a genetically novel, non-*Neotyphodium lolii*, endophyte. E1 is representative of an as yet un-named taxon. This finding is supported by mitochondrial and nuclear genome sequence analysis.

While applicants do not wish to be restricted by theory, on the basis of DNA specific content, the predicted alkaloid profile of E1 indicates that lolitrem B toxins deleterious to animal health are not produced by this endophyte. Endophyte E1 has the mating-type MAT1-1, the opposite mating-type to that carried by the *N. lolii* endophytes previously characterized. Endophyte E1 also has a high inoculation success rate in perennial ryegrass as compared to other endophytes.

Accordingly, in a second aspect, the present invention provides a substantially purified or isolated endophyte selected from the group consisting of E1, NEA10, NEA11 and NEA12, which were deposited at The National Measurement Institute, 1/153 Bertie Street, Port Melbourne, Victoria, Australia, 3207, on 5 Jan. 2010 with accession numbers V10/000001, V10/000002, V10/000003 and V10/000004, respectively. Replacement deposits were made on Apr. 15, 2016 in response to a notification of non-viability, and were assigned the same accession numbers. A replacement deposit for NEA12, having accession number V10/000004, was made at The National Measurement Institute, 1/153 Bertie Street, Port Melbourne, Victoria, Australia 3207, on Sep. 3, 2019 in response to a notification of non-viability, and was assigned the same accession number.

The present invention also provides a substantially purified or isolated endophyte selected from the group consisting of NEA13 and NEA14, which were deposited at the National Measurement Institute, 1/153 Bertie Street, Port Melbourne, Victoria, Australia, 3207, on 23 Dec. 2010 with accession numbers V10/030285 and V10/030284, respectively. Replacement deposits were made on Apr. 15, 2016 in response to a notification of non-viability, and were assigned the same accession numbers. A replacement deposit was also made on Mar. 2, 2017 in response to a notification of non-viability for NEA14, and was assigned the same accession number.

In a further aspect the present invention provides a substantially purified or isolated endophyte having a desired toxin profile. Preferably the endophyte is isolated from a fescue species, preferably tall fescue. Preferably, the endophyte is of the genus *Neotyphodium*, more preferably it is from a species selected from the group consisting of *N. uncinatum*, *N. coenophialum* and N. 10114 most preferably *N. coenophialum*. The endophyte may also be from the genus *Epichloe*, including *E. typhina*, *E. baconii* and *E. festucae*. The endophyte may also be of the non-*Epichloe* out-group. The endophyte may also be from a species selected from the group consisting of FaTG-3 and FaTG-3 like, and FaTG-2 and FaTG-2 like.

By a 'desired toxin profile' is meant that the endophyte produces significantly less toxic alkaloids, such as ergovaline, compared with a plant inoculated with a control endophyte such as standard toxic (ST) endophyte; and/or significantly more alkaloids conferring beneficial properties such as improved tolerance to water and/or nutrient stress and improved resistance to pests and/or diseases in the plant with which the endophyte is associated, such as peramine, N-formylloline, N-acetylloline and norloline, again when compared with a plant inoculated with a control endophyte such as ST or with a no endophyte control plant.

For example, toxic alkaloids may be present in an amount less than approximately 1 μg/g dry weight, for example between approximately 1 and 0.001 μg/g dry weight, preferably less than approximately 0.5 μg/g dry weight, for example between approximately 0.5 and 0.001 μg/g dry weight, more preferably less than approximately 0.2 μg/g dry weight, for example between approximately 0.2 and 0.001 μg/g dry weight.

For example, said alkaloids conferring beneficial properties may be present in an amount of between approximately 5 and 100 μg/g dry weight, preferably between approximately 10 and 50 μg/g dry weight, more preferably between approximately 15 and 30 μg/g dry weight.

In a particularly preferred embodiment, the present invention provides a substantially purified or isolated endophyte selected from the group consisting of NEA16, NEA17, NEA18, NEA19, NEA20, NEA21 and NEA23, which were deposited at The National Measurement Institute, 1/153 Bertie Street, Port Melbourne, Victoria, Australia, 3207, on 3 Apr. 2012 with accession numbers V12/001413, V12/001414, V12/001415, V12/001416, V12/001417, V12/001418 and V12/001419, respectively. Replacement deposits were made on Apr. 15, 2016 in response to a notification of non-viability, and were assigned the same accession numbers. Such endophytes may have a desired toxin profile as hereinbefore described.

In a further aspect the present invention provides an endophyte variant having a desired genetic and metabolic profile. Preferably the endophyte variant is generated by polyploidisation or induced chromosome doubling, for example by treating the endophyte with colchicine or a similar compound. Alternatively, the endophyte variant may be generated by X-ray mutagenesis or exposing the endophyte to ionising radiation, for example from a caesium source.

Preferably the endophyte which is treated to generate the endophyte variant is isolated from a *Lolium* species, preferably *Lolium perenne*. Preferably, the endophyte is of the genus *Neotyphodium*, more preferably it is from a species selected from the group consisting of *N. uncinatum*, *N. coenophialum* and *N. lolii*, most preferably *N. lolii*. The endophyte may also be from the genus *Epichloe*, including *E. typhina*, *E. baconii* and *E. festucae*. The endophyte may also be of the non-*Epichloe* out-group. The endophyte may also be from a species selected from the group consisting of FaTG-3 and FaTG-3 like, and FaTG-2 and FaTG-2 like.

In a preferred embodiment, the endophyte variant may have a desired toxin profile. By a 'desired toxin profile' is meant that the endophyte produces significantly less toxic alkaloids, such as ergovaline, compared with a plant inoculated with a control endophyte such as standard toxic (ST) endophyte; and/or significantly more alkaloids conferring beneficial properties such as improved resistance to pests and/or diseases in the plant with which the endophyte is associated, such as peramine, N-formylloline, N-acetylloline and norloline, again when compared with a plant inoculated with a control endophyte such as ST or with a no endophyte control plant.

For example, toxic alkaloids may be present in an amount less than approximately 1 μg/g dry weight, for example between approximately 1 and 0.001 μg/g dry weight, preferably less than approximately 0.5 μg/g dry weight, for example between approximately 0.5 and 0.001 μg/g dry weight, more preferably less than approximately 0.2 μg/g dry weight, for example between approximately 0.2 and 0.001 μg/g dry weight.

For example, said alkaloids conferring beneficial properties may be present in an amount of between approximately 5 and 100 μg/g dry weight, preferably between approximately 10 and 50 μg/g dry weight, more preferably between approximately 15 and 30 μg/g dry weight.

In a particularly preferred embodiment, the present invention provides an endophyte variant selected from the group consisting of NEA12dh5, NEA12dh6, NEA12dh13, NEA12dh14, and NEA12dh17, which were deposited at The National Measurement Institute, 1/153 Bertie Street, Port Melbourne, Victoria, Australia, 3207, on 3 Apr. 2012 with accession numbers V12/001408, V12/001409, V12/001410, V12/001411 and V12/001412, respectively. Replacement deposits were made on Apr. 15, 2016 in response to notifications of non-viability, and were assigned the same accession numbers. Such endophytes may have a desired genetic and metabolic profile as hereinbefore described.

In a preferred embodiment, the endlphyte may be substantially purified.

By 'substantially purified' is meant that the endophyte is free of other organisms. The term therefore includes, for example, an endophyte in axenic culture. Preferably, the endophyte is at least approximately 90% pure, more preferably at least approximately 95% pure, even more preferably at least approximately 98% pure.

The term 'isolated' means that the endophyte is removed from its original environment (e.g. the natural environment if it is naturally occurring). For example, a naturally occurring endophyte present in a living plant is not isolated, but the same endophyte separated from some or all of the coexisting materials in the natural system, is isolated.

On the basis of the deposits referred to above, the entire genome of an endophyte selected from the group consisting of E1, NEA10, NEA11, NEA12, NEA13, NEA14, NEA21, NEA23, NEA18, NEA19, NEA16, NEA20, NEA12dh5, NEA12dh6, NEA12dh13, NEA12dh14 and NEA12dh17, is incorporated herein by reference.

Thus, in a further aspect, the present invention includes identifying and/or cloning nucleic acids including genes encoding polypeptides or transcription factors, for example transcription factors that are involved in sexual reproduction or vegetative hyphal fusion, in an endophyte. For example, the nucleic acids may encode mating-type genes, such as MAT1-1.

Methods for identifying and/or cloning nucleic acids encoding such genes are known to those skilled in the art and include creating nucleic acid libraries, such as cDNA or genomic libraries, and screening such libraries, for example using probes for genes of the desired type, for example mating-type genes; or mutating the genome of the endophyte of the present invention, for example using chemical or transposon mutagenesis, identifying changes in the production of polypeptides or transcription factors of interest, for example those that are involved in sexual reproduction or vegetative hyphal fusion, and thus identifying genes encoding such polypeptides or transcription factors.

Thus, in a further aspect of the present invention, there is provided a substantially purified or isolated nucleic acid encoding a polypeptide or transcription factor from the genome of an endophyte of the present invention. Preferably, the nucleic acid may encode a polypeptide or transcription factor that is involved in sexual reproduction or vegetative hyphal fusion in an endophyte.

In a preferred embodiment, the nucleic acid may include a mating-type gene, such as MAT1-1, or a functionally active fragment or variant thereof.

In a particularly preferred embodiment, the nucleic acid may include a nucleotide sequence selected from the group consisting of sequences shown in FIG. 1 hereto, and functionally active fragments and variants thereof.

By 'nucleic acid' is meant a chain of nucleotides capable of carrying genetic information. The term generally refers to genes or functionally active fragments or variants thereof and or other sequences in the genome of the organism that influence its phenotype. The term 'nucleic acid' includes DNA (such as cDNA or genomic DNA) and RNA (such as mRNA or microRNA) that is single- or double-stranded, optionally containing synthetic, non-natural or altered nucleotide bases, synthetic nucleic acids and combinations thereof.

By a 'nucleic acid encoding a polypeptide or transcription factor' is meant a nucleic acid encoding an enzyme or transcription factor normally present in an endophyte of the present invention.

By a 'nucleic acid encoding a polypeptide or transcription factor involved sexual reproduction or vegetative hyphal fusion' is meant a nucleic acid encoding an enzyme or transcription factor normally present in an endophyte of the present invention, which catalyses or regulates a step involved in sexual reproduction or vegetative hyphal fusion in the endophyte, or otherwise regulates sexual reproduction or vegetative hyphal fusion in the endophyte.

The present invention encompasses functionally active fragments and variants of the nucleic acids of the present invention. By 'functionally active' in relation to the nucleic acid is meant that the fragment or variant (such as an analogue, derivative or mutant) is capable of manipulating the function of the encoded polypeptide, for example by being translated into an enzyme or transcription factor that is able to catalyse or regulate a step involved in the relevant pathway, or otherwise regulate the pathway in the endophyte. For example, the fragment or variant may be capable of manipulating sexual reproduction or vegetative hyphal fusion in an endophyte, for example by being translated into an enzyme or transcription factor that is able to catalyse or regulate a step involved in sexual reproduction or vegetative hyphal fusion in the endophyte, or otherwise regulate sexual reproduction or vegetative hyphal fusion in the endophyte.

Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or variant corresponds, more preferably at least approximately 90% identity, even more preferably at least approximately 95% identity, most preferably at least approximately 98% identity. Such functionally active variants and fragments include, for example, those having conservative nucleic acid changes. Examples of suitable nucleic acid changes are also shown in FIG. 1 hereto.

Preferably the fragment has a size of at least 20 nucleotides, more preferably at least 50 nucleotides, more preferably at least 100 nucleotides.

By 'conservative nucleic acid changes' is meant nucleic acid substitutions that result in conservation of the amino acid in the encoded protein, due to the degeneracy of the genetic code. Such functionally active variants and fragments also include, for example, those having nucleic acid changes which result in conservative amino acid substitutions of one or more residues in the corresponding amino acid sequence.

By 'conservative amino acid substitutions' is meant the substitution of an amino acid by another one of the same class, the classes being as follows:
Nonpolar: Ala, Val, Leu, Ile, Pro, Met, Phe, Trp
Uncharged polar: Gly, Ser, Thr, Cys, Tyr, Asn, Gln
Acidic: Asp, Glu
Basic: Lys, Arg, His Other conservative amino acid substitutions may also be made as follows:

Aromatic: Phe, Tyr, His
Proton Donor: Asn, Gln, Lys, Arg, His, Trp
Proton Acceptor: Glu, Asp, Thr, Ser, Tyr, Asn, Gln In a further aspect of the present invention, there is provided a genetic construct including a nucleic acid according to the present invention.

By 'genetic construct' is meant a recombinant nucleic acid molecule.

In a preferred embodiment, the genetic construct according to the present invention may be a vector.

By a 'vector' is meant a genetic construct used to transfer genetic material to a target cell.

The vector may be of any suitable type and may be viral or non-viral. The vector may be an expression vector. Such vectors include chromosomal, non-chromosomal and synthetic nucleic acid sequences, e.g. derivatives of plant viruses; bacterial plasmids; derivatives of the Ti plasmid from *Agrobacterium tumefaciens*; derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the target cell.

In a preferred embodiment of this aspect of the invention, the genetic construct may further include a promoter and a terminator; said promoter, gene and terminator being operatively linked.

By a 'promoter' is meant a nucleic acid sequence sufficient to direct transcription of an operatively linked nucleic acid sequence.

By 'operatively linked' is meant that the nucleic acid(s) and a regulatory sequence, such as a promoter, are linked in such a way as to permit expression of said nucleic acid under appropriate conditions, for example when appropriate molecules such as transcriptional activator proteins are bound to the regulatory sequence. Preferably an operatively linked promoter is upstream of the associated nucleic acid.

By 'upstream' is meant in the 3'→5' direction along the nucleic acid.

The promoter and terminator may be of any suitable type and may be endogenous to the target cell or may be exogenous, provided that they are functional in the target cell.

A variety of terminators which may be employed in the genetic constructs of the present invention are also well known to those skilled in the art. The terminator may be from the same gene as the promoter sequence or a different gene. Particularly suitable terminators are polyadenylation signals, such as the (CaMV)35S polyA and other terminators from the nopaline synthase (nos) and the octopine synthase (ocs) genes.

The genetic construct, in addition to the promoter, the gene and the terminator, may include further elements necessary for expression of the nucleic acid, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (nptII) gene, the hygromycin phosphotransferase (hph) gene, the phosphinothricin acetyltransferase (bar or pat) gene], and reporter genes [such as beta-glucuronidase (GUS) gene (gusA) and the green fluorescent protein (GFP) gene (gfp)]. The genetic construct may also contain a ribosome binding site for translation initiation. The genetic construct may also include appropriate sequences for amplifying expression.

Those skilled in the art will appreciate that the various components of the genetic construct are operably linked, so as to result in expression of said nucleic acid. Techniques for operably linking the components of the genetic construct of the present invention are well known to those skilled in the art. Such techniques include the use of linkers, such as synthetic linkers, for example including one or more restriction enzyme sites.

Preferably, the genetic construct is substantially purified or isolated.

By 'substantially purified' is meant that the genetic construct is free of the genes, which, in the naturally-occurring genome of the organism from which the nucleic acid or promoter of the invention is derived, flank the nucleic acid or promoter. The term therefore includes, for example, a genetic construct which is incorporated into a vector; into an autonomously replicating plasmid or virus; or into the genomic DNA of a prokaryote or eukaryote; or which exists as a separate molecule (e.g. a cDNA or a genomic or cDNA fragment produced by PCR or restriction endonuclease digestion) independent of other sequences. It also includes a genetic construct which is part of a hybrid gene encoding additional polypeptide sequence.

Preferably, the substantially purified genetic construct is at least approximately 90% pure, more preferably at least approximately 95% pure, even more preferably at least approximately 98% pure.

The term "isolated" means that the material is removed from its original environment (e.g. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

As an alternative to use of a selectable marker gene to provide a phenotypic trait for selection of transformed host cells, the presence of the genetic construct in transformed cells may be determined by other techniques well known in the art, such as PCR (polymerase chain reaction), Southern blot hybridisation analysis, histochemical assays (e.g. GUS assays), thin layer chromatography (TLC), northern and western blot hybridisation analyses.

The genetic constructs of the present invention may be introduced into plants or fungi by any suitable technique. Techniques for incorporating the genetic constructs of the present invention into plant cells or fungal cells (for example by transduction, transfection, transformation or gene targeting) are well known to those skilled in the art. Such techniques include *Agrobacterium*-mediated introduction, *Rhizobium*-mediated introduction, electroporation to tissues, cells and protoplasts, protoplast fusion, injection into reproductive organs, injection into immature embryos and high velocity projectile introduction to cells, tissues, calli, immature and mature embryos, biolistic transformation, Whiskers transformation, and combinations thereof. The choice of technique will depend largely on the type of plant or fungus to be transformed, and may be readily determined by an appropriately skilled person. For transformation of protoplasts, PEG-mediated transformation is particularly preferred. For transformation of fungi PEG-mediated transformation and electroporation of protoplasts and *Agrobacterium*-mediated transformation of hyphal explants are particularly preferred.

Cells incorporating the genetic constructs of the present invention may be selected, as described below, and then cultured in an appropriate medium to regenerate transformed plants or fungi, using techniques well known in the art. The culture conditions, such as temperature, pH and the like, will be apparent to the person skilled in the art. The resulting plants or fungi may be reproduced, either sexually or asexually, using methods well known in the art, to produce successive generations of transformed plants or fungi.

In a further aspect, the present invention provides a plant inoculated with an endophyte or endophyte variant as hereinbefore described, said plant comprising an endophyte-free host plant stably infected with said endophyte or endophyte variant.

Preferably, the plant is infected with the endophyte or endophyte variant by a method selected from the group consisting of inoculation, breeding, crossing, hybridization and combinations thereof.

In a preferred embodiment, the plant may be infected by isogenic inoculation. This has the advantage that phenotypic effects of endophytes may be assessed in the absence of host-specific genetic effects. More particularly, multiple inoculations of endophytes may be made in plant germplasm, and plantlets regenerated in culture before transfer to soil.

The identification of an endophyte of the opposite mating-type that is highly compatible and stable in planta provides a means for molecular breeding of endophytes for perennial ryegrass. Preferably the plant may be infected by hyper-inoculation.

Hyphal fusion between endophyte strains of the opposite mating-type provides a means for delivery of favourable traits into the host plant, preferably via hyper-inoculation. Such strains are preferably selected from the group including an endophyte strain that exhibits the favourable characteristics of high inoculation frequency and high compatibility with a wide range of germplasm, preferably elite perennial ryegrass and/or tall fescue host germplasm and an endophyte that exhibits a low inoculation frequency and low compatibility, but has a highly favourable alkaloid toxin profile.

It has generally been assumed that interactions between endophyte taxa and host grasses will be species specific. Applicants have surprisingly found that endophyte from tall fescue may be used to deliver favourable traits to ryegrasses, such as perennial ryegrass.

In a further aspect of the present invention there is provided a method of analysing metabolites in a plurality of endophytes, said method including:

providing:
  a plurality of endophytes; and
  a plurality of isogenic plants;
  inoculating each isogenic plant with an endophyte;
  culturing the endophyte-infected plants; and
  analysing the metabolites produced by the endophyte-infected plants.

By 'metabolites' is meant chemical compounds, in particular toxins, produced by the endophyte-infected plant, including, but not limited to, lolines, peramine, ergovaline, lolitrem, and janthitrems, such as janthitrem I, janthitrem G and janthitem F.

By 'isogenic plants' is meant that the plants are genetically identical.

The endophyte-infected plants may be cultured by known techniques. The person skilled in the art can readily determine appropriate culture conditions depending on the plant to be cultured.

The metabolites may be analysed by known techniques such as chromatographic techniques or mass spectrometry, for example LCMS or HPLC. In a particularly preferred embodiment, endophyte-infected plants may be analysed by reverse phase liquid chromatography mass spectrometry (LCMS). This reverse phase method may allow analysis of specific metabolites (including lolines, peramine, ergovaline, lolitrem, and janthitrems, such as janthitrem I, janthitrem G and janthitem F) in one LCMS chromatographic run from a single endophyte-infected plant extract.

In another particularly preferred embodiment, LCMS including EIC (extracted ion chromatogram) analysis may allow detection of the alkaloid metabolites from small quantities of endophyte-infected plant material. Metabolite identity may be confirmed by comparison of retention time with that of pure toxins or extracts of endophyte-infected plants with a known toxin profile analysed under substantially the same conditions and/or by comparison of mass fragmentation patterns, for example generated by MS2 analysis in a linear ion trap mass spectrometer.

In a particularly preferred embodiment, the endophytes may be selected from the group consisting of E1, NEA10, NEA11, NEA12, NEA13, NEA14, NEA21, NEA23, NEA18, NEA19, NEA16 and NEA20.

In a particularly preferred embodiment, the endophyte variant may be selected from the group consisting of NEA12dh5, NEA12dh6, NEA12dh13, NEA12dh14, and NEA12dh17.

In a further aspect, the present invention provides a plant, plant seed or other plant part derived from a plant of the present invention and stably infected with an endophyte or endophyte variant of the present invention.

Preferably, the plant cell, plant, plant seed or other plant part is a grass, more preferably a forage, turf or bioenergy grass, such as those of the genera *Lolium* and *Festuca*, including *L. perenne* and *L. arundinaceum*.

By 'plant cell' is meant any self-propagating cell bounded by a semi-permeable membrane and containing plastid. Such a cell also required a cell wall if further propagation is desired. Plant cell, as used herein includes, without limitation, seeds suspension cultures, embryos, meristematic regions, callus tissue, leaves, roots, shoots, gametophytes, sporophytes, pollen and microspores.

In a further aspect, the present invention provides use of an endophyte or endophyte variant as hereinbefore described to produce a plant stably infected with said endophyte or endophyte variant.

In a still further aspect, the present invention provides a method of quantifying endophyte content of a plant, said method including measuring copies of a target sequence by quantitative PCR.

In a preferred embodiment, the method may be performed using an electronic device, such as a computer.

Preferably, quantitative PCR may be used to measure endophyte colonisation in planta, for example using a nucleic acid dye, such as SYBR Green chemistry, and qPCR-specific primer sets. The primer sets may be directed to a target sequence such as an endophyte gene, for example the peramine biosynthesis perA gene.

The development of a high-throughput PCR-based assay to measure endophyte biomass in planta may enable efficient screening of large numbers of plants to study endophyte-host plant biomass associations.

As used herein, except where the context requires otherwise, the term "comprise" and variations of the term, such as "comprising", "comprises" and "comprised", are not intended to exclude further additives, components, integers or steps.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

Example 1

Identification of Novel Endophytes

A collection of 244 perennial grass accessions was assembled for the discovery of novel endophyte strains. The collection targeted accessions from the Northern Mediterranean and Eastern Europe for endophytes that lack lolitrems, as well as accessions from the Middle East, the proposed centre of origin of perennial ryegrass and *N. lolii*.

Genotypic analysis of endophyte content was performed across a total of 189 accessions. From each accession 1-5 plant genotypes were analysed for endophyte. Endophyte incidence was low, with endophyte detected in 51% of accessions. Endophyte was consistently detected (with 0 SSR markers) in 77 of the accessions.

Endophytes representing five different taxa were detected across the 77 accessions with 18 SSR markers used to investigate endophyte diversity in perennial ryegrass (FIG. 2). *N. lolii* was predominant, occurring in 63 accessions. Also detected, although less common, were LpTG-2 and putatively new taxa.

Genetic variation in *N. lolii* appeared to be low. A total of 22 unique genotypes were detected across the 63 accessions host to *N. lolii*.

The likely toxin profiles of 14 of the 22 genotypes were established from comparisons with genetic and phenotypic data from previous studies. Most of these genotypes (12/14) showed genetic similarity to endophytes known to produce lolitrems.

There were two genotypes that showed genetic similarity to genotypes known to lack lolitrems but produce ergovaline. One of these genotypes was identical to the genotype detected in the endophyte NEA6. The likely toxin profiles of the remaining eight genotypes were not known. These genotypes did not show high levels of genetic similarity to the endophytes AR1, Endosafe, NEA3 or NEA5.

Plants carrying candidate endophytes were subjected to primary metabolic profiling in the endogenous genetic background, through clonal propagation and measurement of toxin levels. A total of 42 genotypes representing four of the five taxa were selected for toxin profiling, including the eight novel genotypes with unknown toxin profiles. The perennial ryegrass genotype North African 6 ($NA_6$), which contains standard toxic (ST) endophyte, was used as a control.

For metabolic profiling, a complete randomised block design was used, with four replicate clones for each plant and using four hydroponics tubs as blocks. Following three months in hydroponics, whole shoot (leaf plus basal region) was harvested from each plant. The fresh and dry weights of each plant were measured and powdered sample material from 80 (20 genotypes×4 replicates) samples (three tillers per sample) analysed for alkaloid content (lolitrem, ergovaline and peramine).

Example 2

Candidate Endophytes

Candidate endophytes for further study were chosen on the basis of their genetic identity and metabolic profile. Host-endophyte combinations producing significant amounts of lolitrem B were eliminated, as the ryegrass staggers syndrome produced by this alkaloid is the most important limitation for livestock production.

The candidate endophyte NEA10 (originating from Spain) was identified as a novel genotype in this analysis with an unknown toxin profile. Its genetic identity is a unique *N. lolii* strain. Following in planta metabolic profiling analysis, candidate endophyte NEA10 was found to produce ergovaline and peramine, and not lolitrem B.

The candidate endophyte NEA11 (originating from France) was identified as a novel genotype in this analysis with an unknown toxin profile. Its genetic identity is a unique LpTG-2 strain. Following in planta metabolic profiling analysis, candidate endophyte NEA11 was found to produce ergovaline and peramine, and not lolitrem B.

The candidate endophyte NEA12 (originating from France) was identified as a novel genotype in this analysis with an unknown toxin profile. NEA12 is a genetically novel, non-*Neotyphodium lolii*, endophyte representative of an as yet un-named taxon. Following in planta metabolic profiling analysis, candidate endophyte NEA12 was found to not produce the three alkaloids assessed (lolitrem B, ergovaline and peramine).

The candidate endophyte E1 was identified as a novel genotype in this analysis with an unknown toxin profile. E1 is a genetically novel, non-*Neotyphodium lolii*, endophyte representative of an as yet un-named taxon. Following in planta metabolic profiling analysis, candidate endophyte E1 was found to not produce the three alkaloids assessed (lolitrem B, ergovaline and peramine).

Example 3

Methodologies for Endophyte Characterisation

Endophyte Isolation

Novel candidate endophytes were isolated from their host plant to establish an in vitro culture. Following isolation, the genotype of each endophyte was confirmed by SSR analysis to ensure a high level of quality control prior to inception of isogenic inoculations.

Establishment of Meristem Cultures for a Diverse Perennial Ryegrass Host Panel

A set of cultivars representing elite germplasm were obtained, including forage and turf types. Meristem cultures from different cultivars were established to evaluate and compare the phenotypic properties of novel endophyte strains in diverse isogenic host backgrounds. Embryogenic genotypes were identified for each of the cultivars through callus induction and proliferation. Subsequent regeneration of embryogenic genotypes identified primary tissue culture responsive (pTCR) genotypes for each of the cultivars. The number of pTCR genotypes with regeneration frequencies ranging from 80-100% varied from 1-4 per cultivar. pTCR genotypes were then prepared for meristem-derived callus induction to identify highly regenerable genotypes for isogeneic endophyte inoculation. Table 1 shows a selection of cultivars developed, and the tissue culture responsive (TCR) genotype, used for isogenic inoculation.

TABLE 1

Summary information for perennial cultivars selected for isogenic inoculation.

| Cultivar | Characteristics | TCR genotype used for inoculation |
|---|---|---|
| Bealey | Tetraploid forage type | Bea 02 |
| Bronsyn | Standard forage type with robust endophyte performance | Bro 08 |
| Impact | Late flowering, dense tillering forage type | Imp 04 |
| Barsandra | Turf type | San 02 |
| Tolosa | Distinct forage type | Tol 03 |

Isogenic Inoculation of Novel Perennial Ryegrass Endophytes

In order to accurately determine the phenotypic effects of different candidate endophytes in the absence of host-specific genetic effects, a system for isogenic inoculation was developed (FIG. 3). The regenerating callus method of inoculation was chosen, as it results in a relatively high rate of inoculation compared to other tested techniques, and the achieved isogenic inoculation rate was similar to the standard inoculation procedure for non-isogenic seedlings. Novel candidate endophytes NEA10, NEA11, NEA12, E1 and control endophyte ST were individually inoculated into elite germplasm. The logistical approach was to inoculate two cultivars at any given time, with one TCR genotype for each variety chosen for inoculation in this initial study. For each cultivar-endophyte combination, 30 replicate inoculations were performed, 25 of these replicates being transferred to soil. Following inoculation and plantlet regeneration in culture, plants were transferred to soil for three months to allow establishment of endophyte and host-plant associations. After this period, three tillers from each plant were sampled and tested for endophyte presence using SSR-based analysis.

A quantitative score was used to assess endophyte inoculation frequency (Table 2). Three diagnostic SSR markers were used to determine endophyte presence and identity and samples were scored on a scale of 0-3.

Of the 570 inoculations tested, 195 (34.2%) could be positively scored with a high degree of confidence (Table 3). Successful inoculations are listed on Table 3.

TABLE 2

SSR screening for endophyte presence in planta.

| Quantitative score | Alleles present and of correct size for given SSR loci |
|---|---|
| 3 | Endophyte present |
| 2 | Endophyte present |
| 1 | Endophyte absent |
| 0 | Endophyte absent |

TABLE 3

Summary statistics for isogenic inoculation of selected candidate endophytes into a targeted perennial ryegrass panel of 5 hosts.

A. Number of positive inoculants

| | NEA10 | NEA11 | NEA12 | E1 | ST | Total |
|---|---|---|---|---|---|---|
| Bea02 | 0 | 12 | 3 | 4 | 8 | 27 |
| Bro08 | 0 | 14 | 1 | 13 | 13 | 41 |
| Imp04 | 3 | 40 | 4 | 10 | 16 | 73 |
| San02 | 0 | 17 | 6 | 6 | 11 | 40 |
| Tol03 | 0 | 3 | 2 | 6 | 3 | 14 |
| Total | 3 | 86 | 16 | 39 | 51 | 195 |

B. Total number of inoculations tested

| | NEA10 | NEA11 | NEA12 | E1 | ST | Total |
|---|---|---|---|---|---|---|
| Bea02 | 24 | 18 | 20 | 19 | 25 | 106 |
| Bro08 | 19 | 15 | 20 | 18 | 25 | 97 |
| Imp04 | 31 | 49 | 21 | 12 | 35 | 148 |
| San02 | 47 | 39 | 24 | 7 | 32 | 149 |
| Tol03 | 17 | 7 | 18 | 17 | 11 | 70 |
| Total | 138 | 128 | 103 | 73 | 128 | 570 |

C. Percent of positive inoculants

| | NEA10 | NEA11 | NEA12 | E1 | ST | Average |
|---|---|---|---|---|---|---|
| Bea02 | 0.0 | 66.7 | 15.0 | 21.1 | 32.0 | 25.5 |
| Bro08 | 0.0 | 93.3 | 5.0 | 72.2 | 52.0 | 42.3 |
| Imp04 | 9.7 | 81.6 | 19.0 | 83.3 | 45.7 | 49.3 |
| San02 | 0.0 | 43.6 | 25.0 | 85.7 | 34.4 | 26.8 |
| Tol03 | 0.0 | 42.9 | 11.1 | 35.3 | 27.3 | 20.0 |
| Average | 2.2 | 67.2 | 15.5 | 53.4 | 39.8 | 34.2 |

Variation in inoculation success according to candidate endophyte identity was observed (Table 3). Endophyte NEA10 (2.2%), for example, exhibited relatively lower success rates as compared to NEA11 (67.2%), or the commercial endophyte ST (39.8%; Table 4) and only formed stable associations with one of the five hosts in the panel (Impact). Endophyte E1 is a highly compatible endophyte, which obtained a high rate of success of inoculation into perennial ryegrass (Table 3) compared to other endophytes examined, including the strain ST.

Variation was also observed between host plant genotypes for successful inoculations (Table 3). Tolosa (20.0%) appears to be more recalcitrant to inoculation compared to host plants such as Bronsyn (42.3%) and Impact (49.3%).

Vegetative Stability of Isogenic Perennial Ryegrass-Fungal Endophyte Associations Fully confirmed endophyte positive plants from the targeted host-endophyte panel (host plants Bealey, Bronsyn, Barsandra, Tolosa and Impact; endophytes ST, NEA10, NEA11, NEA12) were retested 6-12 months after inoculation and 18-24 months after inoculation, to confirm the presence of endophyte and to assess vegetative stability. In this experiment, 3 replicates of 3 tillers each (total of 9 tillers) were collected for SSR-based analysis.

Most of the previously confirmed endophyte positive plants were again confirmed in this study at 6-12 months post inoculation, indicating that each of the host—endophyte combinations were stable (Table 4). Endophyte NEA12 appears to be less stable in planta, as 7 of the 13 previously confirmed samples could not be fully confirmed in this experiment (Table 4). ST also showed lower levels of stability compared to NEAT 1, with 7/21 samples not re-confirmed in this study (Table 4). Following this analysis, up to three independent inoculation events from each host plant-endophyte combination were retained for further study.

At 18-24 months post inoculation, plants were further assessed for long term vegetative stability (Table 4). ST, NEA10 and NEA11 each exhibit stable associations, with most plants retaining endophyte. NEA12 appears to be less stable in some associations, however does form stable long term associations with Tolosa.

TABLE 4

Endophyte frequency in priority ryegrass host panel genotypes in re-sampled plants that were previously fully confirmed. Plants were re-sampled 6-12 months (shown in bold text) post inoculation and again after 18-24 months post inoculation (shown in normal text).

| Plant | Endophyte genotype | | | |
|---|---|---|---|---|
| genotype | ST | NEA10 | NEA11 | NEA12 |
| Impact | 9/10 | 2/3 | 12/12 | 1/4 |
| (Imp04) | 3/3 | 2/2 | 3/3 | 1/1 |
| Barsandra | 4/6 | NA | 7/7 | 2/4 |
| (San02) | 2/3 | | 3/3 | 1/2 |
| Tolosa | 1/2 | NA | 3/3 | 2/2 |
| (Tol03) | 1/1 | | 2/3 | 2/2 |
| Bealey | 3/3 | NA | 9/9 | 0/2 |
| (Bea02) | 2/3 | | 3/3 | 0/1 |
| Bronsyn | 3/6 | NA | 9/9 | 1/1 |
| (Bro08) | 2/2 | | 4/4 | 0/1 |

NA = not applicable, as no fully confirmed plants were previously identified.

Metabolic Profiling of Isogenic Perennial Ryegrass-Fungal Endophyte Associations Metabolic profiling was conducted to determine the stability of the predicted endophyte phenotype in a range of different host genotype backgrounds. Four replicates of three tillers each were grown under optimal conditions in hydroponics for six weeks prior to measuring lolitrem B, ergovaline and peramine levels. Each replicate plant was also tested for the presence/identity of endophyte using SSR-based genotyping in order to correlate toxin profile with endophyte presence, in particular for those instances were toxin profiles were negative for the alkaloids measured.

Table 5 summarises the outcomes of metabolic profiling in hydroponics for both the endophyte discovery phase and the isogenic inoculation phase. Toxin profiles were as predicted from the cluster assignment of the endophyte in the diversity analysis and the toxin profiles measured in the endogenous host plant.

TABLE 5

Metabolic profile of candidate endophytes.

| Endophyte strain | Endogenous toxin profile | Isogenic toxin profile[b] | Origin | Species |
|---|---|---|---|---|
| NEA10 | —/E/n.d[a]/— | —/E/P/— | Spain | N. lolii |
| NEA11 | —/E/n.d/— | —/E/P/— | France | LpTG-2 |
| NEA12 | —/—/—/n.d | —/—/—/J | France | non-N. lolii |
| E1 | n.d | —/—/—/— | | non-N. lolii |
| ST | L/E/P/— | L/E/P/— | | N. lolii |

Toxins are listed in order: L = Lolitrem B; E = Ergovaline; P = Peramine; J = Janthitrems
[a]Peramine not measured in NEA10 and NEA11 samples; Janthitrems not measured in NEA12 samples
[b]Toxin profile in isogenic associations Genome Survey Sequencing of Candidate Fungal Endophytes Nuclear Genome Assembly Genome Survey Sequencing was performed for non-N. lolii strains NEA12 and E1, LpTG-2 strain NEA11 and Neotyphodium lolii strains including Standard Toxic (ST) and NEA10 using GSFLX Titanium (TI-GSFLX) pyrosequencing technology (Roche; as per manufacturers instructions). A further five N. lolii strains were sequenced using either GSFLX Standard or GS20 pyrosequencing technology. Genome assembly for each of the strains was conducted with GSFLX De Novo Assembler (Table 6).

A new genome assembly was performed for N. lolii strain ST (GSFLX De Novo Assembler), combining sequence reads from both GSFLX and TI-GSFLX runs. Table 7 compares the assembly of single and multiple strains. This combined assembly of the ST genome achieves c.12x coverage of the c.32 Mbp haploid genome. The genome is assembled into 7,875 large contigs (0.5 to 47 kb) of which the net length is 31,750,111 bp.

Analysis using Augustus gene prediction software trained for Fusarium graminearum shows that there are 11,517 predicted protein coding genes in the N. lolii genome.

TABLE 6

Summary statistics for GS-FLX based whole genome sequencing of candidate endophytes.

| | N. lolii Lp19 | N. lolii ST | N. lolii NEA3 | N. lolii AR1 | N. lolii E9 | N. lolii G4 |
|---|---|---|---|---|---|---|
| Genome size (Mb) | ~29 | ~29 | ~29 | ~29 | ~29 | ~29 |
| Toxin profile[a] | L + E + P | L + E + P | E + P | P | L + P | L + P |
| 454 Sequencer | GS20 | GSFLX Standard | GSFLX Standard | GSFLX Standard | GSFLX Standard | GSFLX Standard |
| Number of sequencing runs | 1 | 1 | 1 | 1 | 1 | 1 1/2 |
| Number of high quality reads | 449,408 | 288,527 | 361,154 | 437,465 | 344,074 | 631,248 |
| Number of bases in high quality reads | 47,820,858 | 71,810,513 | 84,032,924 | 97,510,674 | 85,419,382 | 146,574,403 |
| Average read length (bases) | 106 | 249 | 232 | 223 | 249 | 215 |
| Origin of reads assembled[b] | nuclear + mt | nuclear + mt | nuclear + mt | nuclear + mt | nuclear + mt | nuclear + mt |
| Large contigs (>500 bases) | | | | | | |
| Number of contigs | 6 | 2,524 | 5,251 | 6,070 | 6,612 | 12,663 |
| number of bases | 99,508 | 1,834,624 | 3,911,733 | 4,650,113 | 5,208,116 | 12,393,467 |
| average contig size | 16,584 | 726 | 744 | 766 | 787 | 978 |
| N50 contig size | 88,709 | 680 | 723 | 751 | 774 | 1039 |
| largest contig size (bases) | 88,709 | 65,108 | 15,473 | 19,024 | 81,839 | 29,071 |

TABLE 6-continued

Summary statistics for GS-FLX based whole genome sequencing of candidate endophytes.

All contigs

| | | | | | | |
|---|---|---|---|---|---|---|
| number of contigs | 29,013 | 28,137 | 33,262 | 33,777 | 33,136 | 32,796 |
| number of bases | 3,532,954 | 7,999,326 | 10,842,510 | 11,755,707 | 12,022,601 | 17,790,671 |

| | N. lolii NEA10 | N. lolii ST | non-N.lolii E1 | non-N.lolii NEA12 | LpTG-2 NEA11 |
|---|---|---|---|---|---|
| Genome size (Mb) | ~29 | ~28 | TBD | TBD | 55 |
| Toxin profile[a] | E + P | L + E + P | TBD | J | E + P |
| 454 Sequencer | GSFLX Titanium | GSFLX Titanium | GSFLX Titanium | GSFLX Titanium | GSFLX Titanium |
| Number of sequencing runs | 112 | 1 | 1/2 | 1/2 | 1/2 |
| Number of high quality reads | 580,060 | 1,220,036 | 539,019 | 399,868 | 456,111 |
| Number of bases in high quality reads | 221,859,987 | 451,459,919 | 202,854,865 | 165,826,144 | 177,307,015 |
| Average read length (bases) | 383 | 370 | 377 | 415 | 389 |
| Origin of reads assembled[b] | nuclear + mt | nuclear | nuclear + mt | nuclear + mt | nuclear + mt |
| Large contigs (>500 bases) | | | | | |
| Number of contigs | 7,272 | 4,198 | 9,139 | 12,399 | 14,791 |
| number of bases | 26,931,240 | 24,382,151 | 27,150,736 | 17,300,350 | 16,306,033 |
| average contig size | 3703 | 5,808 | 2970 | 1,395 | 1,102 |
| N50 contig size | 7668 | 11,026 | 5845 | 1,703 | 1,214 |
| largest contig size (bases) | 50,291 | 90,675 | 40,456 | 16,319 | 59,986 |
| All contigs | | | | | |
| number of contigs | 11,809 | 6,962 | 15,589 | 20,640 | 39,791 |
| number of bases | 28,155,780 | 25,104,969 | 28,916,589 | 19,862,340 | 23,307,237 |

[a]L = Lolitrem B, E = Ergovaline, P = Peramine, J = Janthitrems
[b]Newbler Assembler

TABLE 7

Assembly comparison of single and multiple strains of N. lolii endophyte

| 454 Sequencer | Lp19 GS 20 | ST GS FLX (Standard) | NEA3 GS FLX (Standard) | AR1 GS FLX (Standard) | E9 GS FLX (Standard) | G4 GS FLX (Standard) | ST GS FLX (Titanium) | combined ST GS FLX (Standard + Titanium) | ST + NEA3 + AR1 + E9 + G4 GS FLX (Standard) |
|---|---|---|---|---|---|---|---|---|---|
| Number of sequencing runs | 1 | 1[a] | 1 | 1 | 1[a] | 1[b] | 1 | 2 | 5 |
| Number of reads | 282,604 | 191,848 | 257,331 | 311,444 | 267,445 | 446,017 | 913,566 | 1,105,14 | 1,474,135 |
| Number of bases in reads | 28,628,965 | 46,613,713 | 58,666,512 | 68,947,121 | 65,192,155 | 101,770,051 | 334,946,727 | 381,560,440 | 341,189,552 |
| Large contigs (≥500 bases) | | | | | | | | | |
| number of contigs | 109 | 1,419 | 3,210 | 3,519 | 4,560 | 11,895 | 8,825 | 7,875 | 11,905 |
| number of bases | 124,393 | 909,187 | 2,111,227 | 2,317,893 | 3,041,084 | 9,249,140 | 31,669,111 | 31,150,111 | 26,515,831 |
| average contig size | 1,141 | 640 | 657 | 658 | 666 | 77 | 3,588 | 4,031 | 2,227 |
| N50 contig size[c] | 1,193 | 606 | 632 | 636 | 644 | 774 | 6,142 | 7,231 | 3,436 |
| largest contig size (bases) | 7,867 | 8,639 | 7,382 | 8,816 | 8,016 | 8,226 | 46,664 | 46,668 | 24,527 |
| Q40 plus bases (%)[d] | 90.62 | 93.97 | 93.40 | 93.90 | 93.72 | 94.64 | 98.03 | 98.52 | 98.32 |
| All contigs (≥100 bases) | | | | | | | | | |
| number of contigs | 2,183 | 8,769 | 12,434 | 15,324 | 15,126 | 28,456 | 11,324 | 10,555 | 21,836 |
| number of bases | 500,187 | 2,911,985 | 4,778,407 | 5,584,622 | 6,123,678 | 14,307,808 | 32,350,805 | 32,482,543 | 29,165,397 |

Alkaloid Biosynthetic Gene Content

The content of genes known to be involved in alkaloid production in each of the sequenced endophyte genomes was investigated. Sequence reads for each of the strains were subjected to a BLAST(N) search against each of the known toxin gene sequences (downloaded from NCBI) to determine the degree of gene coverage by sequence reads. Table 8 below shows the correlation between secondary metabolite production and toxin-related gene content in endophyte genomes.

Based on this analysis, endophyte strain E1 is predicted to produce the alkaloids peramine and ergovaline, but not loline or lolitrem B. In planta analysis of alkaloid content has shown that E1 does indeed not produce loline or lolitrem B.

NEA10 and NEA11 produce ergovaline and peramine, but not lolitrem B. The NEA11 sequence provides evidence for 2 peramine biosynthesis genes, as might be expected in a heteroploid genome.

NEA12, known to lack production of ergot alkaloids and lolitrem B, also lacks corresponding biosynthetic genes.

TABLE 8

Correlation between secondary metabolite production and toxin-related gene content in fungal endophyte genomes.

| | Gene | GenBank Accession No | N. lolii Lp19 | N. lolii ST | N. lolii NEA3 | N. lolii AR1 | N. lolii E09 | N. lolii G04 |
|---|---|---|---|---|---|---|---|---|
| Metabolite production in planta Lolitrems | | | L | L | — | — | L | L |
| | ltmB | DQ443465 | + | + | + | + | + | + |
| | ltmQ | DQ443465 | + | + | + | + | + | + |
| | ltmP | DQ443465 | + | + | + | + | + | + |
| | ltmJ | DQ443465 | + | + | ■ | ■ | + | + |
| | ltmE | DQ443465 | + | + | ■ | ■ | + | + |
| | ltmF | DQ443465 | + | + | + | + | + | + |
| | ltmC | DQ443465 | + | + | + | + | + | + |
| | ltmG | AY742903 | + | + | + | + | + | + |
| | ltmM | AY742903 | + | + | + | + | + | + |
| | ltmK | AY742903 | + | + | + | + | + | + |
| Metabolite production in planta Peramine | | | P | P | P | P | P | P |
| | perA | AB205145 | + | + | + | + | + | + |
| Metabolite production in planta Ergot Alkaloids | | | E | E | E | — | — | — |
| | dmaW | AY259837 | + | + | + | + | ■ | ■ |
| | lpsA | AF368420 | + | + | + | + | + | + |
| | lpsB | EF125025 | + | + | + | + | + | + |
| | easA | EF125025 | + | + | + | + | + | + |
| | easE | EF125025 | + | + | + | + | + | + |
| | easF | EF125025 | + | + | + | + | + | + |
| | easG | EF125025 | + | + | + | + | + | + |
| | easH | EF125025 | + | + | + | + | + | + |
| Metabolite production in planta Loline Alkaloids | | | — | — | — | — | — | — |
| | lolC | AY723749 | ■ | ■ | ■ | ■ | ■ | ■ |
| | lolD | AY723749 | ■ | ■ | ■ | ■ | ■ | ■ |
| | lolO | AY723749 | ■ | ■ | ■ | ■ | ■ | ■ |
| | lolA | AY723749 | ■ | ■ | ■ | ■ | ■ | ■ |
| | lolU | AY723749 | ■ | ■ | ■ | ■ | ■ | ■ |
| | lolP | AY723749 | ■ | ■ | ■ | ■ | ■ | ■ |
| | lolT | AY723749 | ■ | ■ | ■ | ■ | ■ | ■ |
| | lolE | AY723749 | ■ | ■ | ■ | ■ | ■ | ■ |

TABLE 8-continued

Correlation between secondary metabolite production and toxin-related gene content in fungal endophyte genomes.

| | Gene | N. lolii NEA10 | LpTG-2 NEA11 | Non-N. lolii NEA12 | Non-N. lolii E1 | E. festucae Ef E2368 |
|---|---|---|---|---|---|---|
| Metabolite production in planta Lolitrems | | — | — | — | — | — |
| | ltmB | presence | presence | presence | presence | presence |
| | ltmQ | presence | presence | presence | presence | presence |
| | ltmP | presence | presence | presence | presence | presence |
| | ltmJ | absence | absence | absence | absence | absence |
| | ltmE | absence | absence | absence | absence | absence |
| | ltmF | presence | presence | presence | presence | presence |
| | ltmC | presence | presence | presence | presence | presence |
| | ltmG | presence | presence | presence | presence | absence |
| | ltmM | presence | presence | presence | presence | absence |
| | ltmK | presence | presence | presence | presence | absence |
| Metabolite production in planta Peramine | | P | P | — | — | — |
| | perA | presence | presence | presence | presence | truncation |
| Metabolite production in planta Ergot Alkaloids | | E | E | — | — | E |
| | dmaW | presence | presence | absence | presence | presence |
| | lpsA | presence | presence | absence | presence | presence |
| | lpsB | presence | presence | absence | presence | presence |
| | easA | presence | presence | absence | presence | presence |
| | easE | presence | presence | absence | presence | presence |
| | easF | presence | presence | absence | presence | presence |
| | easG | presence | presence | absence | presence | presence |
| | easH | presence | presence | absence | presence | presence |
| Metabolite production in planta Loline Alkaloids | | — | — | — | — | Lol |
| | lolC | absence | absence | absence | absence | presence |
| | lolD | absence | absence | absence | absence | presence |
| | lolO | absence | absence | absence | absence | presence |
| | lolA | absence | absence | absence | absence | presence |
| | lolU | absence | absence | absence | absence | presence |
| | lolP | absence | absence | absence | absence | presence |
| | lolT | absence | absence | absence | absence | presence |
| | lolE | absence | absence | absence | absence | presence |

▒ = gene presence

■ = gene absence

▨ = gene truncation

Figure 4:
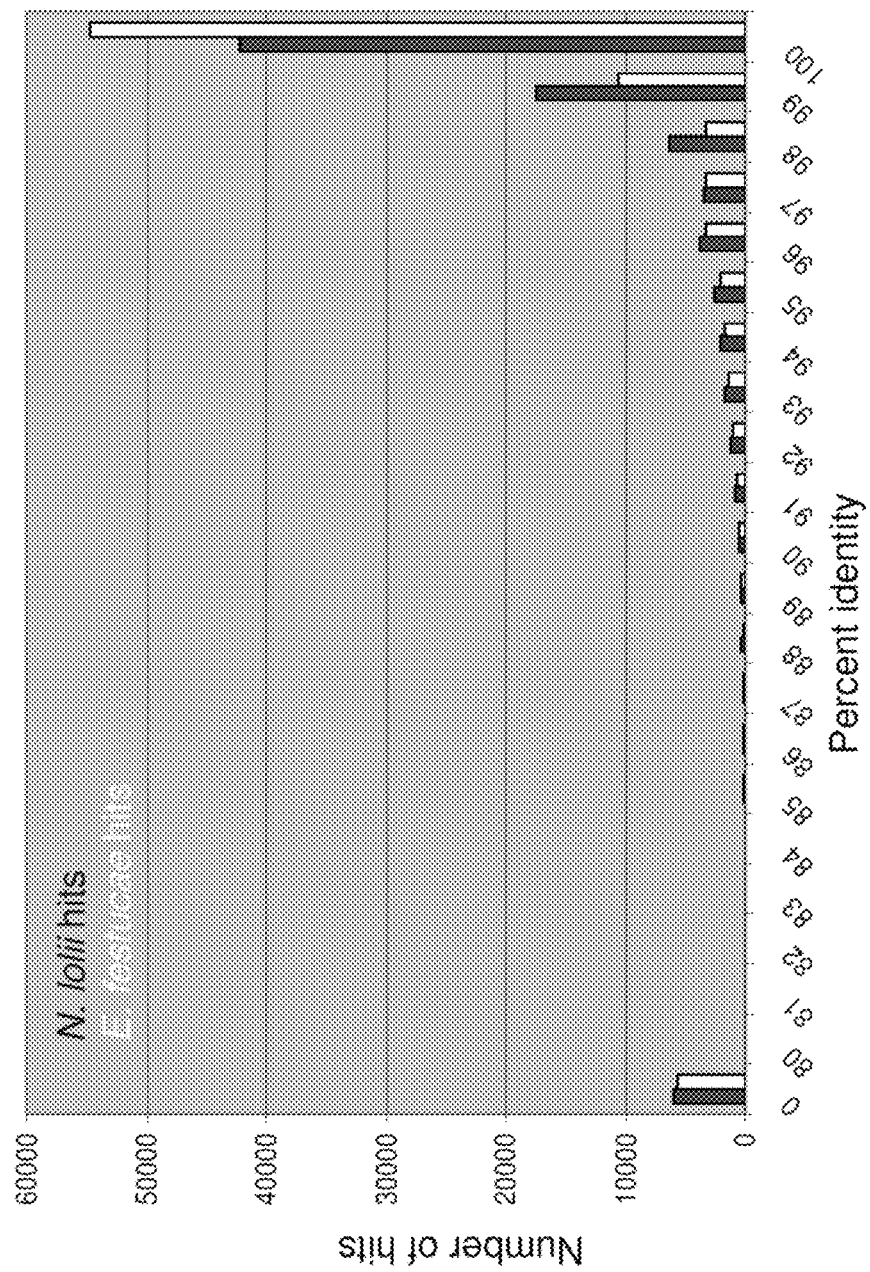
FIG. 4 shows the number of hits showing a given percent identity for 250 bp fragments of the NEA12 genome against the *E. festucae* and *N. lolii* genomes. The X-axis shows the percent identity, the Y-axis shows the number of hits. Black: *N. lolii* strain ST; White: *E. festucae* strain E2368.

Nuclear Genome Comparison
Comparison of the NEA12 Nuclear Genome to *E. festucae* E2368 and *N. lolii* ST To compare the nuclear genome of NEA12 to *E. festucae* and *N. lolii*, the contigs derived from NEA12 were split into 250 bp segments and these segments were used as BLAST (N) queries against *E. festucae* strain E2368 (University of Kentucky, http://www.genome.ou.edu.fungi.html) and *N. lolii* ST contigs. One hit was scored for each 250 bp contig if it was greater than 50 bp long and greater than 80% identity. Summary statistics were taken for NEA12 250 bp fragments against *E. festucae* and *N. lolii* (FIG. 4).

The number of hits showing a given percent identity shows there are more 250 bp segments that give 100 percent identity matches against an *E. festucae* genome than a *N. lolii* genome.

The above statistic is independent of the length of the overlap. An identical 250 bp region would give a 250 bp overlap with a percent identity of 100. The number and proportion of these identical reads is given for the two searches below (Table 9).

TABLE 9

The number and proportion of identical reads between NEA12 and an *E. festucae* genome and a *N. lolii* genome.

|  | ST | *E. festucae* | Total |
|---|---|---|---|
| Number of identical reads (100% identity between 250 by segment) | 16914 | 28866 | 89416 |
| Percent of identical reads (100% identity between 250 by segment) | 18.92 | 32.28 |  |

There are also segments that have no match to either *N. lolii* (6051) or *E. festucae* (5670). These data suggest that NEA12 is a new endophyte taxon that is genetically closer to *E. festucae* than *N. lolii*. This data supports the earlier observation, using SSR-based genetic diversity analysis, that NEA12 is genetically distinct from *N. lolii* and *E. festucae*.

Comparison of E1 Nuclear Genome to NEA12, *E. festucae* E2368 and *N. lolii* ST

Figure 5:
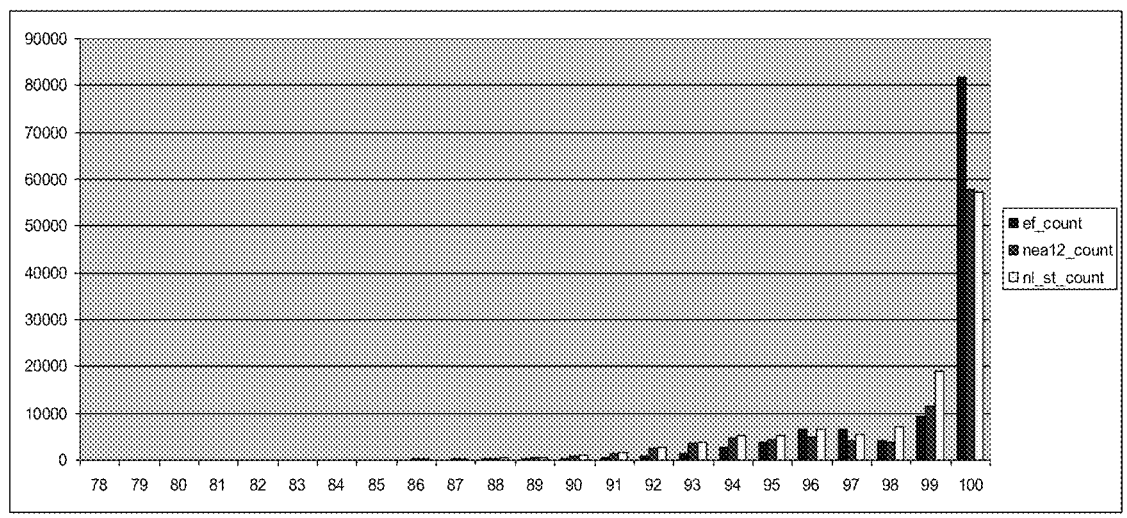
FIG. 5 shows the number of hits showing a given percent identity for 250 bp segments of the E1 genome against the genomes of NEA12, *E. festucae* and *N. lolii*. The X-axis shows the percent identity, the Y-axis shows the number of hits. Black (1st bar in each group): *E. festucae* strain E2368; Grey (2nd bar in each group): Non-*N. lolii* strain NEA12; White (3rd bar in each group): *N. lolii* strain ST.

For comparison at the whole genome level, the contigs from endophyte strain E1 were split into 123,258 250 bp segments. Each 250 bp segment was used as a BLAST(N) query against the assembled whole genome DNA sequences from NEA12, *E. festucae* E2368 and *N. lolii* ST (FIG. 5). A BLAST(N) hit was recorded if there was an overlap of greater than 49 bp. The number of overlaps at a given percent identity was counted for each search. The plot of this data reveals that the genome of endophyte strain E1 is more similar to that of *E. festucae* strain E2368 than to either *N. lolii* strain ST or NEA12.

Figure 6:
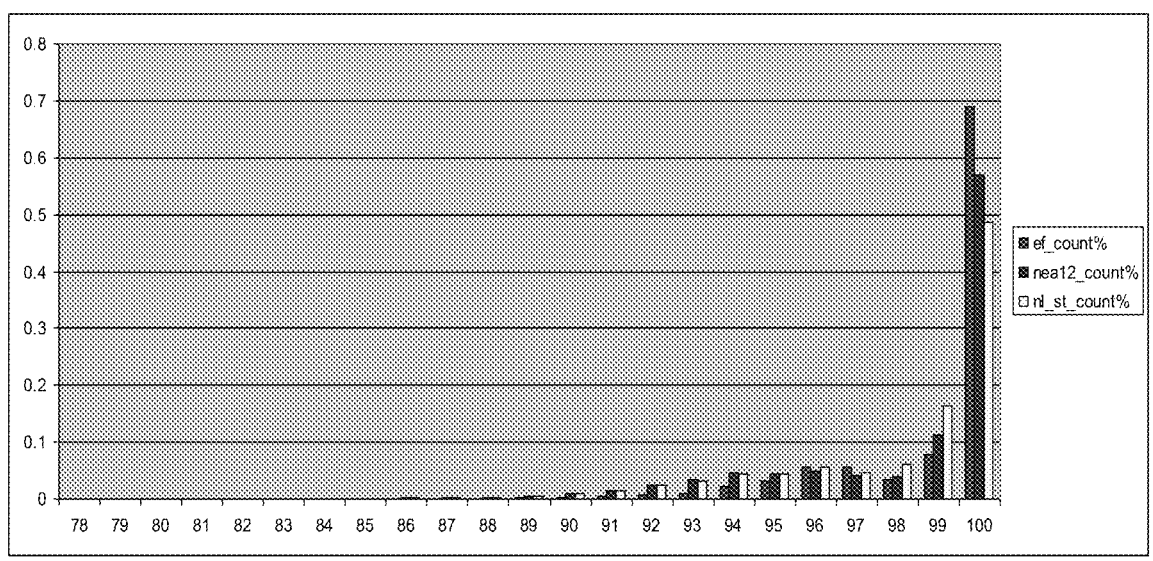
FIG. 6 shows the number of hits showing a given percent identity for 250 bp fragments of E1 against NEA12, *E. festucae* and *N. lolii*. The X-axis shows the percent identity, the Y-axis shows the number of hits expressed as a fraction of the total matches seen per comparison. Grey (1st bar in each group): *E. festucae* strain E2368; Black (2nd bar in each group): Non-*N. lolii* strain NEA12; White (3rd bar in each group): *N. lolii* strain ST.

The assembled contigs from NEA12 sum to c.17.3 Mb, so the level of sequence similarity to that endophyte is probably underestimated due to limited scope for comparison. If the similarity is expressed as a fraction of the total matches observed per comparison, strain E1 is seen to be more similar to strain NEA12 than to *N. lolii* strain ST (FIG. 6). The property of enhance similarity between E1 and *E. festucae* as compared to *N. lolii* is similar to the pattern seen with mitochondrial genome analysis.

LpTG-2 Endophyte NEA11

The LpTG-2 endophyte strain NEA11 is reported to be a hybrid of *N. lolii* and *E. typhina*.

Mitochondrial sequence analysis supports the hybridisation of *E. typhina* with a *N. lolii* with only the *N. lolii* mitochondria being retained.

Figure 7:
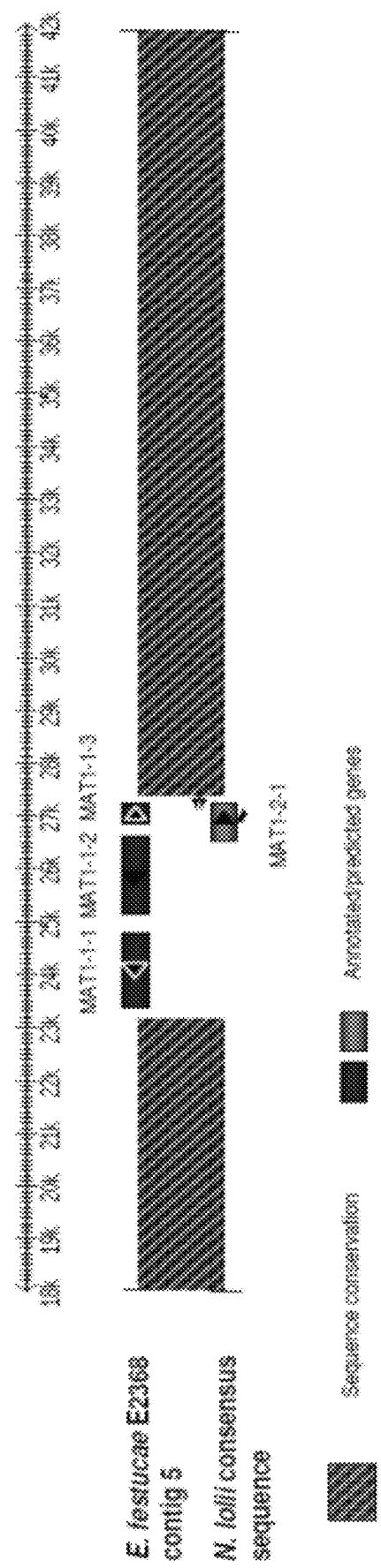
FIG. 7 shows a schematic diagram of the mating-type loci in *Neotyphodium/Epichloë*.
Figure 8:
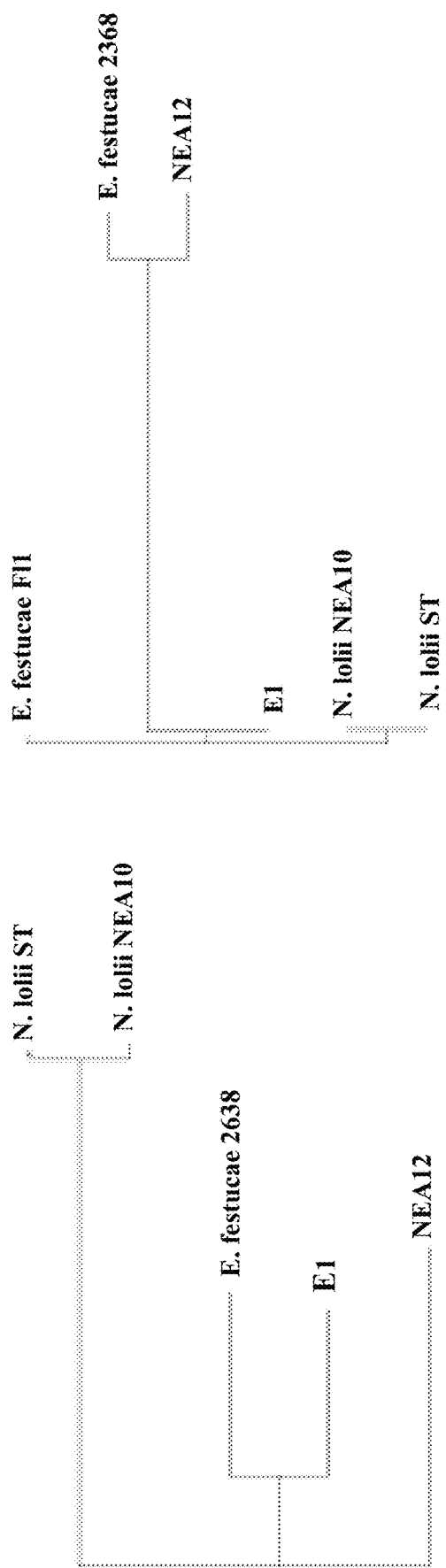
FIG. 8 shows ClustalW analysis trees of the sequence flanking the mating-type loci (left), and the NoxR gene (cloned from *E. festucae* strain FL1 gi117413991; right).

Evidence for the hybrid nuclear genome is seen when nuclear genes are used as a query against contigs from the NEA11 genome assembly (FIGS. 7 and 8).

The panels below show a region of the 'UDP-N-acetyl-glucosaminyltransferase' gene from *E. festucae* being used as a BLAST(N) query against: *E. festucae* (E2368) genome contigs (SEQ ID NO: 13); *N. lolii* (ST) genome contigs (SEQ ID NO: 14); and LpTG-2 (NEA11) genome contigs (SEQ ID NO: 15). This result clearly shows a second variant of this gene in the NEA11 genome that has far more SNPs than the first NEA11 contig hit. This presumably represents the *E. typhina* copy of this gene that has been retained in the NEA11 genome. It is unlikely that this is a localised duplication in NEA11 as neither *E. festucae*, nor *N. lolii* has such a duplication.

```
1: E. festucae (E2368) genome contigs
1_0            1141    accagacgatacaatctcgatagtaaccgcctgcctcatagcgggattgattacacccag    1200
contig01260   42150    ............................................................   42091

1_0            1201    gcagctcatgacagtggtatcaatctccaatataagaccctacgaacggactctgatata    1260
contig01260   42090    ............................................................   42031

1_0            1261    acgccatcgtccccgactcatgatgcccatgtgaaacctttaccagttgccaacgccgtg    1320
contig01260   42030    ............................................................   41971

1_0            1321    tcctcgttagaggtcctgaacaatctgtgtgaacagagtagttggaaatgggtggaaggt    1380
contig01260   41970    ............................................................   41911

1_0            1381    atgttaattggaggctgtcctcaatacggcctagagcgatacgatgatgcgttcaagtcc    1440
contig01260   41910    ............................................................   41851

1_0            1441    ttctcaaggattgtcgcagttgattccaggtaagttgctcgccacaataccctcactcat    1500
contig01260   41850    ............................................................   41791

1_0            1501    ctgcttgatctcacaatcaccggcttcccagccatgttgaagctatcagtcatatgggcg    1560
contig01260   41790    ............................................................   41731

1_0            1561    cagccttgtattgcctcggacgtcaagatgaagcagagaaaaattggctccgggtgataa    1620
contig01260   41730    ............................................................   41671

1_0            1621    agctacgaccaaattatctcgatgccacggaacacttggtgggccatctttataaaaatc    1680
contig01260   41670    ............................................................   41611
```

-continued

```
2: N. lolii (ST) genome contigs
1_0            1141   accagacgatacaatctcgatagtaaccgcctgcctcatagcgggattgattacacccag  1200
contig01260   42150   ............................................................  42091

1_0            1201   gcagctcatgacagtggtatcaatctccaatataagaccctacgaacggactctgatata  1260
contig01260   42090   ............................................................  42031

1_0            1261   acgccatcgtccccgactcatgatgcccatgtgaaacctttaccagttgccaacgccgtg  1320
contig01260   42030   ............................................................  41971

1_0            1321   tcctcgttagaggtcctgaacaatctgtgtgaacagagtagttggaaatgggtggaaggt  1380
contig01260   41970   ............................................................  41911

1_0            1381   atgttaattggaggctgtcctcaatacggcctagagcgatacgatgatgcgttcaagtcc  1440
contig01260   41910   ............................................................  41851

1_0            1441   ttctcaaggattgtcgcagttgattccaggtaagttgctcgccacaataccctcactcat  1500
contig01260   41850   ............................................................  41791

1_0            1501   ctgcttgatctcacaatcaccggcttcccagccatgttgaagctatcagtcatatgggcg  1560
contig01260   41790   ............................................................  41731

1_0            1561   cagccttgtattgcctcggacgtcaagatgaagcagagaaaaattggctccgggtgataa  1620
contig01260   41730   ............................................................  41671

1_0            1621   agctacgaccaaattatctcgatgccacggaacacttggtgggccatctttataaaaatc  1680
contig01260   41670   ............................................................  41611

3: LpTG-2 (NEA11) genome contigs
1_0            1141   accagacgatacaatctcgatagtaaccgcctgccccatagcgggattgattacacccag  1200
contig04703    1281   ............................................................  1340
contig18455     473   .......a..........g....                                          451

1_0            1201   gcagctcatgacagtggtatcaatctccaatataagaccctacgaacggactctgatata  1260
contig04703    1341   ............................................................  1400
contig18455     450   ....t.....t.......................ac.................g..       391

1_0            1261   acgccatcgtccccgactcatgatgcccatgtgaaacctttaccagttgccaacgccgtg  1320
contig04703    1401   ............................................................  1460
contig18455     390   .........................g........c..c.............            331

1_0            1321   tcctcgttagaggtcctgaacaatctgtgtgaacagagtagttggaaatgggtggaaggt  1380
contig04703    1461   ............................................................  1520
contig18455     330   ..t...c..............c...............g.....                    271

1_0            1381   atgttaattggaggctgtcttcaatacggcctagagcgatacgatgatgcgttcaagtcc  1440
contig04703    1521   ............................................................  1580
contig18455     270   ......g................g.....t................a.......        211

1_0            1441   ttttcaaggattgtcgcagttgattccaggtaagttgctcgccacaataccctcactcct  1500
contig04703    1581   ............................................................  1640
contig18455     210   ....................a.......c...c.............t.c..t...g       151

1_0            1501   ctgcttgatctcacaatcaccggcttcccagccatgttgaagctatcagtcatatgggcg  1500
contig04703    1641   ............................................................  1700
contig18455     150   t............g...c.t.......t..........                          91

1_0            1561   cagccttgtattgcctcggacgtcaagatgaagcagag-aaaaattggctccgggtgata  1619
contig04703    1701   .....................................a.....................  1760
contig18455      90   ............c.....c..........c.................g..              32

1_0            1620   aagctacgaccaaattatctcgatgccacggaacacttggtgggccatctttataaaaat  1679
contig04703    1761   ............................................................  1820
contig18455      31   ............c................                                    1
```

The panel below shows the *N. lolii* peramine gene from GenBank used as a query against NEA11 genome assembly contigs. BLAST(N) alignment of LpTG-2 endophyte strain NEA11 reads against the peramine gene (perA) sequence (GenBank accession number: AB205145) (SEQ ID Nos 16-21). The presence of SNP in one set of contigs indicates the presence of two copies of the peramine gene sequence in endophyte strain NEA11.

```
PerA_AB205145.1  1596   gcgcgtcacgatttcccatttaacaccctcagtcacgcggctgatagacccagattcaca  1633
FYGH81301D3U82     24   ............................................................    83
FYGH81301BFIA9     24   ............................................................    83
FYGH81301AC9SL    450   ......                                                          455
FYGH81301CXOSV    247   .............g..............................a..............   306
FYGH81301BMMOF    247   .............g..............................a..............   306
FYGH81301DBHI6    247   .............g..............................a..............   306
FYGH81301CM2KG     52   .............g..............................a...........        1
FYGH81301AWXAQ    231   .............g..............................a..............   320

PerA_AB205145.1  1656   accttttctaaagacgatggtgtttaccggcgagcctctgtctgtggacgatgccacccg  1715
FYGH81301D3U82     94   ............................................................   143
FYGH81301BFIA9     94   ............................................................   143
FYGH81301CXOSV    307   ...cg.c..c..................................................   366
FYGH81301BMMOF    307   ...cg.c..c..................................................   366
FYGH81301DBHI6    307   ...cg.c..c..................................................   366
FYGH81301AWXAQ    311   ...cg.c..c................                                     335

PerA_AB205145.1  1716   atggtggggaaaggtcgacgtcgtcaacgaatatgggcctgcagagtgcaccatcaacac  1775
FYGH81301D3U82    144   ............................................................   203
FYGH81301BFIA9    144   ............................................................   203
FYGH81301CXOSV    367   ............................................................   426
FYGH81301BMMOF    367   ............................................................   426
FYGH81301DBHI6    367   ............................................................   426

PerA_AB205145.1  1776   tgtcaacagccgacctatcagtcctgaagctgctacgaacatagggctgccggttggagt  1835
FYGH81301D3U82    204   ............................................................   263
FYGH81301BFIA9    204   ............................................................   263
FYGH81301CXOSV    427   ............................c...g...........................   436
FYGH81301BMMOF    427   ............................c...g...........................   436
FYGH81301DBHI6    427   ............................c...g...........................   436

PerA_AB205145.1  1856   ggccgcttggattaccgacccggaaaaccatcaagtactcgttccgatcggctgtgttgg  1895
FYGH81301D3U82    264   .......................................................       323
FYGH81301BFIA9    264   .......................................................       323
FYGH81301CXOSV    487   ...............a...........                                     513
FYGH81301BMMOF    487   ...............a...........                                     513
FYGH81301DBHI6    487   ...............                                                 301
FYGH81301EQ6ID      4             ..........tg.................a..............            47
```

Mating-Type Analysis

In heterothallic fungi, such as *Epichloë* spp, strains must be of opposite mating-type for sexual reproduction to proceed. In *Epichloë* spp, sexual development is regulated by alternative MAT1-1 (comprising MAT1-1-1, MAT1-1-2 and MAT1-1-3) and MAT1-2 (comprising MAT1-2-1) genes at the MAT locus. Although the flanking regions of MAT1-1 and MAT1-2 are homologous, the nucleotide sequences of MAT1-1 and MAT1-2 idiomorphs are highly dissimilar (FIG. 7).

The mating-type locus of *E. festucae* E2368 was contained in contig 5 of the original assembly (University of Kentucky, http://www.genome.ou.edu.fungi.html). This contig was aligned with contigs derived from *N. lolii* endophyte strain ST. The MAT1-1 mating-type locus genes found in *E. festucae* (MAT1-1-1, MAT1-1-2, MAT1-1-3) were demonstrated to be absent in the *N. lolii* consensus sequence (FIG. 7). In the corresponding location a single gene for the opposite mating type (MAT1-2) was identified. This opposite mating type gene (MAT1-2-1) was found in all the *N. lolii* strains sequenced as well as NEA12 (Table 10).

TABLE 10

GS-FLX based sequence analysis of mating-type loci. Endophyte strain E1 is of the same mating-type as *E. festucae* strain E2368.

| | | Mating Type MAT1-1 | | | Mating Type MAT1-2 |
|---|---|---|---|---|---|
| | | MAT-1-1 | MAT-1-2 | MAT-1-3 | MAT-2-1 |
| *N. lolii* | ST | | | | |
| | Lp19 | | | | |
| | AR1 | | | | |
| | NEA3 | | | | |
| | E9 | | | | |
| | G4 | | | | |
| | NEA10 | | | | |
| LpTG-2 | NEA11 | | | | |
| non-*N. lolii* | NEA12 | | | | |
| non-*N. lolii* | E1 | | | | |
| *E. festucae* | E2368 | | | | |

= Gene Presence
= Gene Absence

To assess the mating type of endophyte strain E1, the two possible mating type contigs were compared to E1 contigs. This activity proved that E1 contained the same three (MAT1-1-1, MAT1-1-2, MAT1-1-3) mating-type genes as *E. festucae* E2368 and is thus of the MAT1-1 mating-type. This is in contrast to the mating type gene of non-*N. lolii* strain NEA12, which is of the MAT1-2, *N. lolii*-like, mating-type.

Cluster analysis based on sequence nucleotide diversity shows that endophyte strains E1 and NEA12 cluster with *E. festucae* strain E2368, with their position in the tree switching between analysis based on the mating-type loci flanking sequence and the NoxR gene respectively, and suggesting that recombination has occurred in these lineages (FIG. 8).

The identification of an endophyte strain of the opposite mating-type to previously characterised perennial ryegrass endophyte strains provides a means for molecular breeding of endophytes to deliver favourable traits into the plant endophyte symbiotum through the use of the novel E1 strain endophyte.

Mitochondrial Genome Analysis

The mitochondrial genome of *N. lolii* endophyte strain Lp19 was present as a single c.88.7 kb contig. This sequence was used to identify contigs containing mitochondrial DNA sequences in the other *N. lolii* strains sequenced through BLAST(N)-based sequence similarity. Homology searches identified mitochondrial contigs in the *E. festucae* strain E2368 assembly the two non-*N. lolii* genomes and the LpTG-2 genome that were sequenced.

Figure 12:
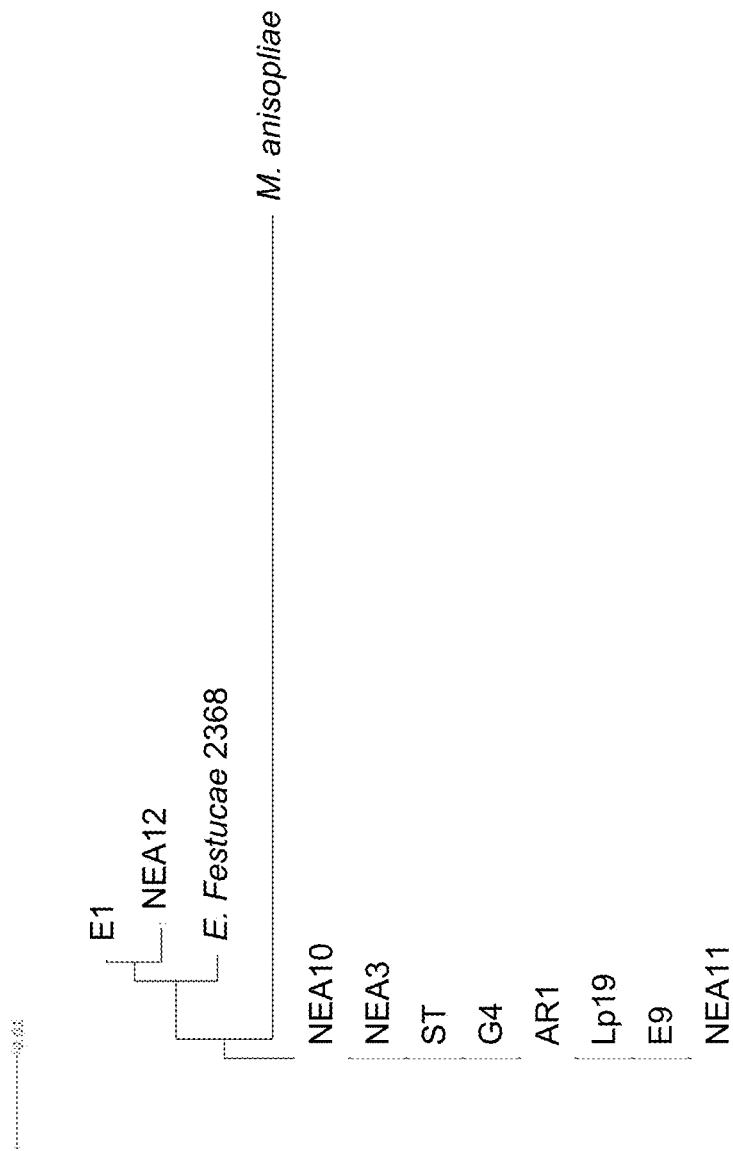
FIG. 12 shows a mitochondrial genome comparison. Neighbour joining tree analysis using ClustalW from a DNA alignment of the 40 blocks of sequence (~40 kb) that are shared across the 10 perennial ryegrass endophyte strains sequenced, *E. festucae* strain E2368 and *Metarhizium anisopliae*.
Figure 13A:
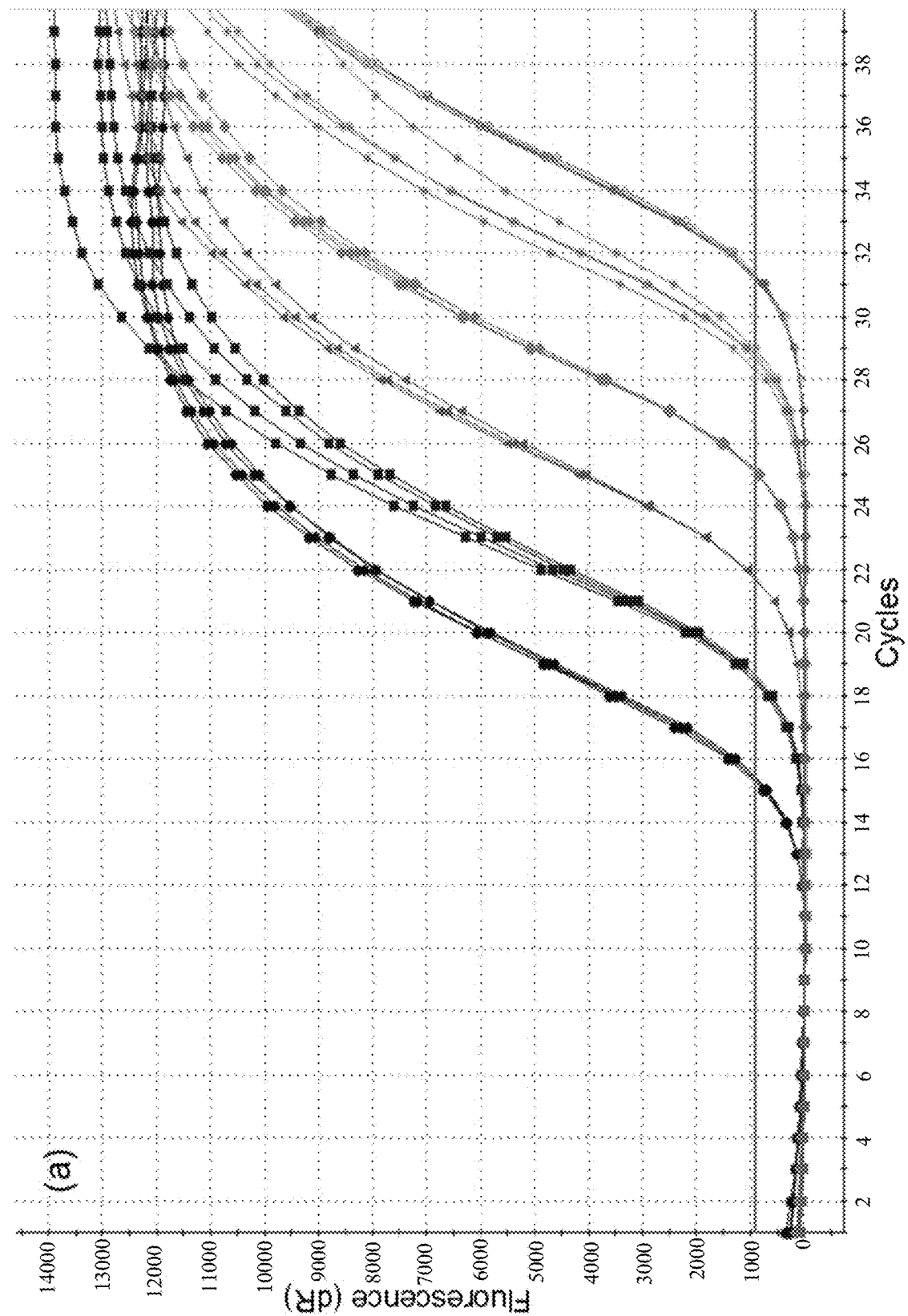
FIGS. 13 A-C show standard curves for quantitative assessment of endophyte colonisation (copy number relative to total plant gDNA). (A) Tight clustering of amplification curves (4 technical replicates) ranging from $2\times10^2$ to $2\times10^6$ copies of the 73 bp perA amplicon. (B) Dissociation curve analysis of the amplification curves shown in (A), with the presence of a single peak indicating primer pair specificity. (C) Assay performance is determined in terms of efficiency, precision and sensitivity. For a typical reaction, a slope of −3.1 to −3.6 and $R^2$ value 0.985 is acceptable. This assay recorded a slope of −3.2 and $R^2$ value of 0.999.
Figure 13B:
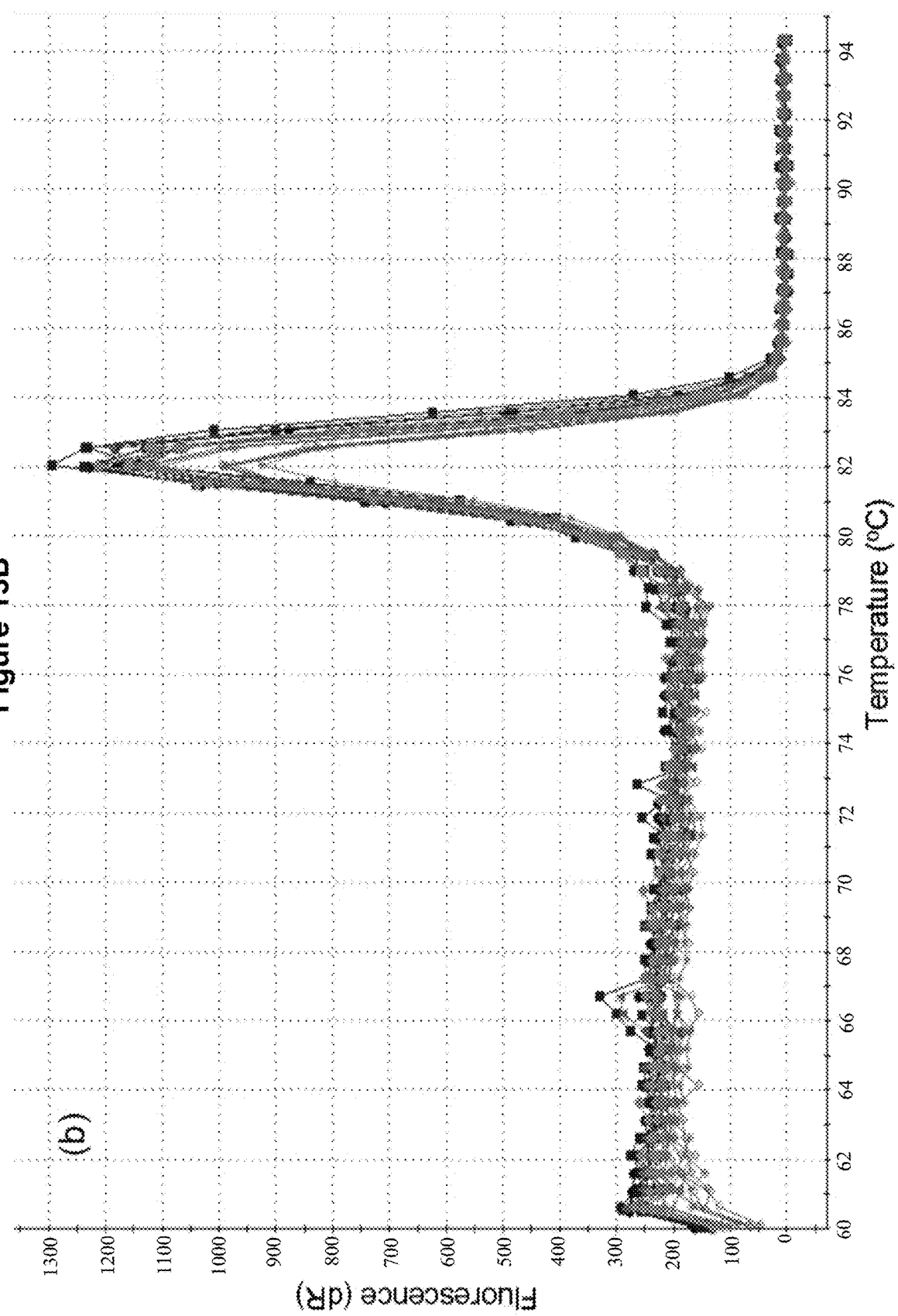
Figure 13C:
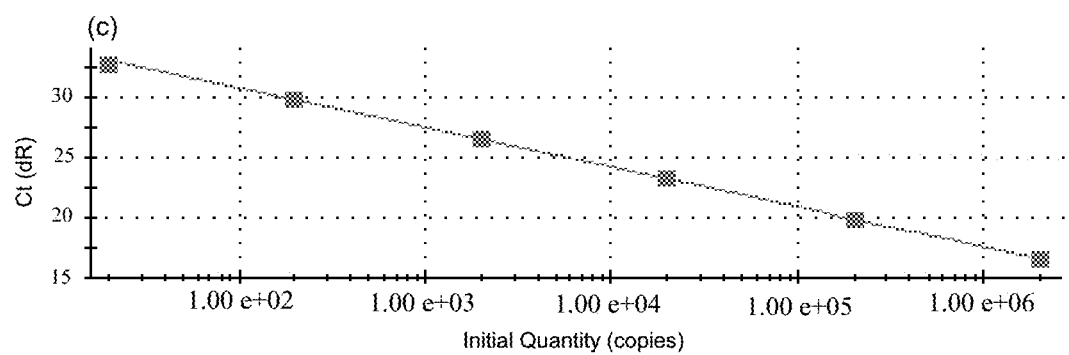
Figure 14A:
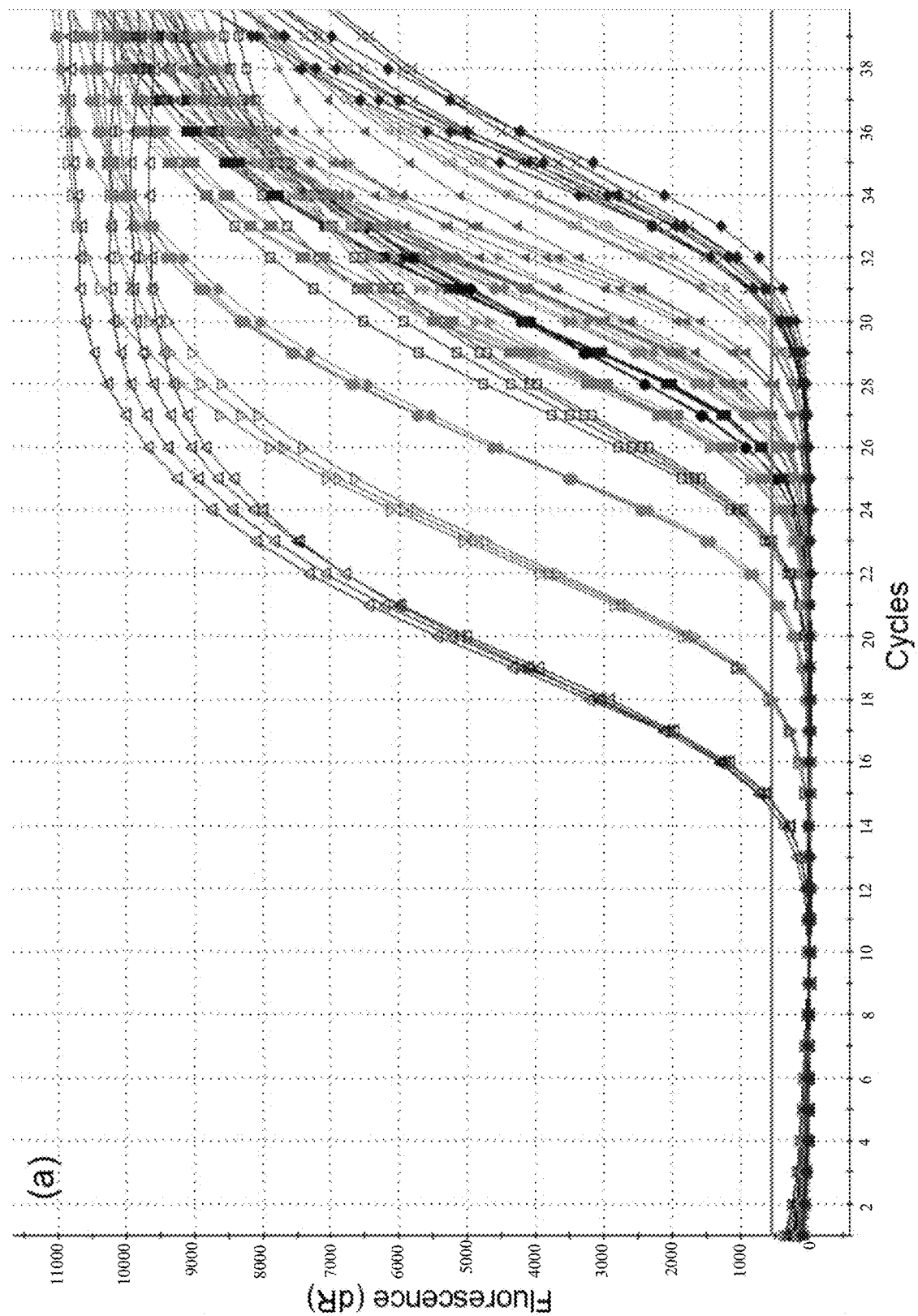
FIGS. 14 A-C show quantitative assessment of endophyte colonisation in diverse ryegrass host panel. (A) Standard curve of perA target sequence ($2\times10^2$ to $2\times10^6$) and amplification curves of the unknown samples. (B) Dissociation curve analysis of the amplification curves shown in (A). (C) Standard curve for perA target (■) and unknown samples (▲).
Figure 14B:
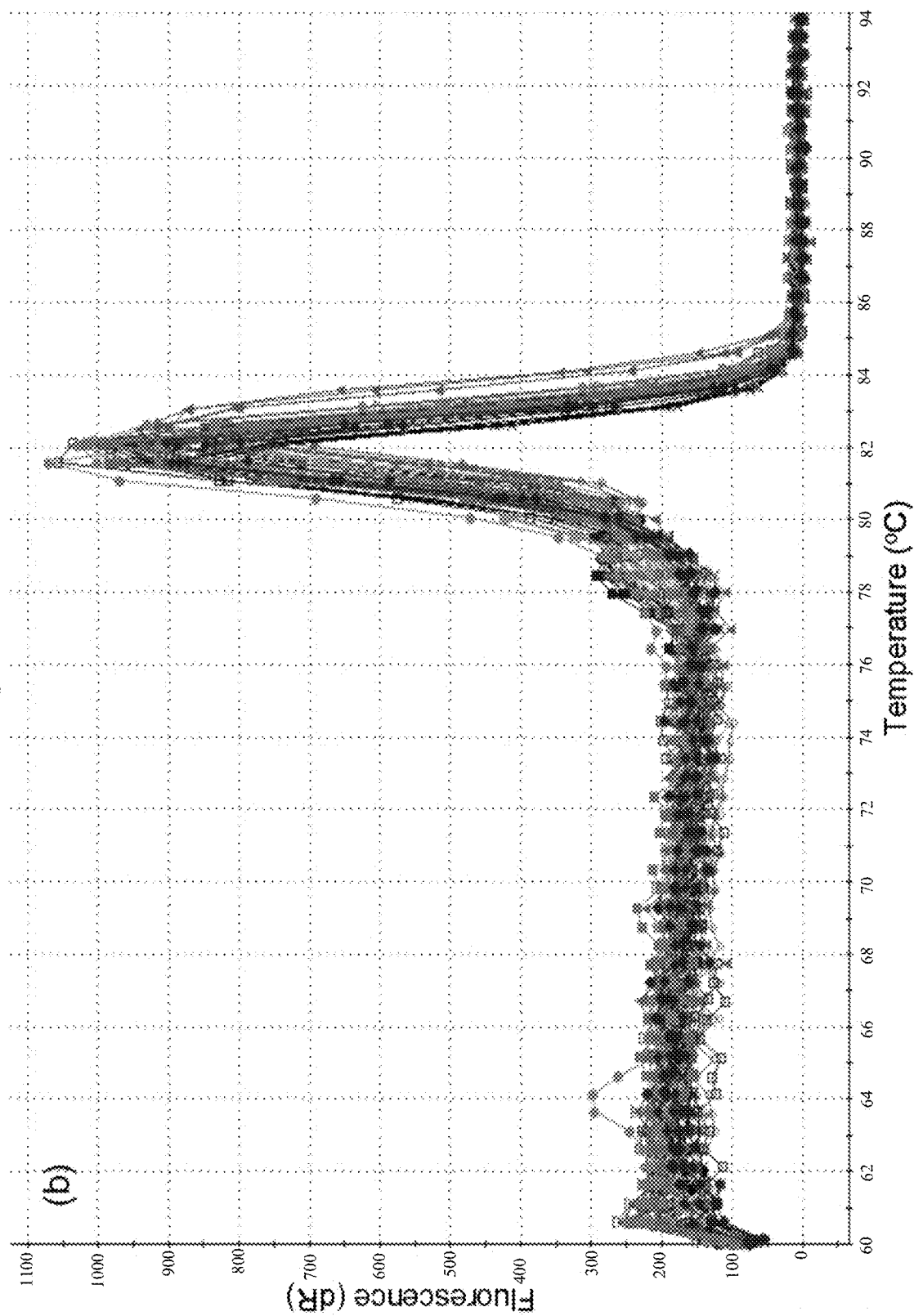
Figure 14C:
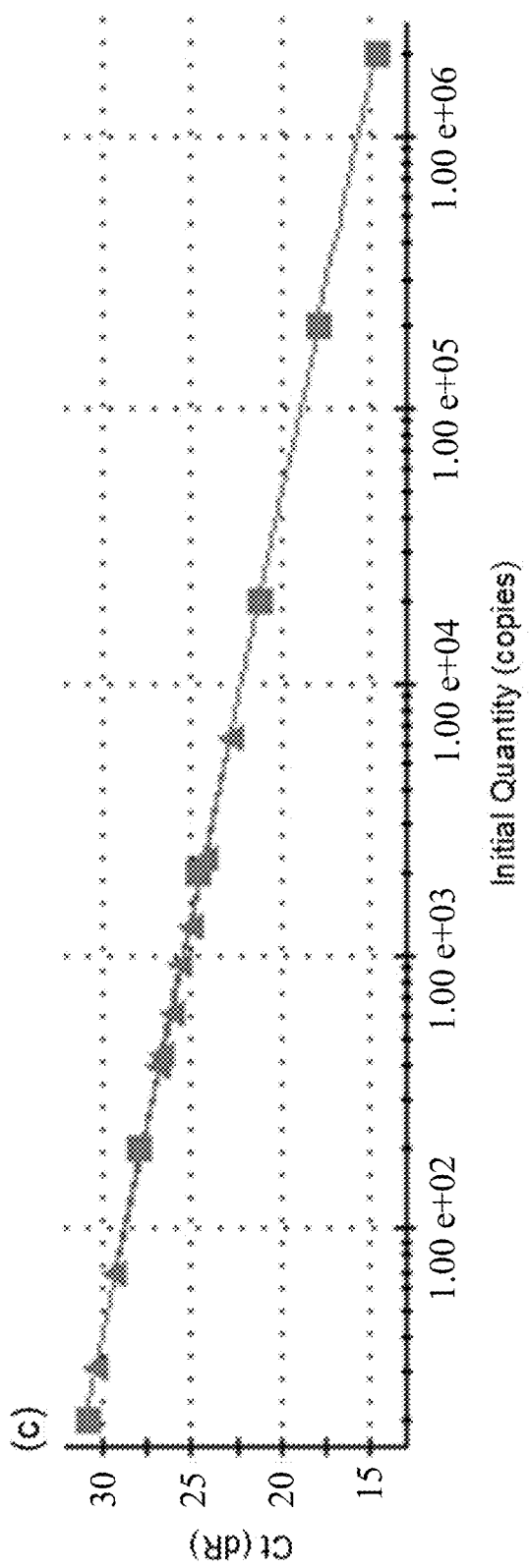
Figure 15:
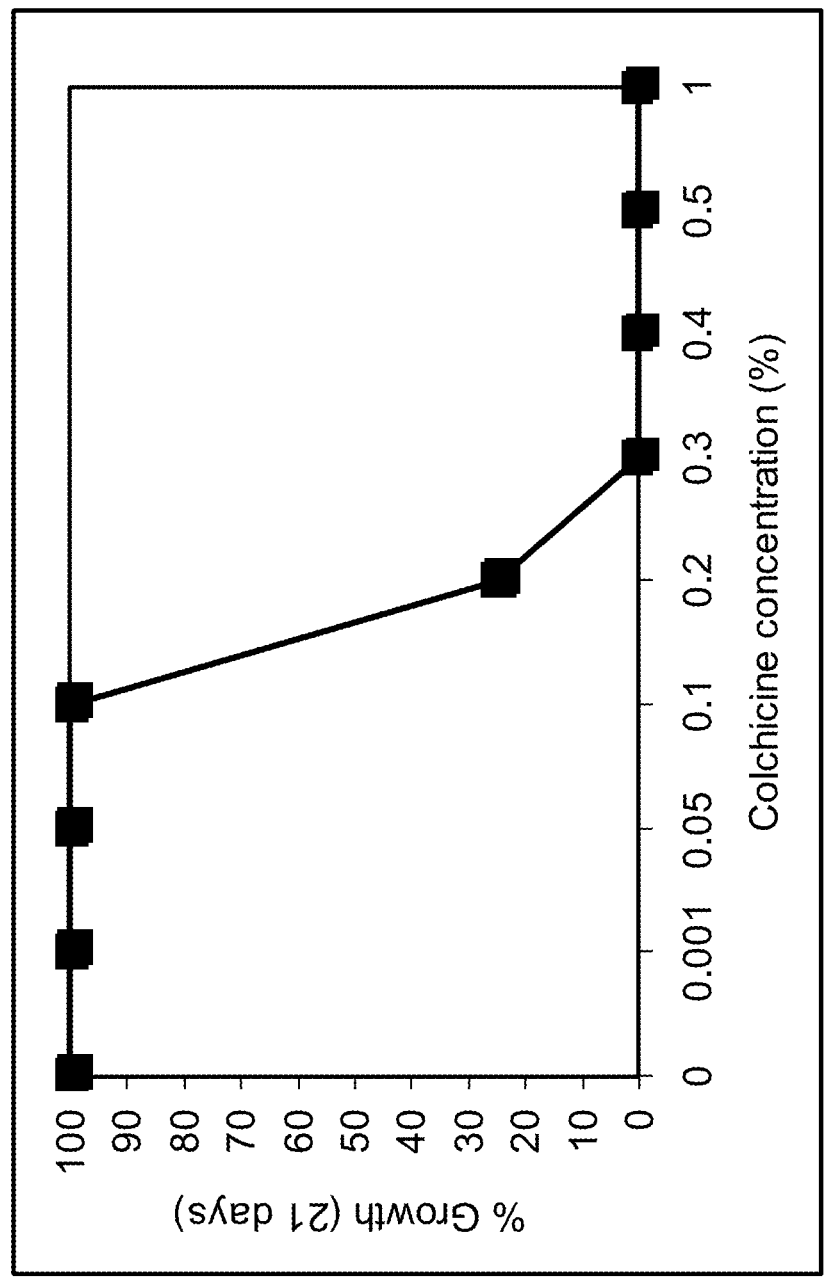
FIG. 15 shows a colchicine kill curve of endophyte strain ST mycelia grown in potato dextrose broth at 22° C., 150 rpm for 21 days.

The mitochondrial genome sizes for each of the fungal endophytes sequenced in this study as well as the *E. festucae* strain E2368 are shown on Table 11. A representative of the Clavicipitaceae, *Metarhizium anisopliae* (Genbank reference number NC 008068.1), is shown for comparison. The *N. lolii* mitochondrial genomes are similar in size, ranging from 88,377 bp for G4 to 88,740 bp for AR1. LpTG-2 representative, NEA11 has a mitochondrion genome similar in size to *N. lolii*. The two non-*N. lolii* genomes, E1 (63,218 bp) and NEA12 (57,818 bp), have relatively smaller mitochondrial genomes more similar in size to that of *E. festucae* strain E2368 (69,614 bp) than that of *N. lolii*.

phyte species (c. 40 kb; FIG. 12). There are still gaps present in the *Metarhizium anisopliae* sequence in this alignment.

A Quantitative PCR Method for Assaying Endophyte Biomass in Planta

Figure 16:
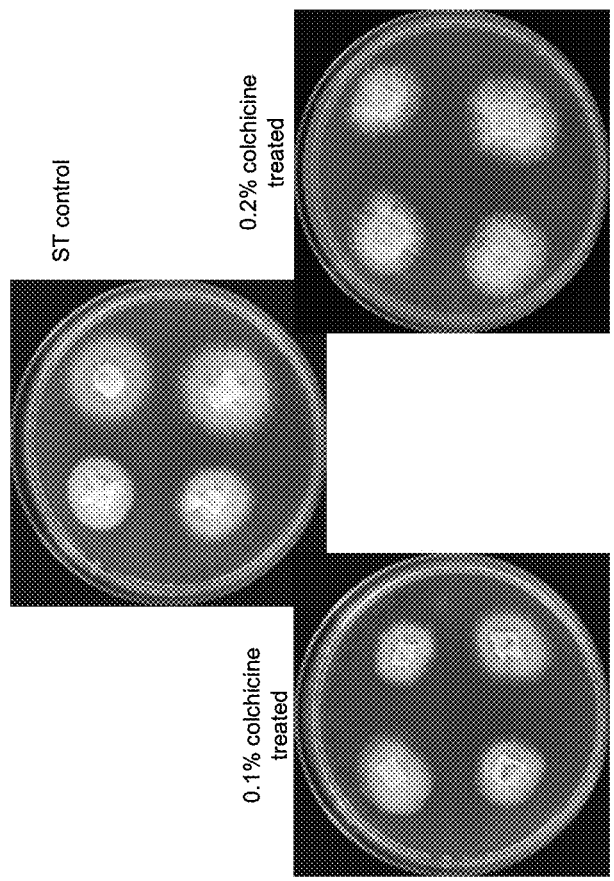
FIG. 16 shows phenotype of colchicine treated colonies (0.1 and 0.2%) of endophyte strain ST compared to the untreated ST control. Mycelia were grown on potato dextrose agar at 22° C. in dark.
Figure 17A:
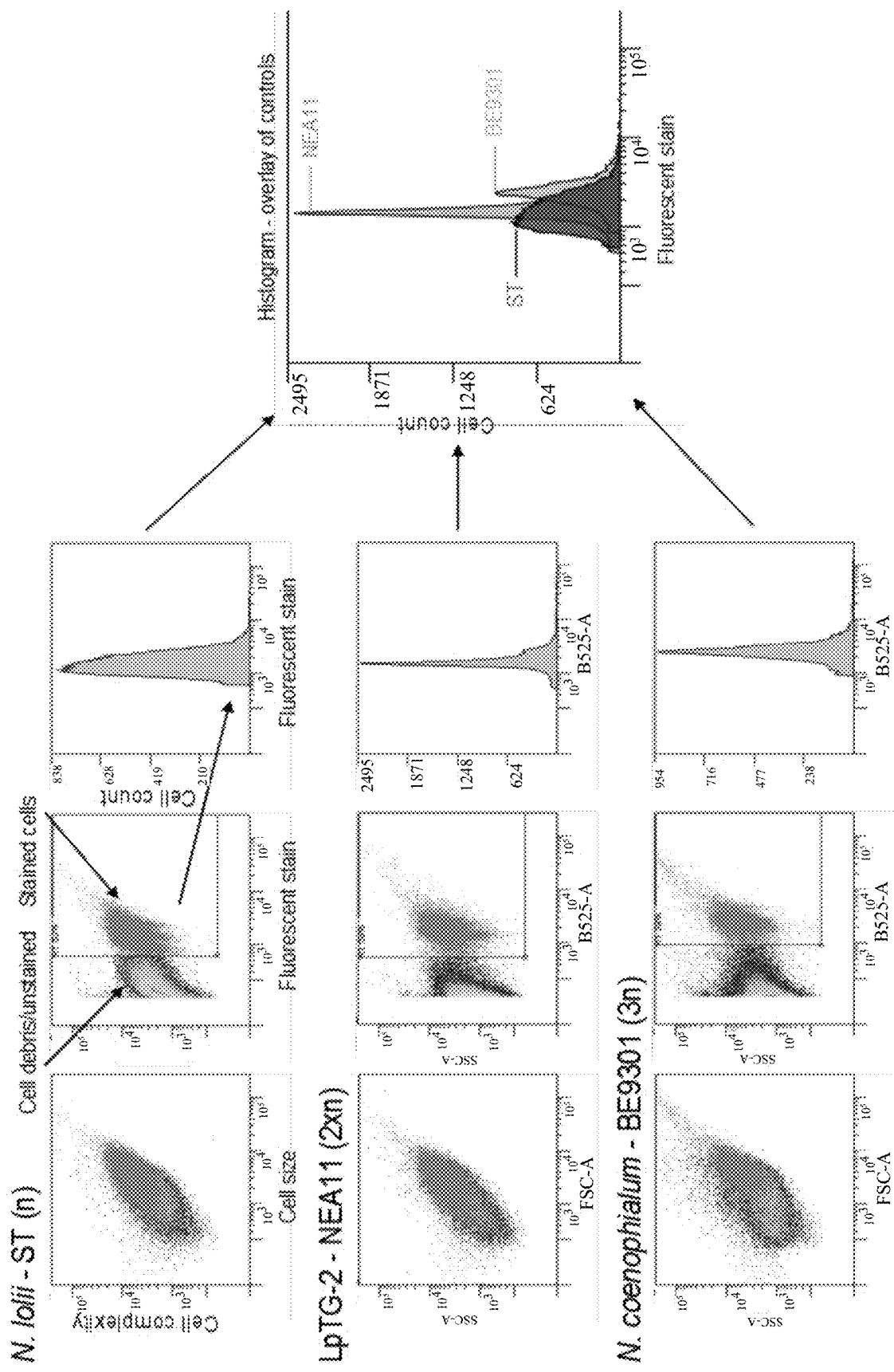
FIGS. 17 A and B show assessment for changes in ploidy level by flow cytometry. A) Dot plots and histogram overlay of control samples, ST, BE9301 and NEA11. B) Dot plots and histogram overlay of two individual ST colonies (13 and 14), showing a shift in peak location relative to the controls.
Figure 17B:
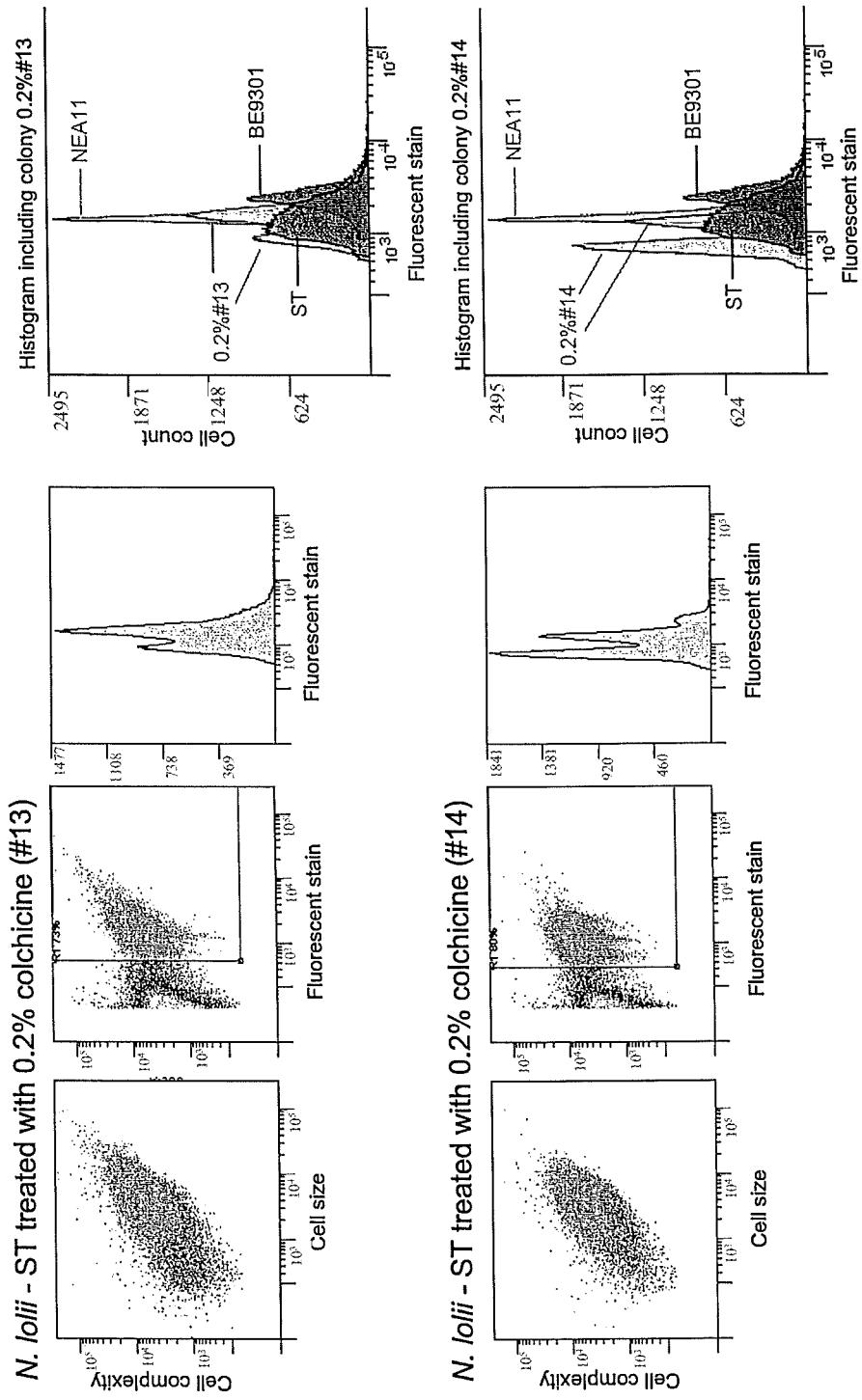

A quantitative PCR (qPCR) method for assaying endophyte biomass in planta has been developed and successfully implemented. The development of a high-throughput PCR-based assay to measure endophyte biomass in planta enables efficient screening of large numbers of plants to study endophyte-ryegrass biomass associations. qPCR-specific primer sets have been designed for the peramine biosynthesis gene (perA). To quantitatively assess in planta endophyte biomass, a standard curve, ranging from $2 \times 10^2$ to $2 \times 10^6$ copies of the target sequence, has been generated from endophyte DNA template (FIG. 16). The standard curve is used to quantitatively determine in planta endophyte biomass of unknown samples (FIG. 17).

A proof-of-concept study was conducted using a subset of plants which had been previously analysed using established SSR methodology. The analysis clearly shows a correlation between the quantitative SSR allele scoring and the presence of endophyte in planta (Table 12).

TABLE 11

Mitochondrial genome size of the 10 fungal endophyte strains sequenced in this study, *E. festucae* strain E2368 and *Metarhizium anisopliae*.

| | N. lolii Lp19 | N. lolii ST | N. lolii NEA3 | N. lolii AR1 | N. lolii E9 | N. lolii G4 | N. lolii NEA10 | non-N.lolii E1 | non-N.lolii NEA12 | LpTG-2 NEA11 | Epichloë festucae 2368 | Metarhizium anisopliae |
|---|---|---|---|---|---|---|---|---|---|---|---|---|
| Approximate Mitochondrial Genome Lengths (bp) | 88709 | 88711 | 87526 | 88740 | 88738 | 88377 | 88734 | 63219 | 57818 | 88692 | 69614 | 24674 |

Figure 9:
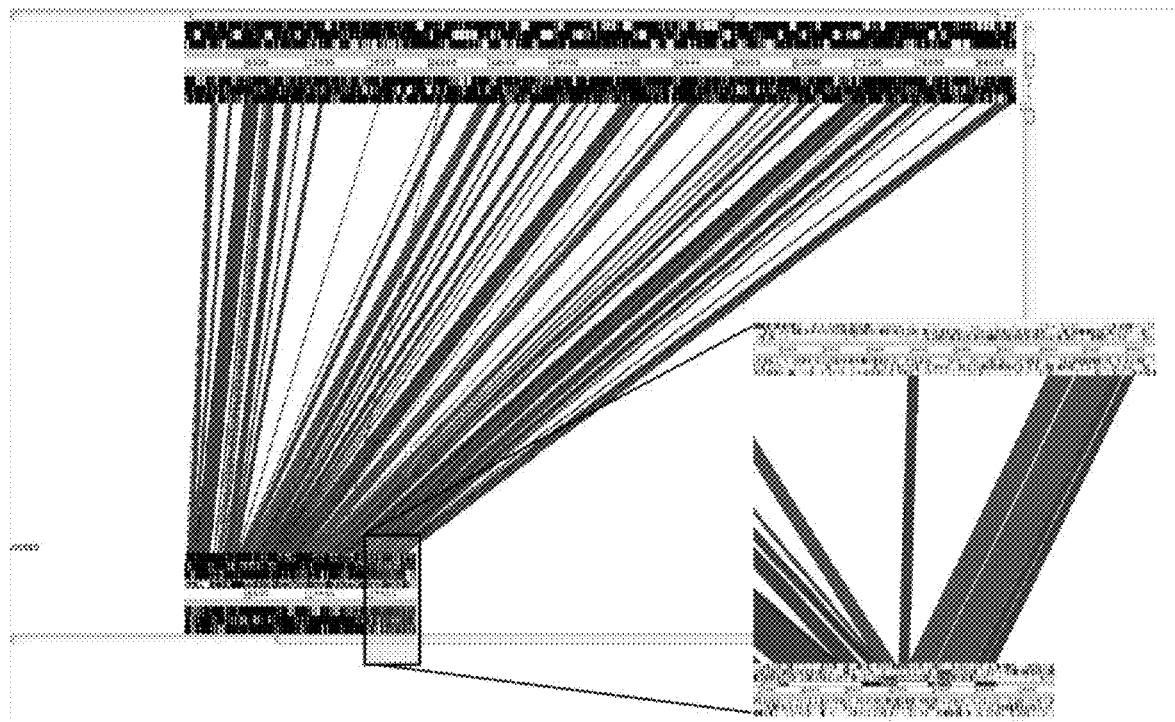
FIG. 9 shows an alignment between mitochondrial genome of *N. lolii* strain Lp19 and a representative of the Clavicipitaceae, *Metarhizium anisopliae* (Genbank reference number NC_008068.1). While the two mitochondrial genomes vary in size, the genes are present in the same order and strand sense, with differences being due to variable insertions in the *N. lolii* mitochondrial genome.
Figure 10:
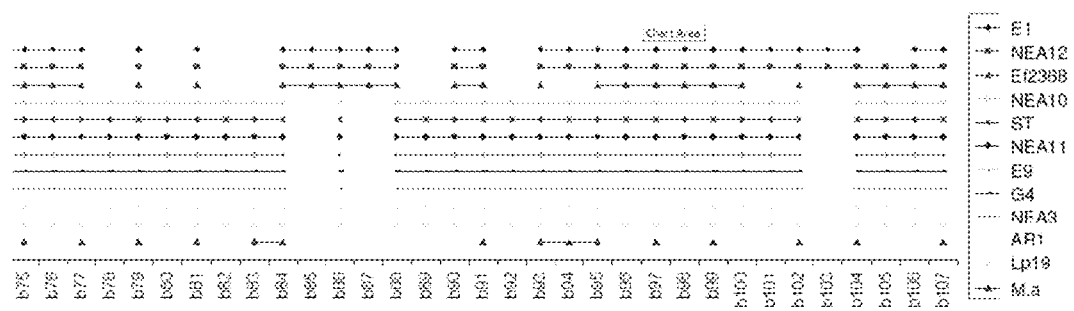
FIG. 10 shows a depiction of part of the block structure of the mitochondrial genomes for each of the fungal endophytes sequenced in this study, as well as *E. festucae* strain E2368 and *Metarhizium anisopliae* for comparison. A shared block (e.g. b84) is present in all 12 mitochondria whereas block 85 is present only in the mitochondria of *E. festucae* strain E2368, and Non-*N. lolii* strains E1 and NEA12.

The multiple mitochondrial DNA sequences were used to generate a mitochondrial genome alignment along with the mitochondrial genome sequence of the Clavicipitaceae fungus *Metarhizium anisopliae*. The alignment demonstrated that while the different mitochondrial genomes vary in size, the genes are present in the same order and strand sense in all genomes, with differences being due to variable insertions in each strain (FIGS. 9 and 10).

Figure 11:
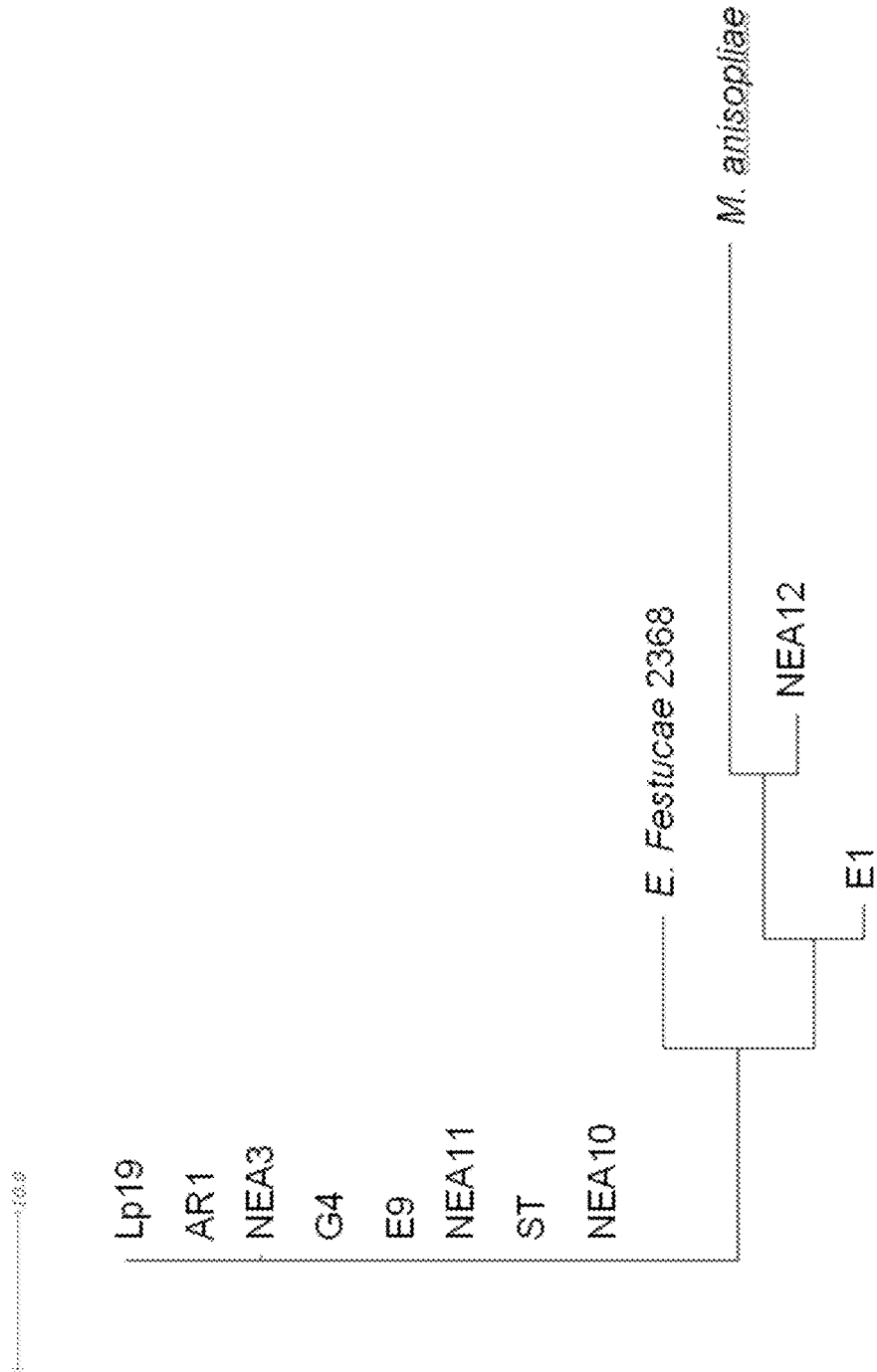
FIG. 11 shows a mitochondrial genome comparison. Parsimony tree of the relationships between the mitochondrial genomes of the 10 perennial ryegrass endophyte strains sequenced, *E. festucae* strain E2368 and *Metarhizium anisopliae*.

Scoring block presence as 1 and absence as 0, a matrix was created to generate a parsimony tree of the relationships between the mitochondrial genomes (FIG. 11). This tree places the E1 and NEA12 mitochondria on a branch with the *E. festucae* strain E2368 mitochondrial genome, these three genomes showing greater variation than that of the *N. lolii* mitochondria. The mitochondrial tree shows that endophyte strains NEA12 and E1 are neither *E. festucae* nor *N. lolii*, but are more similar to *E. festucae* than *N. lolii*. Endophyte LpTG-2 NEA11 has a mitochondrial genome that is genetically a *N. lolii* type, being in a Glade with NEA3 and AR1, within the *N. lolii* cluster.

A similar pattern is observed if a neighbour joining tree is constructed using ClustalW from a DNA alignment of only the 40 blocks of sequence that are shared across all endo-

TABLE 12

Association between SSR-based analysis of endophyte presence and endophyte colonisation as determined by qPCR-based analysis. Each host genotype-endophyte combination represented three independent biological replicates. An SSR-based quality score was used to assess endophyte presence, a score of 3 indicated 3 out of 3 SSR markers were efficiently amplified and of the correct size.

| Host plant-endophyte combination | SSR-based assay | qPCR results (copies/ng gDNA) |
|---|---|---|
| 1 | 1 | Negative |
| 2 | 3 | 16.638 |
| 3 | 3 | 68.98 |
| 4 | 1 | Negative/very low |
| 5 | 3 | 24.3 |
| 6 | 3 | 1.48 |
| 7 | 3 | 14.386 |
| 8 | 2 | 0.7646 |

Example 4

Molecular Breeding—E1 as a Vehicle for Trait Delivery into Perennial Ryegrass by Hyper-Inoculation Endophyte E1 is a genetically novel, non-*Neotyphodium lolii* endophyte. E1 is representative of an as yet un-named taxon This supposition is supported by mitochondrial and nuclear genome sequence analysis On the basis of DNA specific content, the predicted alkaloid profile of E1 indicates that the lolitrem B toxins deleterious to animal health are not produced by this endophyte.

The E1 endophyte does not produce lolitrem B, ergovaline, peramine, lolines or janthitrems in planta.

Endophyte E1 has the mating-type MAT1-1, the opposite mating-type to that carried by all *N. lolii* endophytes previously characterised Endophyte E1 has a high inoculation success rate in perennial ryegrass as compared to other endophytes The identification of an endophyte of the opposite mating-type that is highly compatible and stable in planta provides a means for molecular breeding of endophytes for perennial ryegrass through hyper-inoculation Hyphal fusion between endophyte strains of the opposite mating-type provides a means for delivery of favourable traits into the host plant via hyper-inoculation. Such strains would include: 1) an endophyte strain that exhibits the favourable characteristics of high inoculation frequency and high compatibility with a wide range of elite perennial ryegrass host germplasm and; 2) an endophyte that exhibits a low inoculation frequency and low compatibility, but has a highly favourable alkaloid toxin profile.

The E1 endophyte strain is genetically novel and is compatible with a wide range of elite germplasm as it can be inoculated with a high degree of success. E1 also is of the opposite mating-type to all of the previously characterised perennial ryegrass endophytes. Molecular breeding may therefore be applied by combining the highly compatible E1 endophyte traits with the favourable toxin profile traits of endophytes such as NEA12.

The process of molecular breeding through vegetative (hyphal) fusion may occur in planta by co-inoculation of two endophyte into the same plant. However, molecular breeding may be more efficiently achieved through vegetative fusion in in vitro culture of endophytes of the opposite mating-type, followed by hyper-inoculation of the resultant endophyte.

The following experimental design is applied for molecular breeding of fungal endophytes 1. Determine vegetative compatibility of known endophytes using established co-culturing methodologies.
2. Generation of auxotrophic mutants (e.g. by gene silencing techniques such as RNAi) for two strains of endophyte, such as E1 and NEA12, exhibiting opposite mating-types.
3. Development of vegetative (hyphal) fusion protocol using a combination of cell well degrading enzymes and PEG-4000.
4. Screen for regenerated endophytes based on survival (indicating complementarity of auxotrophic mutations).
5. Genetic screen using SSR and/or mating-type markers to confirm presence of the hybrid genome in a single nuclear compartment.
6. Inoculation and compatibility/stability assessment of endophytes using established methodologies.
7. Phenotypic assessment of endophyte-host associations using established methodologies.

Example 5

Generation of Artificial Polyploids of Fungal Endophytes

Colchicine has been widely used for induction of polyploidy in plant species such as perennial ryegrass, as compared to the application to fungi, which has been limited to a few species.

The mitotic spindle inhibitor colchicine is capable of inducing autopolyploidisation, and may be applicable to the production of artificial polyploid endophytes.

Artificial polyploids were generated by colchicine induced chromosome doubling of the endophyte strains ST and NEA12.

NEA12, a janthitrem only producing endophyte, with superior bioprotective properties forms stable associations with a limited range of perennial ryegrass hosts. An artificial polyploid of NEA12 that is non-toxic to mammals, with enhanced bioprotective properties, that is broadly compatible and highly stable is highly desirable to industry.

Generation of Artificial Polyploids

Experiments were conducted to determine the range of colchicine concentrations in which the mycelia of the fungal endophyte *N. lolii* (strain ST) would grow successfully. Mycelia were grown in colchicine concentrations ranging from 0% to 1% for 21 days and monitored for growth (FIG. 15). At greater than or equal to 0.2% colchicine mycelium growth halted whereas at 0.1% or less colchicine mycelium growth was prolific.

Artificial polyploids were generated for endophyte strains ST and NEA12. Endophyte strains ST and NEA12 (n) were grown in 0, 0.1 and 0.2% colchicine and potato dextrose broth for 21 days followed by a 7-10 day recovery period in potato dextrose broth only. Protoplasts were generated from all colchicine concentrations and single colonies isolated (FIG. 16).

*N. coenophialum* strain BE9301 and LpTG-2 strain NEA11 which are natural heteroploids (3n and 2xn fused respectively) have been utilised as control material for assessment of ploidy changes using flow cytometry. An optimised protocol was established allowing analysis of fungal protoplasts via flow cytometry. A number of colonies have been identified with changes in nuclear DNA content relative to the control samples (FIGS. 20 and 21).

TABLE 13

Summary of individual endophyte colonies, ST and NEA12, treated with colchicine and subjected to flow cytometry analysis.

| Endophyte | Colchicine treatment (%) | Number of colonies | Number colonies analysed |
|---|---|---|---|
| *N. lolii* ST | 0.2 | 12 | 12 |
| *N. lolii* NEA12 | 0.1 | 60 | 2 |
| *N. lolii* NEA12 | 0.2 | 60 | 18 |

Example 6

Generation of Novel Endophyte Variation Using Ionising Radiation

Summary

Lolitrem B is the major alkaloid leading to ryegrass staggers in grazing animals.

Figure 18:
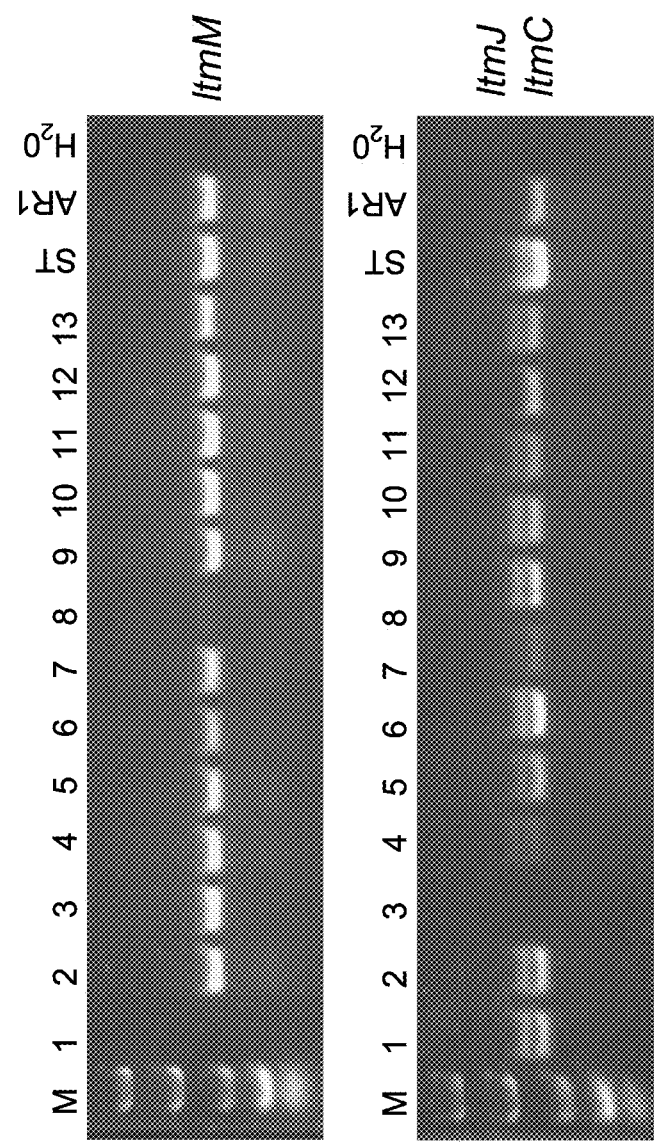
FIG. 18 shows high throughput PCR screening method for detection of lolitrem B gene deletion mutants. The lolitrem genes targeted include: ItmM (480 bp), ItmJ (734 bp) and ItmC (583 bp). M: EasyLadder1 (100-2000 bp); 1-13: Individual putative lolitrem B gene deletion mutants; ST: ST DNA (positive control for ItmM, ItmJ and ItmC); AR1: AR1 DNA (positive control for ItmM and ItmC, negative control for ItmJ); $H_2O$ PCR control.

B gene cluster, which contains 10 genes all required for synthesis of lolitrem B, were targeted to identify individual *N. lolii* colonies with deletions (Young et al, 2005). A high throughput PCR screening method was developed to detect for the presence and absence of the three lolitrem B genes (FIG. 18).

TABLE 14

Analysis of ionising radiation experiments. Protoplast regeneration, concentration of recovered protoplasts and number of PCR analysed colonies.

| Endophyte strain | Age of Culture | Dose (Gy) | Irradiation events | Protoplast regeneration | Concentration | Colonies plated | PCR screened colonies |
|---|---|---|---|---|---|---|---|
| ST | 2 wks | 0 | 1 | ✓ | $1.8 \times 10^8$ pp/ml | — | — |
| ST | 2 wks | 10 | 1 | ✓ | $5.8 \times 10^5$ pp/ml | 700 | 450 |
| ST | 2 wks | 15 | 1 | ✓ | $7.5 \times 10^5$ pp/ml | 200 | 200 |
| ST | 2 wks | 20 | 1 | ✓ | $2.2 \times 10^6$ pp/ml | 2950 | 400 |
| ST | 2 wks | 30* | 1 | — | — | — | — |
| ST | 2 wks | 30 | 1 | ✓ | $1.94 \times 10^7$ pp/ml | 400 | 350 |
| ST | 2 wks | 0 | 2 | ✓ | $1.1 \times 10^8$ pp/ml | — | — |
| ST | 2 wks | 10 | 2 | ✓ | $2.6 \times 10^8$ pp/ml | 150 | 150 |
| ST | 2 wks | 15 | 2 | slow/reduced numbers | $2.2 \times 10^7$ pp/ml | 200 | 200 |
| ST | 2 wks | 20 | 2 | ✓ | $1.38 \times 10^7$ pp/ml | — | — |
| ST | 2 wks | 30/25 | 2 | ✓ | $6.38 \times 10^5$ pp/ml | 1000 | 750 |
| ST | 2 wks | 30 | 2 | ✓ | $1.3 \times 10^8$ pp/ml | 900 | 300 |
| ST | 4 Days | 0 | 1 | ✓ | $2.5 \times 10^6$ pp/ml | — | — |
| ST | 4 Days | 10 | 1 | slow/reduced numbers | $3.75 \times 10^6$ pp/ml | 200 | 200 |
| ST | 4 Days | 15 | 1 | slow/reduced numbers | $1.38 \times 10^8$ pp/ml | 200 | 200 |
| ST | 4 Days | 20 | 1 | slow/reduced numbers | $2.7 \times 10^5$ pp/ml | — | — |
| ST | 4 Days | 25 | 1 | slow/reduced numbers | $1.38 \times 10^5$ pp/ml | 50 | 50 |
| ST | 4 Days | 30 | 1 | slow/reduced numbers | $1.38 \times 10^7$ pp/ml | — | — |
| | | | | | Total | 6950 | 3250 |

*30 Gy dose for first irradiation

A method has been developed to eliminate the production of the detrimental alkaloid lolitrem B, using X-ray mutagenesis induced deletion of genes in the lolitrem B biosynthetic gene cluster, in the ST endophyte.

Such an endophyte would be advantageous over existing commercial endophytes, as ST is highly stable and broadly compatible.

Introduction

Ionising radiation is capable of introducing a broad range of mutagenic lesions and has been found to be very effective in many species. Published methods are available to readily detect deletion mutants in targeted plant genes (Li et al, 2002). Experiments have been performed to determine if *N. lolii* mycelia are amenable to production of mutagenic lesions by ionising radiation, in particular deletion mutations.

Generation of Novel Endophyte Variation Using Ionising Radiation

*N. lolii* strain ST was grown in potato dextrose broth for different periods of time ranging from 2-14 days before exposure to ionising radiation. Radiation from a caesium source was applied to the liquid cultures in doses ranging from 10-30 Gy. Following a recovery period (10-14 days) the radiation dose was repeated. Protoplasts were generated and recovery of individual colonies monitored over a 4-6 week period.

Lolitrem B is the major alkaloid leading to ryegrass staggers in grazing animals. Three genes within the lolitrem

Example 7

Tall Fescue Endophyte Discovery and Characterisation

Summary

Tall Fescue Endophyte Discovery

The strategies implemented for perennial ryegrass endophyte discovery were extended to the resident endophytes of tall fescue (including the FaTG-2 and FaTG-3 taxonomic groups).

A targeted collection of tall fescue germplasm was made from throughout the range of natural growth and domesticated cultivation.

A total of 568 tall fescue accessions obtained from 40 different countries were tested for endophyte incidence using endophyte-specific simple sequence repeat (SSR) genetic markers. Twelve to twenty seeds from each accession were tested for endophyte presence. Total genomic DNA was extracted from two independent seed bulks of 6-10 seeds from each accession and endophytes were detected by PCR amplification with six endophyte-specific SSR markers.

Endophyte was detected in 40% (228/568) of the tall fescue accessions tested.

Figure 19:
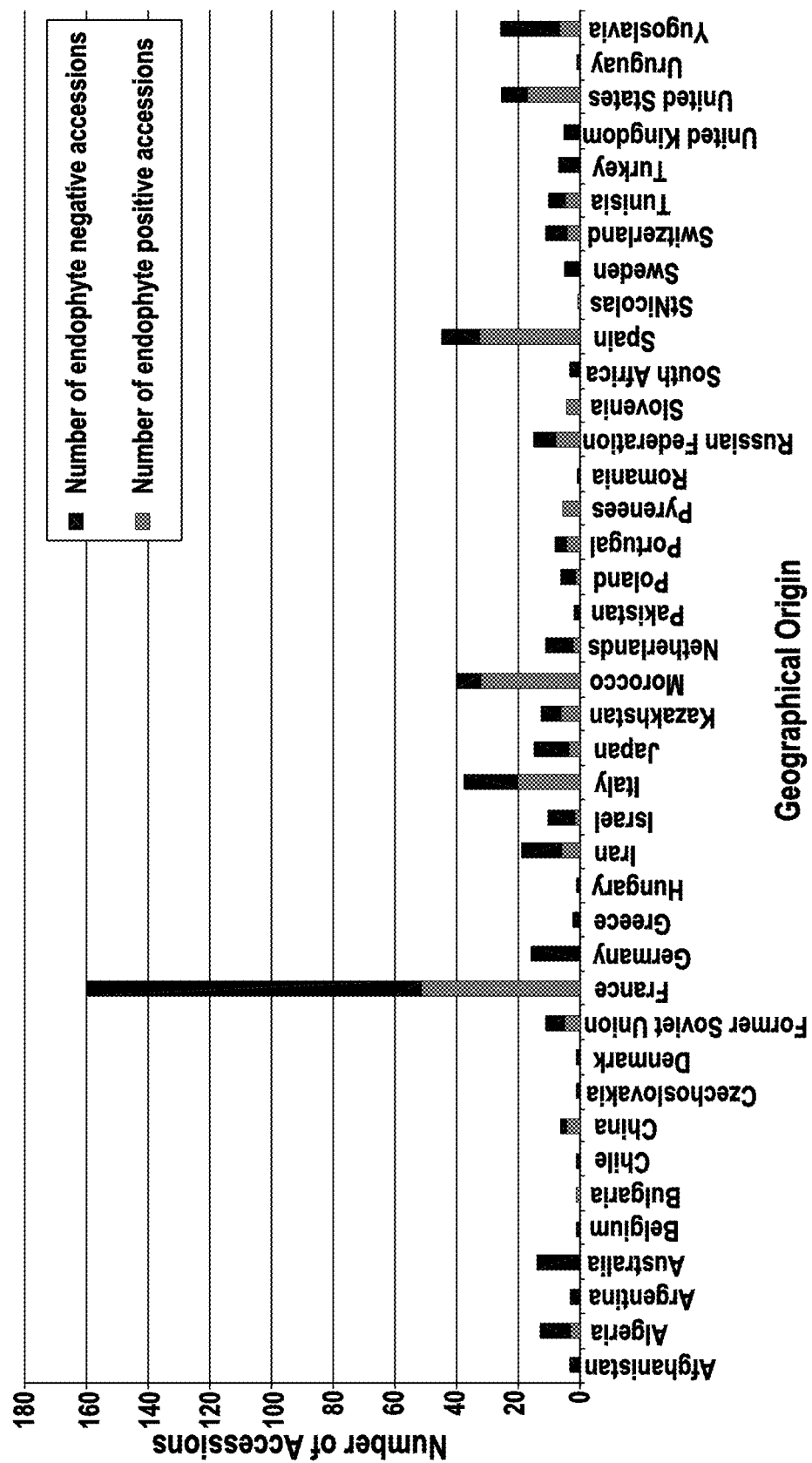
FIG. 19 shows geographical origins represented in the tall fescue endophyte incidence assessment. This graph shows the 40 different geographic origins represented in the incidence assessment. The X axis gives geographic origins in the alphabetical order and the Y axis shows the number of accessions. The number of negative accessions is shown with black and the number of positive accessions is shown in grey.

Furthermore, accessions from 23 out of the 40 countries screened were endophyte positive (FIG. 19) showing the highest incidence in Morocco and Pyrenees, where the majority of accessions tested (80%-100%) were endophyte positive. Accessions originating from Italy, Spain, and United States exhibited a higher endophyte incidence among the tall fescue accessions tested.

A subset of selected endophyte positive samples, were selected for further analysis using 32 endophyte-specific SSR markers. The selected genotypes represent a broad range of known geographical origins, hence representing an effective survey of tall fescue endophyte genotypic variation. A set of 52 reference isolates representing several endophyte species, including the resident endophyte of tall fescue and meadow fescue were also included to the diversity analysis.

Figure 20:
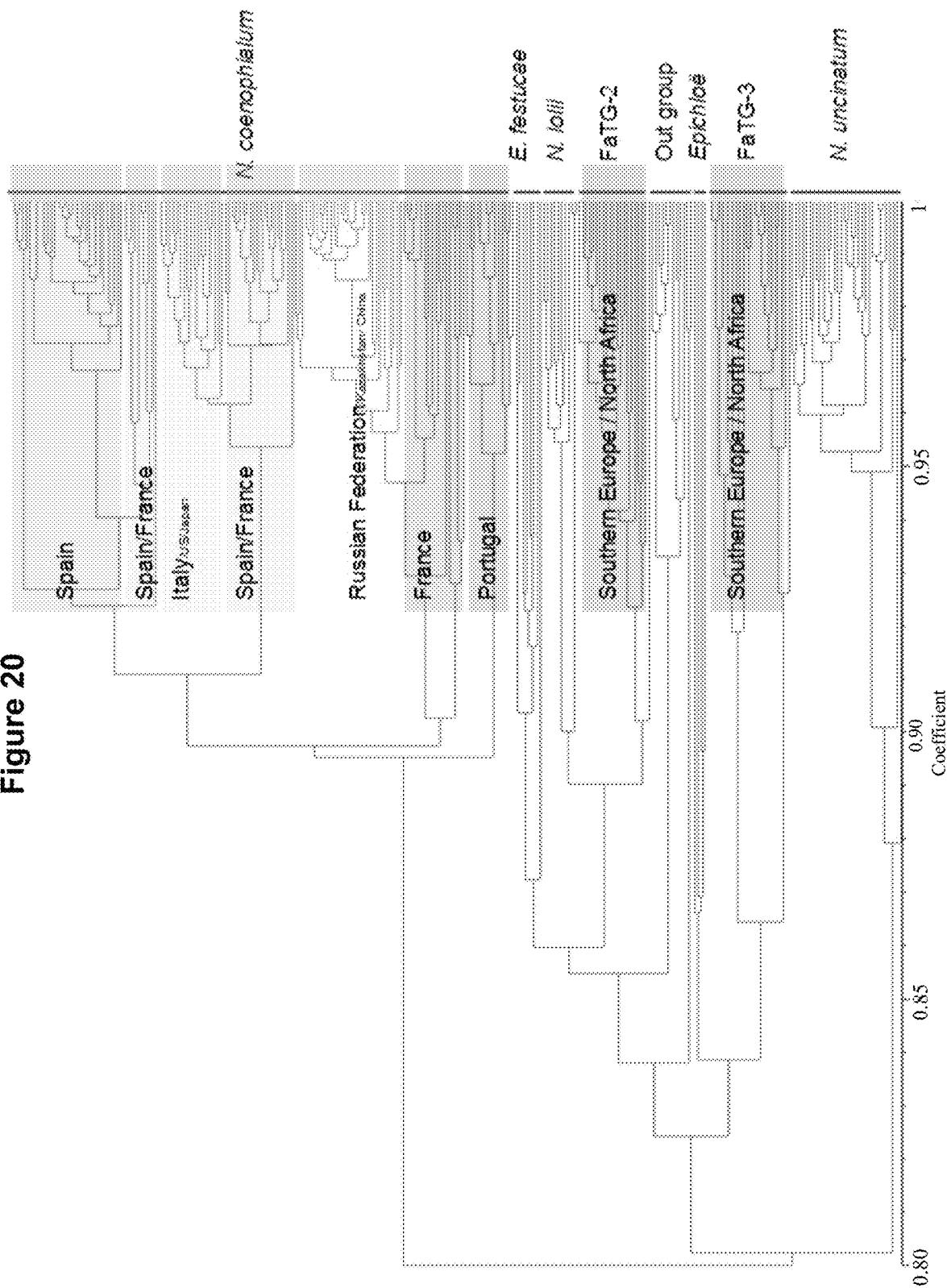
FIG. 20 shows UPGMA phenogram of genetic relationships among endophytes in tall fescue accessions of diverse origins and reference *Neotyphodium, Epichloë*, FaTG-2 and FaTG-3 species.

The UPGMA phenogram, constructed using average taxonomic distance based on SSR polymorphism across 203 endophyte positive accessions, represented six different known taxa, and two out-grouped clusters (FIG. 20). The phenogram was supported by Mantel test statistics showing a high correlation coefficient (r=0.95) which indicated a high goodness-of-fit for the data. Endophytes representing six different taxa were detected in the 203 accessions (FIG. 20). The majority of endophytes (60%; 122/203) appeared to belong to the taxon *Neotyphodium* coenophialum, clustering in the phenogram with *N. coenophialum* isolates from the reference endophyte collection (FIG. 20). This species occurred in 72% (122/170) of tall fescue collection accessions.

As defined by the *N. coenophialum* reference isolates, the *N. coenophialum* cluster comprised five main sub-clusters, of which the fifth sub-cluster is rather out grouped from the other four (FIG. 20).

The genetic variation observed within *N. coenophialum* was high when comparing it with other taxonomic groups. In the phenogram *N. coenophialum* strains clustered for the most part according to their geographical origin (FIG. 20). The first sub-cluster of *N. coenophialum* comprised mainly tall fescue accessions from Spain (28) and few accessions from Pyrenees (3) and France (4) (FIG. 20). Italian (7) and French (14) accessions were clustered in the second sub-cluster (FIG. 20). The third sub-cluster clearly shows the genetic similarity among accessions collected from geographic area surrounding Russian Federation [Slovenia (3), Russian Federation (6), Kazakhstan (7), Former Soviet Union (4) and China (3)] (FIG. 20). Furthermore within the third sub-cluster a set of accessions from France (11) and Pyrenees (1) have formed a separate cluster from Russian Federation and its surrounding geographic origins. The fourth sub-cluster comprises only five endophytes of which two are Moroccan accessions and two are AR endophytes (AR542 and AR584) which were initially isolated from tall fescue originated in Morocco (Latch et al, 2000). The accessions collected from Portugal (4) have formed a distinct sub-cluster which is separated from all the other four sub-clusters (FIG. 20).

FaTG-2 accessions formed a cluster close, but distinct from isolates of *N. lolii* (FIG. 20). There were 20 FaTG-2 endophyte genotypes tall fescue collection which clustered with the FaTG-2 reference genotype. Among them, a set of six accessions formed sub-clusters having lesser genetic similarity to the FaTG-2 reference genotype. Therefore, the endophytes of those sub-clusters were named "FaTG-2 like" endophyte genotypes.

A set of six endophyte genotypes formed a distinct cluster with putative FaTG-3 reference isolates as defined by the previously-analysed AR endophytes. Furthermore, 13 accessions primarily originating from Morocco (9/13) formed a sub-cluster with putative FaTG-3 isolates and those unidentified accessions, forming a cluster distinct to putative FaTG-3 were named "FaTG-3 like" endophytes (FIG. 20).

The identities of selected putative FaTG-2 and FaTG-3 accessions are largely consistent with geographical provenance, as these taxa are known to be characteristic of populations from southern Europe and North Africa.

Two out grouped clusters were also identified and they were named as "out-group I" and "out-group II" (FIG. 20). Accessions of Mediterranean origin primarily clustered in "out-group I", whereas one accession from Former Soviet Union formed the second out-group. Moreover, within "out-group I" Italian accessions clearly group separately from Moroccan and Algerian accessions.

A number of candidate novel endophytes have been identified.

Metabolic Profiling of Tall Fescue-Endophyte Associations

Representative tall fescue-endophyte associations were selected for metabolic profiling analysis in order to determine the endophyte derived alkaloid profile, in particular, lolitrem B, ergot alkaloids, peramine and lolines.

Analysis of metabolite production was assessed under controlled conditions using a growth chamber. Tall fescue-endophyte associations were each replicated four times by clonal splitting and arranged in a randomised block design in the growth chamber. Plants were maintained in soil for six weeks, with trimming every two weeks to encourage growth. Following 6 weeks growth, pseudostem tissue was harvested and freeze dried prior to performing a metabolite extraction and LCMS analysis. The perennial ryegrass—*N. lolii* designer association Bronsyn-ST was used as a control as ST is known to produce lolitrem B, ergovaline and peramine. For each of the accessions, the presence and identity of the resident endophyte was confirmed through SSR analysis of the plant material harvested for metabolic profile analysis and endophyte negative samples were removed from further analysis.

Figure 21:
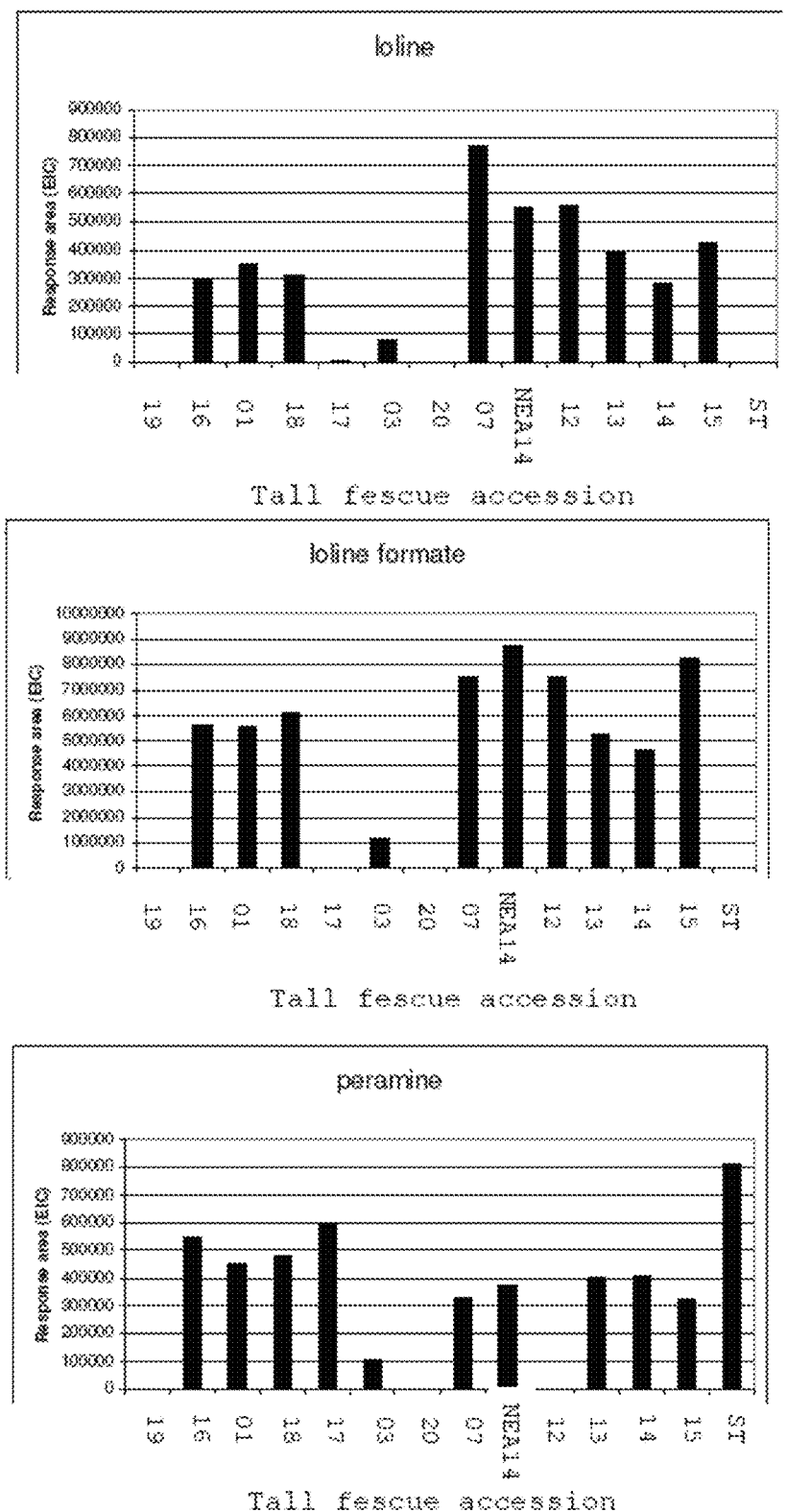
FIG. 21 shows production of the insecticidal alkaloids loline, loline formate and peramine by tall fescue endophytes in their endogenous host.
Figure 22:
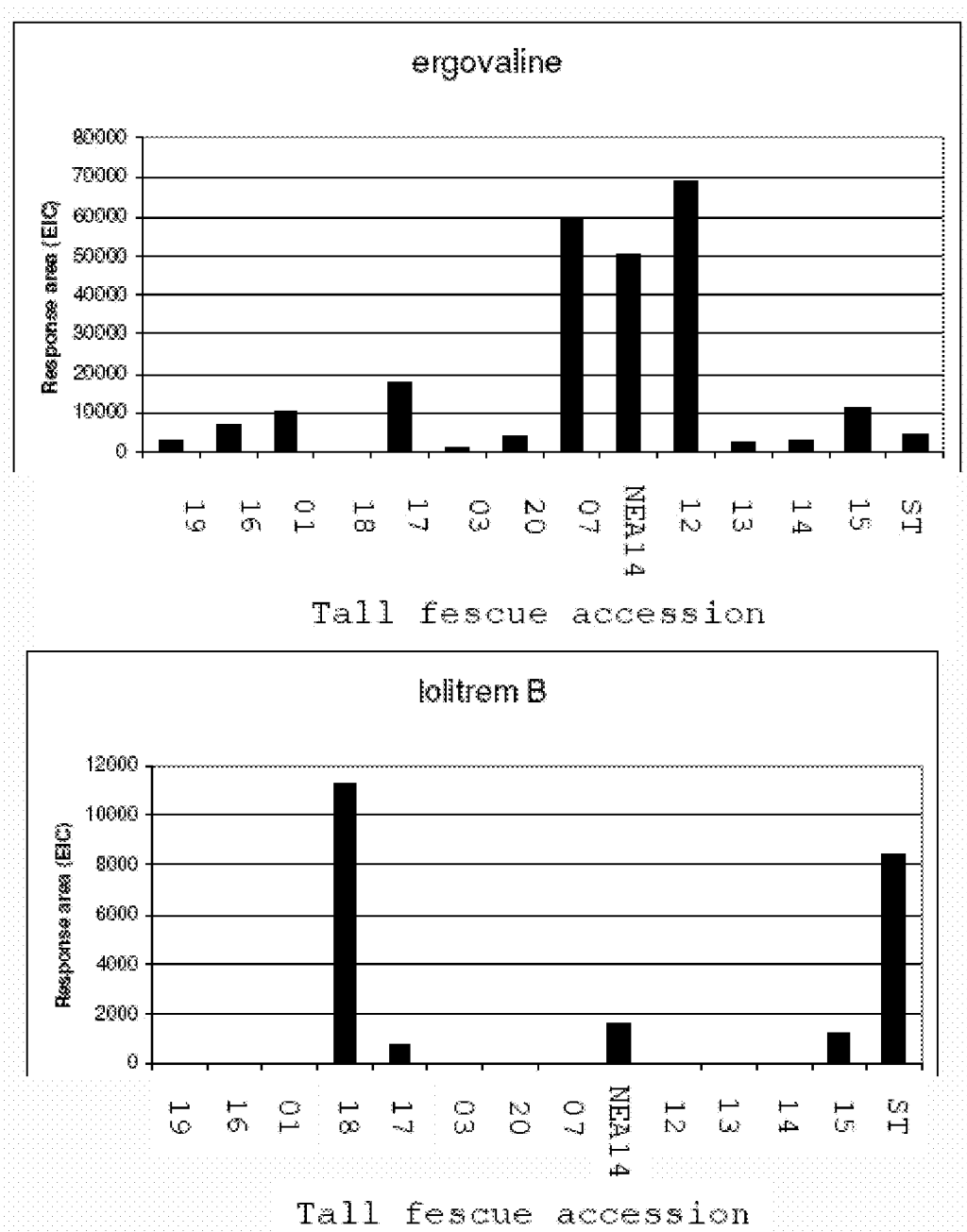
FIG. 22 shows production of the anti-mammalian alkaloids ergovaline and lolitrem B by tall fescue endophytes in their endogenous host.

The results of the qualitative assessment alkaloid of production for 20 novel tall fescue endophytes are summarized in Table 15. Relative quantitation data for Batch three, comprising 13 endophytes assessed in their endogenous hosts, are shown in FIG. 21 and FIG. 22. A number of novel endophytes with favourable toxin profiles (low/no ergovaline production combined with loline and peramine production) have been identified.

TABLE 15

Summary of alkaloid profiles for selected tall fescue endophytes in their endogenous host.

| Tall fescue accession details | | Batch # | | | | | |
|---|---|---|---|---|---|---|---|
| Tall fescue accession | Endophyte species | for alkaloid profiling | Alkaloid profile | | | | Confirmed profile |
| | | | Lolines | Peramine | Ergovaline* | Lolitrem B | |
| 1 | *N. coenophialum* | 1 & 3 | + | + | $+^M$ | − | Y |
| NEA13 | *N. coenophialum* | 2 | n.d | + | + | n.d | n.a |

TABLE 15-continued

Summary of alkaloid profiles for selected tall fescue endophytes in their endogenous host.

| Tall fescue accession details | | Batch # for alkaloid profiling | Alkaloid profile | | | | Confirmed profile |
|---|---|---|---|---|---|---|---|
| Tall fescue accession | Endophyte species | | Lolines | Peramine | Ergovaline* | Lolitrem B | |
| 3 | N. coenophialum | 3 | + | + | + | − | n.a |
| 4 | N. coenophialum | 1 | n.d | + | +$^L$ | n.d | n.a |
| 5 | N. coenophialum | 2 | n.d | + | + | n.d | n.a |
| 6 | N. coenophialum | 2 | n.d | − | + | n.d | n.a |
| 7 | N. coenophialum | 2 & 3 | + | + | +$^H$ | − | Y |
| 8 | N. coenophialum | 2 | n.d | + | + | n.d | n.a |
| 9 | N. coenophialum | 2 | n.d | + | + | n.d | n.a |
| 10 | N. coenophialum | 2 | n.d | − | + | n.d | n.a |
| NEA14 | N. coenophialum | 1 & 3 | + | + | +$^H$ | − | Y |
| 12 | N. coenophialum | 2 & 3 | + | − | +$^H$ | − | Y |
| 13 | N. coenophialum | 1 & 3 | + | + | +$^L$ | − | Y |
| 14 | N. coenophialum | 2 & 3 | + | + | +$^L$ | − | Y |
| 15 | N. coenophialum | 1 & 3 | + | + | +$^M$ | − | Y |
| 16 | FaTG-2 | 3 | + | + | +$^M$ | − | n.a |
| 17 | FaTG-2 | 2 & 3 | − | + | +$^M$ | − | N |
| 18 | FaTG-3 | 3 | + | + | − | + | n.a |
| 19 | Out group 1 | 2 & 3 | − | − | +$^L$ | − | Y |
| 20 | Out group 1 | 1 & 3 | − | − | +$^L$ | − | Y |
| ST | N. lolii | 3 | − | + | + | + | Y |

*Relative quantitation of ergovaline levels: $^L$= Low; $^M$= Medium; $^H$= High.

Establishment of Meristem Cultures for a Diverse Fescue Host Panel

Tissue culture responsive genotypes from selected germplasm material have been generated (Drover, Dovey, Bariane, Barolex). Table 16 shows the host cultivars, and their tissue culture responsive genotype, selected for further study. Each of the selected genotypes has a regeneration frequency greater than 80%

TABLE 16

Establishment of meristem cultures for a diverse tall fescue host panel.

| Cultivar | TCR genotype used for inoculation | Species | Characteristics |
|---|---|---|---|
| Bariane | BARI 27 | L. arundinaceum | Soft leaved, later maturing, highly palatable |
| Dovey | DOV 24 | L. arundinaceum | High yielding, fast establishing |
| Quantum | QUAN 17 | L. arundinaceum | Soft leaved with improved rust resistance |
| Jesup | JESS 01 | L. arundinaceum | Cool season perennial forage |
| Bronsyn | BRO 08 | L. perenne | Standard perennial ryegrass forage type |

Tall Fescue Endophyte Isolation

Selected novel endophytes were isolated from tall fescue accessions (Table 17).

TABLE 17

Summary of endophytes isolated from tall fescue accessions

| Endophyte Accession | Origin | Taxon |
|---|---|---|
| 1 | Spain | N. coenophialum |
| NEA13 | | N. coenophialum |
| 4 | Pyrenees | N. coenophialum |
| 5 | Pyrenees | N. coenophialum |
| 6 | Catalunya (Spain) | N. coenophialum |
| 7 | Corsica (France) | N. coenophialum |
| 8 | Corsica (France) | N. coenophialum |
| 9 | Corsica (France) | N. coenophialum |
| 10 | Aragon (Spain) | N. coenophialum |
| NEA14 | PaySardegna (France) | N. coenophialum |
| 12 | Aragon (Spain) | N. coenophialum |
| 13 | Gaurda (Portugal) | N. coenophialum |
| 14 | Gaurda (Portugal) | N. coenophialum |
| 15 | Aragon (Spain) | N. coenophialum |
| 17 | Spain | FaTG-2 |
| 18 | Tunisia | FaTG-3 |
| 19 | Algeria | outgroup1 |
| 20 | Sardegna (NW Italy) | outgroup1 |
| 21 | Catalunya (Spain) | N. coenophialum |

Isogenic Inoculation of Novel Tall Fescue Endophytes

A set of ten novel tall fescue endophytes were selected for inoculation based on genetic novelty using SSR-based diversity analysis and the toxin profile based on qualitative metabolic profiling (Table 18). Included in the set was the endophyte AR542 a commercial endophyte in use globally.

AR542 was discovered and isolated by AgResearch NZ and is marketed as MaxP™ and MaxQ™.

TABLE 18

Endophytes selected for isogenic inoculation based on analysis of genetic diversity and metabolic profile

| Tall fescue accession details | | Alkaloid profile | | | |
|---|---|---|---|---|---|
| Tall fescue accession | Endophyte species | Lolines | Peramine | Ergovaline | Lolitrem B |
| NEA13 | N. coenophialum | n.d | + | + | n.d |
| 3 | N. coenophialum | + | + | +$^L$ | − |

TABLE 18-continued

Endophytes selected for isogenic inoculation based on analysis of genetic diversity and metabolic profile

| Tall fescue accession details | | Alkaloid profile | | | |
|---|---|---|---|---|---|
| Tall fescue accession | Endophyte species | Lolines | Peramine | Ergovaline | Lolitrem B |
| 22 | N. coenophialum | n.d | n.d | n.d | n.d |
| NEA14 | N. coenophialum | + | + | +$^H$ | − |
| 13 | N. coenophialum | + | + | +$^L$ | − |
| 15 | N. coenophialum | + | + | +$^M$ | − |
| 17 | FaTG-2 | − | + | +$^M$ | − |
| 19 | Out group 1 | − | − | +$^L$ | − |
| 20 | Out group 1 | − | − | +$^L$ | − |
| AR542* | N. coenophialum | n.d | n.d | − | n.d |

*toxin profile from Bouton et al, 2002.

In order to accurately determine the phenotypic effects of different candidate endophytes in the absence of host-specific genetic effects, a system for isogenic inoculation was used. Novel candidate endophytes were individually inoculated into elite tall fescue germplasm as well as the perennial ryegrass host genotype Bronsyn (Bro08). Following inoculation and plantlet regeneration in culture, plants were transferred to soil for three months to allow establishment of endophyte and host-plant associations. After this period, three tillers from each plant were sampled and tested for endophyte presence using SSR-based analysis.

Of the 498 isogenic inoculations tested, 109 (21.9%) could be positively scored with a high degree of confidence. Successful inoculations are listed on Table 19.

Variation in inoculation success according to candidate endophyte identity was observed. Endophyte strain 3 (4.3%), for example, exhibited relatively lower success rates as compared to strain 20 (51.1%), or the commercial endophyte AR542 (44.4%; Table 19) and only formed stable associations with one of the five hosts (Bariane). No successful inoculations were identified for endophyte strain 15. FaTG-2 endophyte, strain 17, is a highly compatible endophyte which obtains a high rate of success of inoculation into tall fescue (Table 19) compared to other endophytes examined, and is comparable to AR542. Out-group 1 endophyte strain 20 exhibits the highest level of compatibility as measured by its ability to be inoculated.

Both tall fescue endophytes inoculated into perennial ryegrass host Bro08, strain NEA13 and strain NEA14, were taken up successfully, establishing that endophyte inoculation across a range of host species is possible.

TABLE 19

Summary statistics for isogenic inoculations of selected candidate endophytes in a targeted isogenic tall fescue and perennial ryegrass panel of 5 hosts.
C. Percent of successful inoculations

| Host plant genotype | Endophyte strain | | | | | | | | | | |
|---|---|---|---|---|---|---|---|---|---|---|---|
| | 22 | 3 | NEA13 | 15 | NEA14 | AR542 | 13 | 17 | 20 | 19 | Total |
| BARI 24 | 13.0 | 12.5 | 22.2 | 0.0 | 0.0 | 42.3 | 16.7 | 56.5 | 54.5 | 8.3 | 24.3 |
| BRO 08 | TBD | TBD | 18.2 | TBD | 11.8 | TBD | TBD | TBD | TBD | TBD | 14.3 |
| DOV 24 | 30.0 | 0.0 | TBD | TBD | TBD | TBD | TBD | TBD | TBD | TBD | 12.5 |
| JESS 01 | 30.4 | 0.0 | 17.9 | 0.0 | 35.0 | 47.4 | 20.0 | 10.0 | 41.7 | 20.0 | 22.2 |
| QUAN 17 | 37.5 | 0.0 | 10.0 | 0.0 | TBD | TBD | TBD | TBD | TBD | TBD | 17.5 |
| Total | 25.0 | 4.3 | 17.9 | 0.0 | 13.4 | 44.4 | 18.2 | 41.5 | 51.1 | 13.6 | 21.9 |
| Species | | | N. coenophialum | | | | | FaTG-2 | Outgroup 1 | | |

TBD Be Determined

Example 8

Antifungal Activity of Neotyphodium/Epichloë Endophytes

Introduction

Neotyphodium endophytes at present are largely unexplored in terms of their production of novel antimicrobials.

While some Epichloë/Neotyphodium endophytes have been shown to inhibit the growth of plant-pathogenic fungi in vitro, the inhibitory substances produced have not been identified.

Endophytes with anti-fungal properties may benefit host plants by preventing pathogenic organisms from colonizing them and causing disease. This is of particular interest to the turf grass industry.

A Bioassay to Assess Antifungal Activity of Neotyphodium Endophytes

To determine if endophytes of the species Neotyphodium produce anti-fungal substances in vitro representative species/strains from Neotyphodium were tested for the presence of anti-fungal activity against eight species of fungal plant pathogens.

Figure 23:
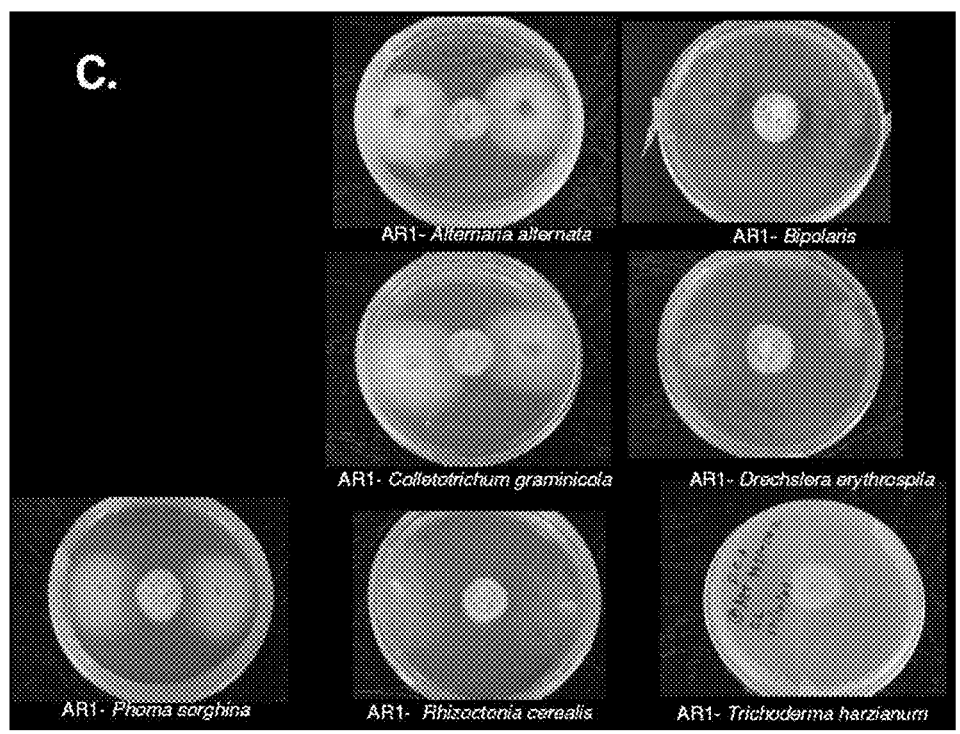
FIG. 23 shows an example of antifungal bioassay of inhibition reactions. Testing for antifungal activity of endophyte NEA12, ST and AR1 against 8 species of pathogenic fungi.

Three types of inhibition reactions were observed. In the first reaction, pathogenic fungal growth was unaffected. In the second, growth of the pathogenic fungi was initially unaffected, but growth ceased when the colony margin approached a "critical" distance from the central endophyte colony. In the third stronger reaction type, the overall growth of the colony of the pathogenic fungi was reduced. Examples of inhibition reactions are shown in FIG. 23.

Variation was observed within and between endophyte taxa. Non-N. lolii strain NEA12 exhibits the strongest and most broad spectrum antifungal activity. Variation was also observed among genetically distinct strains of N. lolii.

Within *N. lolii*, strains with strongest to weakest effects were ST>AR1>NEA3>NEA10. ST exhibited the broadest spectrum of antifungal activity, inhibiting the growth of 7/8 fungi strains tested.

The bioassay results showed that endophytes in vitro exhibit variation in anti-fungal activity that does not correlate with known toxin production (specifically, lolitrem B, ergovaline and peramine). For example NEA12 does not produce lolitrem B, ergovaline and peramine and has strong antifungal activity and ST does produce lolitrem B, ergovaline and peramine and also has strong antifungal activity.

Figure 27:
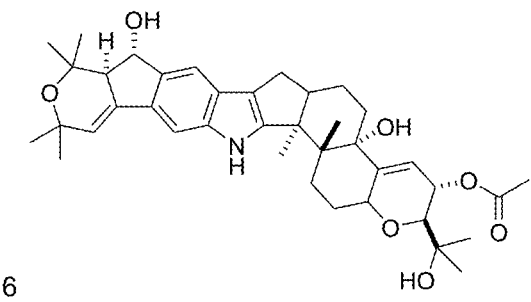
FIG. 27 shows structures of endophyte metabolites
1 peramine (MW 247.3);
2 ergovaline (MW 533.6);
3 lolitrem B (MW 685.9);
4 janthitrem I (MW 645.8);
5 janthitrem G (MW 629.8);
6 janthitrem F (MW 645.8).

I (4) (11,12-epoxy janthitrem G (janthitrem G (5)) by LCMS. Janthitrem G is an isomer of the previously described janthitrem F (6) and its structure was determined by NMR in the original patent describing AR37 (Latch et al, 2000; structures shown in FIG. 27).

Figure 28:
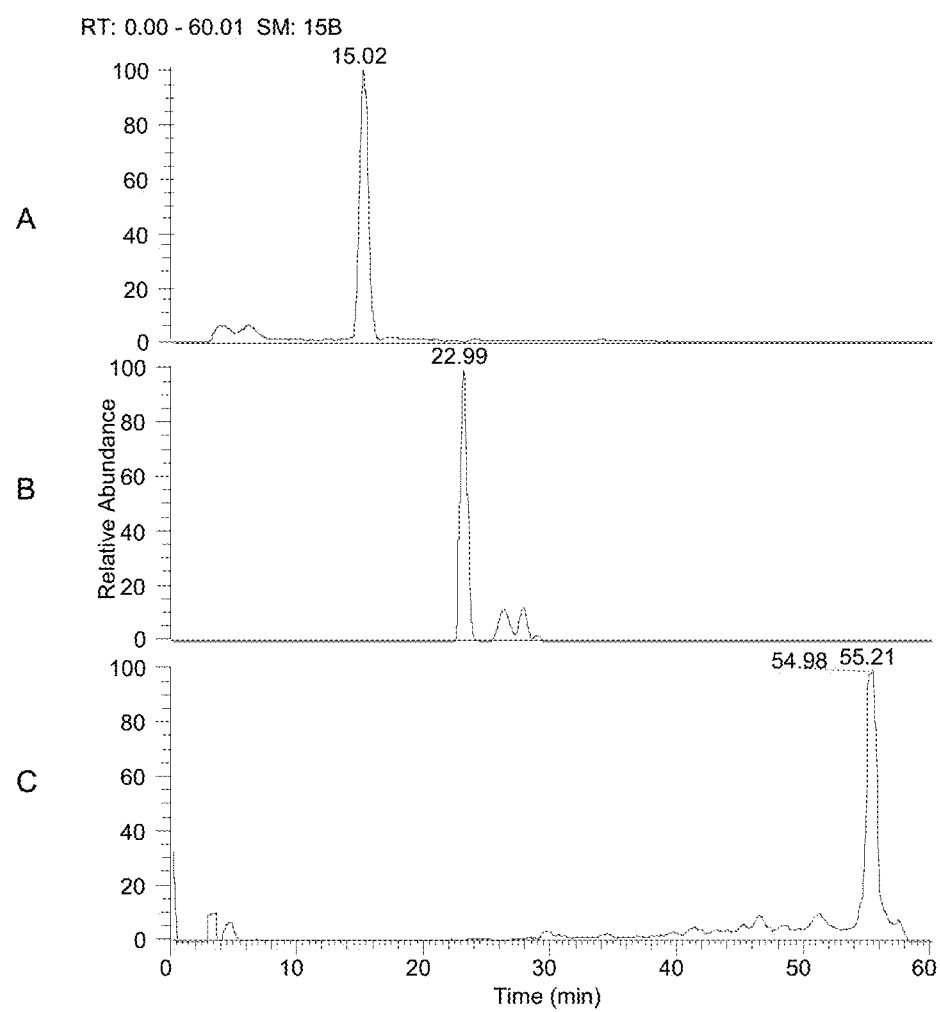
FIG. 28 shows LCMS analysis of standard materials displaying extracted ion chromatogram for the toxins:
  A. peramine
  NL: 7.47E4
  Base Peak m/z=47.50-248.50 F: ITMS+c ESI Full ms [150.00-2000.00] MS
  B. ergovaline
  NL: 1.64E6
  Base Peak m/z=533.40-534.40 F: ITMS+c ESI Full ms [150.00-2000.00] MS
  C. lolitrem B
  NL: 2.25E3
  Base Peak m/z=685.50-687.00 F: ITMS+c ESI Full ms [150.00-2000.00] MS

Standards were analysed to provide reference for the perennial ryegrass analyses. The lolitrem B standard had deteriorated significantly but a peak matching the expected m/z and approximate retention time could be found (FIG. 28).

TABLE 20

Antifungal activity exhibited by representative strains of N. lolii and related endophyte taxa.
Assays were scored visually from 0-5. NT—not tested.

| | | Fungal species | | | | | | | |
|---|---|---|---|---|---|---|---|---|---|
| Endophyte strain | Endophyte species | *Alternaria alternata* | *Colletrichum graminicola* | *Rhizoctonia cerealis* | *Trichoderma harzianum* | *Phoma sorghina* | *Botrytis cinerea* | *Bipolaris portulaceae* | *Drechslera brizae* |
| AR510 | FaTG-3 | 0 | 0 | 5 | 1 | NT | NT | NT | NT |
| NEA11 | LpTG-2 | 0 | 1 | 2 | 0 | NT | NT | NT | NT |
| AR1 | *N. lolii* | 0 | 0 | 3 | 0 | 2 | 0 | 1 | 1 |
| NEA10 | *N. lolii* | 0 | 0 | 0 | 0 | 0 | 0 | 1 | 1 |
| NEA3 | *N. lolii* | 0 | 0 | 1 | 1 | 1 | 0 | 0 | 0 |
| ST | *N. lolii* | 0 | 1 | 3 | 2 | 2 | 2 | 4 | 3 |
| NEA12 | Non-*N. lolii* | 3 | 4 | 4 | 3 | 3 | 3 | 3 | 2 |

Samples are scored visually from 0-5. 0 is no antifungal activity, 1 is low antifungal activity, 5 is strong antifungal activity.
NT—not tested Mass Spectrometry for Identification of Antifungal Metabolites Mass spectrometry was used to determine the relationship between antifungal activity and metabolite expression.

Figure 24:
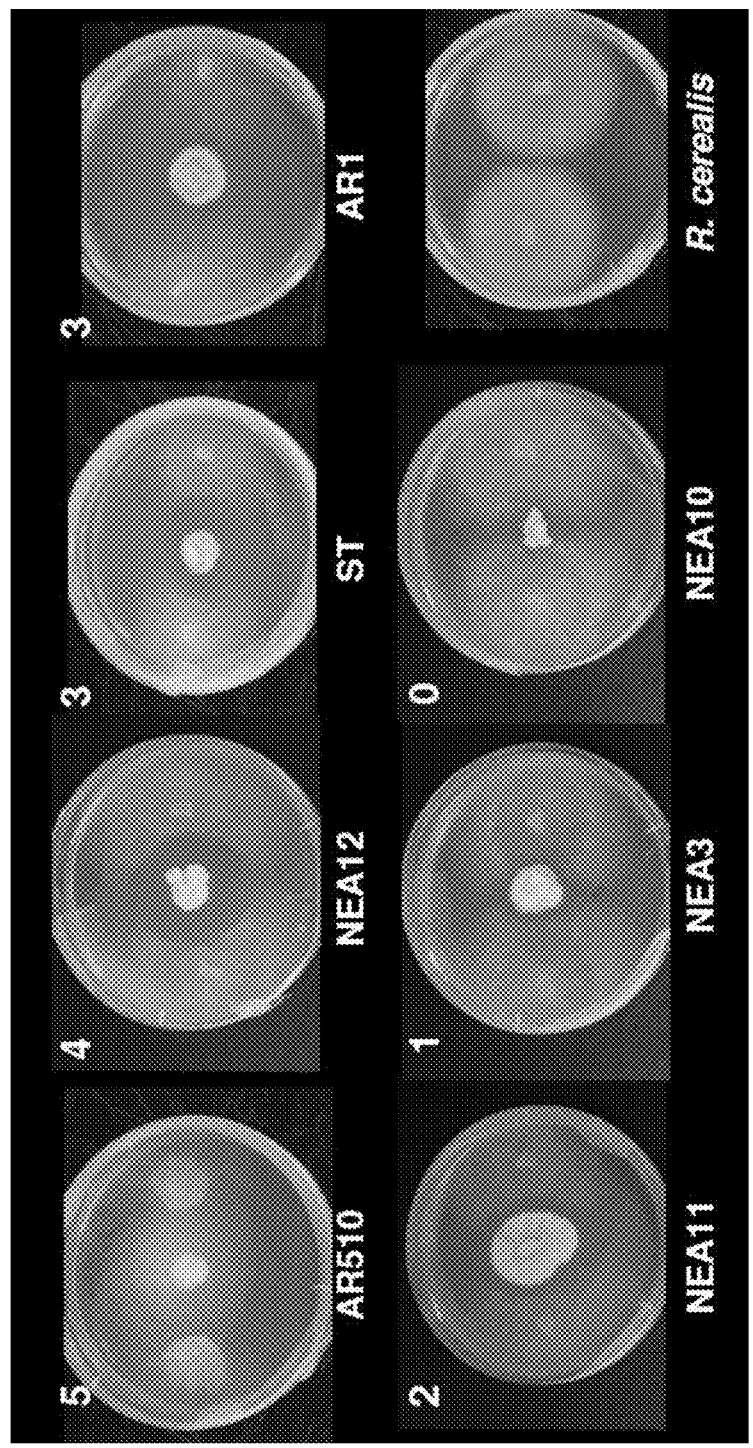
FIG. 24 shows endophytes selected for metabolic profiling in in vitro culture. Shown in the top left hand corner is the inhibition score.

Endophyte strains representing the full spectrum of antifungal activity were selected for analysis in order to identify those alkaloids that may be associated with antifungal activity (FIG. 24).

Figure 25:
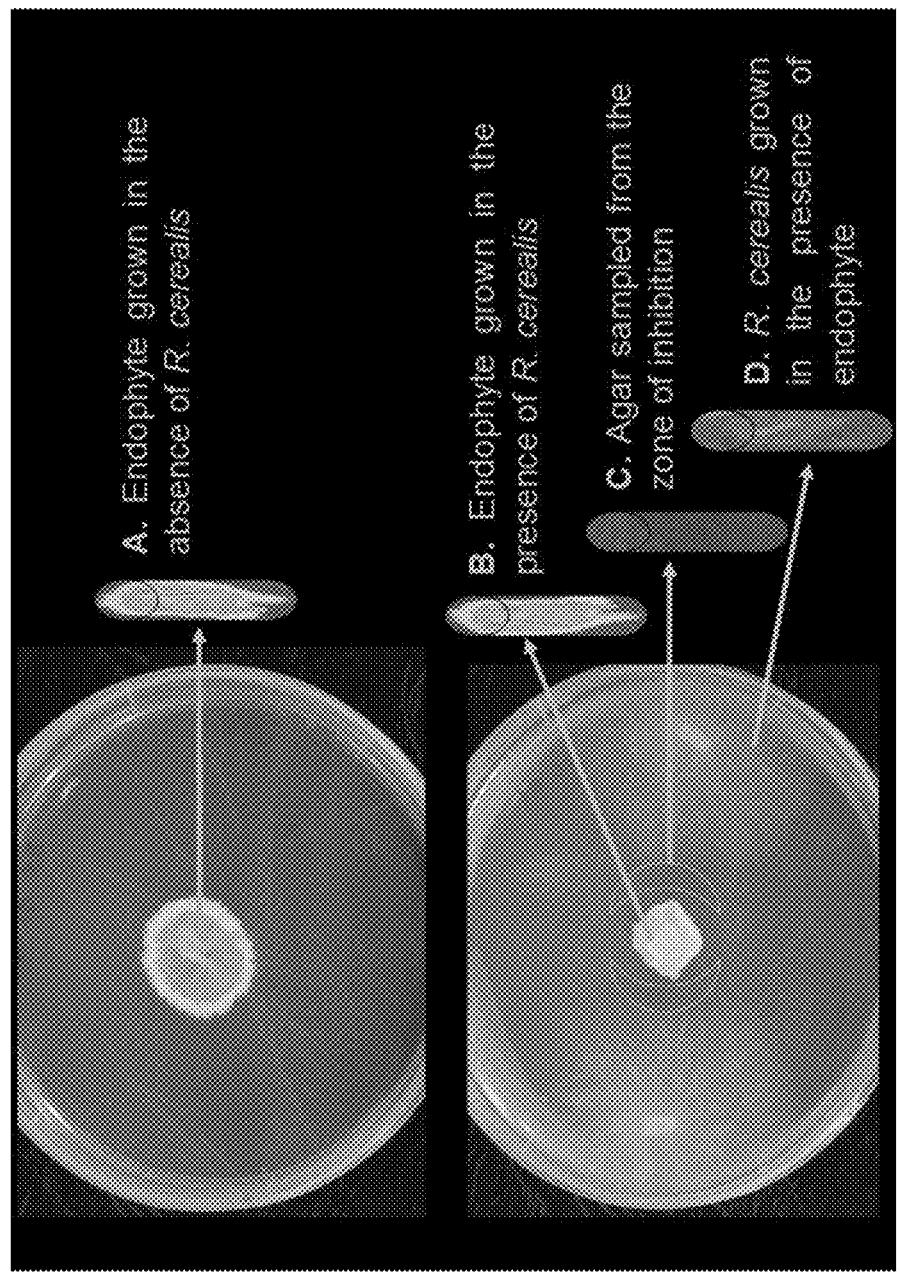
FIG. 25 shows a method for sampling material for LCMS analysis.

Endophyte strains were grown both in the presence and absence of the pathogenic fungi *Rhizoctonia cerealis* (FIG. 25). Freeze dried endophyte mycelia was then extracted for metabolic profiling analysis.

Figure 26:
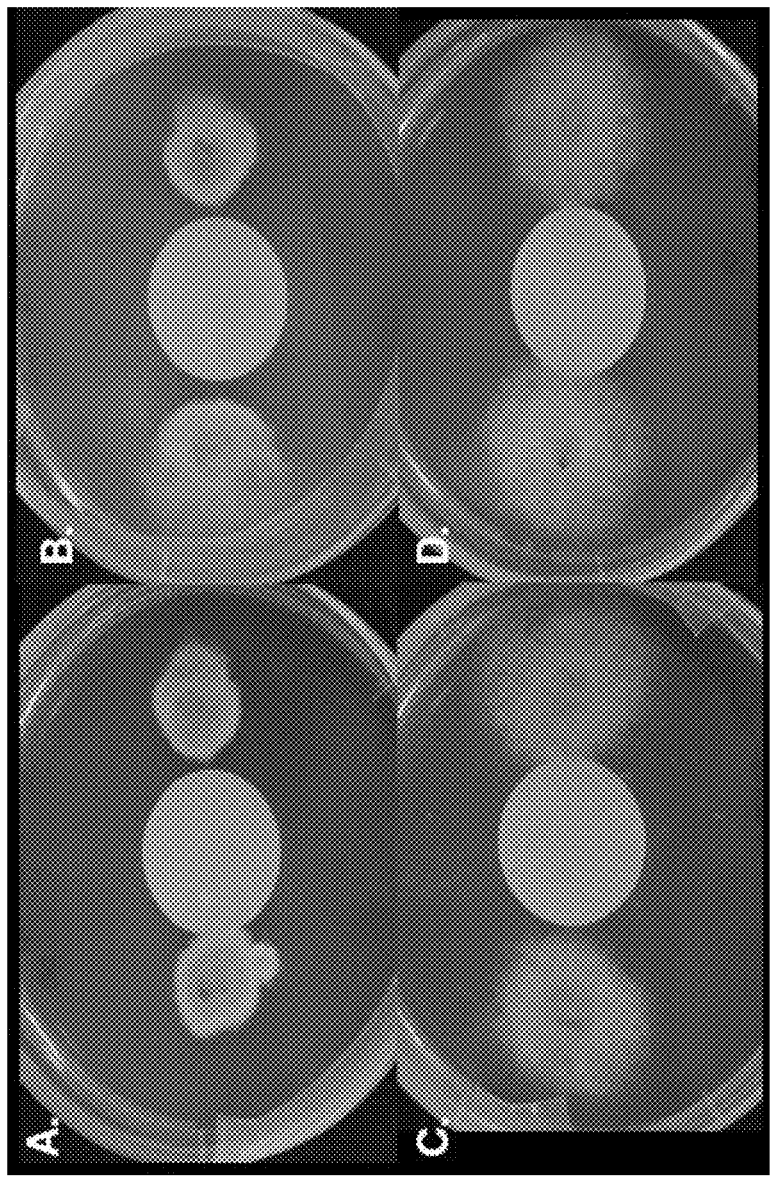
FIG. 26 shows a validation assay. *Rhizoctonia cerealis* was grown in the presence of methanol extracts of endophyte mycelia. Shown is an example using the endophyte strain ST. A. Methanol extract of ST grown in the absence of *R. cerealis*; B. Methanol extract ST grown in presence of *R. cerealis*; C. Water only control; D. Methanol only control.

Following extraction, a validation assay was done to ensure that the alkaloids associated with antifungal activity had been appropriately extracted (FIG. 26). The antifungal activity of the extract used for LCMS analysis was confirmed. The expression of antifungal alkaloids is constitutive as extracts taken from endophyte in the absence of *Rhizoctonia cerealis* also exhibit antifungal activity (FIG. 26).

Example 9

Metabolic Profiling

Summary

Perennial ryegrass cultivars inoculated with the NEA12 endophyte were analysed using LCMS. The toxins peramine, ergovaline and lolitrem B were not detected in the extract. The AR37 metabolite 11,12-epoxy janthitrem G was detected and its structure assigned based on retention time and MS analysis of an extract of the AR37 inoculated perennial ryegrass.

Metabolic Profiling of Endophyte NEA12 in Perennial Ryegrass.

Figure 29:
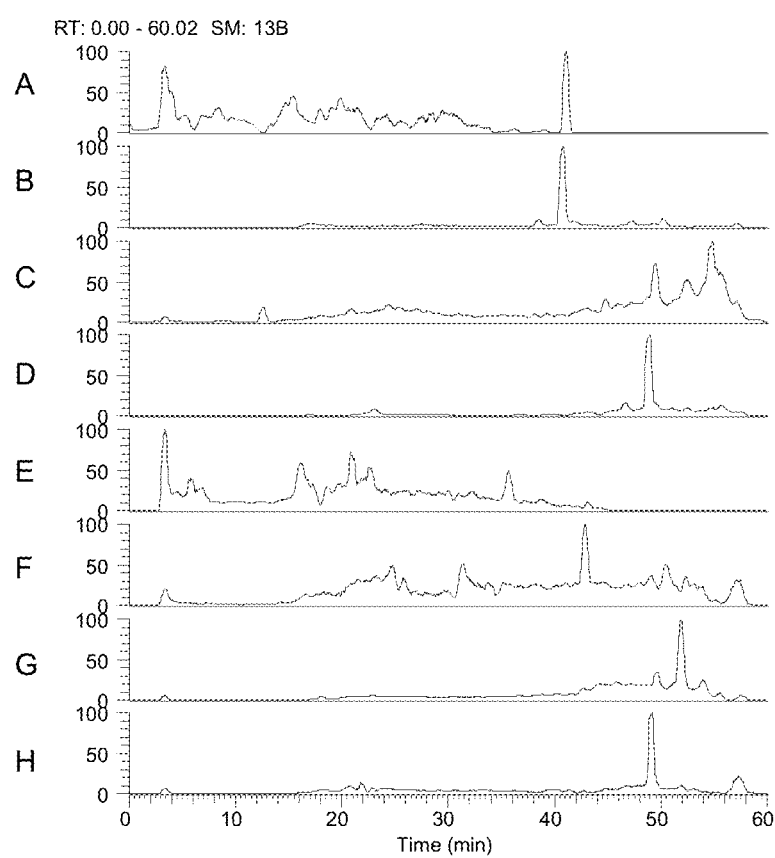
FIG. 29 shows an LCMS comparison of AR37 inoculated perennial ryegrass with NEA12 inoculated perennial ryegrass (IMP04 NEA12 20).
  A. AR37 no peramine
  NL: 3.14E3
  Base Peak m/z=247.50-248.50 F: ITMS+c ESI Full ms [150.00-2000.00] MS
  B. AR37 no ergovaline
  NL: 7.39E4
  Base Peak m/z=533.40-534.40 F: ITMS+c ESI Full ms [150.00-2000.00] MS
  C. AR37 no lolitrem B
  NL: 1.32E4
  Base Peak m/z=685.50-687.00 F: ITMS+c ESI Full ms [150.00-2000.00] MS
  D. AR37 janthitrem
  NL: 8.68E4
  Base Peak m/z=645.50-646.50 F: ITMS+c ESI Full ms [150.00-2000.00] MS
  E. NEA12 no peramine
  NL: 6.18E3
  Base Peak m/z=247.50-248.50 F: ITMS+c ESI Full ms [150.00-2000.00] MS
  F. NEA12 no ergovaline
  NL: 4.10E3
  Base Peak m/z=533.40-534.40 F: ITMS+c ESI Full ms [150.00-2000.00] MS
  G. NEA12 no lolitrem B
  NL: 1.32E4
  Base Peak m/z=685.50-687.00 F: ITMS+c ESI Full ms [150.00-2000.00] MS
  H. NEA12 janthitrem
  NL: 1.04E4
  Base Peak m/z=645.50-646.50 F: ITMS+c ESI Full ms [150.00-2000.00] MS
Figure 30:
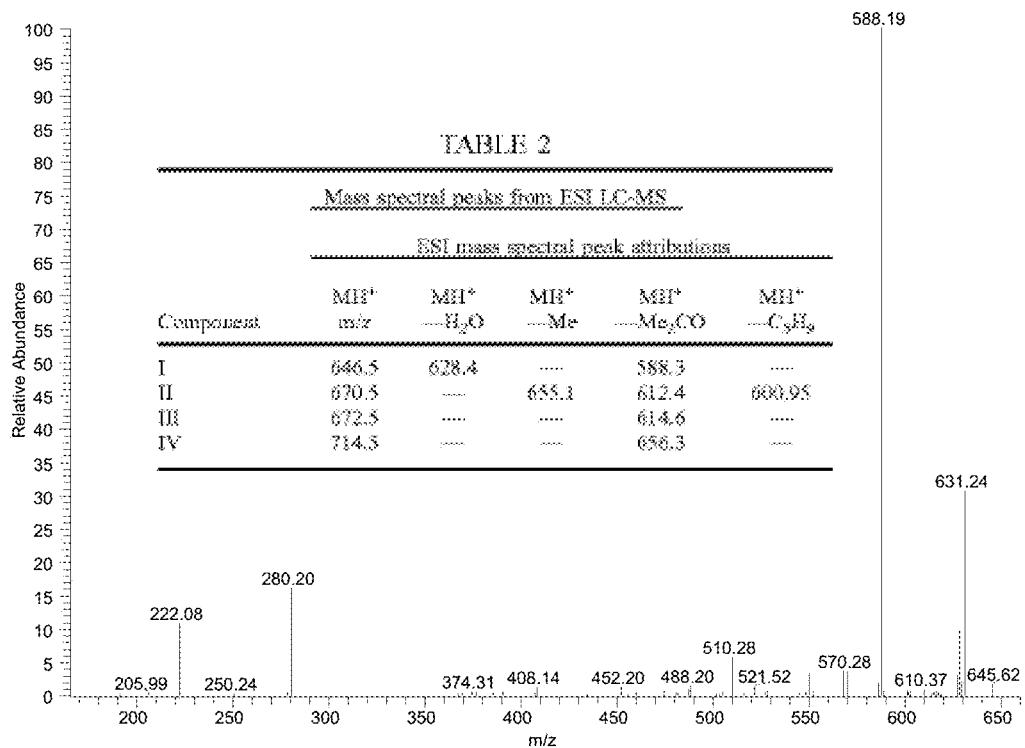
FIG. 30 shows an MSMS analysis of NEA12 insulated perennial ryegrass metabolite 4. Inset is Table 2 from International patent application WO2004/106487 describing the fragmentations of the janthitrems found. Data for NEA12 metabolite 4 is in good agreement with that of component I in the table. (endo15June09-010 #3184 RT: 49.01 AV: 1 NL: 5.02E2, T: ITMS+cESId Full ms2 646.51@cid35.00 [165.00-660.00])

Perennial ryegrass cultivars inoculated with different endophytes were analysed for peramine (1), ergovaline (2), lolitrem B (3) and the AR37 isolated metabolites janthitrem Data for AR37 inoculated endophyte and NEA12-inoculated ryegrass gave comparable results. Neither contained detectable levels of peramine, ergovaline or lolitrem B. Both contained 11,12-epoxy-janthitrem G (4) (FIG. 29). MSMS analysis of the ion m/z 646 (4) is shown in FIG. 30. The data is a good match for that described in the original patent application.

Figure 31:
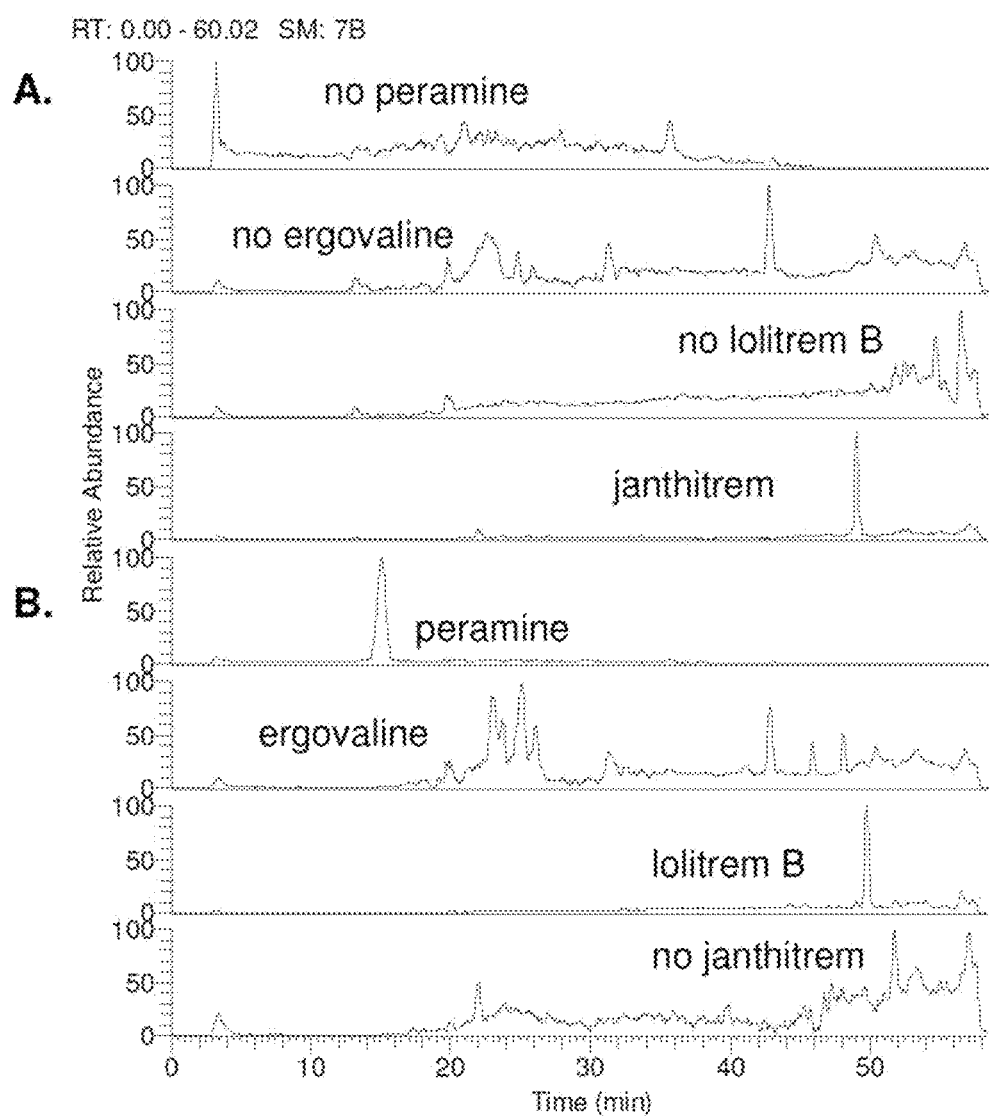
FIG. 31 shows Reverse phase liquid chromatography mass spectrometry (LCMS) analysis of A. TOL03 NEA12 and B. TOL03 ST. Profiles show the presence and absence of specific metabolites including peramine, ergovaline, lolitrem, and janthitrems.
Figure 32:
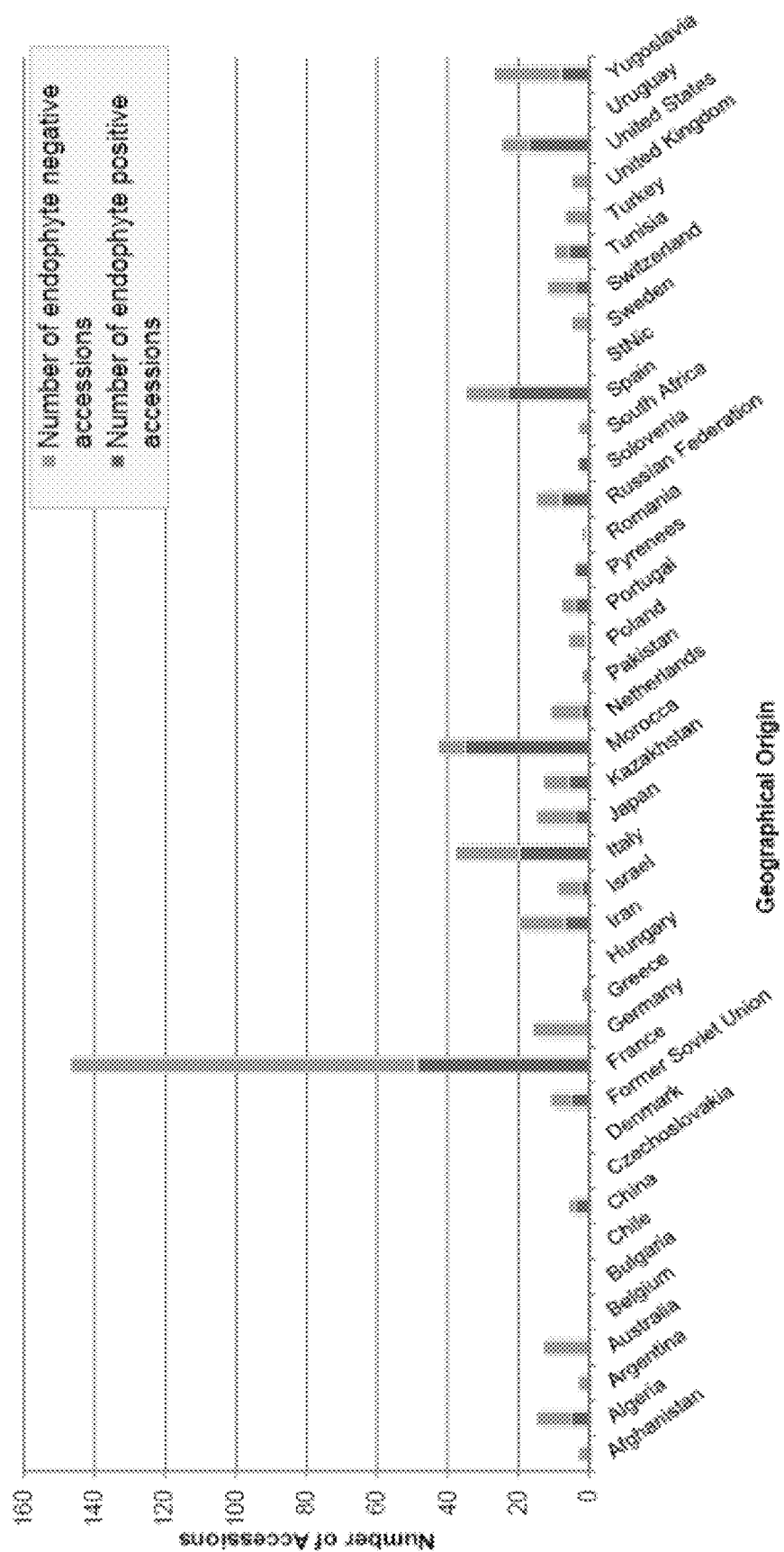
FIG. 32 shows genotypic analysis of endophyte content in accessions from a targeted fescue germplasm collection.

Analysis of NEA12 was carried out in a number of perennial ryegrass cultivars. It was present to a greater or lesser extent in the majority of those examined (Table 21). No attempt was made to quantitate the amount found. A standard toxic (ST) endophyte was analysed in the same perennial ryegrass cultivars. The ST endophyte produced peramine and ergovaline but not janthitrems (Table 21). The toxin profiles for ST and NEA12 are shown in FIG. 31.

TABLE 21

Analysis of endophytes in different perennial ryegrass cultivars.

| Endophyte | Perennial ryegrass cultivar/inoculation event | alkaloids detected |
|---|---|---|
| NEA12 | IMP04 20 | janthitrem |
| NEA12 | TOL03 18 | janthitrem |
| NEA12 | TOL03 16 | janthitrem |
| ST | TOL03 01 | peramine, ergovaline, lolitrem B |
| ST | TOL03 12 | peramine, ergovaline, lolitrem B |
| ST | IMP04 44 | peramine, ergovaline, lolitrem B |
| ST | IMP04 04 | peramine, ergovaline, lolitrem B |
| ST | BRO08 02 | peramine, ergovaline, lolitrem B |
| ST | BRO08 01 | peramine, ergovaline, lolitrem B |

The NEA12 endophyte appears to have the same alkaloid profile as AR37 and is distinctly different from the ST endophyte.

Example 10

Tall Fescue Endophyte Discovery

The objectives of this work on discovery and characterization of endophytes in tall fescue (*Lolium arundinaceum*) were:
1. Identification and characterisation of novel tall fescue endophytes for evaluation in germplasm.
2. Development and evaluation of optimised associations between novel endophytes and elite germplasm.

The endophyte discovery was based on screening 568 accessions to identify endophyte positive plants followed by genotyping 210 endophytes to identify novel endophytes in tall fescue.

The characterisation in planta of novel endophytes from tall fescue was based on the following steps:
- Meristem cultures for tall fescue cultivars were established for isogenic host panel
- Endogenous metabolic profiles were determined for 48 samples
- Isolation of 38 endophytes was undertaken
- Inoculation of 15-20 endophytes into isogenic host panel was undertaken
- Isogenic host-endophyte associations were characterised Genotypic Analysis of Endophyte Content in Accessions from a Targeted Fescue Germplasm Collection Initially, 472 accessions from 30 countries were tested for endophyte incidence; with 2 replicates of 6-10 seeds in each bulk per accession used in the analysis and endophyte incidence assessed with 6 SSRs.

New accessions were included in the analysis from the under-represented geographic origins; with a total of 568 accessions from 40 countries tested for endophyte incidence.

TABLE 22

Genotypic analysis of endophyte content in accessions from a targeted fescue germplasm collection

| | Number of geographic origins | | Percentage positive accessions | |
|---|---|---|---|---|
| | FEtc collection | GRIN collection | FEtc collection | GRIN collection |
| Incidence assessment 01 | 7 | 23 | 96% | 30% |
| Incidence assessment 02 | — | 10 | — | 45% |

Genotypic analysis of endophyte content in accessions from a targeted fescue germplasm collection is shown in Table 22. 233 endophyte positive accessions (41%) were detected. The geographical origins are represented in the endophyte incidence assessment.

Figure 33:
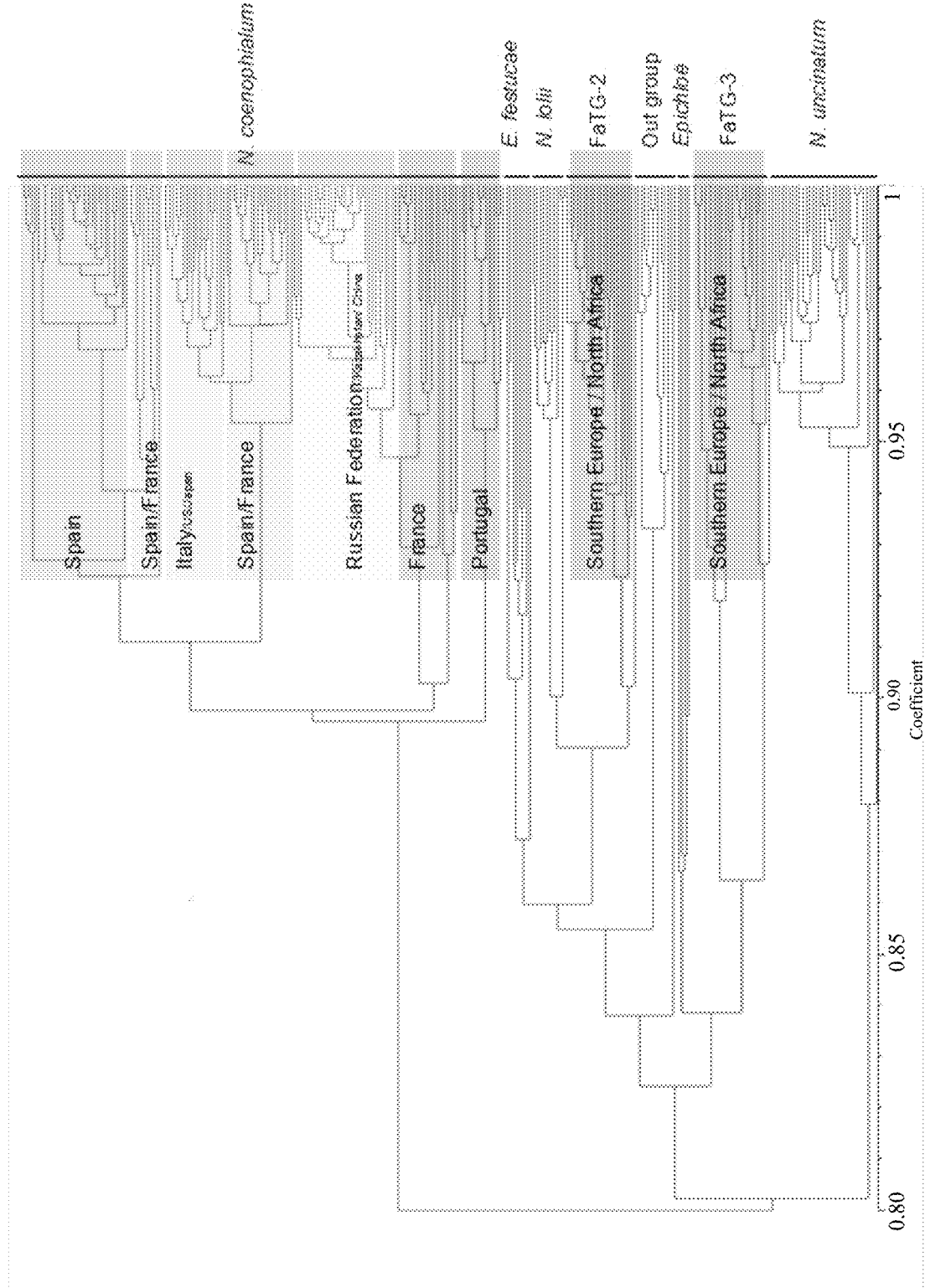
FIG. 33 shows genetic diversity analysis of tall fescue endophytes.

A genetic diversity analysis of tall fescue endophytes is shown in FIG. 33. A selected set of 210 accessions were used to assess genetic diversity of tall fescue endophytes. Genetic diversity was assessed with 38 SSR markers. Six different taxa were detected. The majority were *N. coenophialum*. Twenty were FaTG-2. Six were putative FaTG-3. Thirteen were FaTG-3 like.

Figure 34:
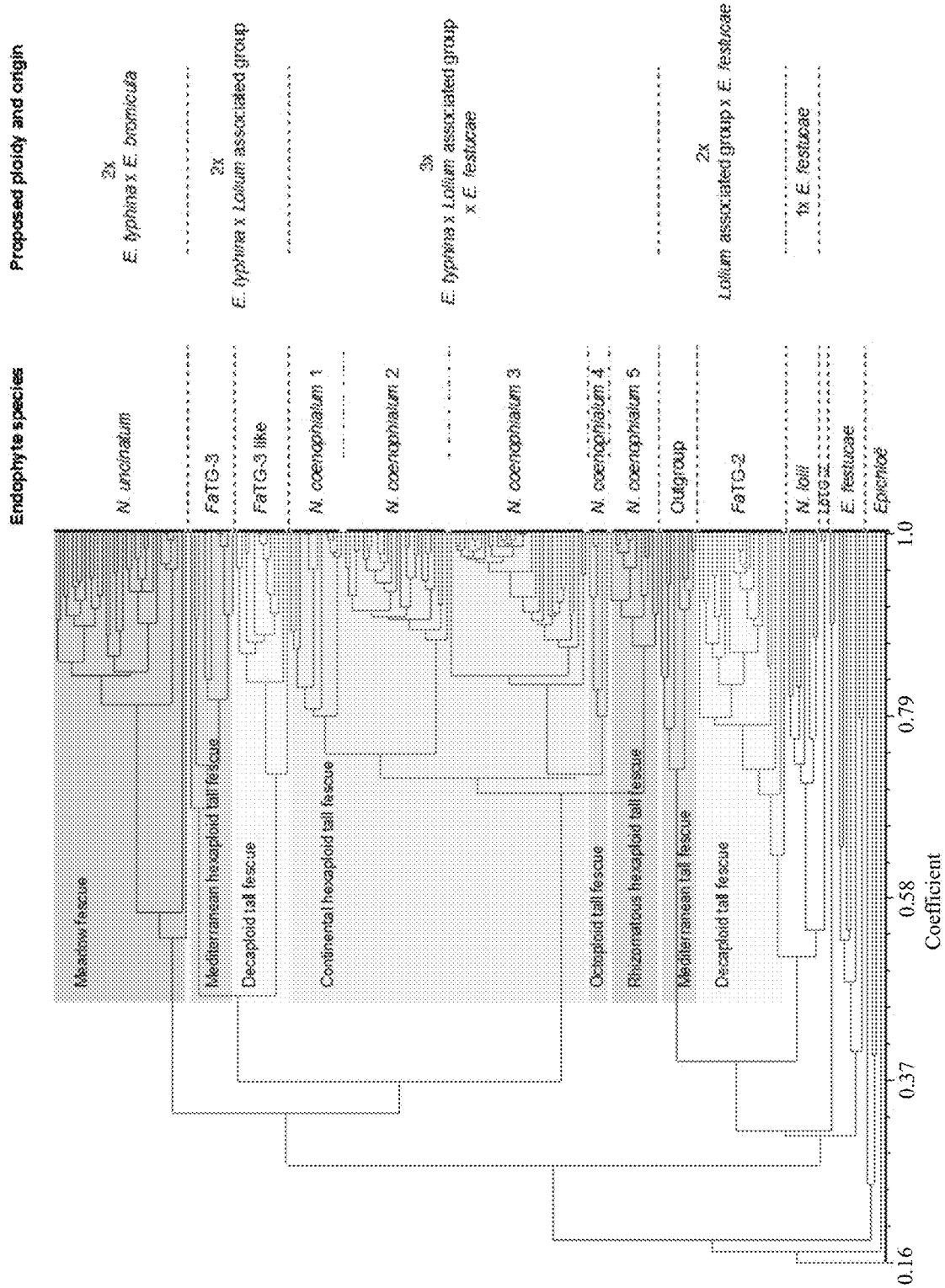
FIG. 34 shows diversity analysis of host and endophyte.

Diversity of Host and Endophyte is Shown in FIG. 34.

Figure 35:
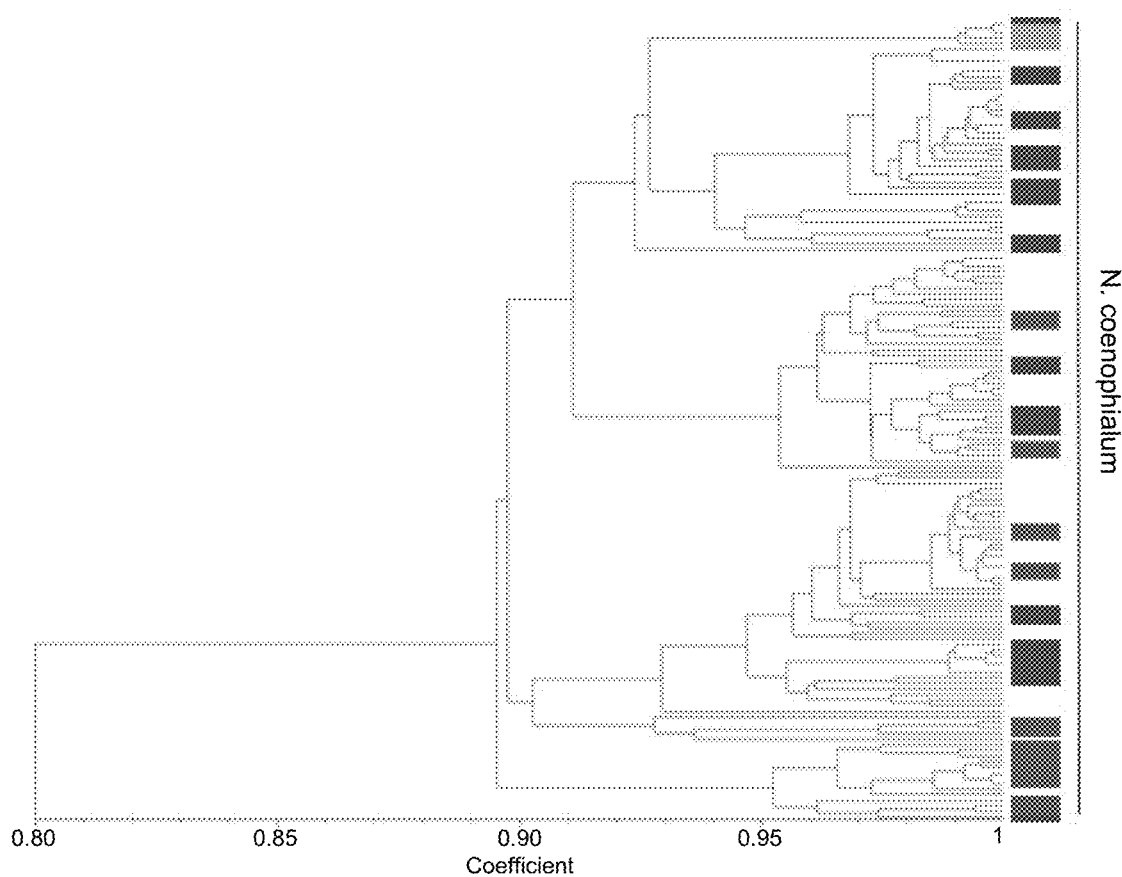
FIG. 35 shows selection of fescue-endophyte combinations for metabolic profiling, endophyte isolation and isogenic inoculation.

Selection of fescue-endophyte combinations for metabolic profiling, endophyte isolation and isogenic inoculation is shown in FIG. 35. 52 accessions were initially selected for metabolic profiling and endophyte isolation. Endophyte presence was consistently detected in 25 accessions (red). An additional 48 accessions from under-represented clusters were established in the glasshouse and screened for endophyte presence. 20 accessions were endophyte positive (blue) and were selected for further analysis.

Figure 36:
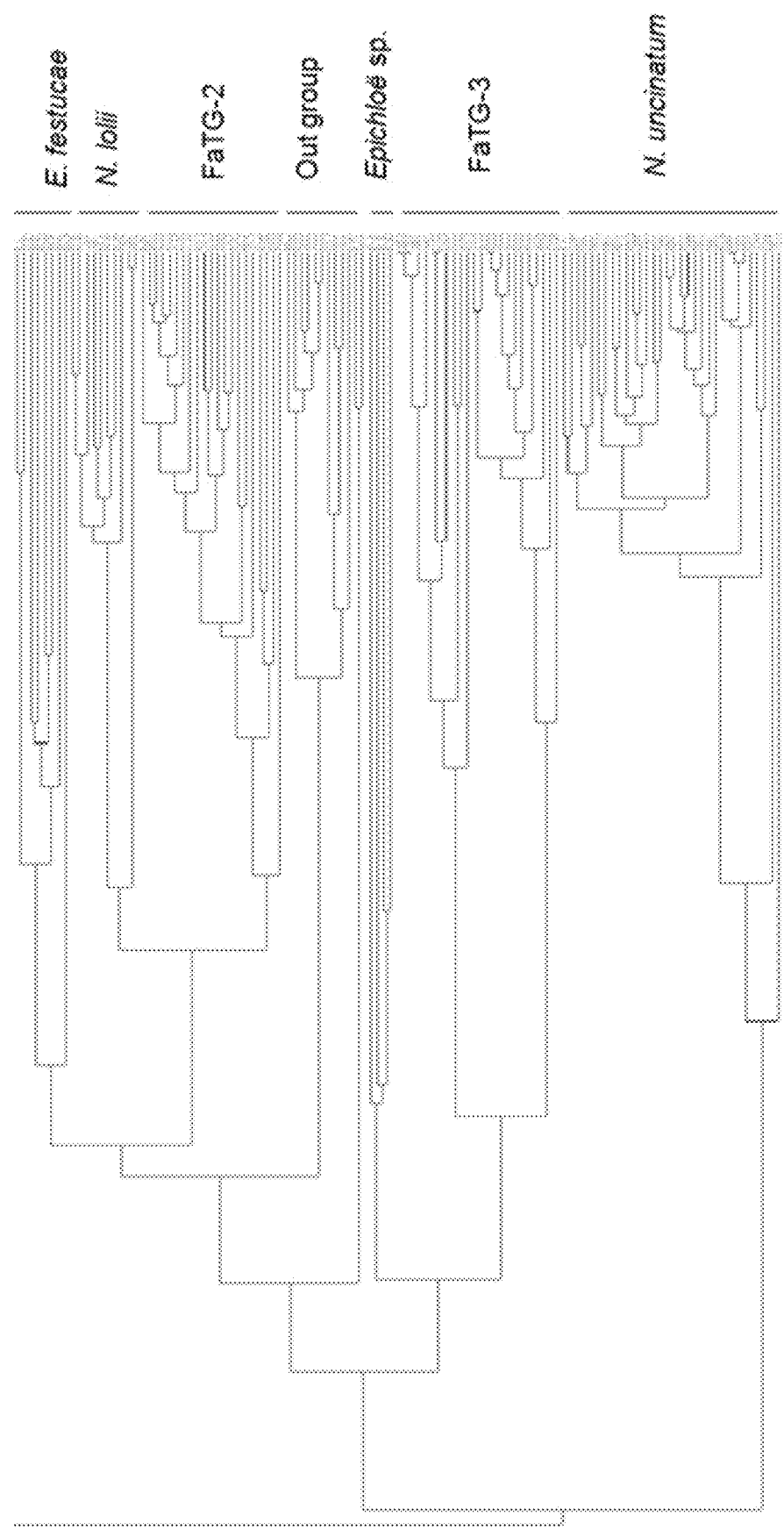
FIG. 36 shows selection of fescue-endophyte combinations for metabolic profiling, endophyte isolation and isogenic inoculation.

Selection of fescue-endophyte combinations for metabolic profiling, endophyte isolation and isogenic inoculation is shown in FIG. 36. Initial selections are shown in red. Additional selections are shown in blue.

Figure 37:
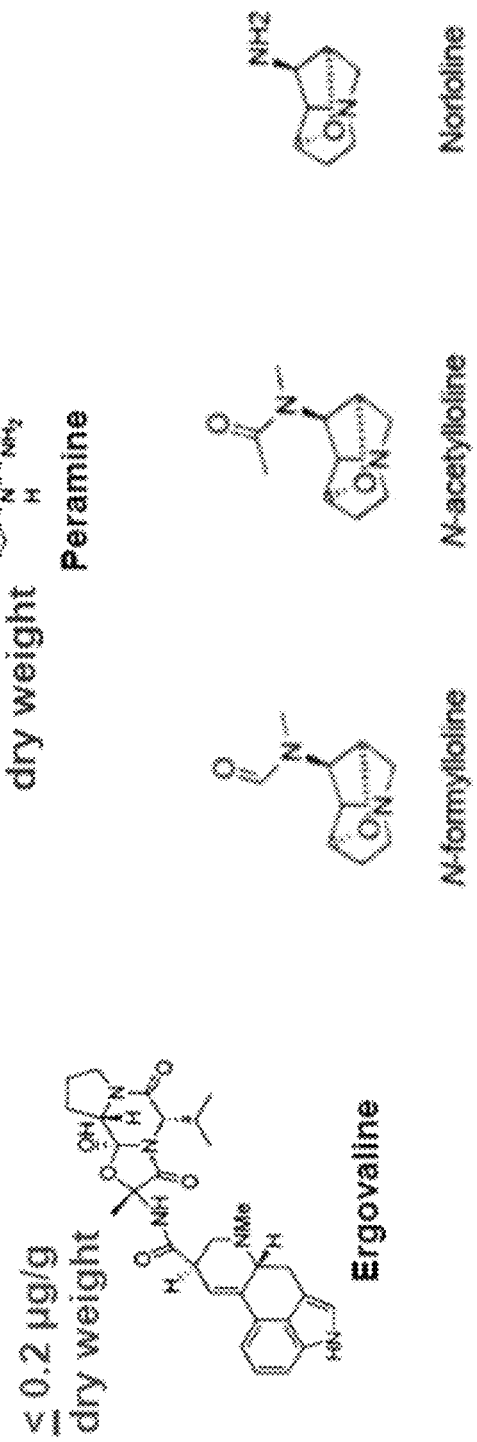
FIG. 37 shows a desired toxin profile of tall fescue endophytes.

The desired toxin profile of tall fescue endophytes is shown in FIG. 37.

Example 11

Metabolic Profiling

The experimental design used for semi-quantitative metabolic profile analysis of tall fescue-endophyte associations for the detection of alkaloid production in the endogenous host background is described below.

Experimental Design for Semi-Quantitative Analysis of Metabolites

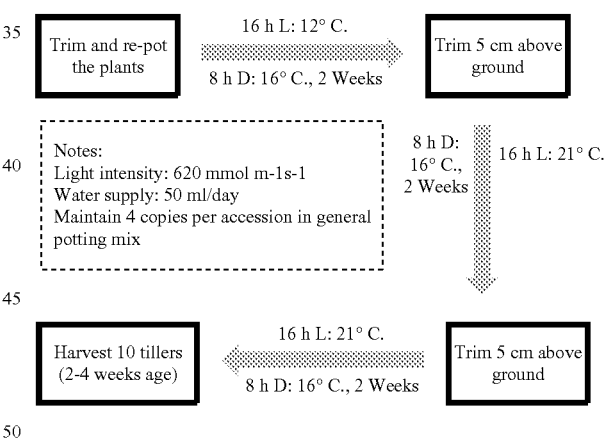

Figure 38:
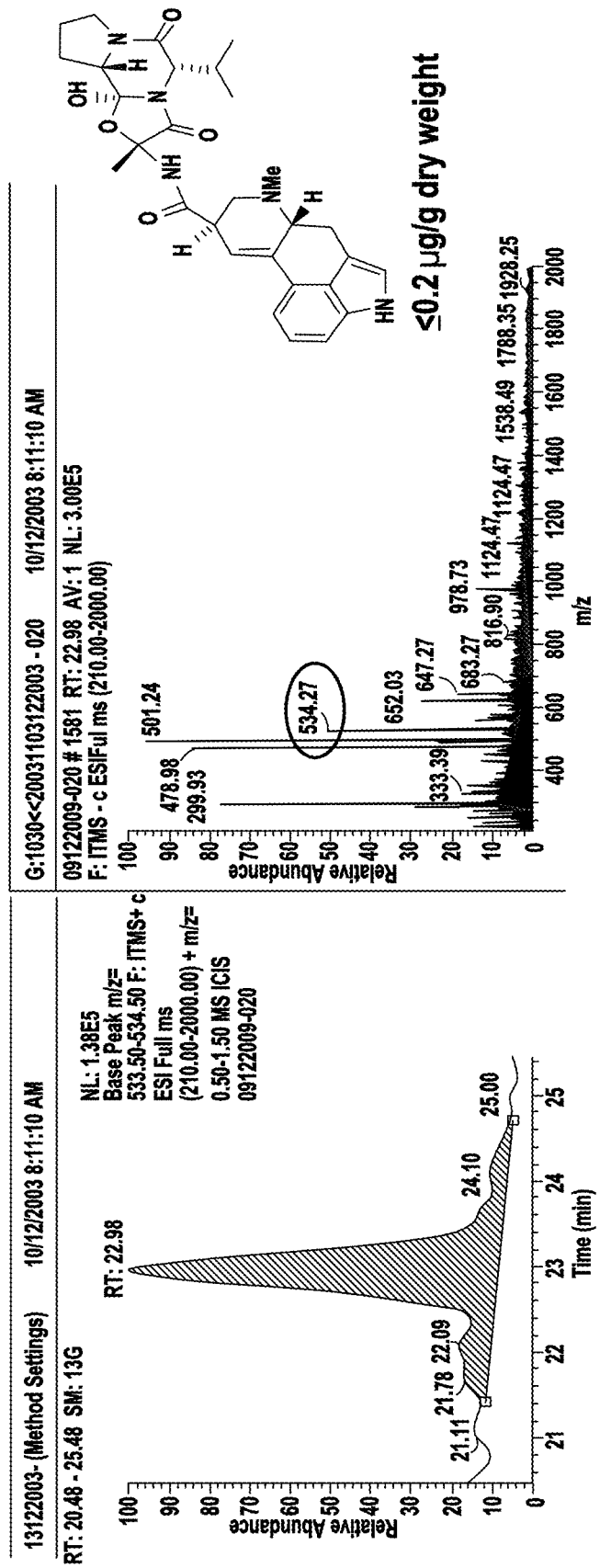
FIG. 38 shows a metabolic profile analysis.
Figure 38:
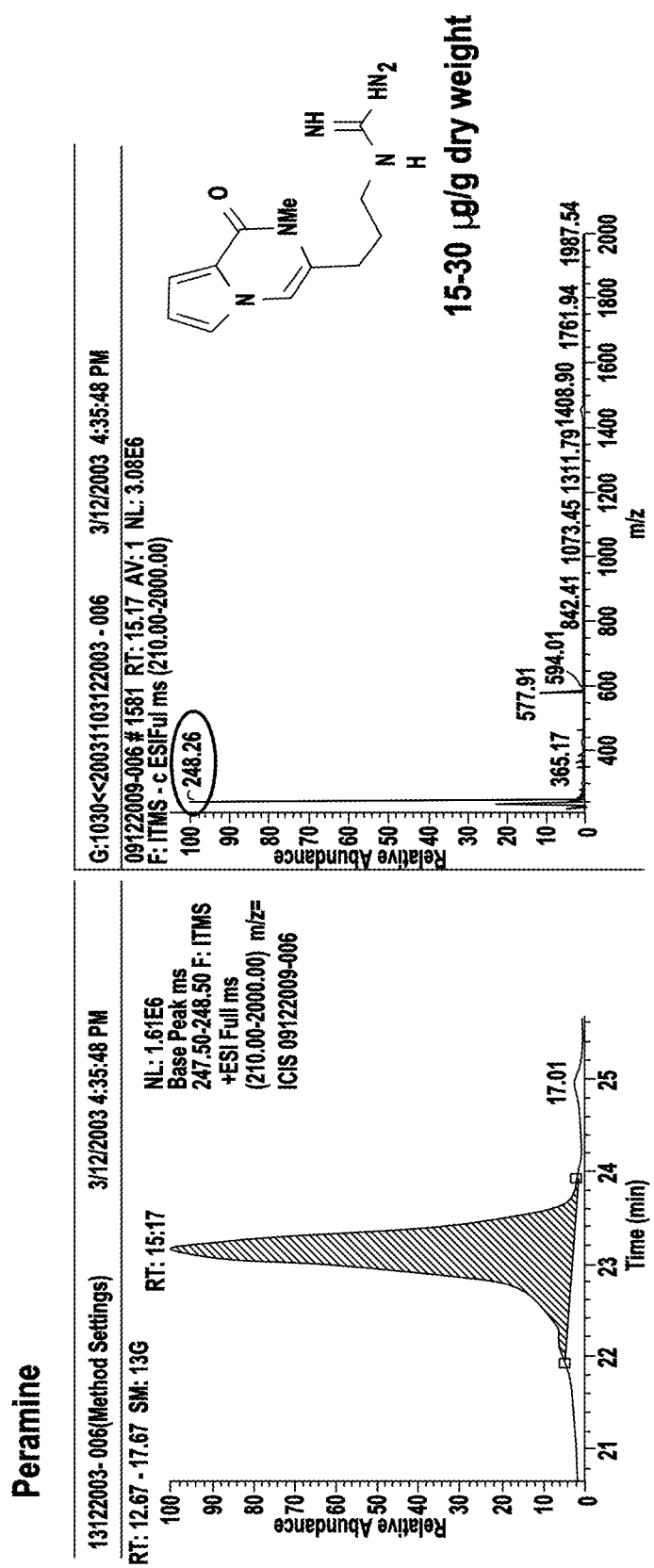

A metabolic profile analysis for detection of ergovaline and peramine is shown in FIG. 38.

Figure 39:
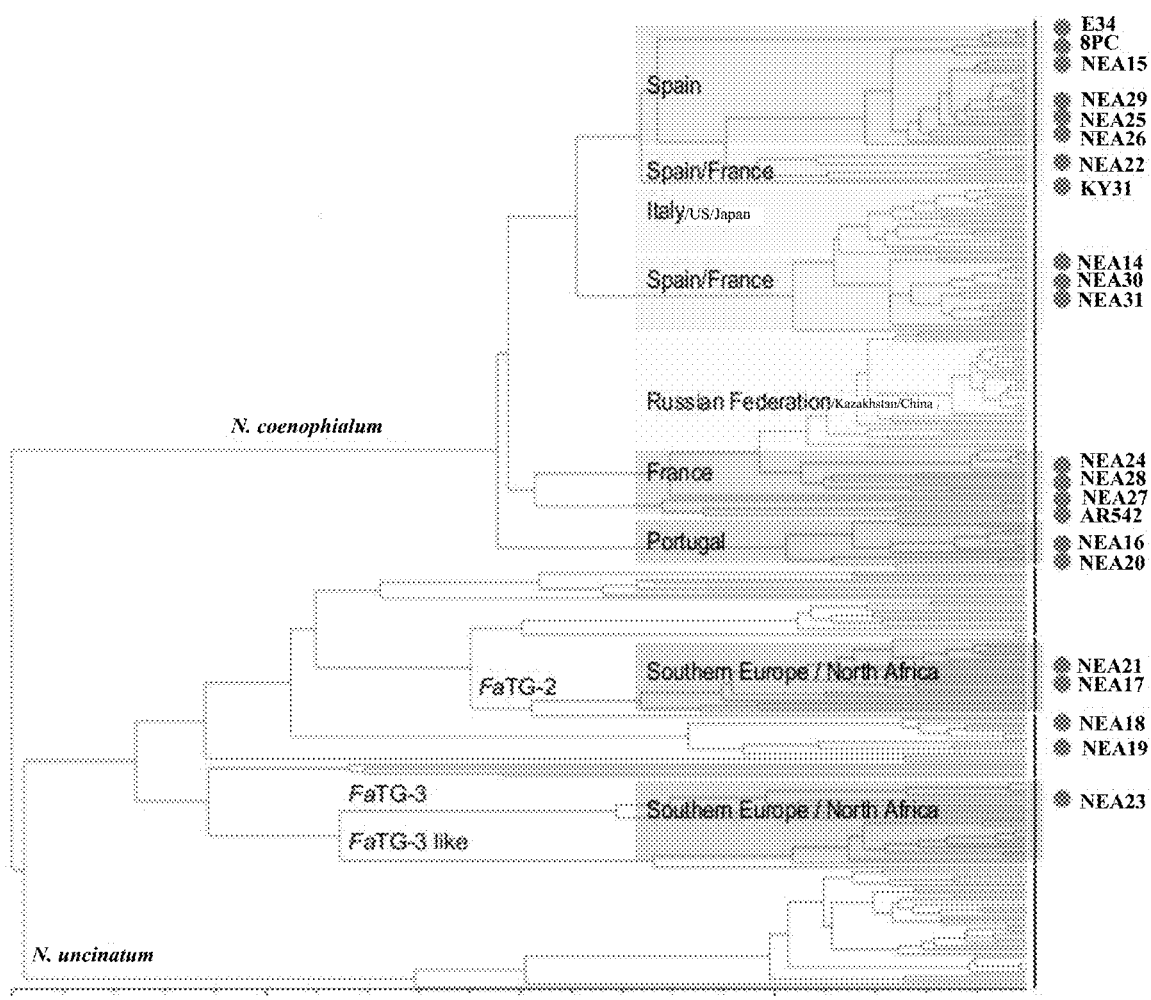
FIG. 39 shows endophytes selected for semi-quantitative analysis of metabolites.

Endophytes selected for semi-quantitative analysis of metabolites are shown in FIG. 39.

Figure 40:
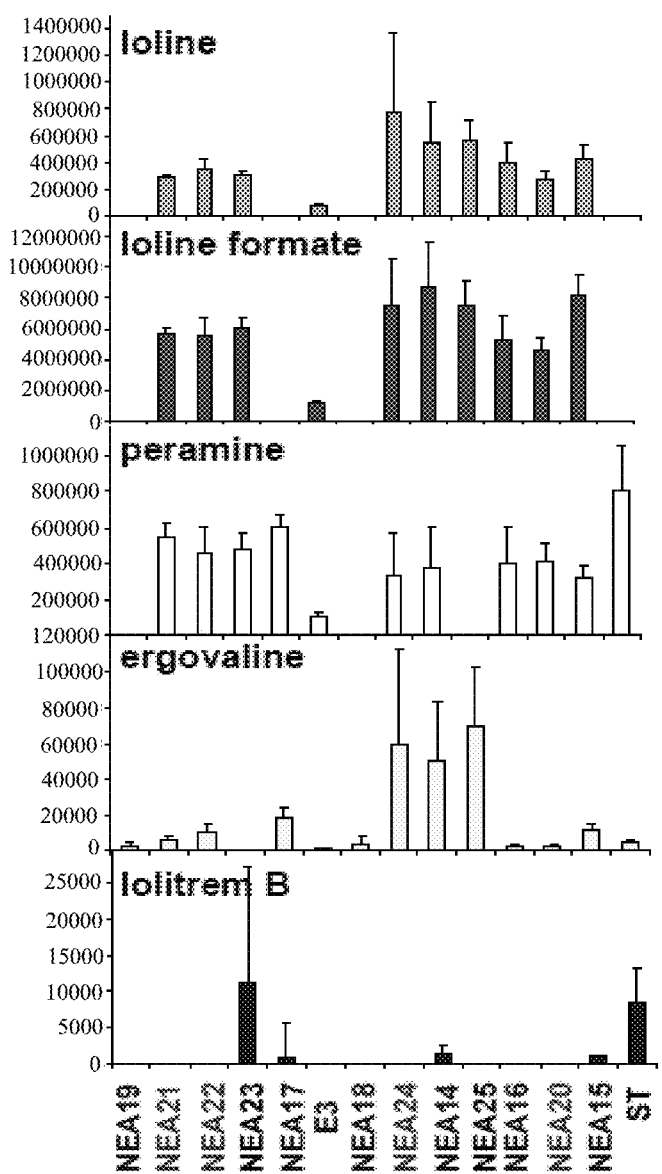
FIGS. 40 and 41 show metabolomics analyses of fescue endophytes.

Metabolic Profile Analysis for the Detection of Alkaloid Production of Different Fescue Endophytes A metabolic analysis of tall fescue-endophyte associations for the detection of alkaloid production including loline, loline formate, peramine, ergovaline and lolitrem B in the endogenous host background is shown in FIG. 40. The alkaloid profile (i.e. lolines, peramine, ergovaline and lolitrem B) of tall fescue-endophyte associations in the endogenous host background for a range of endophyte strains belonging to different endophyte species is shown in Table 23.

TABLE 23

Alkaloid profile (i.e. lolines, peramine, ergovaline and lolitrem B) of tall fescue-endophyte associations in the endogenous host background for a range of endophyte strains belonging to different endophyte species

| Tall fescue accession details | | | Alkaloid profile | | | |
|---|---|---|---|---|---|---|
| Tall fescue accession | Endophyte strain | Endophyte species | Lolines | Peramine | Ergovaline* | Lolitrem B |
| BE9301 | E34 | *N. coenophialum* | + | + | +$^L$ | − |
| 8PC | NEA13 | *N. coenophialum* | n.d | + | + | n.d |
| FEtc7-180 | NEA14 | *N. coenophialum* | + | + | +$^H$ | − |
| FEtc7-58 | NEA15 | *N. coenophialum* | + | + | +$^M$ | − |
| FEtc7-342 | NEA16 | *N. coenophialum* | + | + | − | − |
| FEtc7-343 | NEA20 | *N. coenophialum* | + | + | − | − |
| 234746 | NEA22 | *N. coenophialum* | + | + | +$^M$ | − |
| FEtc6-83 | NEA24 | *N. coenophialum* | + | + | +$^H$ | − |
| FEtc7-289 | NEA25 | *N. coenophialum* | + | − | +$^H$ | − |
| FEtc6-68 | NEA26 | *N. coenophialum* | + | + | + | − |
| FEtc6-85 | NEA27 | *N. coenophialum* | n.d | + | + | n.d |
| FEtc6-87 | NEA28 | *N. coenophialum* | n.d | + | + | n.d |
| FEtc7-127 | NEA29 | *N. coenophialum* | + | + | + | − |
| FEtc6-128 | NEA30 | *N. coenophialum* | + | + | + | − |
| FEtc6-129 | NEA31 | *N. coenophialum* | + | + | + | − |
| 287819 | NEA17 | FaTG-2 | − | + | +$^M$ | |
| 231557 | NEA21 | FaTG-2 | + | + | − | − |
| 269850 | NEA23 | FaTG-3 | + | + | − | − |
| 231553 | NEA19 | Out group 1 | − | − | − | − |
| FEtc6-75 | NEA18 | Out group 1 | − | − | − | − |
| ST | ST | *N. lorii* | − | + | + | + |
| AR542* | AR542 | *N. coenophialum* | + | + | − | − |
| KY31* | KY31 | *N. coenophialum* | + | + | + | − |
| E77* | E77 | *N. coenophialum* | + | + | + | − |

(*Published data; nd = not determined).

Figure 41:
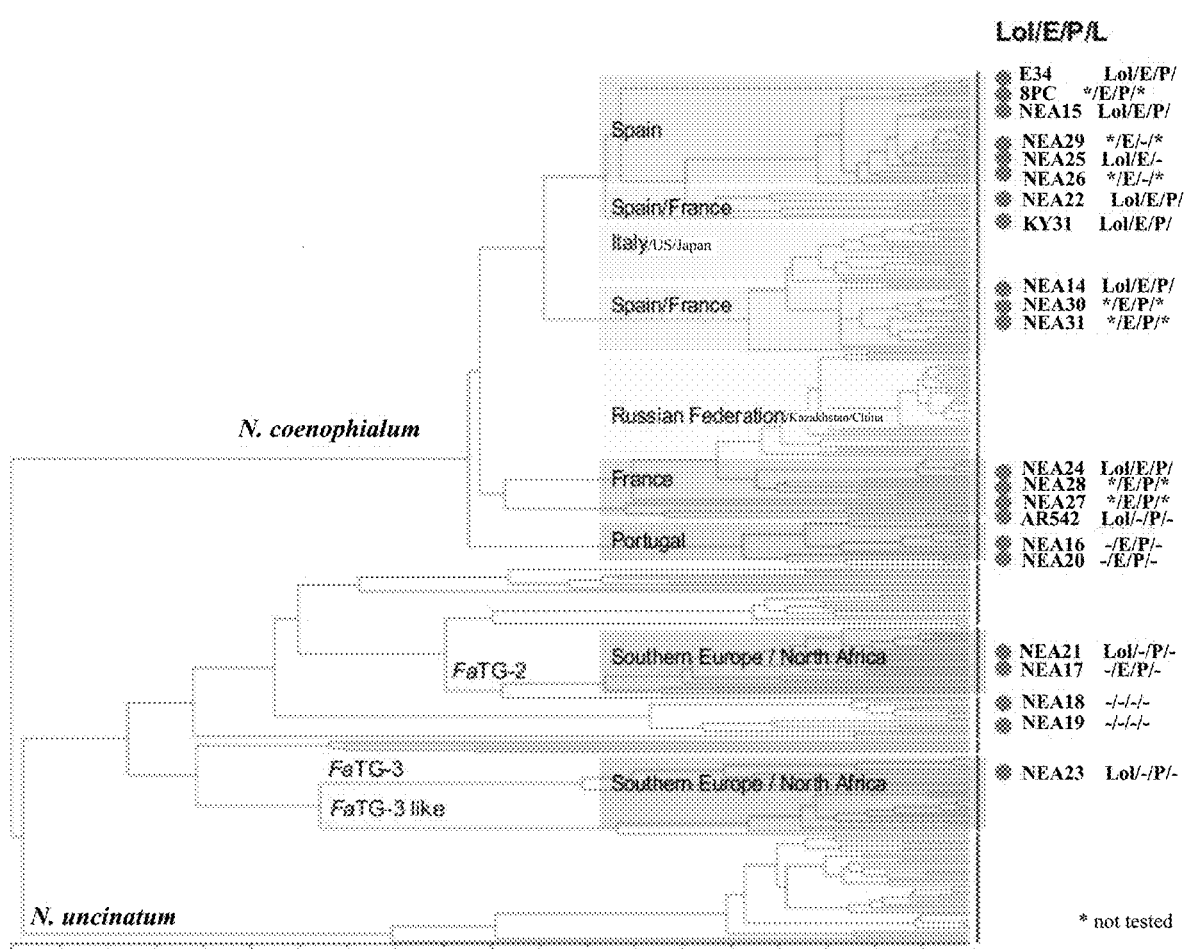

Further metabolic analysis of the fescue endophytes is shown in FIG. 41.

Example 12

Semi-Quantitative Analysis of Metabolic Profile Under Temperature/Water Stress In addition to the metabolic analysis of tall fescue-endophyte associations grown under standard conditions, for the detection of alkaloid production conferred by the endopohytes in the endogenous host background (FIGS. 38-41), a semi-quantitative analysis of metabolic profiles of tall fescue-endophyte associations grown under high temperature and water stress conditions was undertaken. Corresponding tall fescue-endophyte associations were grown under 16 h Light and 30° C.; 18 h Dark and 20° C., and then sampled for alkaloid profile analysis as described below:

Harvest (control)→freeze dry→50 mg pseudostem material→80% methanol extraction→LCMS analysis
Recovery and water stress
Second harvest (stress)→freeze dry→SSR confirm all of the plant material again.

This was performed in a controlled (growth chamber) environment simulating summer conditions, with light watering as required. Nine copies per accession were planted in general potting mix. A Randomized Complete Block with subsampling was used.

Figure 42:
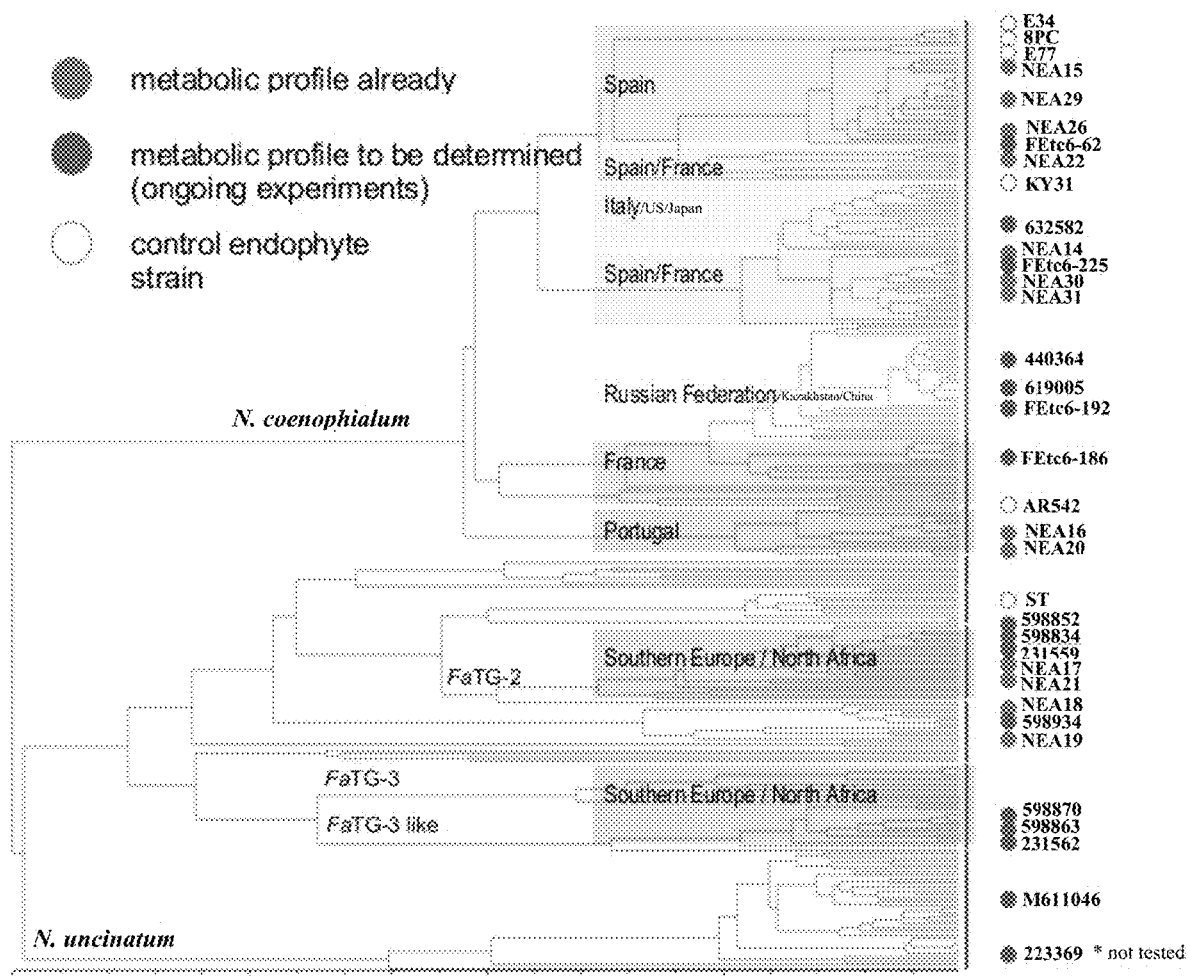
FIG. 42 shows a semi-quantitative analysis of metabolic profile under temperature/water stress.

FIG. 42 shows a semi-quantitative analysis of metabolic profile of tall fescue-endophyte associations grown under high temperature and water stress conditions.

Example 13

In Planta Isogenic Inoculation in Tall Fescue with Novel Endophytes

Summary:
A total of 36 fescue endophytes have been isolated from a range of fescue accessions from different geographic origin as described in Table 24, and found to belong to different taxa as follows: 19 of them being *N. coenophialum*; 5 of them being FaTG-2; 3 of them being Outgroup; 3 of them being FaTG-3; 3 of them being FaTG-3 like; and 3 of them being *N. uncinatum*

TABLE 24

Isolation of fungal endophyte cultures from endophyte-containing fescue accessions
Establishment of Meristem Cultures for Diverse Host Panel for In Planta Inoculation of Fescue Endophytes

| | Fescue Accession | Endophyte Strain | Origin | Cluster | Taxon |
|---|---|---|---|---|---|
| 1 | 8PC | 8PC | | C01.1 | N. coenophialum |
| 2 | BE9301 | E34 | | C01.1 | N. coenophialum |
| 3 | E77 | E77 | | C01.2 | N. coenophialum |
| 4 | FEtc6-62 | | Catalunya (Spain) 4 | C01.2 | N. coenophialum |
| 5 | FEtc6-68 | NEA26 | Catalunya (Spain) 14 | C01.2 | N. coenophialum |
| 6 | FEtc7-127 | NEA29 | Aragon (Spain)14 | C01.2 | N. coenophialum |
| 7 | FEtc7-289 | NEA25 | Aragon (Spain)14 | C01.2 | N. coenophialum |
| 8 | FEtc7-58 | NEA15 | Aragon (Spain) 1 | C01.2 | N. coenophialum |
| 9 | 234746 | NEA22 | Spain | C01.2 | N. coenophialum |
| 10 | 632582 | | Italy | C02.1 | N. coenophialum |
| 11 | Kentucky 31 | KY31 | | C02.1 | N. coenophialum |
| 12 | FEtc6-128 | NEA30 | Pyrenees13 | C02.2 | N. coenophialum |
| 13 | FEtc6-129 | NEA31 | Pyrenees17 | C02.2 | N. coenophialum |
| 14 | FEtc7-180 | NEA14 | PaySardegna (Basque (Fran | C02.2 | N. coenophialum |
| 15 | 440364 | | Kazakhstan | C03 | N. coenophialum |
| 16 | 619005 | | China | C03 | N. coenophialum |
| 17 | FEtc6-83 | NEA24 | Corsica (France)7 | C04 | N. coenophialum |
| 18 | FEtc6-85 | NEA27 | Corsica (France) 15 | C04 | N. coenophialum |
| 19 | FEtc6-87 | NEA28 | Corsica (France) 17 | C04 | N. coenophialum |
| 20 | AR542 | AR542 | Morocco | C05 | N. coenophialum |
| 21 | FEtc7-342 | NEA16 | Gaurda (Portugal) | C06 | N. coenophialum |
| 22 | FEtc7-343 | NEA20 | Gaurda (Portugal) | C06 | N. coenophialum |
| 23 | 231557 | NEA21 | Morocco | C09 | FaTG-2 |
| 24 | 287819 | NEA17 | Spain | C09 | FaTG-2 |
| 25 | 598834 | | Morocco | C09 | FaTG-2 |
| 26 | 231559 | | Morocco | C09 | FaTG-2 |
| 27 | 598852 | | Morocco | C09 | FaTG-2 |
| 28 | 598934 | | Italy | C10 | Outgroup |
| 29 | 231553 | NEA19 | Algeria | C10 | Outgroup |
| 30 | FEtc6-75 | NEA18 | Sardegna (NW Italy) 5 | C10 | Outgroup |
| 31 | 269850 | NEA23 | Tunisia | C12 | FaTG-3 |
| 32 | 610918 | | Tunisia | C12 | FaTG-3 |
| 33 | 610919 | | Tunisia | C12 | FaTG-3 |
| 34 | 598829 | | Morocco | C13 | FaTG-3 like |
| 35 | 598863 | | Morocco | C13 | FaTG-3 like |
| 36 | 598870 | | Morocco | C13 | FaTG-3 like |
| 37 | M311046 | | Russion Federation | C14 | N. uncinatum |
| 38 | M595026 | | United Kingdom | C14 | N. uncinatum |
| 39 | M611046 | | Russion Federation | C14 | N. uncinatum |

Table 25 shows selected tall fescue and perennial ryegrass cultivars used to identify representative plant genotypes included in the diverse host panel for in planta inoculation of fescue endophytes. All the selected plant genotypes have a high regeneration frequency of >80%.

TABLE 25

Selected tall fescue and perennial ryegrass cultivars used to identify representative plant genotypes included in the diverse host panel for in planta inoculation of fescue endophytes

| Cultivar | Genotype code | Species | Characteristics |
|---|---|---|---|
| Bariane | BARI 27 | L. arundinaceum | Soft leaved, later maturing, highly palatable |
| Dovey | DOV 24 | L. arundinaceum | High yielding, fast establishing |
| Quantum | QUAN 17 | L. arundinaceum | Soft leaved with improved rust resistance |
| Jesup | JES 01 | L. arundinaceum | Cool season perennial forage |
| Bronsyn | BRO 08 | L. perenne | Standard perennial ryegrass forage type |

Figure 43:
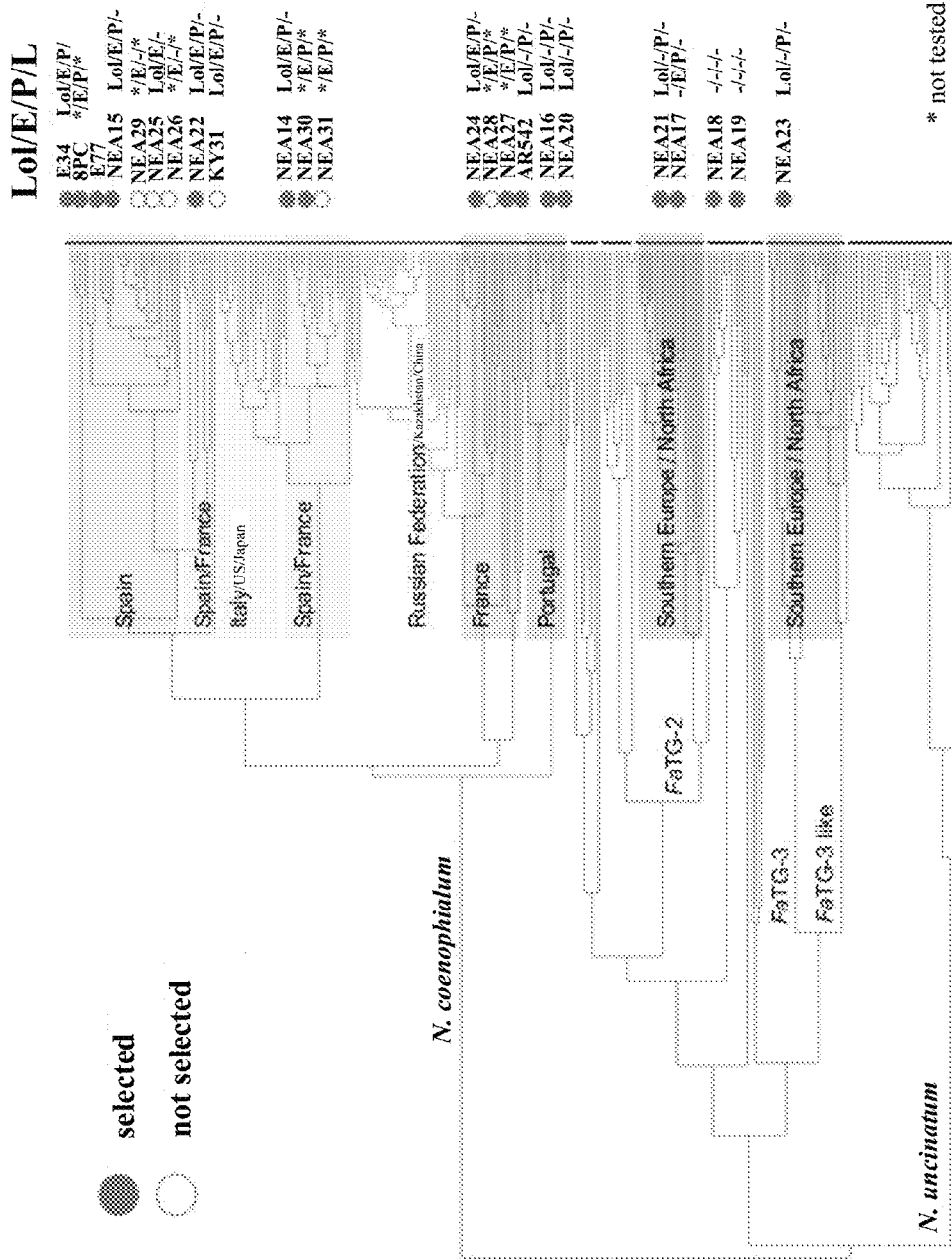
FIG. 43 shows endophytes selected for isogenic inoculation.
Figure 44:
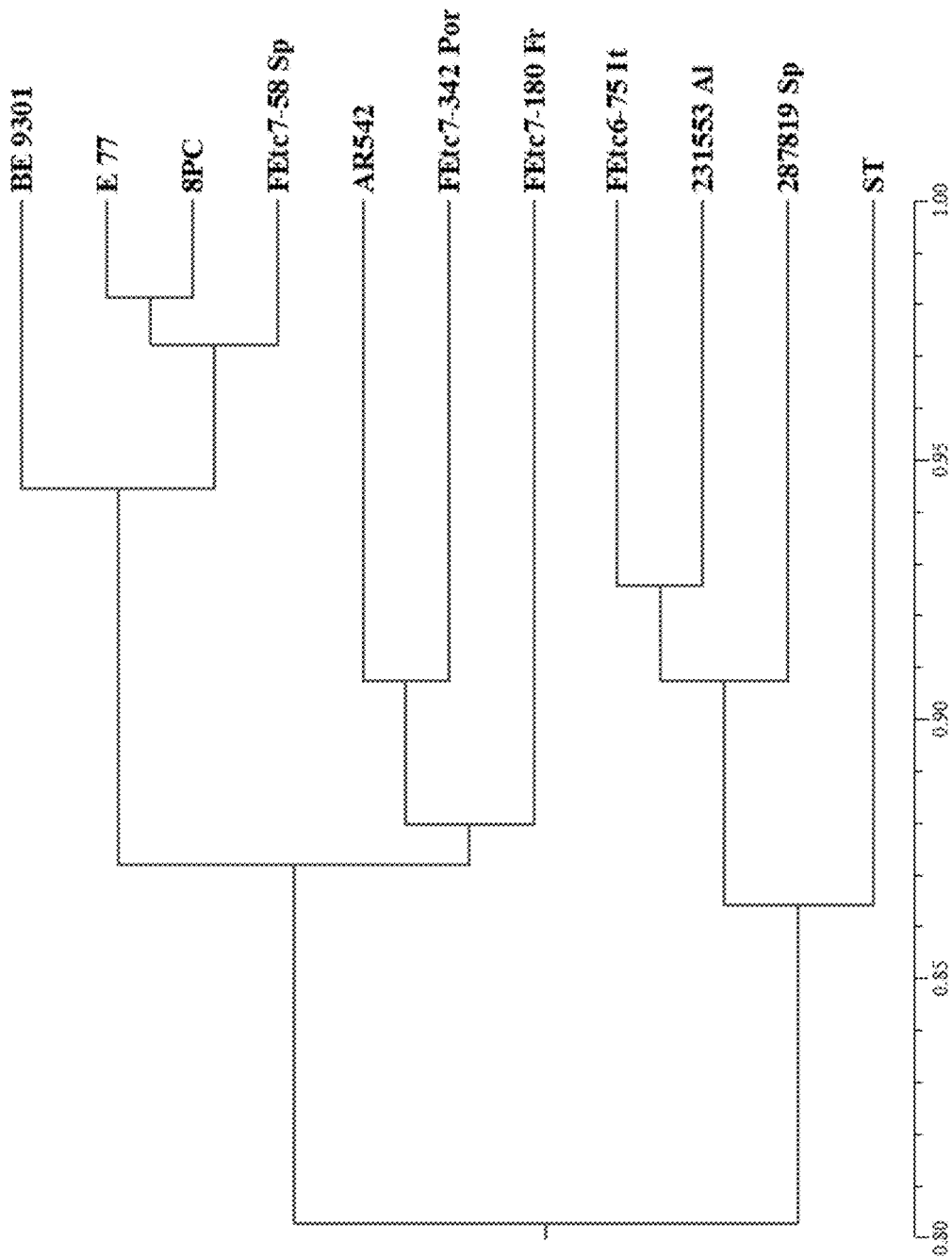
FIG. 44 shows SSR-based genotyping of isolated endophytes cultures prior to isogenic inoculation.

Isolated fungal endophytes from endophyte-containing fescue accessions selected for in planta isogenic inoculation into the diverse host panel are shown in FIG. 43. FIG. 44 shows SSR-based genotyping of isolated endophyte cultures prior to in planta isogenic inoculation to confirm their identity.

Results from the SSR genotyping indicating the allele number and sizes for different SSR markers for the different fescue endophyte strains are shown in Table 26.

TABLE 26

Presence of alleles in endophyte strains

| Endophyte Strain ID | Tall Fescue Accession ID | NCESTA1DH04 (FAM) | | | NLESTA1TA10 (FAM) | | | NCESTA1HA02 (HEX) | | | NCESTA1CC10 (HEX) | | |
|---|---|---|---|---|---|---|---|---|---|---|---|---|---|
| | | Allele 1 | Allele 2 | Allele 3 | Allele 1 | Allele 2 | Allele 3 | Allele 1 | Allele 2 | Allele 3 | Allele 1 | Allele 2 | Allele 3 |
| AR542 | — | 212 | 218 | 227 | 165 | 175 | | 322 | 327 | 330 | 198 | 201 | 211 |
| E34 | BE_9301 | 212 | 218 | 224 | 165 | 175 | | 322 | 329 | 330 | 198 | 201 | 211 |
| E77 | — | 212 | 218 | 224 | 165 | 175 | | 308 | 322 | 330 | 197 | 201 | 211 |
| NEA13 | 8PC | 212 | 218 | 224 | 165 | 175 | | 322 | 330 | | 197 | 200 | 210 |
| NEA14 | FEtc7-180 | 215 | 218 | 229 | 165 | 175 | | 322 | 329 | 330 | 198 | 201 | |
| NEA15 | FEtc7-58 | 212 | 218 | 224 | 165 | 175 | | 322 | 329 | 330 | 197 | 201 | 211 |
| NEA16 | FEtc7-342 | 215 | 227 | | 165 | 175 | | 309 | 322 | 330 | 198 | 201 | 211 |
| NEA17 | 287819 | 215 | 221 | 227 | 171 | 175 | | 322 | | | 201 | 203 | |
| NEA18 | FEtc6-75 | 218 | 227 | | 171 | 175 | | 304 | 322 | | 201 | | |
| NEA19 | 231553 | 221 | 227 | | 171 | 175 | | 304 | 325 | | 201 | | |

Results from the in planta isogenic inoculation into the diverse host panel of selected isolated fungal endophytes from endophyte-containing fescue accessions are shown in Table 27. Data on number of inoculations tested, number of successful inoculations and % of successful inoculations are provided in Table 6 to illustrate the inoculation ability of tall fescue endophytes in tall fescue and perennial ryegrass hosts.

different tall fescue and perennial host genotypes (i.e. BRO 08, BARI 27, DOV 24) was assessed, showing that:

Several tall fescue endophytes (e.g. NEA17, NEA18, NEA19) were stable in perennial ryegrass (BRO08).

BARI27 formed stable associations with all endophytes except for NEA15.

TABLE 27

Inoculation Ability of Tall Fescue Endophytes in Tall Fescue and Perennial Ryegrass Hosts

| | E77 E77 | E34 BE9301 | NEA13 8PC | NEA15 Fetc7-58 | NEA14 FEtc7-180 | AR542 AR542 | NEA16 FEtc7-342 | NEA17 287819 | NEA18 FEtc6-75 | NEA19 231553 | Total |
|---|---|---|---|---|---|---|---|---|---|---|---|
| A. Number of inoculations tested | | | | | | | | | | | |
| BARI 27 | 23 | 25 | 30 | 34 | 38 | 38 | 24 | 32 | 40 | 27 | 311 |
| BRO 08 | 39 | 31 | 24 | 27 | 35 | 36 | 30 | 33 | 48 | 22 | 325 |
| DOV 24 | 10 | 14 | NI | NI | NI | 17 | 8 | 18 | 14 | 16 | 97 |
| JESS 01 | 23 | 23 | 39 | 27 | 20 | 36 | 33 | 17 | 28 | 14 | 260 |
| QUAN 17 | 8 | 31 | 20 | 15 | 17 | 21 | 18 | 16 | 15 | 8 | 169 |
| Total | 103 | 124 | 113 | 103 | 110 | 148 | 113 | 116 | 145 | 87 | 1162 |
| B. Number of successful inoculations | | | | | | | | | | | |
| BARI 27 | 3 | 3 | 4 | 0 | 1 | 11 | 3 | 17 | 18 | 2 | 62 |
| BRO 08 | 0 | 0 | 2 | 0 | 2 | 0 | 0 | 4 | 2 | 5 | 15 |
| DOV 24 | 3 | 0 | NI | NI | NI | 1 | 0 | 1 | 4 | 0 | 9 |
| JESS 01 | 7 | 0 | 5 | 0 | 7 | 10 | 3 | 2 | 1 | 2 | 37 |
| QUAN 17 | 3 | 0 | 1 | 0 | 0 | 0 | 0 | 6 | 5 | 3 | 18 |
| Total | 16 | 3 | 12 | 0 | 10 | 22 | 6 | 30 | 30 | 12 | 141 |
| C. Percent of successful inoculations | | | | | | | | | | | |
| BARI 27 | 13.0 | 12.0 | 13.3 | 0.0 | 2.6 | 28.9 | 12.5 | 53.1 | 45.0 | 7.4 | 18.8 |
| BRO 08 | 0.0 | 0.0 | 8.3 | 0.0 | 5.7 | 0.0 | 0.0 | 12.1 | 4.2 | 22.7 | 5.3 |
| DOV 24 | 30.0 | 0.0 | NI | NI | NI | 5.9 | 0.0 | 5.6 | 28.6 | 0.0 | 10.0 |
| JESS 01 | 30.4 | 0.0 | 12.8 | 0.0 | 35.0 | 27.8 | 9.1 | 11.8 | 3.6 | 14.3 | 14.5 |
| QUAN 17 | 37.5 | 0.0 | 5.0 | 0.0 | 0.0 | 0.0 | 0.0 | 37.5 | 33.3 | 37.5 | 15.1 |
| Total | 22.2 | 2.4 | 9.9 | 0.0 | 10.8 | 12.5 | 4.3 | 24.0 | 22.9 | 16.4 | 12.7 |
| Cluster | 1 | 1 | 1 | 1 | 2 | 3 | 3 | 7 | 8 | 8 | |
| Species | | | N. coenophialum | | | | | FaTG-2 | Outgroup 1 | | |

NI Not inoculated

Example 14

Endophyte Vegetative Stability in Tall Fescue and Perennial Ryegrass Host Genotypes Following in planta isogenic inoculation with a range of selected isolated endophytes from fescue accessions, the endophyte vegetative stability of these endophytes in the NEA15 failed to form stable associations with any of host genotypes tested.

DOV24 formed few stable associations.

The stability of these associations of novel tall fescue endophytes inoculated in different tall fescue and perennial ryegrass genotypes from the diverse host panel was assessed 12 months post-inoculation. Corresponding results are shown in Table 28.

TABLE 28

Stability of associations of novel tall fescue endophytes (e.g. NEA13, NEA14, NEA15, NEA16, NEA17, etc.) inoculated in different tall fescue and perennial ryegrass genotypes (BARI 27, BRO 08, DOV 24, JESS 01 and QUAN 17) from the diverse host panel assessed 12 months post-inoculation.

| Plant Genotype | E77 E77 | E34 8E9301 | NEA13 8PC | NEA15 Fetc7-58 | NEA14 FEtc7-180 | AR542 AR542 | NEA16 FEtc7-342 | NEA17 287819 | NEA18 FEtc6-75 | NEA19 231553 |
|---|---|---|---|---|---|---|---|---|---|---|
| BARI 27 | 1/2 | 2/2 | 1/4 | NA | 1/1 | 7/7 | 1/1 | 1/2 | 8/10 | 1/1 |
| BRO 08 | NA | NA | 0/1 | NA | 0/2 | NA | NA | 5/5 | 2/2 | 3/5 |
| DOV 24 | 1/2 | NA | NI | NI | NI | 0/1 | NA | 2/2 | 2/4 | NA |
| JESS 01 | 5/5 | NA | 4/6 | NA | 5/6 | 5/10 | 2/3 | 0/1 | 0/1 | 3/3 |
| QUAN 17 | 2/3 | NA | 0/1 | NA | NA | NA | NA | 3/6 | 3/5 | 1/2 |

Figure 45:
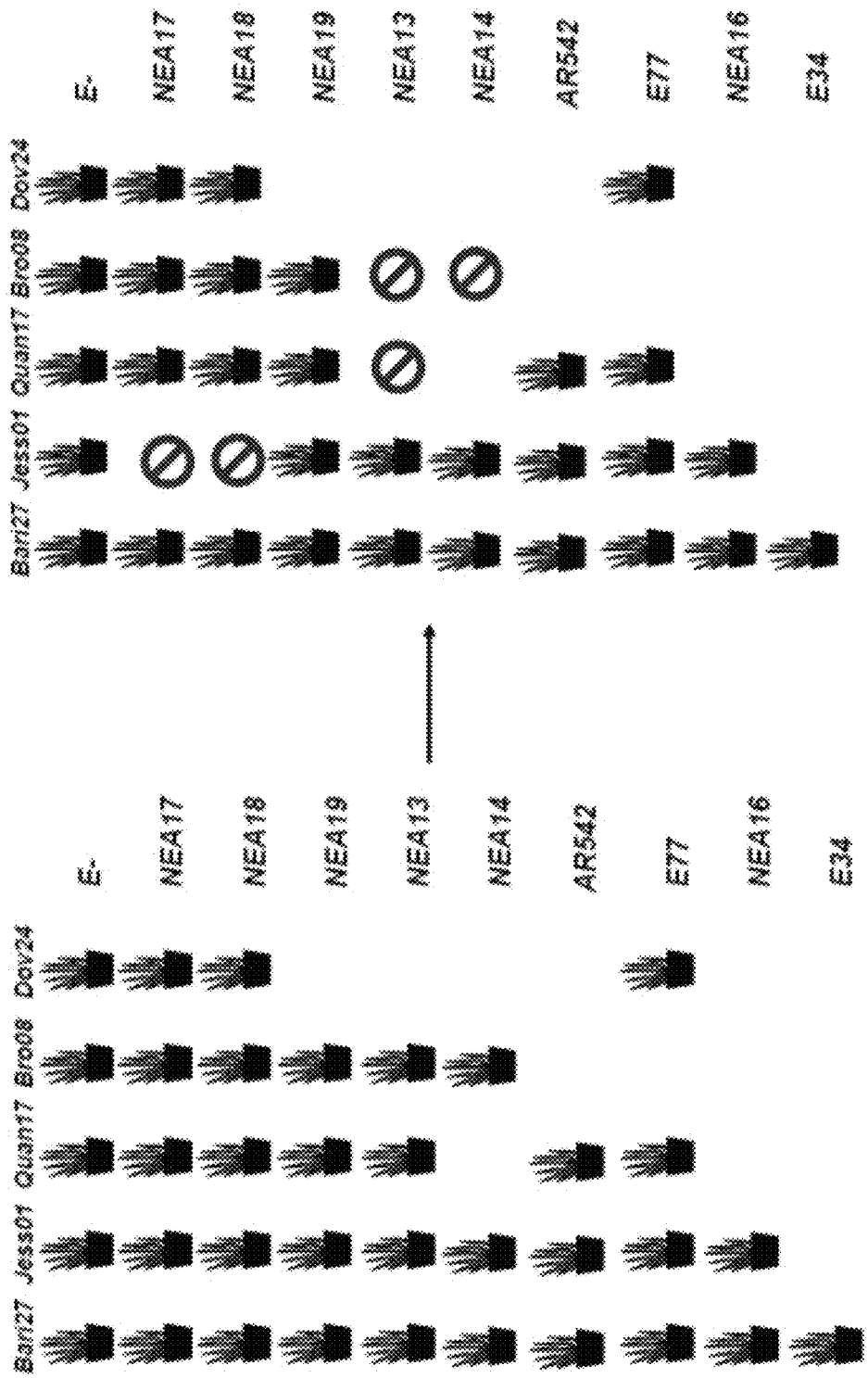
FIG. 45 shows endophyte vegetative stability in tall fescue and perennial ryegrass host genotypes (stability at 12 months post inoculation).

NA—not applicable,
NI—not inoculated,
number of stable association/number of associations FIG. 45 shows stability at 12 months post inoculation of selected endophytes in tall fescue and perennial ryegrass host genotypes from the diverse host panel.

Figure 46:
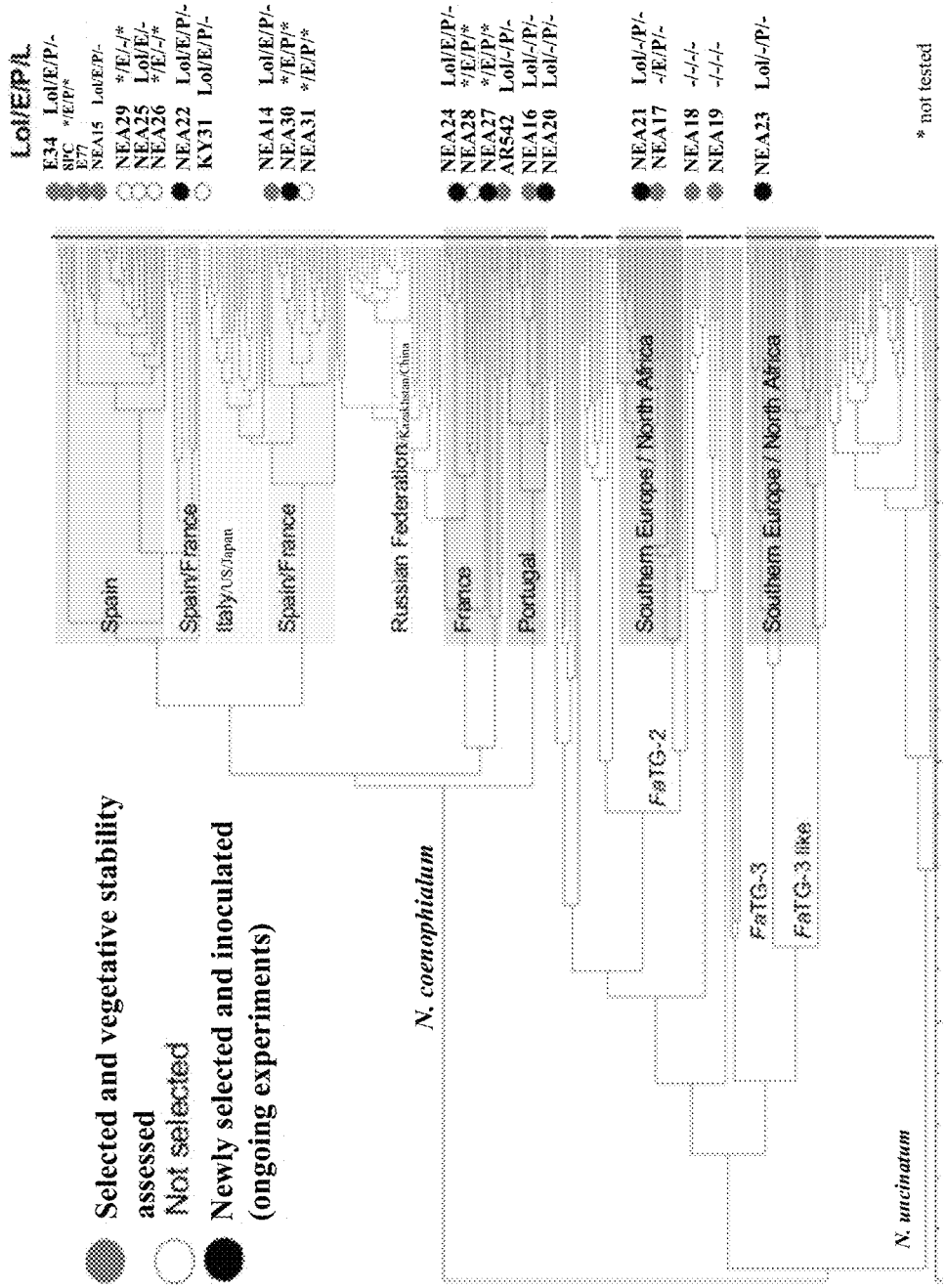
FIG. 46 shows endophytes selected for isogenic inoculation.

The range of novel fescue endophytes selected for in planta isogenic inoculation is shown in FIG. 46.

Table 29 shows additional novel tall fescue endophytes (e.g. NEA20, NEA21, NEA22, etc.) selected for in planta isogenic inoculations in tall fescue genotypes (i.e. BARI 27, JESS 01 and QUAN 17) from the diverse host panel, based on the following selection criteria:
1. Produce little or no ergovaline
2. Produce no lolitrem B
3. Produce lolines and/or peramine

TABLE 29

Additional novel tall fescue endophytes (e.g. NEA20, NEA21, NEA22, etc.) selected for in planta isogenic inoculations in tall fescue genotypes (i.e. BARI 27, JESS 01 and QUAN 17) from the diverse host panel.

| | NEA20 FEtc7-343 Nco Lol/-/ P/- | NEA21 231557 FaTG-3 Lol/-/ P/- | NEA22 234746 Nco Lol/E/ P/- | NEA23 269850 FaTG-3 Lol/-/ P/- | NEA24 FEtc6-83 Nco Lol/E/ P/- | NEA27 FEtc6-85 Nco ?/E/P/? | NEA30 FEtc6-128 Nco ?/E/P/? |
|---|---|---|---|---|---|---|---|
| BARI 27 | 28 | 30 | 30 | TBI | 30 | 25 | 30 |
| JESS 01 | 23 | 20 | 20 | TBI | 20 | 20 | 30 |
| QUAN 17 | 30 | 30 | 40 | TBI | 30 | 35 | 25 |

Nco = *N. coenophialum*;
? = alkaloid profile not tested;
TBI = To Be Inoculated.

Example 15

Figure 47:
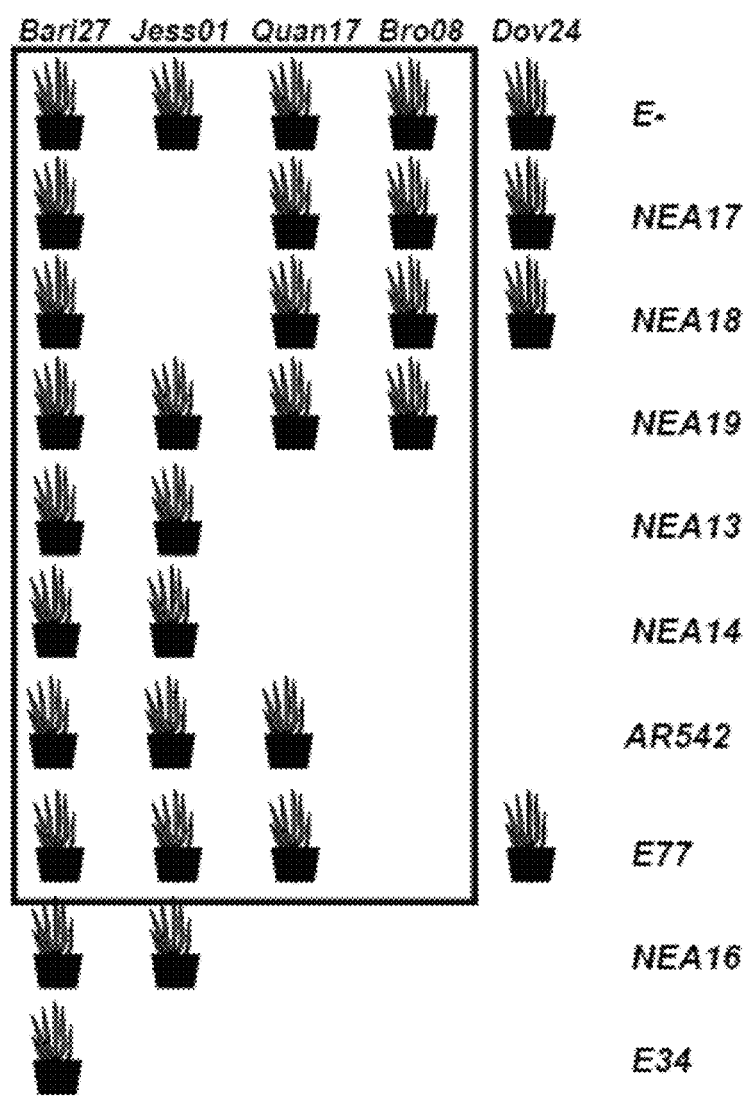
FIGS. 47-50 show metabolic profiling of isogenic tall fescue-endophyte associations.
Figure 49:
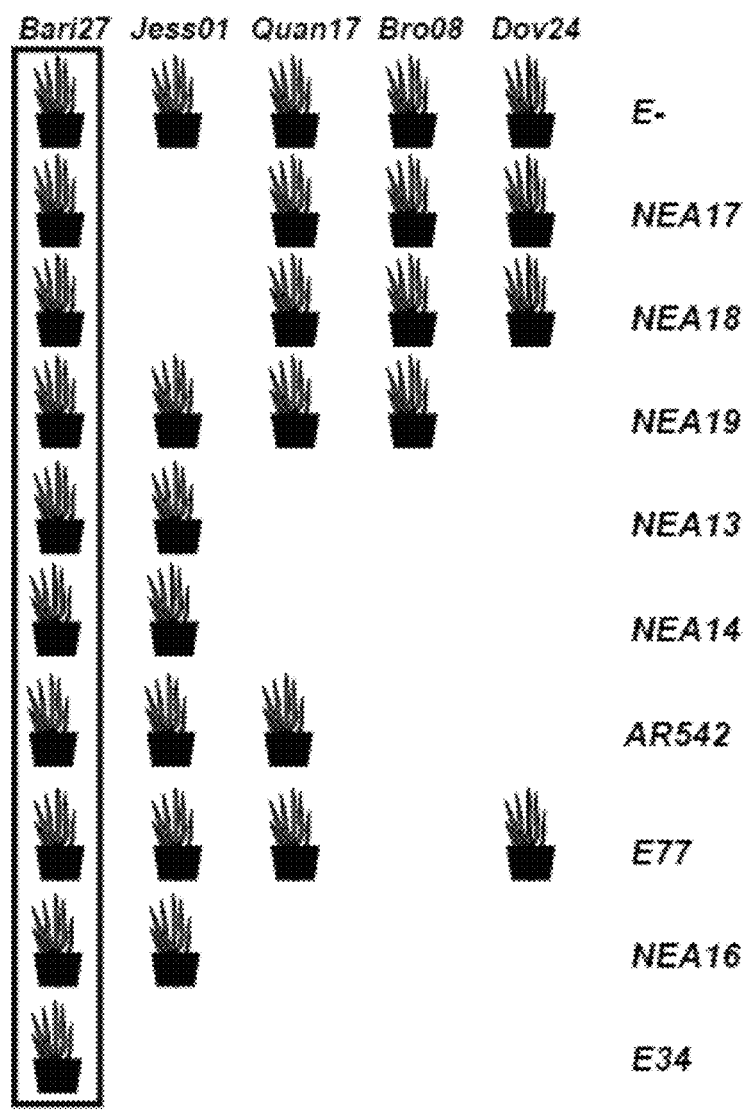
Figure 50:
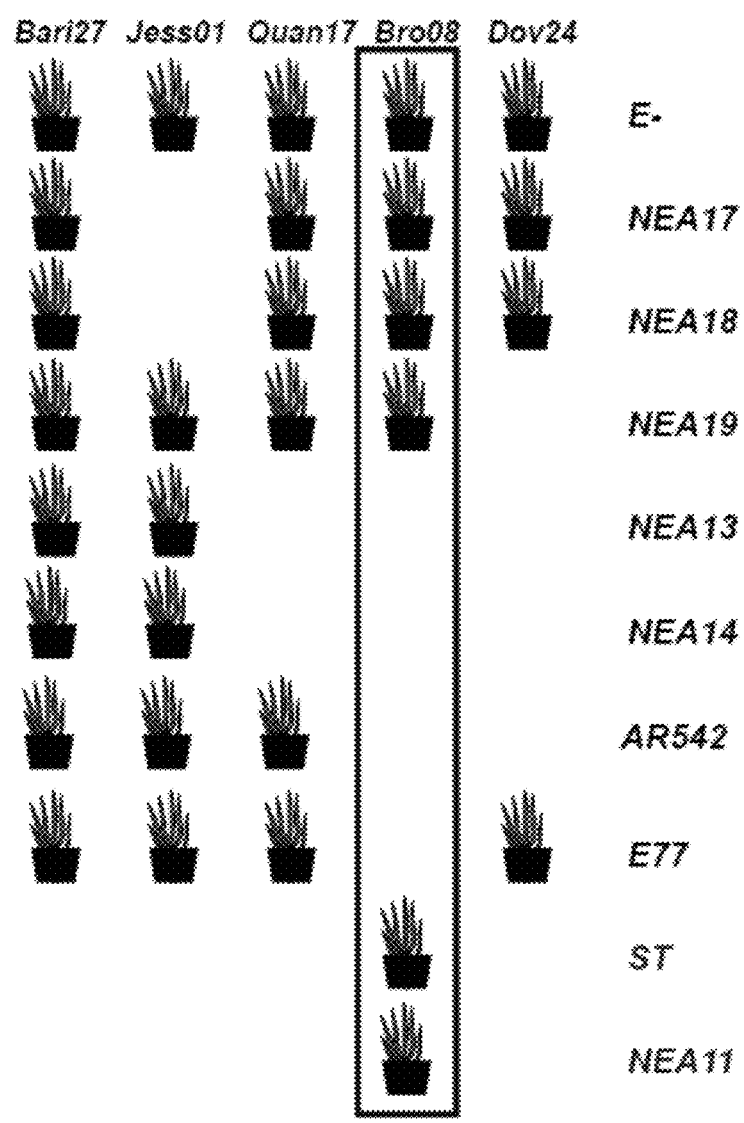

Metabolic Profiling of Endophyte-Tall Fescue Associations Established Following in Planta Isogenic Inoculations of Novel Tall Fescue Endophytes in Tall Fescue Genotypes from the Diverse Host Panel Metabolic profiling of endophyte-tall fescue associations established following in planta isogenic inoculations of novel tall fescue endophytes in tall fescue genotypes from the diverse host panel is shown in FIGS. 47, 49 and 50. These figures:
- Compare semi-quantitative alkaloid profiles of selected endophytes across different isogenic hosts
- Compare semi-quantitative alkaloid profiles for diverse endophytes in an isogenic host
- Compare semi-quantitative alkaloid profiles of tall fescue and perennial ryegrass endophytes in the perennial ryegrass genotype Bro08

Figure 48:
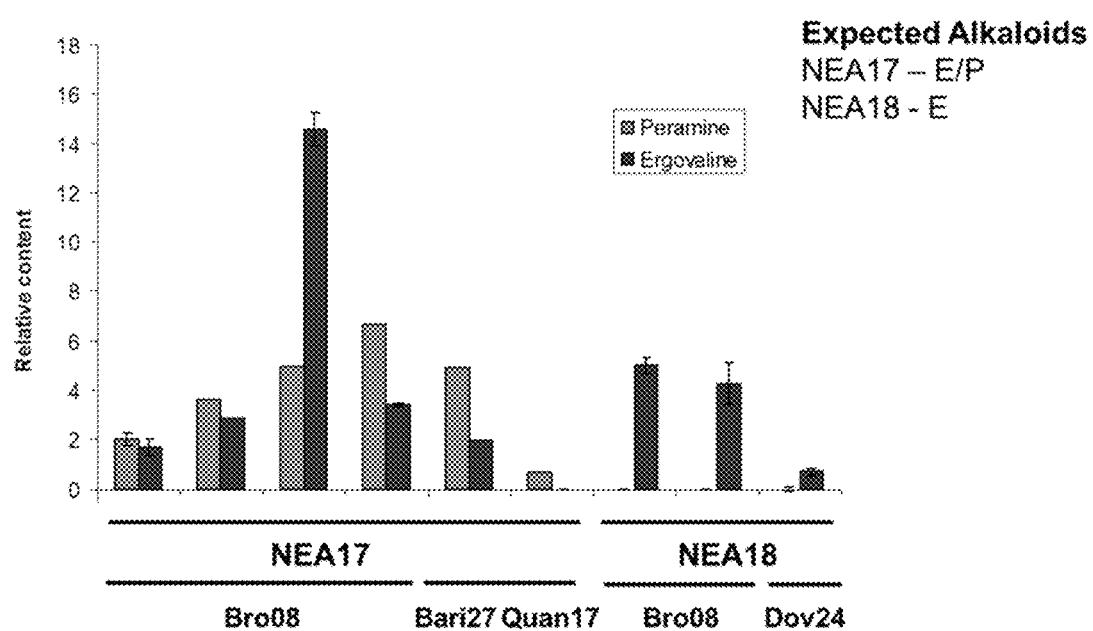

FIG. 48 shows the presence of peramine and ergovaline in endophyte-tall fescue associations established following in planta isogenic inoculations of novel tall fescue endophytes in tall fescue genotypes from the diverse host panel.

Table 30 shows metabolic profiling of endophyte-tall fescue associations established following in planta isogenic inoculations of novel tall fescue endophytes in tall fescue genotypes from the diverse host panel. Confirmed endophyte positive (E+) plants were split to 5 replicates and regularly trimmed to promote tillering. Four months later E+ plants were re-potted in 12 replicates. One month later E+ plants were re-potted if less than 9 positive copies were available at the time. Endophyte status was tested using SSR markers after each re-potting.

TABLE 30

Endophyte-tall fescue associations established following in planta isogenic inoculations of novel tall fescue endophytes in tall fescue genotypes from the diverse host panel used for metabolic profiling.

| | Endophyte genotype | | | | | | | | | | | |
|---|---|---|---|---|---|---|---|---|---|---|---|---|
| Host genotypes | NEA19 231553 | NEA17 287819 | 8PC | AR542 | E34 BE9301 | E77 | NEA18 FEtc6-75 | NEA14 Fetc7-180 | NEA16 Fetc7-342 | NEA15 Fetc7-58 | | |
| Bariane (Bari27) | 2/5 | 2/5 | 3/3 11/11 | 3/3 10/11 | 5/5 10/10 | 1/4 8/12 | NA 9/14 | 5/5 12/12 | 3/4 5/12 | 1/4 1/6 | 16/25 | |
| Dovey (DOV 24) | NA | 2/5 | 8/8 NA | NA | NA | NA | 3/5 6/12 | 3/5 3/12 | NA | NA | NA | |
| Jessup (Jess01) | 2/4 | 4/8 | NA | 3/3 12/12 | 4/4 12/12 | NA | 2/3 8/11 | NA | 2/4 7/19 | 2/3 12/12 | NA | |

TABLE 30-continued

Endophyte-tall fescue associations established following in planta isogenic inoculations of novel tall fescue endophytes in tall fescue genotypes from the diverse host panel used for metabolic profiling.

| Host genotypes | NEA19 231553 | NEA17 287819 | 8PC | AR542 | E34 BE9301 | E77 | NEA18 FEtc6-75 | NEA14 Fetc7-180 | NEA16 Fetc7-342 | NEA15 Fetc7-58 |
|---|---|---|---|---|---|---|---|---|---|---|
| Quantum (Quan17) | 2/5 | 8/7 | 4/5 | 12/12 | NA | NA | 4/5 12/12 | 2/4 5/12 | NA | NA | NA |
| Bronsyn (Bro08) | 9/9 | 10/11 | 5/5 | 11/12 | 1/9 0/8 | NA | NA | 3/4 7/7 | 0/5 | NA | NA |

A range of endophyte-tall fescue associations established following in planta isogenic inoculations of novel tall fescue endophytes in tall fescue genotypes from the diverse host panel were selected for metabolic profiling (Table 30). In total, 29 isogenic host-endophyte associations were subject to LCMS analysis, following the experimental design described below:

Experimental Design
  Trim and re-pot plants
  16 h Light, 30° C.; 18 h Dark, 20° C.
  Harvest (control)→freeze dry→50 mg pseudostem material→80% methanol extraction→LCMS analysis
  Recovery and water stress
  Second harvest (stressed)→freeze dry→50 mg pseudostem material→80% methanol extraction→LCMS analysis.

This was performed in a controlled (growth chamber) environment simulating summer conditions, with light watering as required. Nine copies per accession were planted in general potting mix. A Randomized Complete Block with subsampling was used.

Example 16

Bio-Protective Properties of Fescue Endophytes

Figure 51:
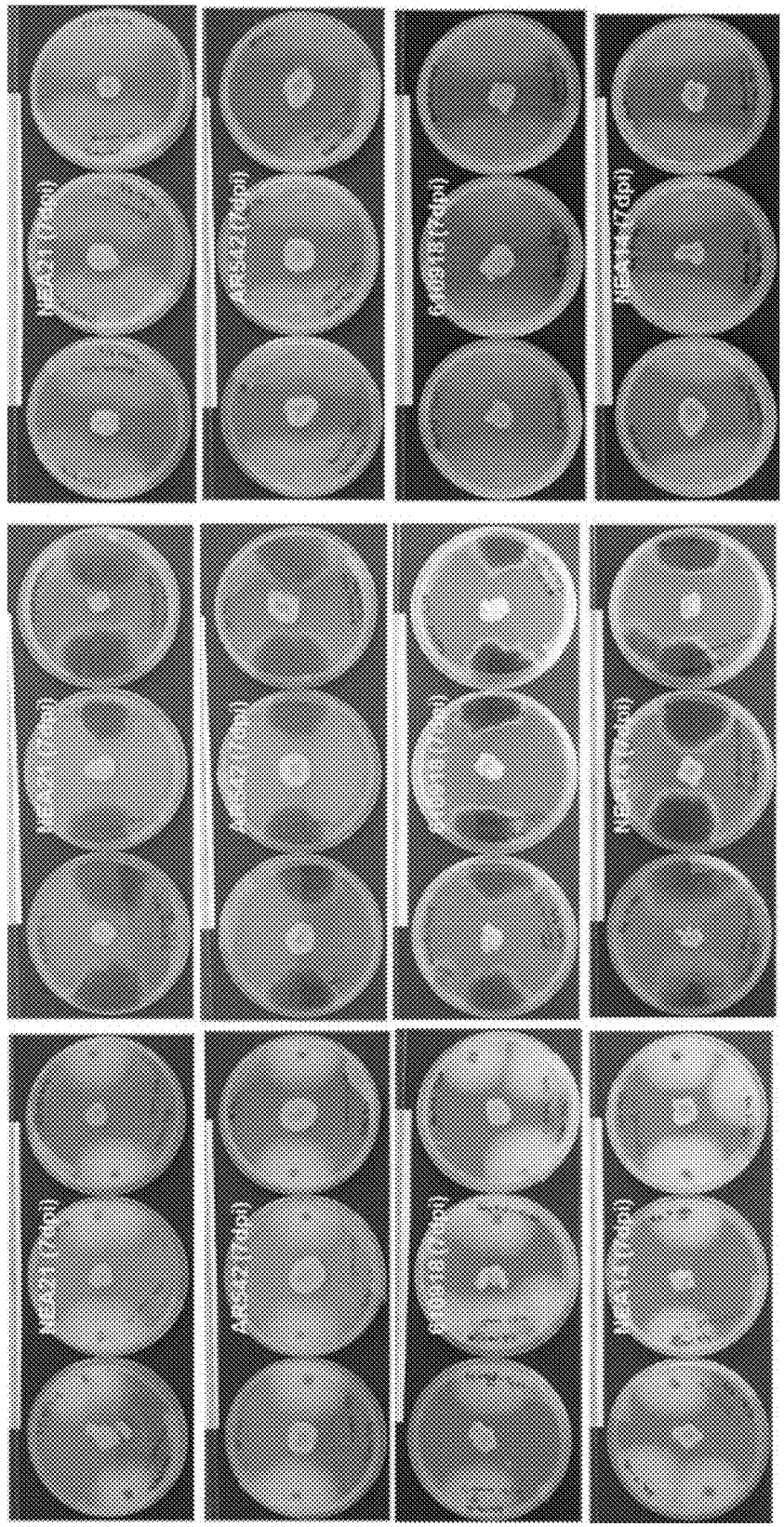
FIG. 51 shows anti-fungal bioassays of fescue endophytes. Column 1 *Colletotrichum graminicola*, Column 2 *Drechslera brizae*, Column 3 *Rhizoctonia cerealis*.

Three fungal pathogens (i.e. *Colletrotrichum graminicola, Drechslera brizae* and *Rhizoctonia cerealis*)—causing a range of fungal diseases and infecting a range of different plant hosts—were included in antifungal bioassays used to analyse the potential anti-fungal activities of isolated fescue endophytes. FIG. 51 shows results from anti-fungal bioassays of isolated fescue endophytes. Results of anti-fungal bioassays are also shown in Table 31. A range of endophytes were found to have high (H) and medium (M) antifungal activity (Table 31).

TABLE 31

Anti-fungal bioassays of isolated novel fescue endophytes

| Tall Fescue endophytes | | | Antifungal activity against | | |
|---|---|---|---|---|---|
| Strain ID | Accession | Taxon | Colletrotrichum graminicola | Drechslera brizae | Rhizoctonia cerealis |
| 1 440364 | | N. coenophialum | H | H | H |
| 2 AR542 | AR542 | N. coenophialum | M | H | H |
| 3 E34 | BE9301 | N. coenophialum | M | M | H |
| 4 NEA13 | 8PC | N. coenophialum | M | H | H |
| 5 NEA14 | FEtc7-180 | N. coenophialum | M | M | H |
| 6 NEA15 | FEtc7-58 | N. coenophialum | M | H | H |
| 7 NEA16 | FEtc7-342 | N. coenophialum | M | H | H |
| 8 NEA22 | 234746 | N. coenophialum | H | M | M |
| 9 NEA27 | FEtc6-85 | N. coenophialum | L | M | L |
| 10 NEA30 | FEtc6-128 | N. coenophialum | M | H | H |
| 11 E1 | | Non-N. lolii | L | L | M |
| 12 NEA18 | FEtc6-75 | Outgroup 1 | M | H | H |
| 13 598852 | | FaTG-2 | M | H | H |
| 14 610918 | | FaTG-3 | M | H | H |
| 15 NEA21 | 231557 | FaTG-3 | M | H | M |
| 16 598829 | | FaTG-3 like | M | L | M |

Antifungal activity: Low, Medium, High

Example 17

Genome Survey Sequencing of Novel Tall Fescue Endophytes

A range of novel tall fescue endophtyes were subjected to genome survey sequencing (GSS).

Figure 52:
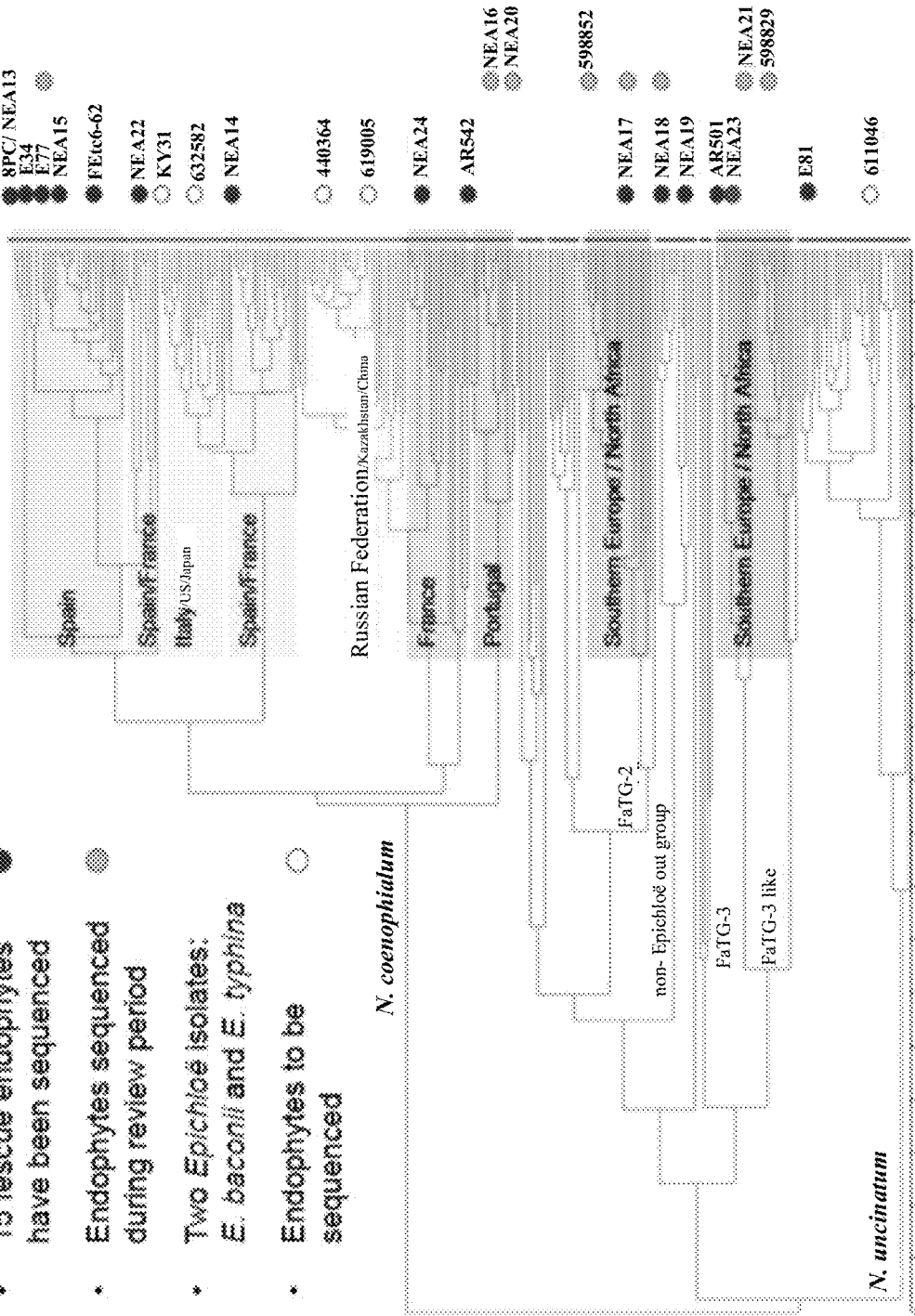
FIG. 52 shows sequencing of selected novel fescue endophytes.

FIG. 52 shows a strategy for GSS of selected novel fescue endophytes. The alkaloid profiles of novel fescue endophytes subjected to GSS analysis are shown in Table 32.

TABLE 32

Alkaloid profiles of sequenced endophytes.

Tall fescue accession details

| Endophyte strain | Accession No/isolated ID | Endophyte species | Alkaloid profile in Endogenous Host | | | |
|---|---|---|---|---|---|---|
| | | | Lolines | Peramine | Ergovaline | Lolitrem B |
| E34 | BE9301 | N. coenophialum | + | + | + | − |
| NEA13 | 8PC | N. coenophialum | ND | + | + | ND |
| NEA14 | FEtc7-180 | N. coenophialum | + | + | + | − |
| NEA15 | FEtc7-58 | N. coenophialum | + | + | + | − |
| NEA16 | FEtc7-342 | N. coenophialum | + | + | − | − |
| NEA20 | FEtc7-343 | N. coenophialum | + | + | − | − |
| NEA22 | 234746 | N. coenophialum | + | + | + | − |
| NEA24 | FEtc6-83 | N. coenophialum | + | + | + | − |
| NEA17 | 287819 | FaTG-2 | − | + | + | − |
| NEA21 | 231557 | FaTG-3 | + | + | − | − |
| NEA23 | 269850 | FaTG-3 | + | + | − | − |
| NEA19 | 231553 | non-Epichloë out-group | − | − | − | − |
| NEA18 | FEtc6-75 | non-Epichloë out-group | − | − | − | − |
| AR542* | AR542* | N. coenophialum | + | + | − | − |
| E77* | E77* | N. coenophialum | + | + | + | − |
| 598852 | 598852 | FaTG-2 | ND | ND | ND | ND |
| AR501* | AR501* | FaTG-3 | + | + | − | − |
| 598829 | 598829 | FaTG-3 like | ND | ND | ND | ND |
| E81 | E81 | N. uncinatum | ND | ND | ND | ND |
| 9340 | 9340 | E. typhina | ND | ND | ND | ND |
| 9707 | 9707 | E. baconii | ND | ND | ND | ND |

Figure 53:
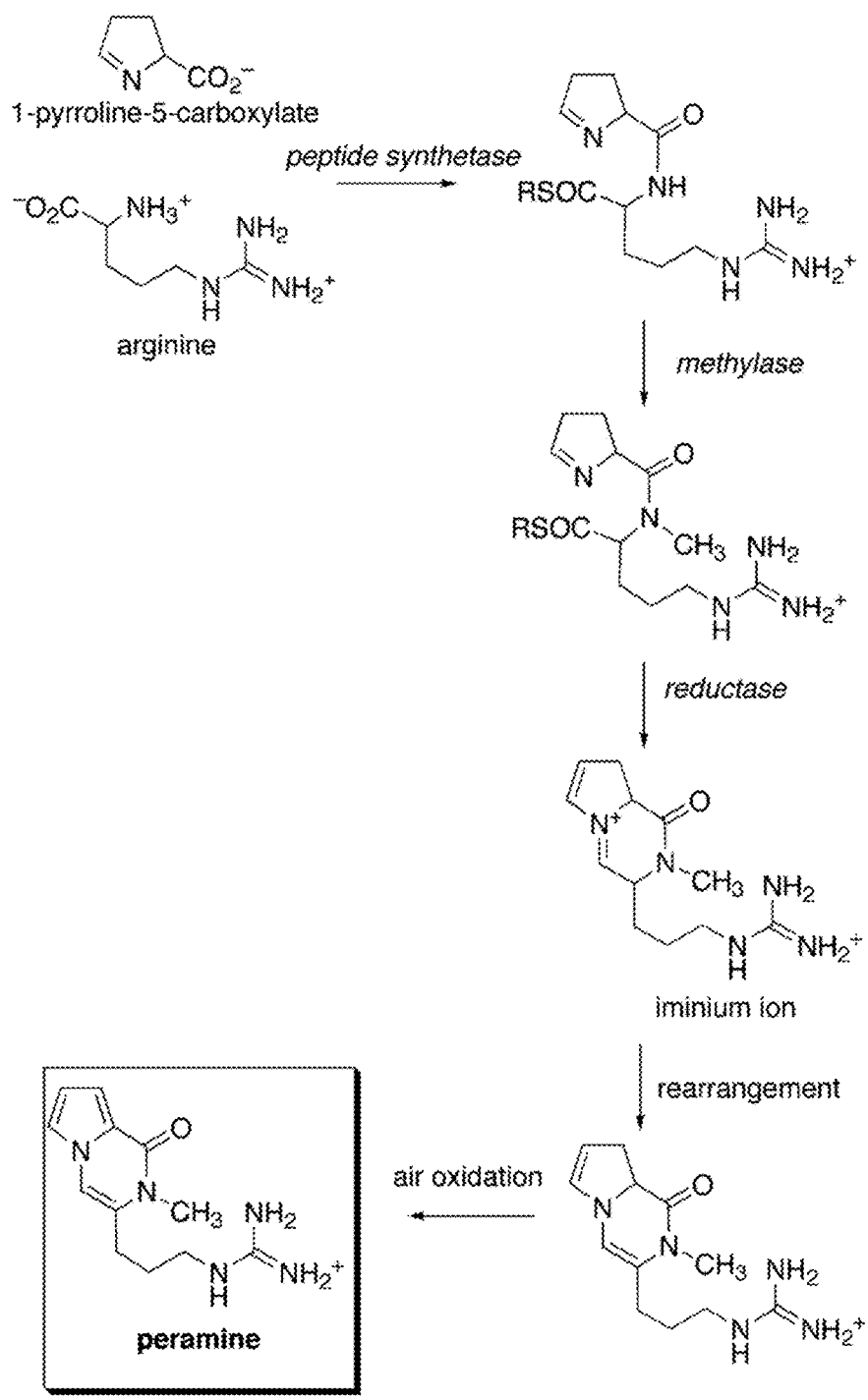
FIG. 53 shows peramine biosynthetic pathway.
Figure 54A:
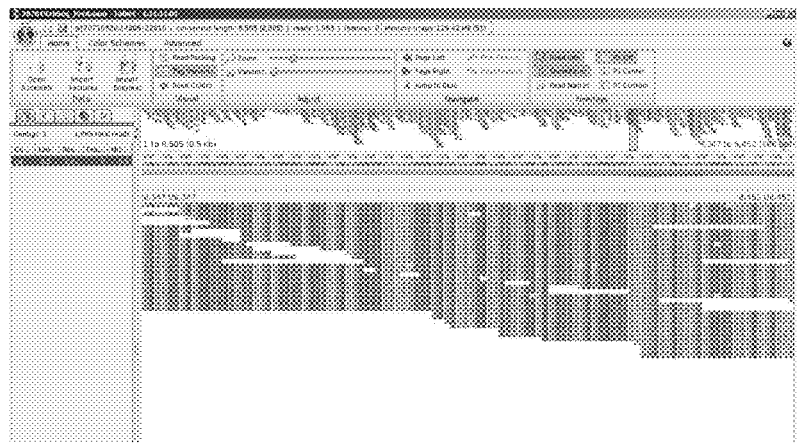
FIGS. 54 A-C show presence of perA gene within non-*Epichloe* out-group endophytes (FIG. 54A NEA17.
FIG. 54B NEA18.
FIG. 54C NEA19). P
Figure 54B:
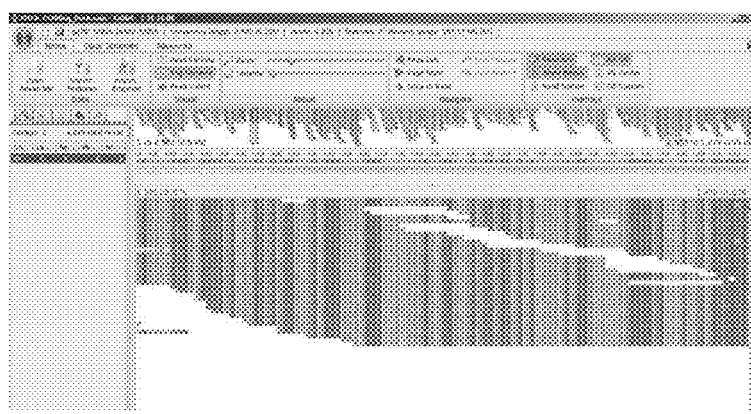
Figure 54C:
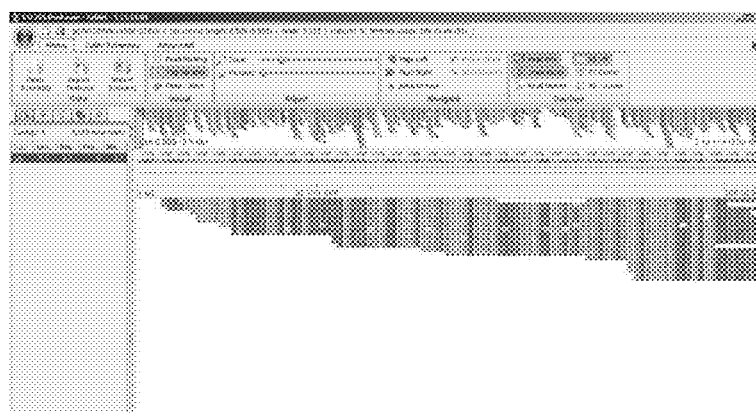

+ Alkaloid present,
− Alkaloid absent,
ND: alkaloid profile not determined
* Profiles are taken from published data +Alkaloid present, − Alkaloid absent, ND: alkaloid profile not determined
* Profiles are taken from published data FIG. 53 shows the peramine biosynthetic pathway. PerA encodes a single multifunctional enzyme that catalyses all the biosynthetic steps. GenBank accession Number: AB205145. The presence of the perA gene in non-*Epichloe* out-group endophytes is shown in FIG. 54.

Figure 55:
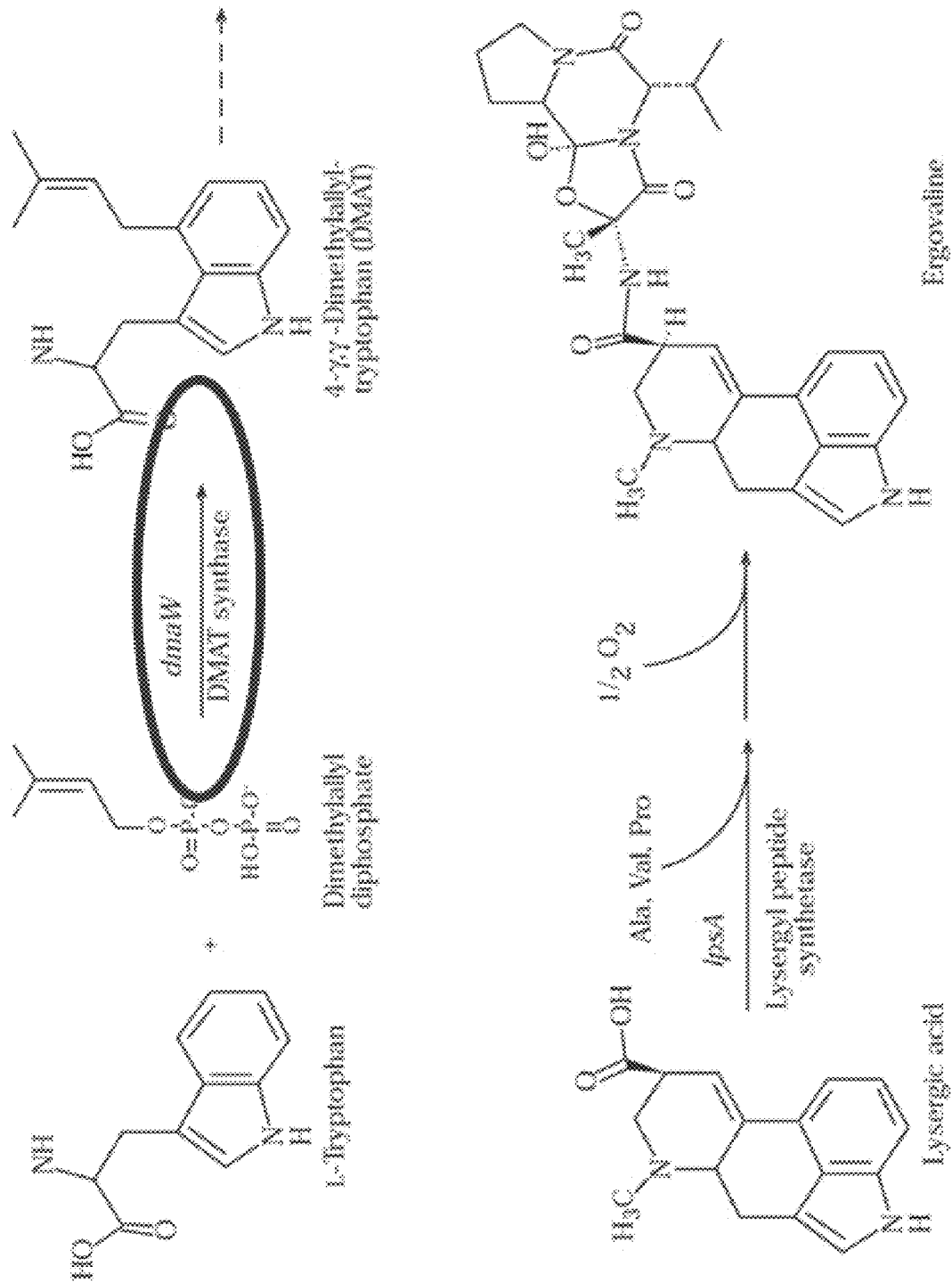
FIG. 55 shows ergovaline biosynthetic pathway.
Figure 56:
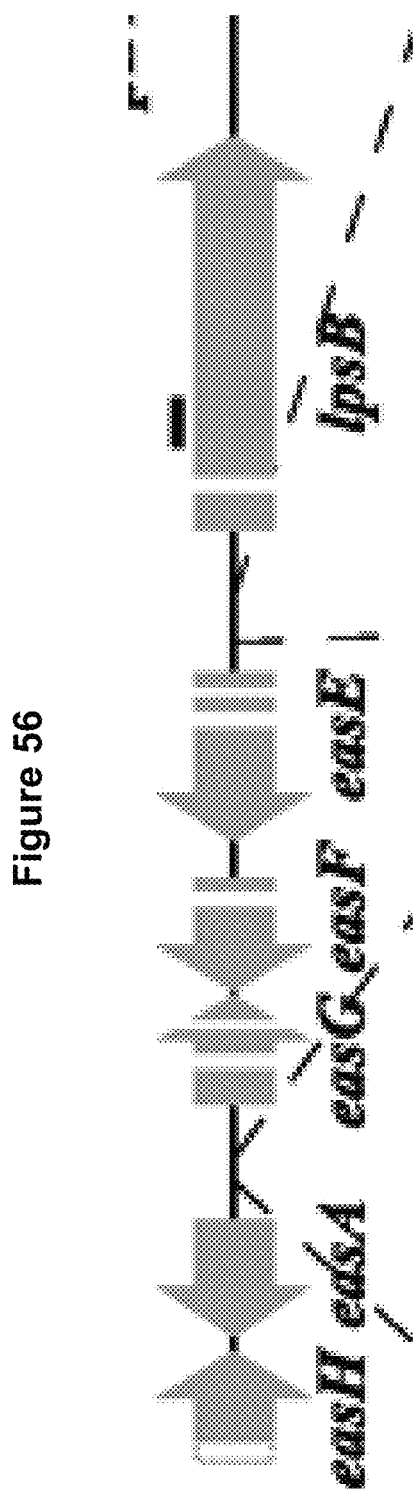
FIG. 56 shows genes in the eas gene cluster.
Figure 57A:
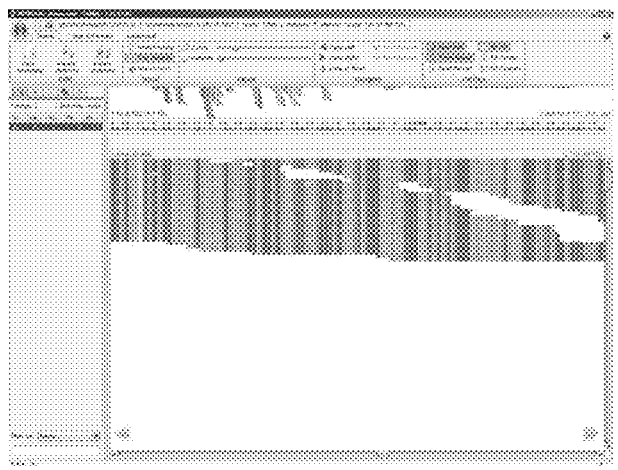
FIGS. 57 A-D show presence of dmaW gene for ergovaline biosynthesis in endophyte strains (FIG. 57A NEA17.
FIG. 57B NEA16.
FIG. 57C AR542.
FIG. 57D NEA20).
Figure 57B:
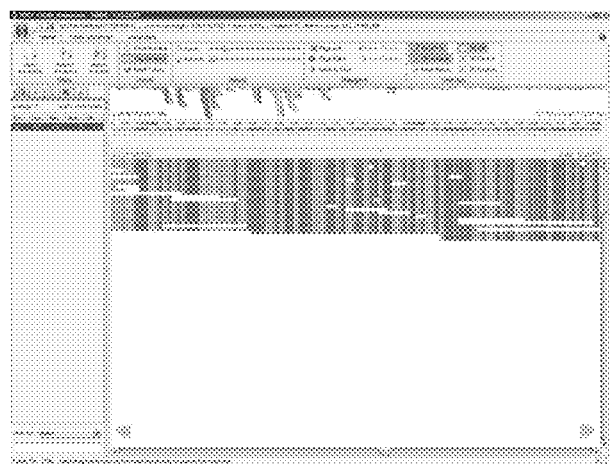
Figure 57C:
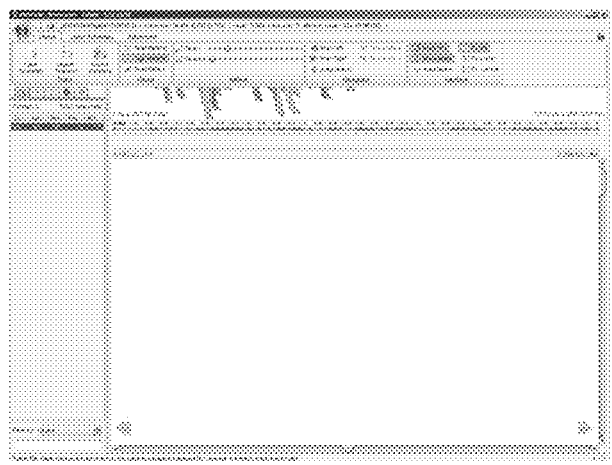
Figure 57D:
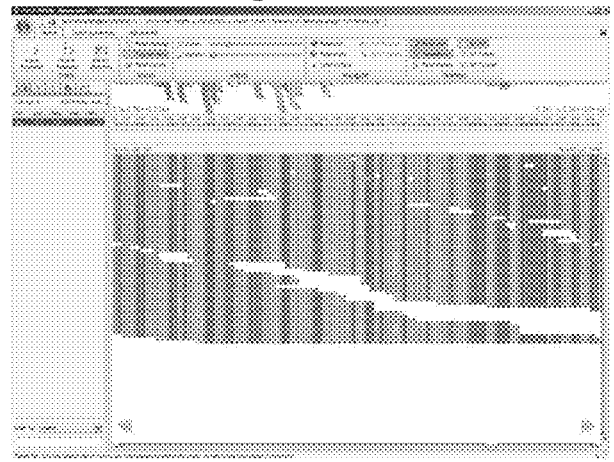
Figure 58A:
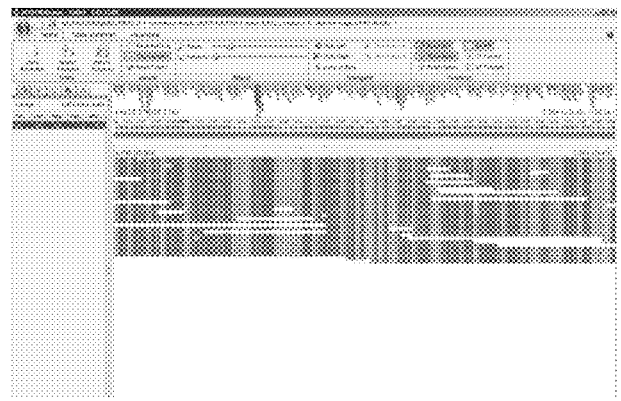
FIG. 58A FaTG-2 NEA17 (287819)
Figure 58B:
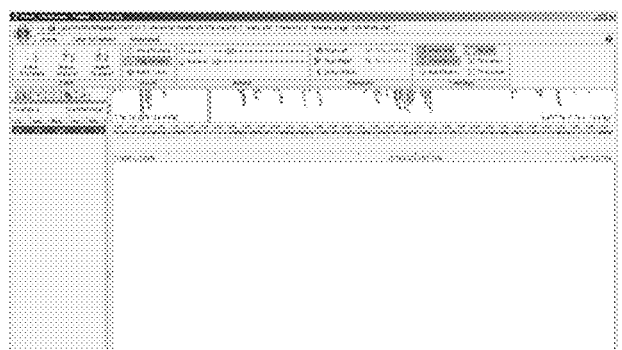
FIG. 58B non-*Epichloe* out-group NEA18 (FEtc6-75)
Figure 58C:
FIG. 58C FATG-3 NEA21 (231557)
Figure 58D:
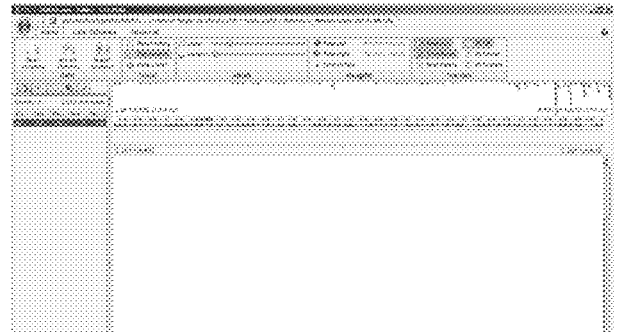
FIG. 58D *N. coenophia*/um NEA16 (FEtc7-342).

FIG. 55 shows the ergovaline biosynthetic pathway. Genes in the eas gene cluster which are involved in ergovaline biosynthesis are shown in FIG. 56 and Table 33. The dmaW gene encodes DMAT synthase enzyme, which catalyzes the first committed step in ergovaline biosynthesis. Presence of the dmaW gene in novel fescue endophytes is shown in FIG. 57 and presence of the eas gene cluster in novel fescue endophytes is shown in FIG. 58.

TABLE 33

Genes in the eas cluster

| Gene Cluster | Gene | GenBank Accession No |
|---|---|---|
| eas gene cluster | dmaW | AY259838 |
| | easA | EF125025 |
| | easE | EF125025 |
| | easF | EF125025 |
| | easG | EF125025 |
| | easH | EF125025 |
| | lpsA | AF368420 |
| | lpsB | EF125025 |

Figure 59:
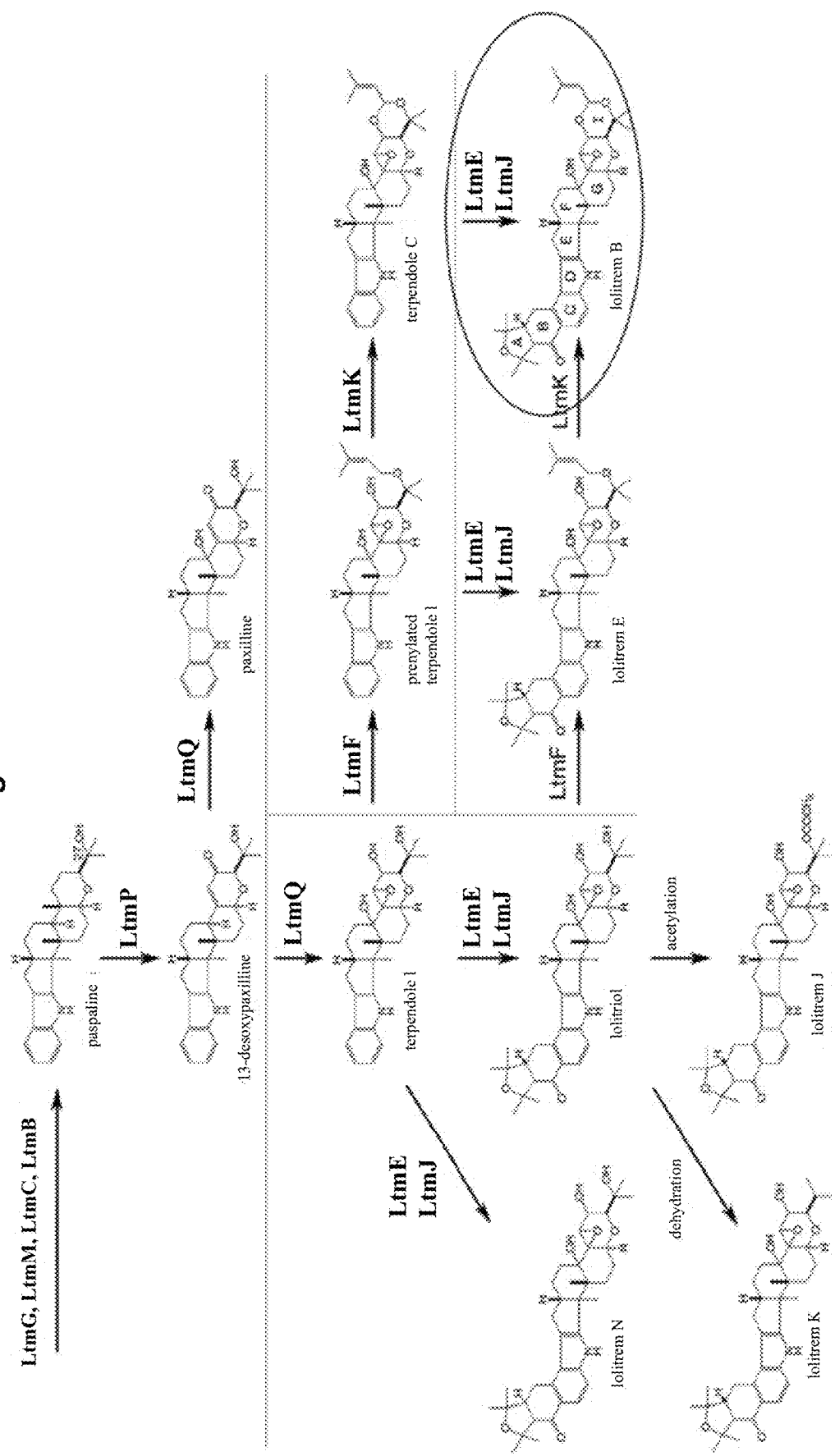
FIG. 59 shows the Lolitrem B biosynthetic pathway.
Figure 60:
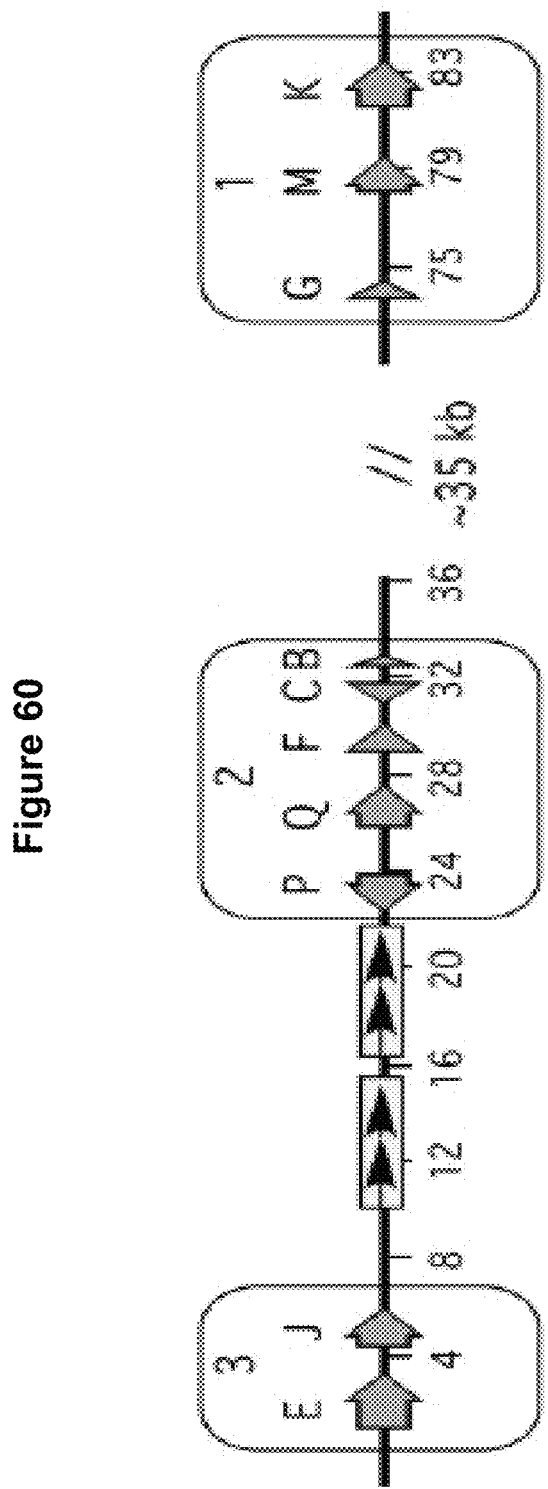
FIG. 60 shows genes in the Lolitrem B biosynthetic gene cluster.
Figure 61A:
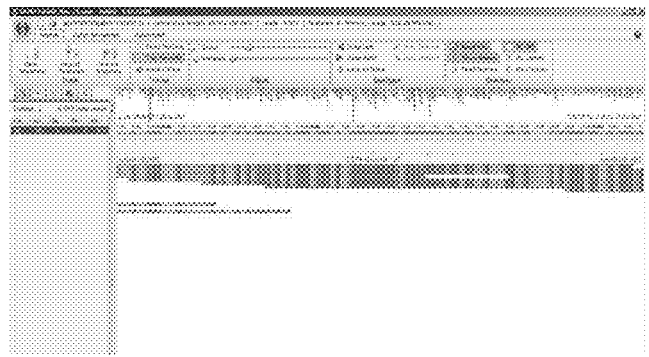
FIG. 61A FaTG-2 NEA17 (287819)
Figure 61B:
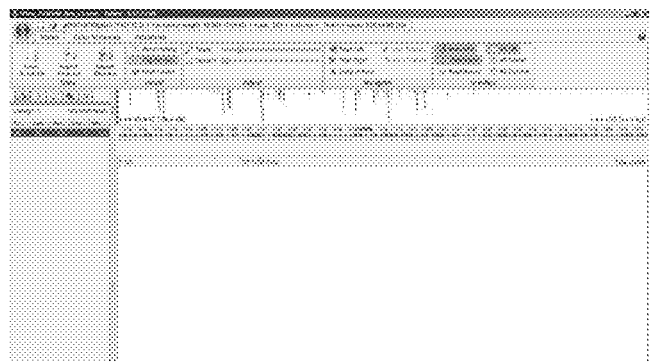
FIG. 61B non-*Epichloe* out-group NEA18 (FEtc6-75)
Figure 61C:
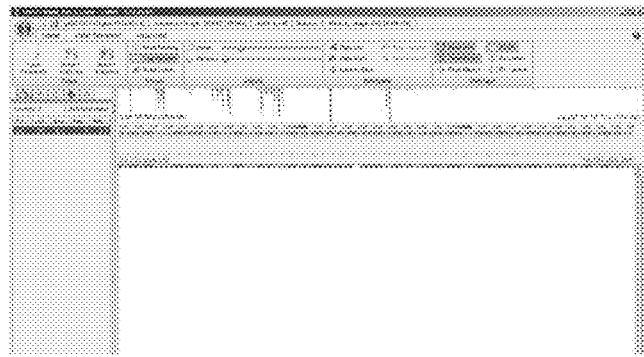
FIG. 61C FATG-3 NEA21 (231557)
Figure 61D:
FIG. 61D *N. coenophialum* NEA16 (FEtc7-342).
Figure 62A:
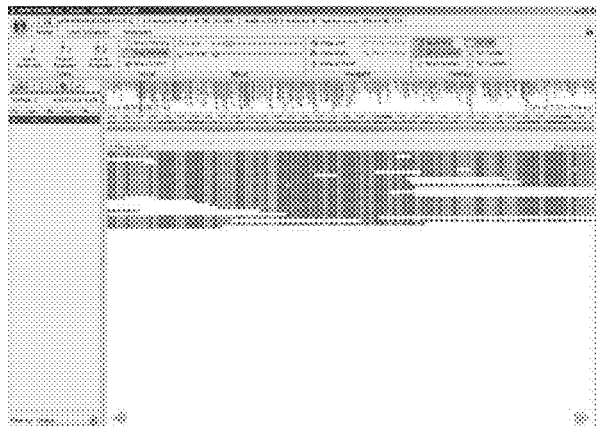
FIG. 62A FaTG-2 NEA17 (287819); FIG.
Figure 62B:
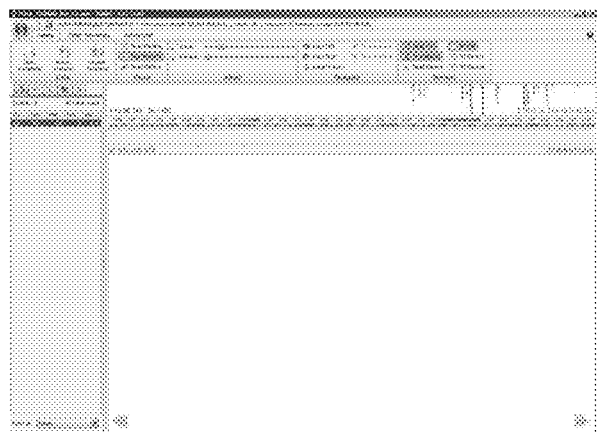
FIGS. 62 A-D show presence of Lolitrem B biosynthetic gene cluster 2 (ItmB, ItmQ, ItmP, ItmF and ItmC) in endophyte strains.
FIG. 62C FATG-3 NEA21 (231557)
FIG. 62D *N. coenophialum* NEA16 (FEtc7-342).
Figure 62C:
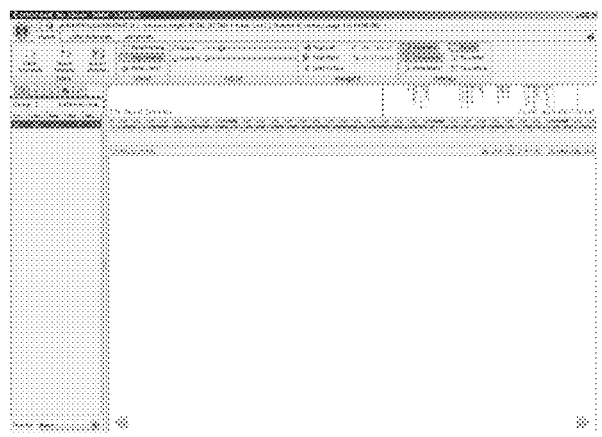
Figure 62D:
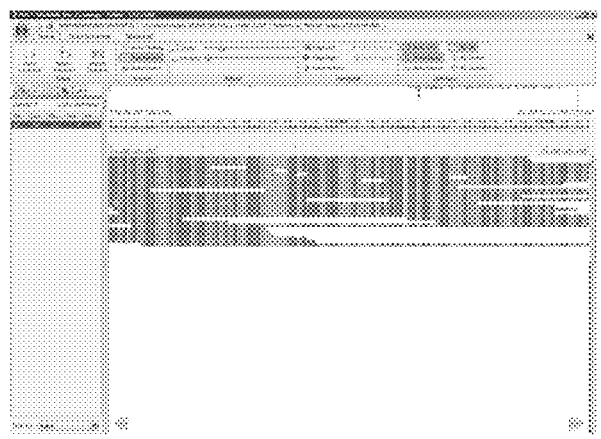
Figure 63A:
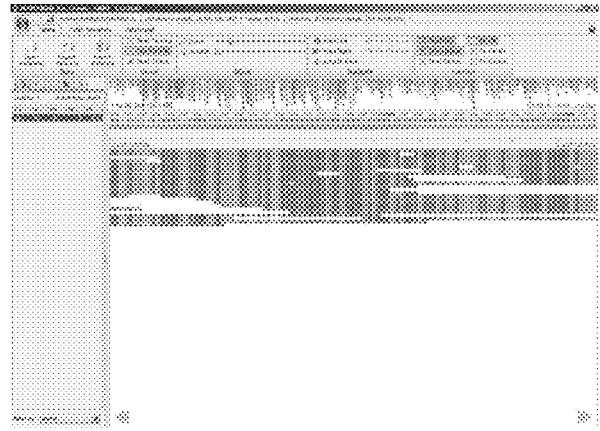
FIG. 63A FaTG-2 NEA17 (287819)
Figure 63B:
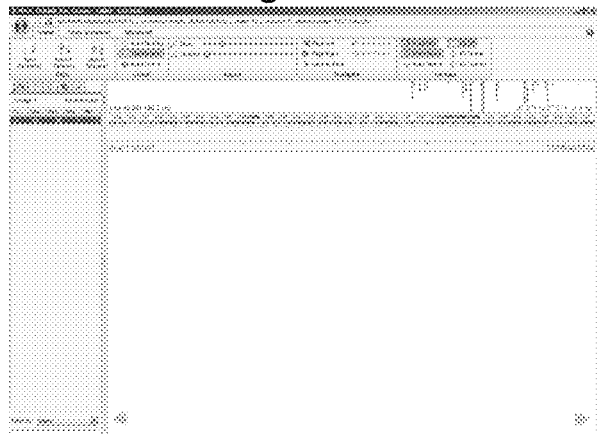
FIG. 63B non-*Epichloe* out-group NEA18 (FEtc6-75)
Figure 63C:
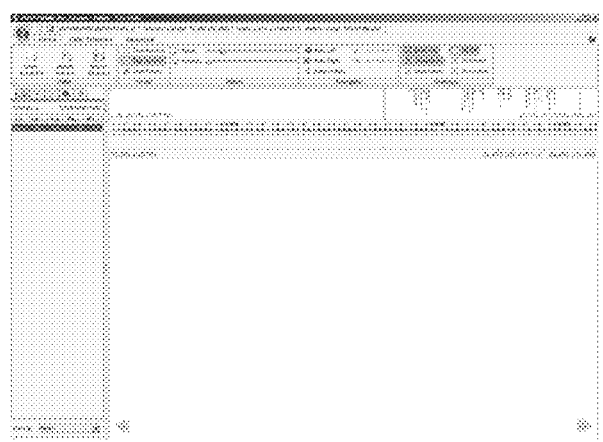
FIG. 63C FATG-3 NEA21 (231557)
Figure 63D:
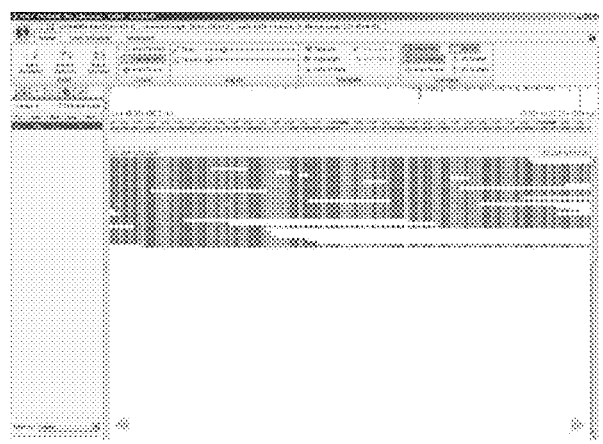
FIG. 63D *N. Coenophialum* NEA16 (FEtc7-342).

FIG. 59 shows the Lolitrem B biosynthetic pathway. Genes in the gene cluster which are involved in Lolitrem B biosynthesis are shown in FIG. 60 and Table 34. Presence of gene cluster 1 (ItmG, ItmM and ItmK) in endophytes is shown in FIG. 61, presence of gene cluster 2 (ItmB, ItmQ, ItmP, ItmF and ItmC) is shown in FIG. 62 and presence of gene cluster 3 (ItmE and ItmJ) is shown in FIG. 63.

TABLE 34

Genes in the gene cluster involved in Lolitrem B biosynthesis

| Gene Cluster | Gene | Gen Bank Accession No |
|---|---|---|
| gene cluster 01 | ltmG | AY742903 |
| | ltmM | AY742903 |
| | ltmK | AY742903 |
| gene cluster 02 | ltmB | DQ443465 |
| | ltmQ | DQ443465 |
| | ltmP | DQ443465 |
| | ltmF | DQ443465 |
| | ltmC | DQ443465 |
| gene cluster 03 | ltmJ | DQ443465 |
| | ltmE | DQ443465 |

Figure 64:
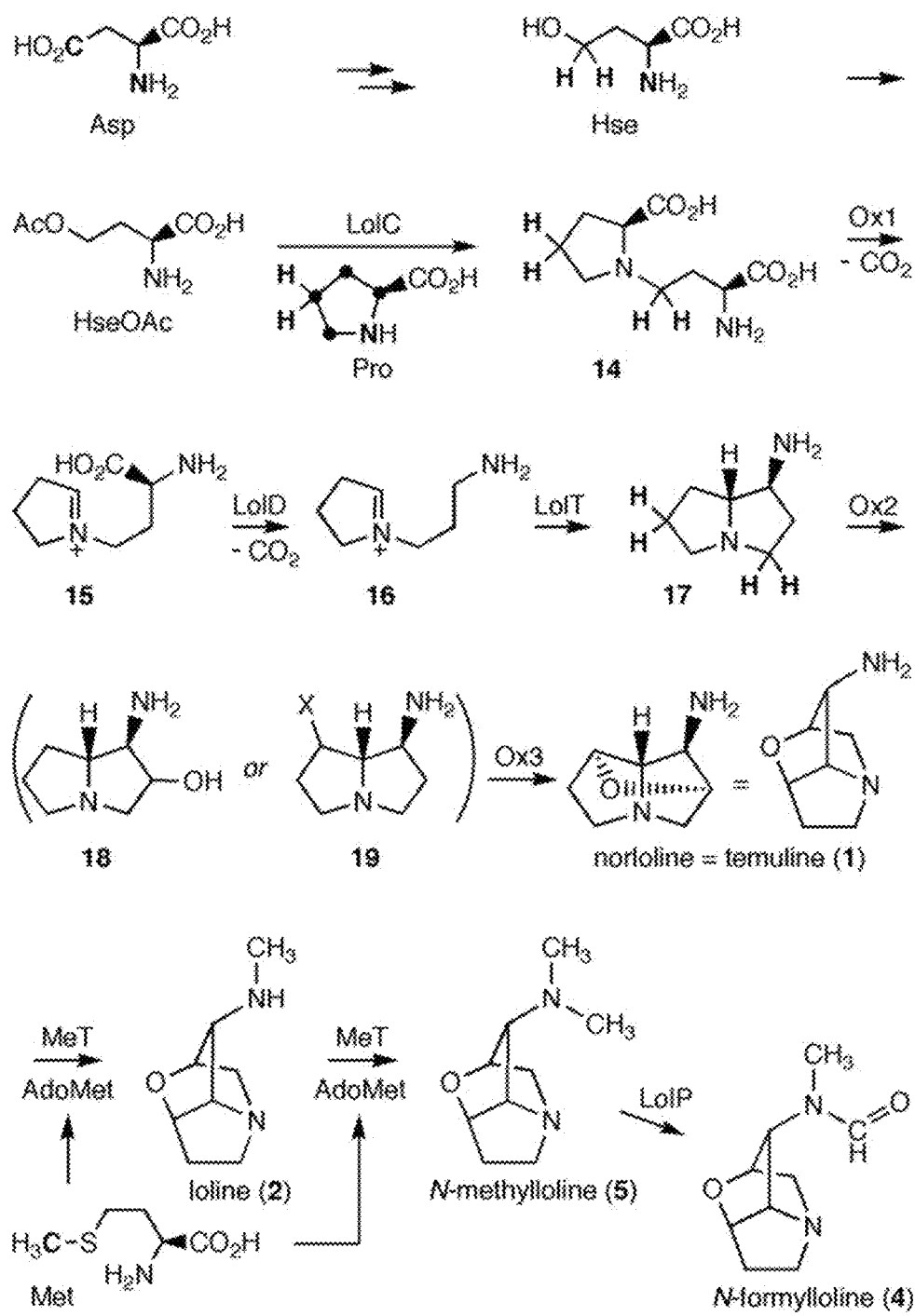
FIG. 64 shows the loline biosynthetic pathway.
Figure 65:
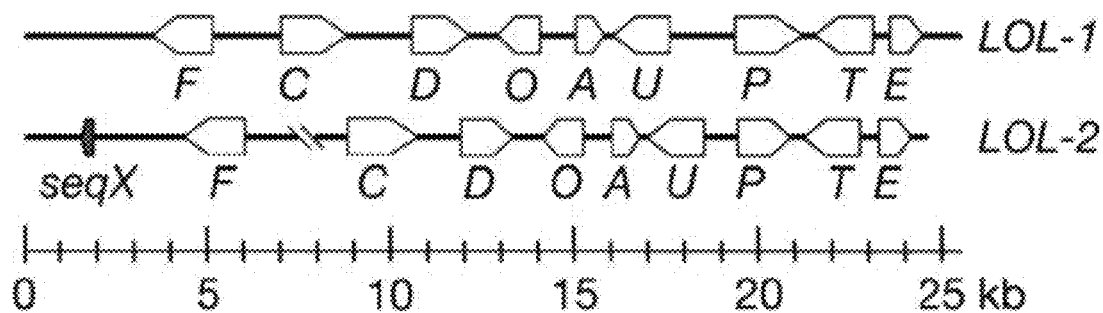
FIG. 65 shows the loline biosynthetic gene cluster.
Figure 66A:
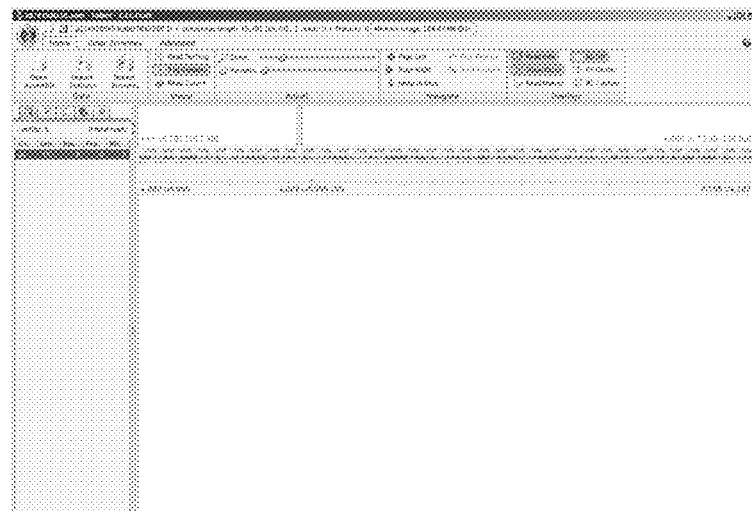
FIG. 66A FaTG-2 NEA17 (287819)
Figure 66B:
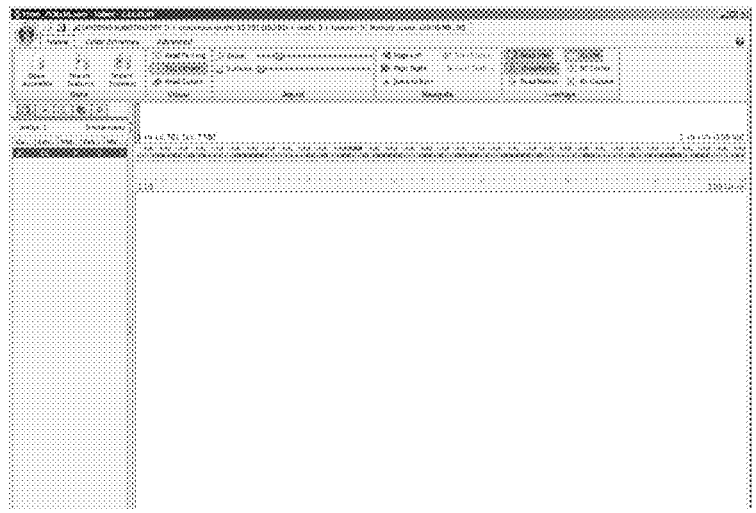
FIG. 66B non-*Epichloe* out-group NEA18 (FEtc6-75)
Figure 66C:
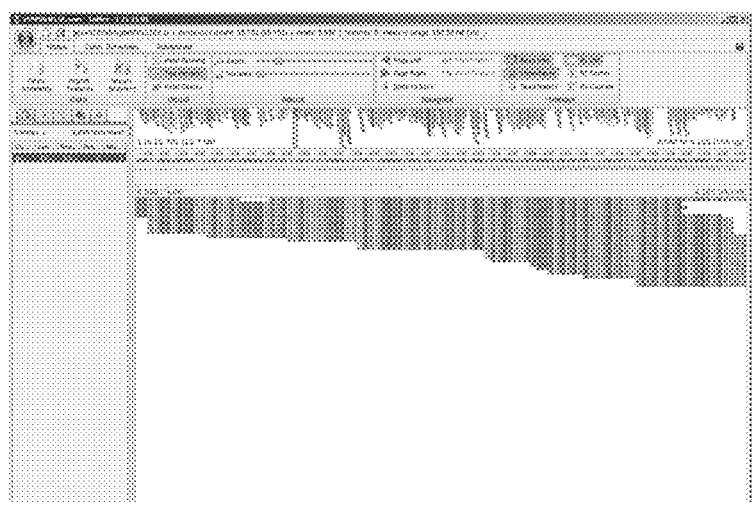
FIG. 66C FATG-3 NEA21 (231557)
Figure 66D:
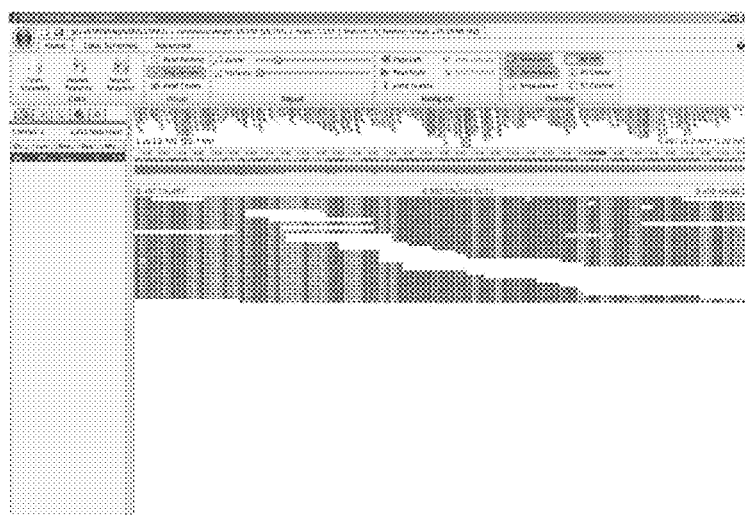
FIG. 66D *N. coenophialum* NEA16 (FEtc7-342).
Figure 67A:
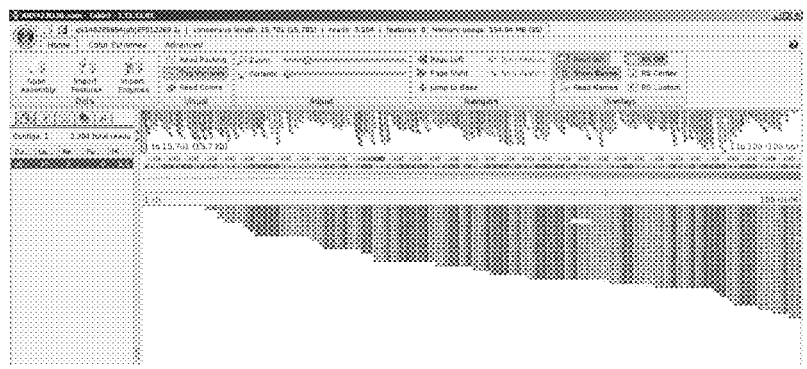
FIG. 67A Presence of loline gene cluster.
Figure 67B:
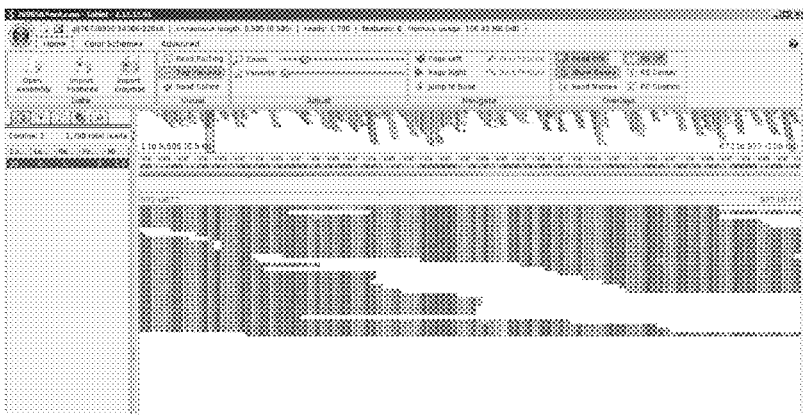
FIG. 67B Presence of peramine gene.
Figure 67C:
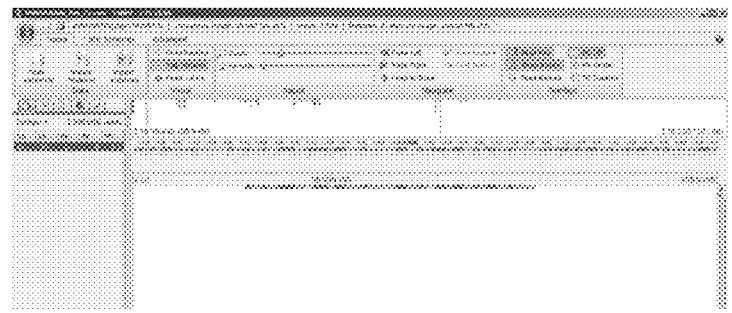
FIG. 67C Analysis of Lolitrem gene cluster 01.
Figure 67D:
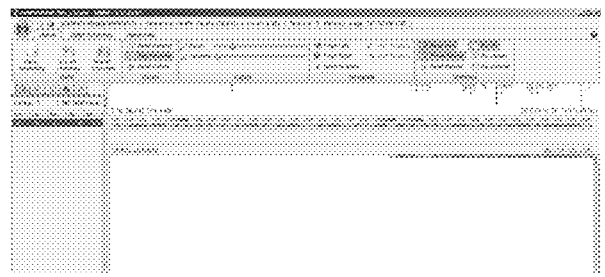
FIG. 67D Analysis of Lolitrem gene clusters 02 and 03.
Figure 67E:
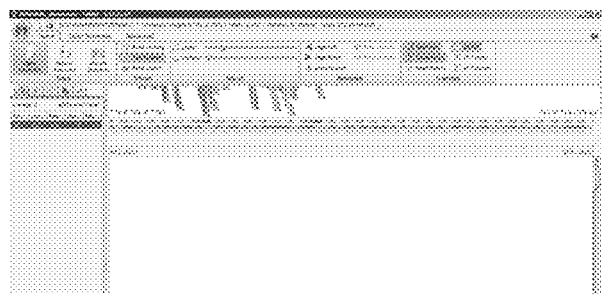
FIG. 67E Analysis of dmaW gene for ergovaline production.
Figure 67F:
FIG. 67F Analysis of eas gene cluster for ergovaline production.

FIG. 64 shows the Loline biosynthetic pathway. Genes in the gene cluster which are involved in Loline biosynthesis are shown in FIG. 65 and Table 35. Presence of Loline biosynthetic gene cluster in novel fescue endophytes is shown in FIG. 66.

TABLE 35

Genes in the Loline biosynthetic gene cluster

| Gene Cluster | Gene | GenBank Accession No |
|---|---|---|
| LOL gene cluster | lolF | EF012269 |
| | lolC | EF012269 |
| | lolD | EF012269 |
| | lolO | EF012269 |

TABLE 35-continued

Genes in the Loline biosynthetic gene cluster

| Gene Cluster | Gene | GenBank Accession No |
|---|---|---|
| | lolA | EF012269 |
| | lolU | EF012269 |
| | lolP | EF012269 |
| | lolT | EF012269 |
| | lolE | EF012269 |

FIG. 67 shows an alkaloid biosynthetic gene analysis for endophyte strain NEA23. Tables 36 and 37 show alkaloid biosynthetic gene analyses for various endophyte strains. Table 36 shows results from the assessment of alkaloid biosynthetic gene presence/absence for different endophytes by mapping genome survey sequence reads corresponding to the different alkaloid biosynthetic genes/gene clusters.

TABLE 36

Assessment of alkaloid biosynthetic gene presence/absence for different endophytes by mapping genome survey sequence reads corresponding to the different alkaloid biosynthetic genes/gene clusters.

| | | GenBank Accession No | N. coenophialum | | | | | | | | FaTG-2 | FaTG-3 | | | non-Epichloë out-group | |
|---|---|---|---|---|---|---|---|---|---|---|---|---|---|---|---|---|
| | Gene | | BE9301 | 8PC | NEA14 | NEA15 | NEA16 | NEA20 | AR542 | NEA22 | NEA17 | NEA21 | NEA23 | AR501 | NEA19 | NEA18 |
| Metabolite production in planta | | | Lol | nd | Lol | Lol | Lol | Lol | Lol | Lol | — | Lol | Lol | Lol | — | — |
| Loline alkaloids | gene cluster | EF012269 | | | | | | | | | | | | | | |
| Metabolite production in planta | | | P | P | P | P | P | P | P | P | P | P | P | P | — | — |
| Peramine | PerA | AB205145 | | | | | | | | | | | | | | |
| Metabolite production in planta | | | E | E | E | E | — | — | — | E | E | — | — | — | — | — |
| Ergot Alkaloids | dmaW | AY259838 | | | | | | | | | | | | | | |
| | eas gene cluster | EF125025 | | | | | | | | | | | | | | |
| Metabolite production in planta | | | — | nd | — | — | — | — | — | — | — | — | — | — | — | — |
| Lolitrems | gene cluster 01 | AY742903 | | | | | | | | | | | | | | |
| | gene cluster 02 | DQ443465 | | | | | | | | | | | | | | |
| | gene cluster 03 | DQ443465 | | | | | | | | | | | | | | |

■ Gene/gene cluster present
▨ Gene/gene cluster absent
▧ Gene/gene cluster partially present
(—) No alkaloid detected
(nd) Not determined Table 37 shows results from the assessment of alkaloid biosynthetic gene presence/absence for different endophytes by mapping genome survey sequence reads corresponding to the different alkaloid biosynthetic genes/gene clusters as well as corresponding alkaloid profile observed for corresponding tall fescue-endophyte associations.

TABLE 37

Alkaloid biosynthetic gene and alkaloid production analysis.

| Tall fescue accession details | | | Alkaloid profile and Gene presence | | | |
|---|---|---|---|---|---|---|
| Endophyte strain | Accession No/isolated ID | Endophyte species | Lolines | Peramine | Ergovaline* | Lolitrem B |
| E34 | BE9301 | N. coenophialum | A+G+ | A+G+ | A+G+ | A−PG+ |
| 8PC | 8PC | N. coenophialum | G+ | A+G+ | A+G+ | PG+ |
| NEA14 | FEtc7-180 | N. coenophialum | A+G+ | A+G+ | A+G+ | A−PG+ |
| NEA15 | FEtc7-58 | N. coenophialum | A+G+ | A+G+ | A+G+ | A−PG+ |

TABLE 37-continued

Alkaloid biosynthetic gene and alkaloid production analysis.

Tall fescue accession details

| Endophyte strain | Accession No/isolated ID | Endophyte species | Alkaloid profile and Gene presence | | | |
|---|---|---|---|---|---|---|
| | | | Lolines | Peramine | Ergovaline* | Lolitrem B |
| NEA16 | FEtc7-342 | N. coenophialum | A+G+ | A+G+ | A-G- | A-PG+ |
| NEA20 | FEtc7-343 | N. coenophialum | A+G+ | A+G+ | A-G- | A-PG+ |
| NEA22 | 234746 | N. coenophialum | A+G+ | A+G+ | A+G+ | A-PG+ |
| NEA24 | FEtc6-83 | N. coenophialum | A+ | A+ | A+ | A- |
| NEA17 | 287819 | FaTG-2 | A-G- | A+G+ | A+G+ | A-G+ |
| NEA21 | 231557 | FaTG-3 | A+G+ | A+G+ | A-G- | A-G- |
| NEA23 | 269850 | FaTG-3 | A+G+ | A+G+ | A-G- | G- |
| NEA19 | 231553 | non-Epichloë out-group | A-G- | A-G+ | A-G- | A-G- |
| NEA18 | FEtc6-75 | non-Epichloë out-group | A-G- | A-G+ | A-G- | A-G- |
| AR542* | AR542* | N. coenophialum | A+G+ | A+G+ | A-G- | A-PG+ |
| E77* | E77* | N. coenophialum | A+ | A+ | A+ | A- |
| 598852 | 598852 | FaTG-2 | | | | |
| AR501* | AR501* | FaTG-3 | A+G+ | A+G+ | A-G- | A-G- |
| 598829 | 598829 | FaTG-3 like | | | | |
| E81 | E81 | N. uncinatum | | | | |
| 9340 | 9340 | E. typhina | | | | |
| 9707 | 9707 | E. baconii | G- | PG+ | G- | G- |

A+: alkaloid present,
A-: Alkaloid absent,
Grey: alkaloid profile not determined,
*Profiles are taken from published data,
G+ = gene/gene cluster present,
G- = gene/gene cluster absent,
PG+ = gene/gene cluster partially present Table 38 shows novel fescue endophytes (NEA16, NEA18, NEA19, NEA20, NEA21 and NEA23) with favourable toxin profiles.

TABLE 38

Novel fescue endophytes (NEA16, NEA18, NEA19, NEA20, NEA21 and NEA23) with favourable toxin profiles and antifungal activities observed in bioassays.

| Tall fescue accession | Taxon | Alkaloid profile (Lol/P/E/L) | Antifungal |
|---|---|---|---|
| NEA21 | FaTG-3 | +/+/-/- | High |
| NEA23 | FaTG-3 | +/+/-/- | Not tested |
| AR501* | FaTG-3 | +/+/-/- | — |
| NEA18 | Non-Epichloë Outgroup | -/-/-/- | High |
| NEA19 | Non-Epichloë Outgroup | -/-/-/- | Not tested |
| NEA16 | N. coenophialum | +/+/-/- | High |
| NEA20 | N. coenophialum | +/+/-/- | Not tested |
| AR542* | N. coenophialum | +/+/-/- | — |

*Control commercial endophyte

Figure 68:
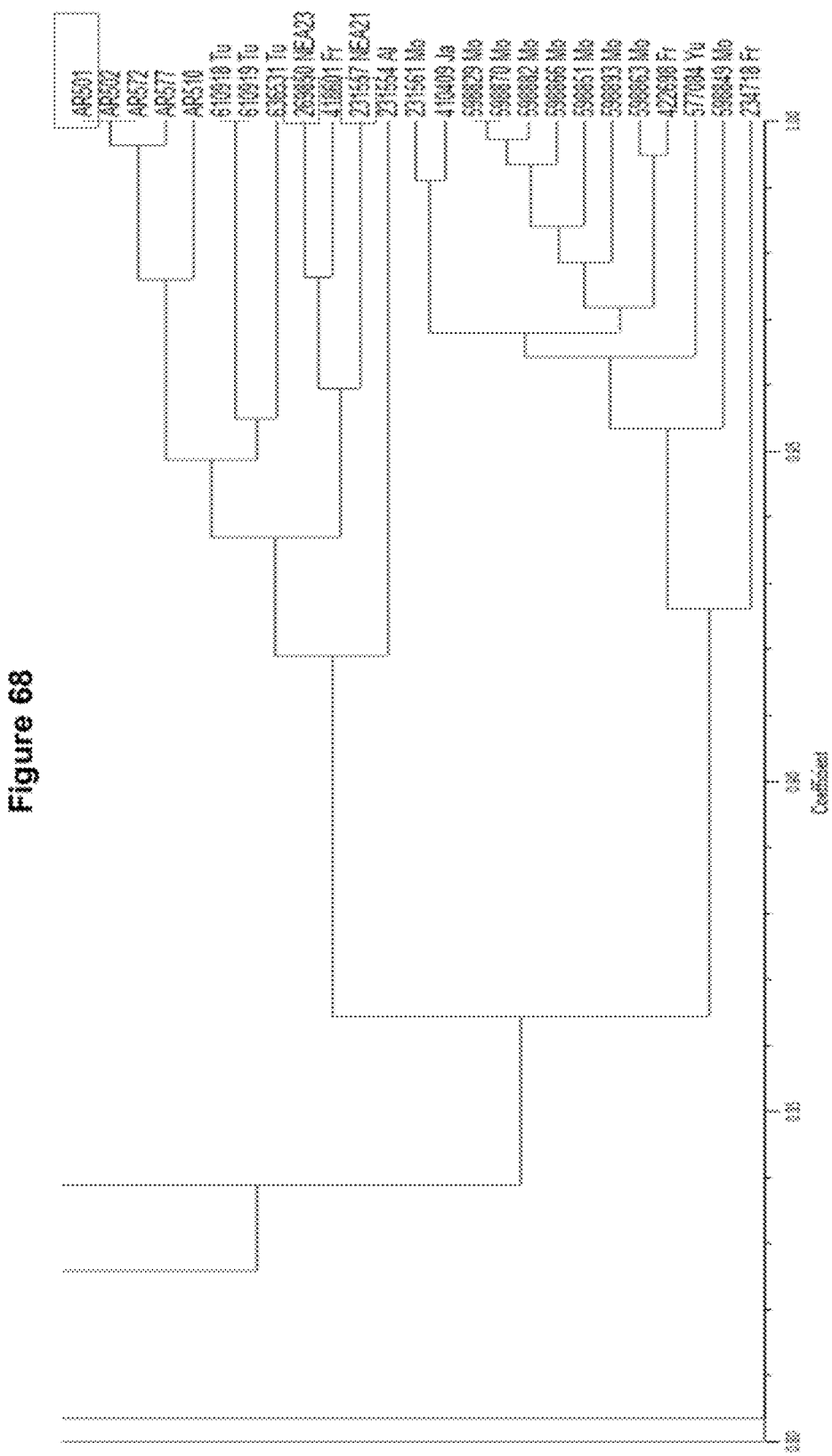
FIG. 68 shows genotypic analysis of NEA23 and NEA21.
Figure 69:
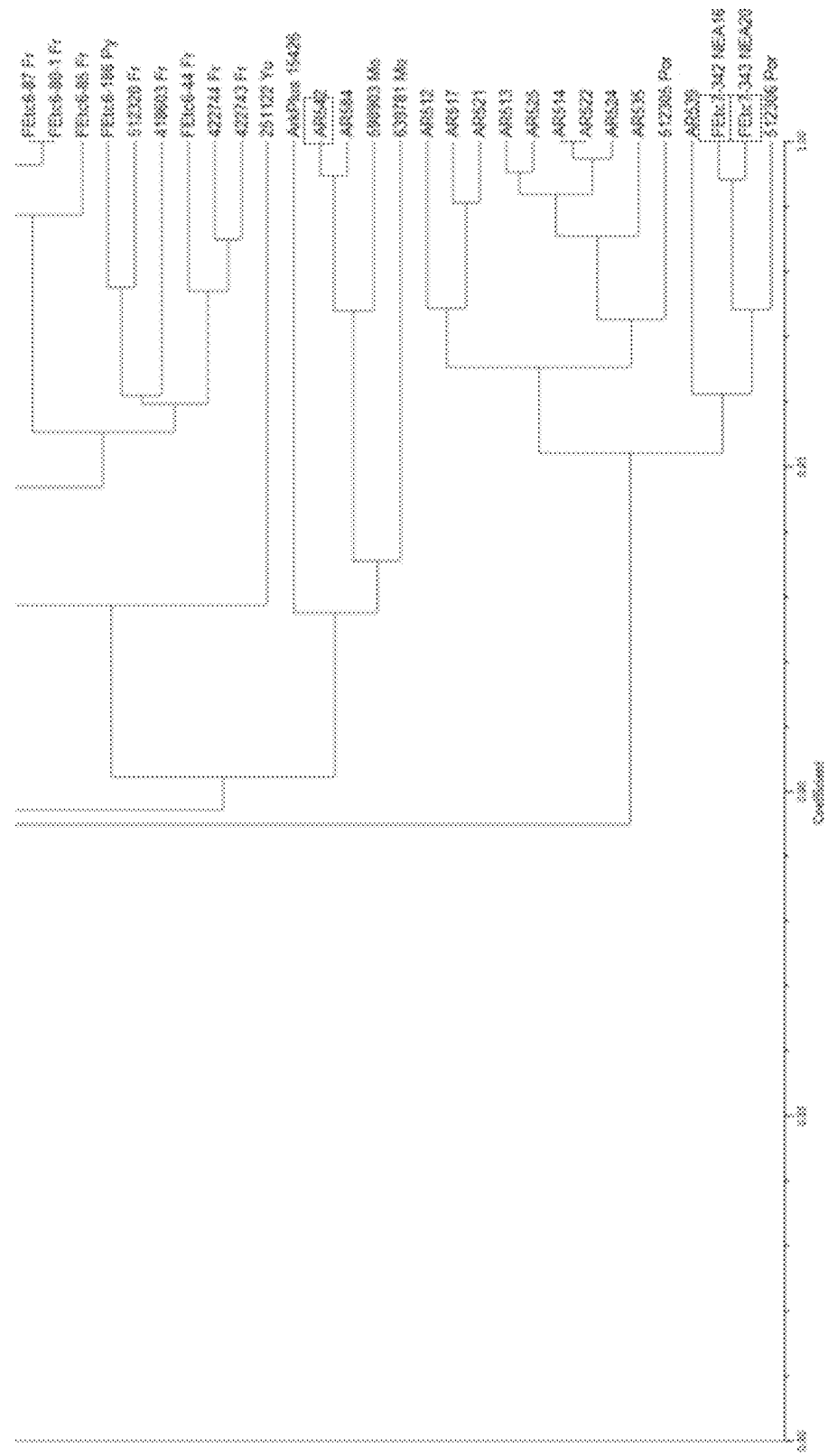
FIG. 69 shows genotypic analysis of NEA16 and NEA20.
Figure 70:
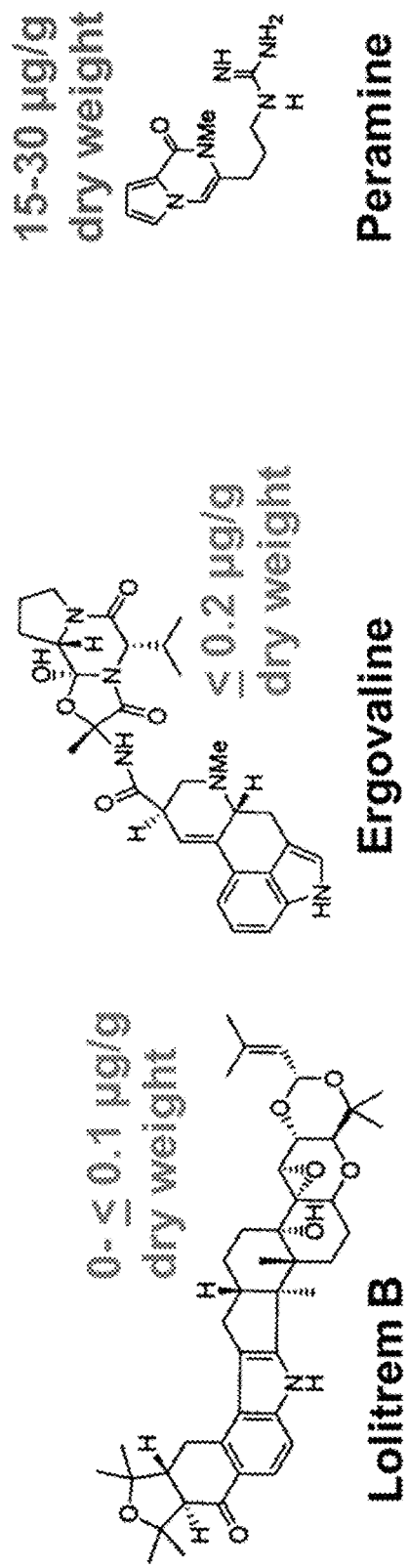
FIG. 70 shows the structures of Lolitrem B, Erogvaline and Peramine, with desirable toxin profiles indicated.

A genotypic analysis of the novel fescue endophytes NEA23 and NEA21 is shown in FIG. 68.

Example 18

Overview of Generation of Novel Designer *Neotyphodium* Endophyte Variant Strains Through Mutagenesis The objective of this work was to create novel variants of the perennial ryegrass endophyte, *Neotyphodium lolii*, through induced polyploidisation and mutagenesis, with desirable properties such as enhanced bioactivities (e.g. antifungal activity), and/or altered plant colonization ability and stability of grass host—endophyte variant associations (e.g. altered in vitro growth), and/or altered growth performance (e.g. enhanced plant vigour, enhanced drought tolerance, enhanced water use efficiency) of corresponding grass host—endophyte variant associations. These grass host—endophyte variant associations are referred to as novel 'designer' grass-endophyte associations.

Experimental Strategies for the Generation and Characterisation of Novel Designer *Neotyphodium* Endophyte Variant Strains Through Mutagenesis The experimental activities thus included:

1. Establishment of phenotypic screens for novel 'designer' grass-endophyte associations such as:

Enhanced biotic stress tolerance

Enhanced drought tolerance and enhanced water use efficiency

Enhanced plant vigour

2. Targeted generation (i.e. polyploidisation and X-ray mutagenesis) and characterisation (i.e. antifungal bioassays, in vitro growth rate, genome survey sequencing [GSS]) of novel 'designer' endophytes 3. Breeding of 'designer' grass-endophyte associations Delivery of 'designer' endophytes into grass (e.g. perennial ryegrass) germplasm development process.

Example 19

Figure 71:
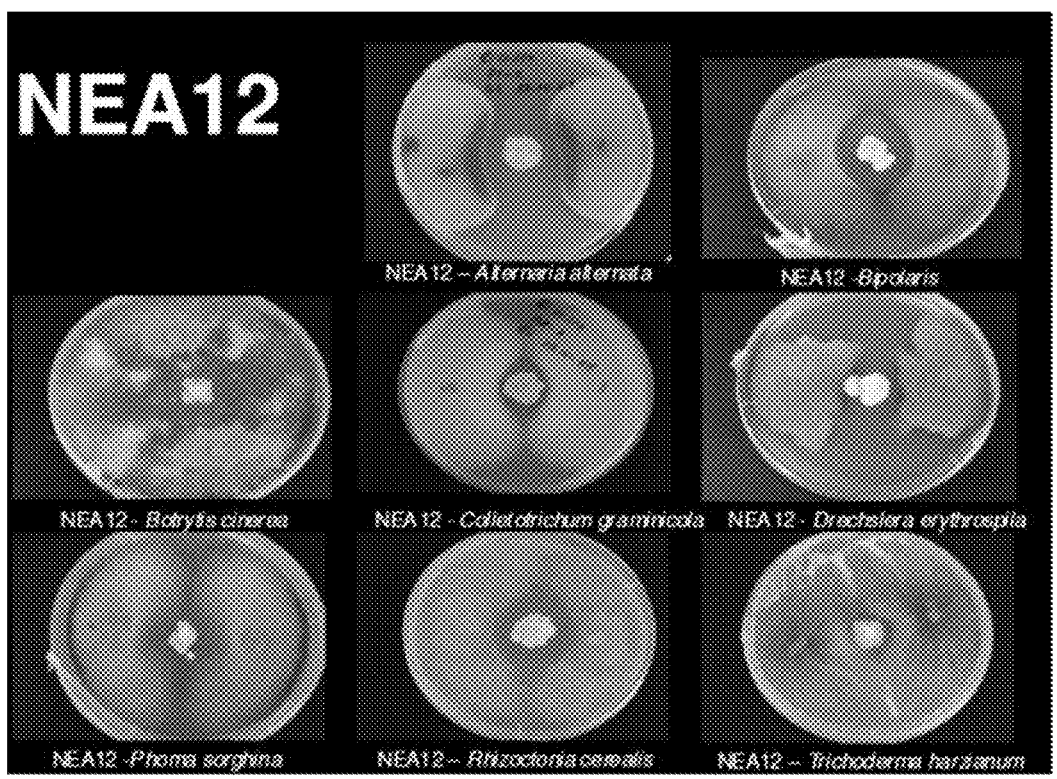
FIG. 71 shows in vitro bioassays to assess antifungal activity of *Neotyphodium* endophytes.
Figure 72:
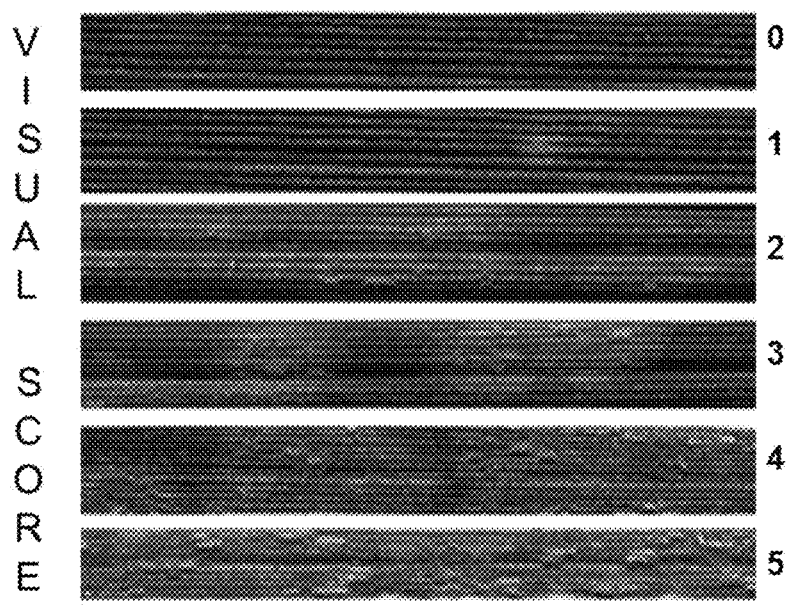
FIG. 72 shows a detached leaf assay to assess resistance to crown rust (*Puccinia coronata* f. sp. *Lolii*) of perennial ryegrass plants with and without *Neotyphodium* endophytes.

Establishment of Phenotypic Screens for Novel 'Designer' Grass-Endophyte Associations Assessment of enhanced biotic stress tolerance using NEA12 is shown in FIGS. 71 and 72. FIG. 71 shows in vitro bioassays to assess antifungal activity of *Neotyphodium* endophytes. FIG. 72 shows a detached leaf assay to assess resistance to crown rust (*Puccinia coronata* f. sp. *lolii*).

Figure 73:
FIG. 73 shows glasshouse and field trial screens for drought tolerance and water use efficiency of perennial ryegrass plants with and without *Neotyphodium* endophytes.

Assessment of enhanced drought tolerance and enhanced water use efficiency is shown in FIG. 73. This involved glasshouse and field trial screens for drought tolerance, survival and recovery, regrowth after drought, metabolic profiling and detailed phenotypic characterisation including multiple trait dissection (based on assessments and measurements associated with plant morphology, plant physiology, plant biochemistry).

Example 20

Generation of Designer *N. lolii* Genotypes by Polyploidisation

Figure 74:
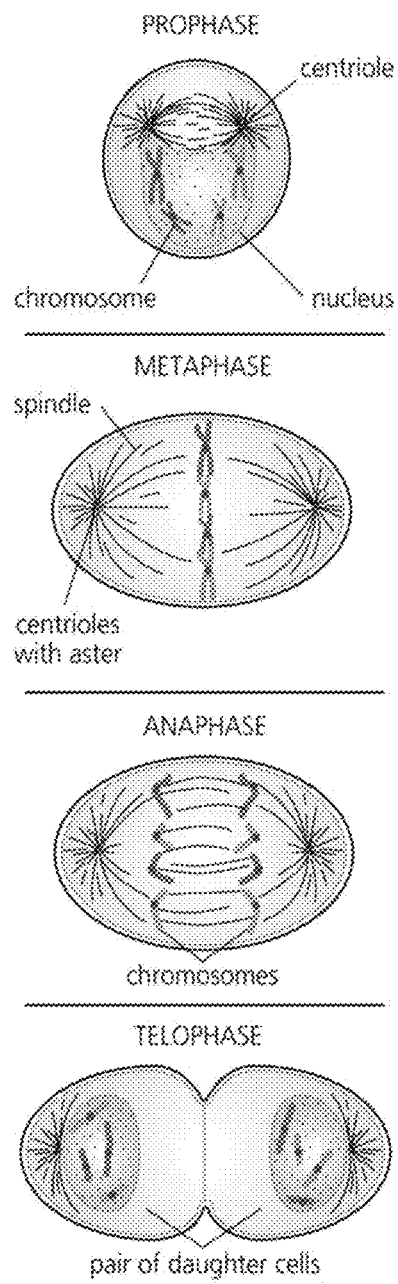
FIG. 74 shows the steps involved in cell division.

This involved creation of novel variation in *Neotyphodium* endophytes without the use of transgenic technology. Colchicine has been widely and successfully used for chromosome doubling in plants, e.g. perennial ryegrass. It inhibits chromosome segregation during mitosis inducing autopolyploidisation (chromosome doubling; see FIG. 74). This enables the generation of novel endophytes through induced chromosome doubling and may be applicable to the production of artificial polyploid endophytes.

Figure 75:
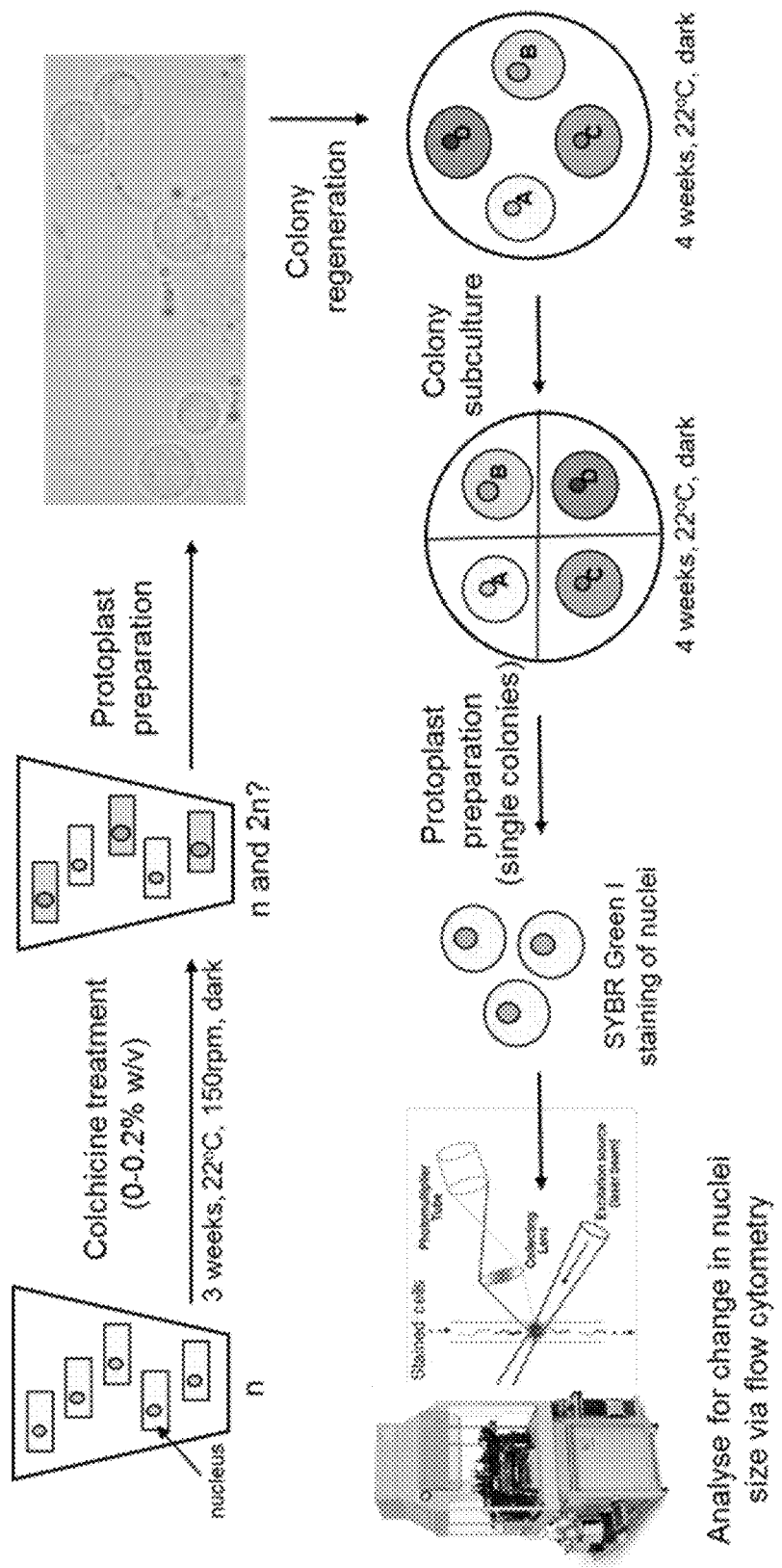
FIG. 75 shows experimental work flow for chromosome doubling of endophyte cells.

The experimental work flow for chromosome doubling is shown in FIG. 75.

Figure 76:
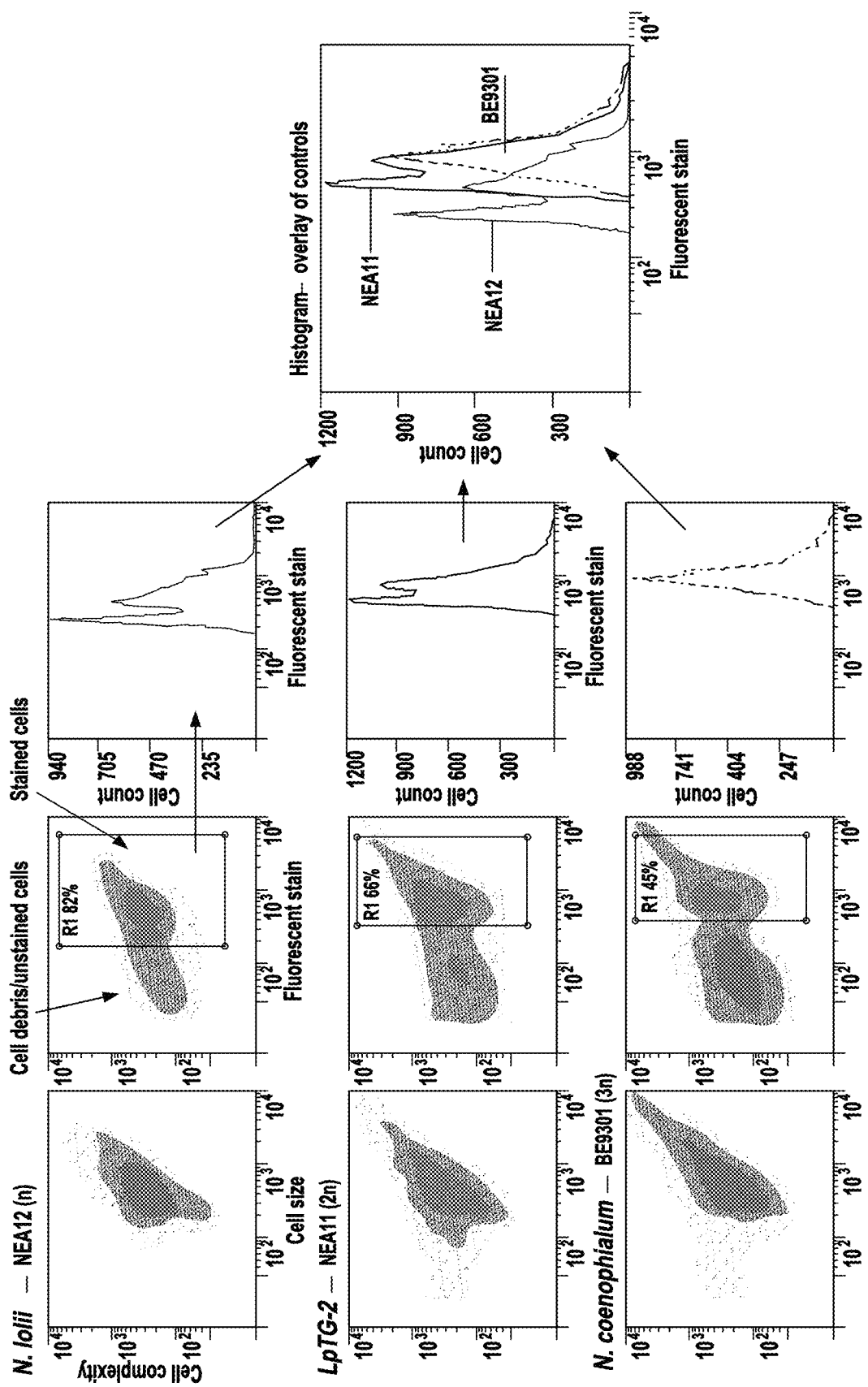
FIG. 76 shows flow cytometry calibrations for DNA content assessment in *Neotyphodium* endophyte strains. Peaks indicate relative nuclear DNA content.

Flow cytometry calibrations to assess DNA content in *Neotyphodium* endophytes are shown in FIG. 76. Peaks indicate relative nuclear DNA content.

Figure 77:
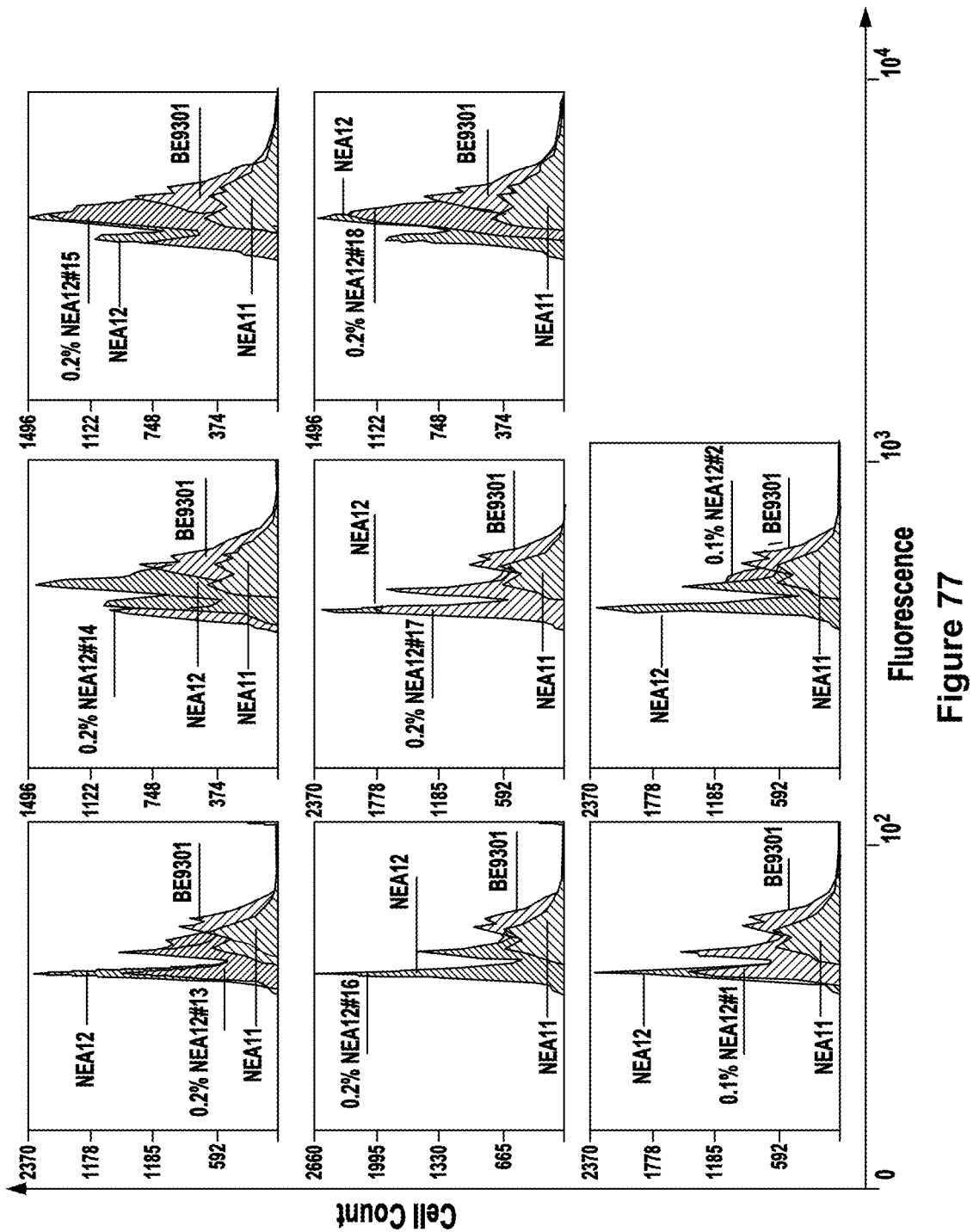
FIG. 77 shows flow cytometry analysis of NEA12dh *Neotyphodium* endophyte strains.

Flow cytometry analysis of NEA12$^{dh}$ strains is shown in FIG. 77 and Table 39.

1. ST endophyte strain is highly stable, broadly compatible and produces lolitrems, peramine and ergovaline. 2. NEA12 endophyte strain produces janthitrem only. 3. AR1 produces peramine only.

TABLE 39

Colchicine treated endophyte strains (ST, NEA12 and AR1 endophyte strains) subjected to colchicine treatments (at different colchicine concentrations in %) leading to the recovery of endophyte colonies (# of colonies) used for flow cytometry analysis

| Endophyte | Colchicine treatment (%) | # of colonies | # colonies analysed |
| --- | --- | --- | --- |
| *N. lolii* ST | 0.2 | 12 | 12 |
| *N. lolii* NEA12 | 0.1 | 60 | 2 |
| *N. lolii* NEA12 | 0.2 | 60 | 18 |
| *N. lolii* AR1 | 0.1 | 60 | 0 |
| *N. lolii* AR1 | 0.2 | 60 | 0 |

Example 21

Figure 78:
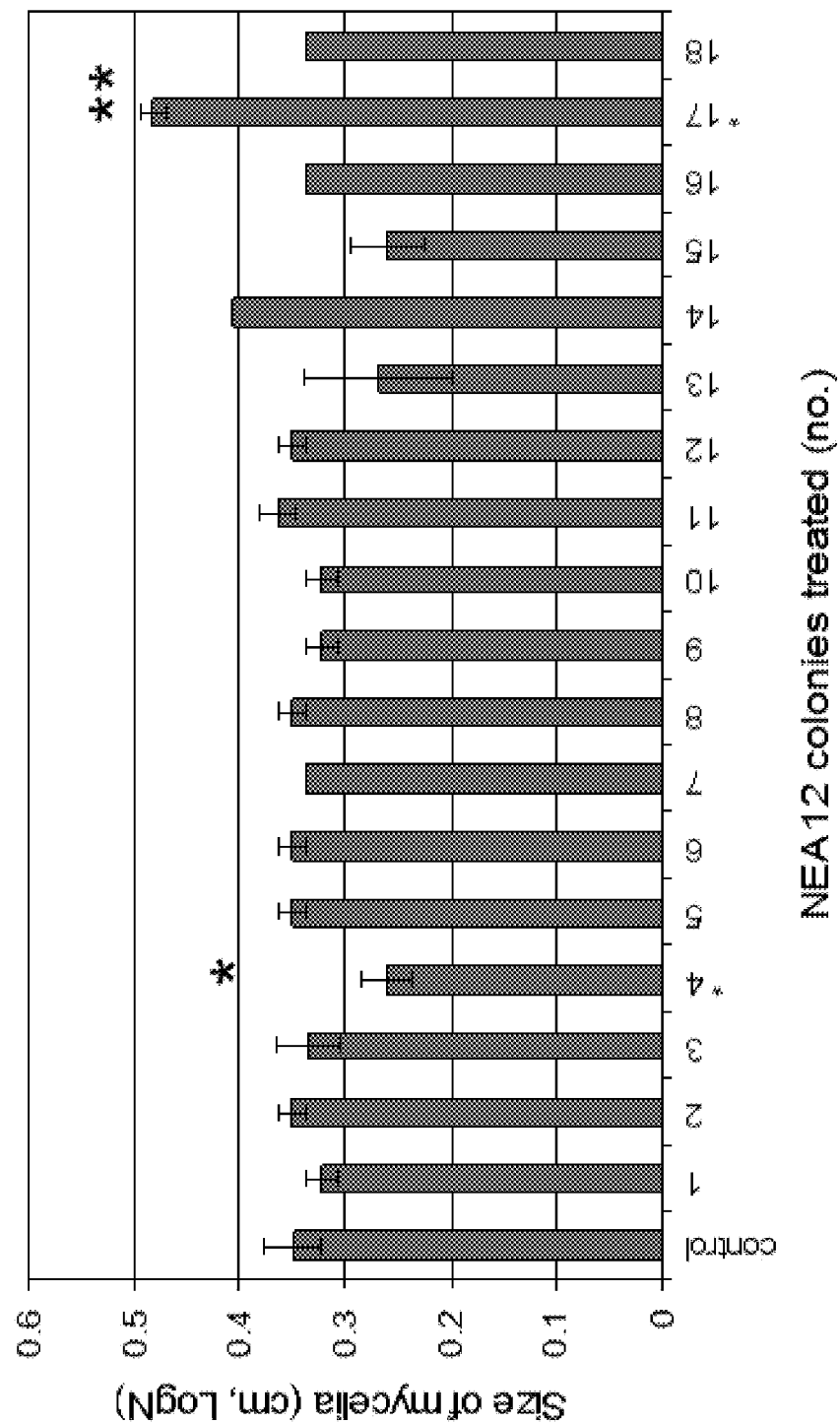
FIG. 78 shows analysis of growth rate in culture after 8 weeks of NEA12$^{dh}$ *Neotyphodium* endophyte strains compared to control endophyte strains.
Figure 79:
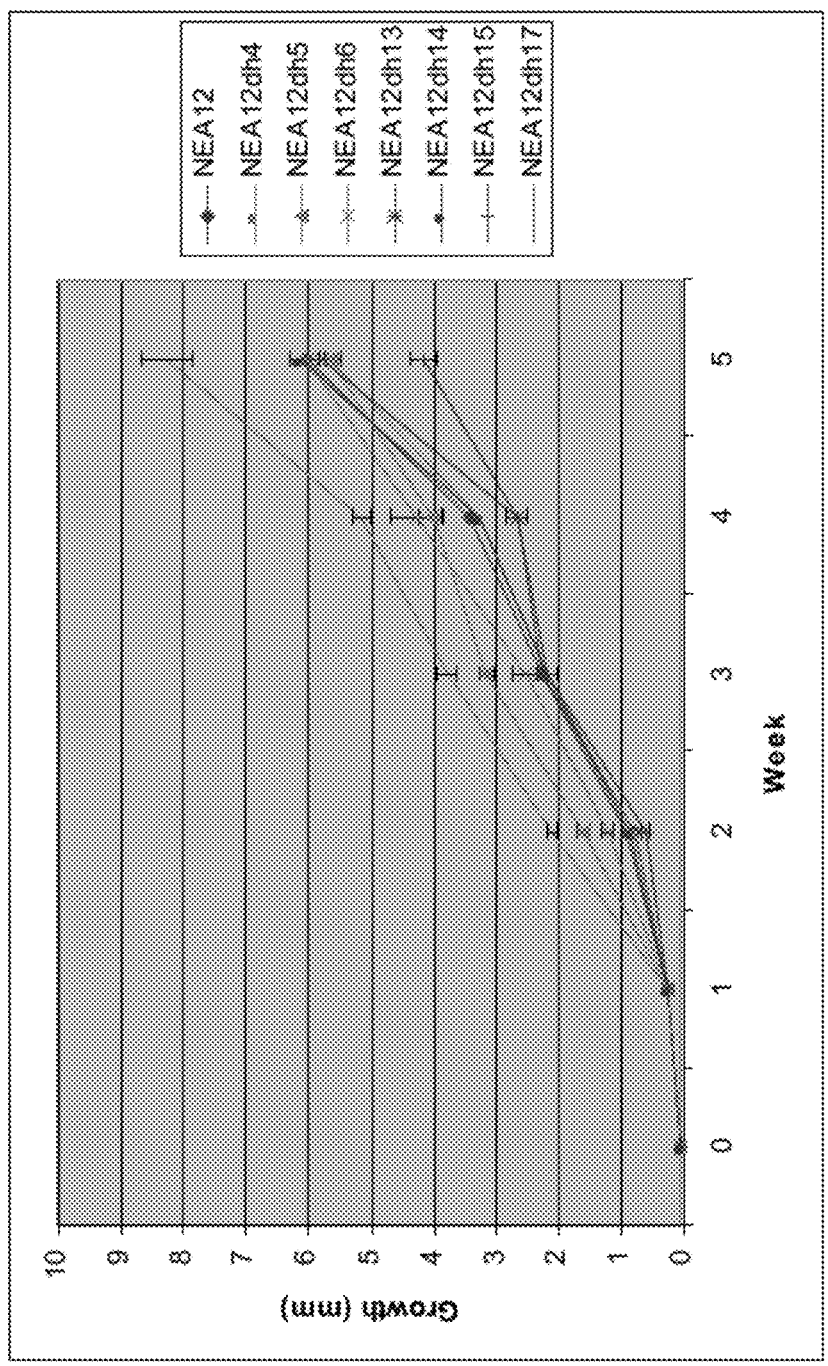
FIG. 79 shows analysis of growth rate in culture over 5 weeks of NEA12$^{dh}$ *Neotyphodium* endophyte strains compared to control endophyte strains.

Analysis of In Vitro Growth of NEA12$^{dh}$ *Neotyphodium* Variant Endophyte Strains Analysis of growth rate of NEA12$^{dh}$ *Neotyphodium* variant endophyte strains in in vitro culture after 8 weeks is shown in FIG. 78. In an initial screen, analysis of variance identified two NEA12$^{dh}$ *Neotyphodium* variant endophyte strains (NEA12$^{dh17}$ and NEA12$^{dh4}$) showing significantly different in vitro growth rate to the control NEA12 endophyte:

NEA12$^{dh17}$ grows significantly faster (p<0.01**)
NEA12$^{dh4}$ grows significantly slower (p<0.05*)

Analysis of growth rate of NEA12$^{dh}$ *Neotyphodium* variant endophyte strains in in vitro culture over 5 weeks is shown in FIG. 10. In a validation screen, Student's t-tests identified two NEA12$^{dh}$ *Neotyphodium* variant endophyte strains (NEA12$^{dh17}$ and NEA12$^{dh15}$) showing significantly different in vitro growth rate to the control NEA12 endophyte:

NEA12$^{dh17}$ grows significantly faster (p<0.01**)
NEA12$^{dh15}$ grows significantly slower (p<0.01**)

Example 22

Antifungal Bioassays of NEA12$^{dh}$ *Neotyphodium* Variant Endophyte Strains A list of fungal pathogens (causing a range of fungal diseases and infecting a range of different plant hosts) that were included in antifungal bioassays used to analyse NEA12$^{dh}$ *Neotyphodium* variant endophyte strains to assess their spectrum of antifungal activities is shown in Table 40.

TABLE 40

Fungal pathogens (causing a range of fungal diseases and infecting a range of different plant hosts) included in antifungal bioassays to analyse NEA12$^{dh}$ *Neotyphodium* variant endophyte strains to assess their spectrum of antifungal activities

| Fungus | Disease | Hosts |
| --- | --- | --- |
| *Alternaria alternata* | leaf spot, rot, blight | Numerous (dead plant materials) |
| *Bipolaris portulacae* | Damping-off | Asteraceae (daisies), Portulacaceae (purslane) |
| *Botrytis cinerea* | Stem rot, mould, seedling wilt | Many dicots, few monocots |
| *Colletotrichum graminicola* | Leaf spot, stalk rot | Poaceae (especially *Zea mays*) |
| *Drechslera brizae* | Leaf blight | Poaceae (*Briza* spp.) |
| *Phoma sorghina* | Spot (leaf, glume, seed), Root rot, Dying-off | Poaceae (grasses) |
| *Rhizoctonia cerealis* | Spot (wheat), Yellow patch (turfgrass) | Poaceae (grasses) |
| *Trichoderma harzianum* | Green mould, Parasite of other fugni | Many dicots, few monocots, Fungi |

Figure 81:
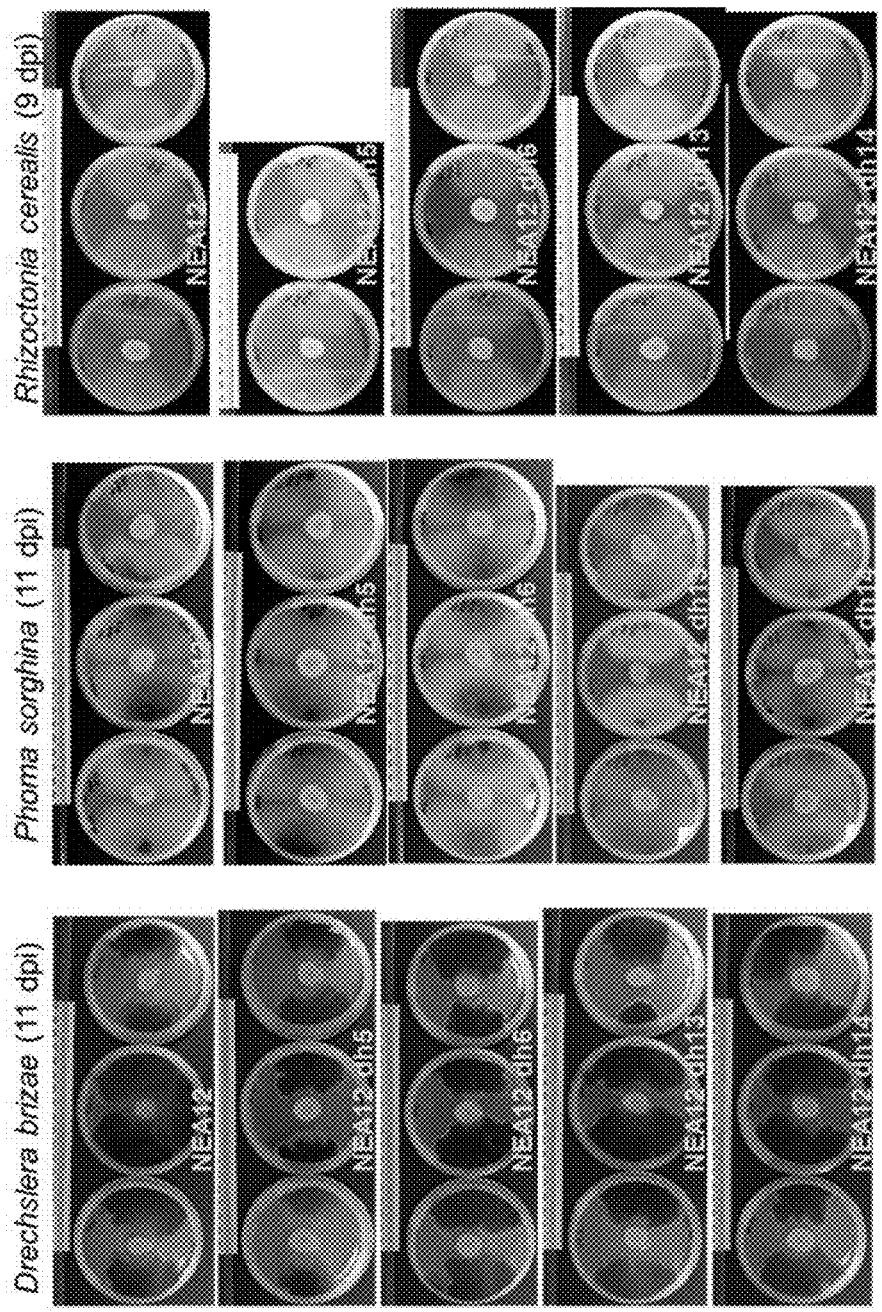
FIG. 81 shows antifungal bioassays of NEA12$^{dh}$ *Neotyphodium* endophyte strains.

Antifungal bioassays of NEA12$^{dh}$ *Neotyphodium* variant endophyte strains are shown in FIGS. 80 and 81. Twenty NEA12$^{dh}$ strains were screened for changes in antifungal activity. Four NEA12$^{dh}$ strains (i.e. dh5, dh6, dh13 and dh14) were identified as having greater antifungal activity compared to NEA12.

Example 23

Genome Survey Sequencing and Sequence Analysis of NEA12$^{dh}$ *Neotyphodium* Variant Endophyte Strains NEA12$^{dh}$ *Neotyphodium* variant endophyte strains with enhanced antifungal activity, showing faster in vitro growth rate and higher DNA content were subjected to genome survey sequencing (GSS). Sequence data was generated for 10 NEA12$^{dh}$ strains and control NEA12 strain (highlighted in blue on Table 41).

TABLE 41

List of NEA12$^{dh}$ Neotyphodium variant endophyte strains showing different antifungal activity [higher than control or equal to control (standard, Std)] and different in vitro growth [slower than control, faster than conrol or equal to control (standard, Std)] compared to control NEA12 strain

| Endophyte | Antifungal | Growth |
|---|---|---|
| NEA12 | Std | Std |
| NEA12dh1 | Std | Std |
| NEA12dh2 | Std | Std |
| NEA12dh3 | Std | Std |
| NEA12dh4 | Std | Slower |
| NEA12dh5 | Higher | Std |
| NEA12dh6 | Higher | Std |
| NEA12dh7 | Std | Std |
| NEA12dh8 | Std | Std |
| NEA12dh9 | Std | Std |
| NEA12dh10 | Std | Std |
| NEA12dh11 | Std | Std |
| NEA12dh12 | Std | Std |
| NEA12dh13 | Higher | Std |
| NEA12dh14 | Higher | Std |
| NEA12dh15 | Std | Slower |
| NEA12dh16 | Std | Std |
| NEA12dh17 | Std | Faster |
| NEA12dh18 | Std | Std |
| NEA12dh19 | Std | Std |
| NEA12dh20 | Std | Std |

Figure 82:
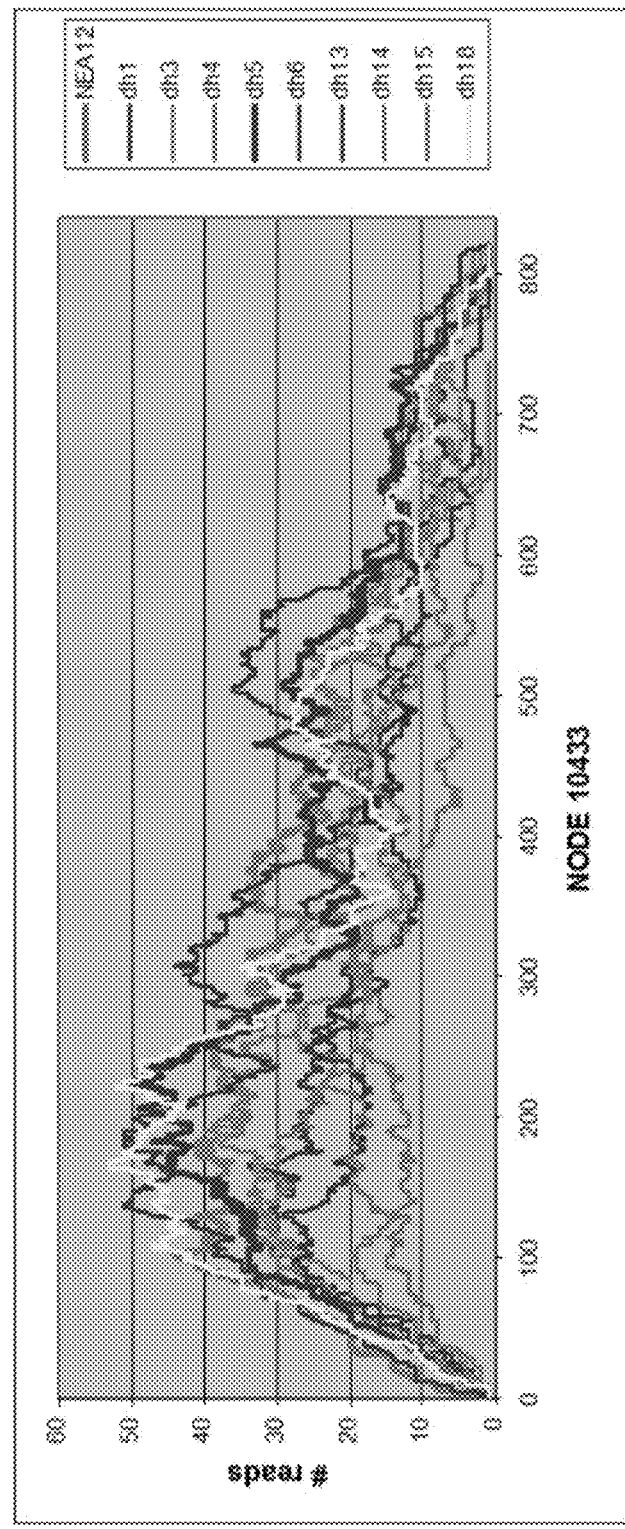
FIG. 82 shows analysis of genome survey sequencing read depth of colchicine-treated *Neotyphodium* endophyte strains.

Genome survey sequencing (GSS) data obtained for NEA12$^{dh}$ Neotyphodium variant endophyte strains derived from colchicine treated NEA12 control strain (highlighted in blue on Table 41) were analysed as follows:
- De-novo assembly of the GSS data from NEA12 control strain—to act as a reference genome sequence for the analysis of the NEA12$^{dh}$ Neotyphodium variant endophyte strains
- Map the GSS data sequence reads from the NEA12$^{dh}$ Neotyphodium variant endophyte strains to the NEA12 reference genome sequence
- Identify potentially duplicated regions, i.e. regions with higher than expected sequence coverage
- Identify gene sequences that may have been duplicated Analysis of GSS read depth of NEA12$^{dh}$ Neotyphodium variant endophyte strains is shown in FIG. 82. Analysis of sequence contigs that appeared to have higher than expected read depth indicates that no major duplication event has occurred (excepting whole genome events). The patterns of read depth across these contigs are not identical between strains. This suggests there are differences between the NEA12$^{dh}$ Neotyphodium variant endophyte strains and the control NEA12 strain.

Analysis of GSS sequence assemblies for the NEA12$^{dh}$ Neotyphodium variant endophyte strains and the control NEA12 strain is shown in Table 42.

TABLE 42

Analysis of GSS sequence assemblies for the NEA12$^{dh}$ Neotyphodium variant endophyte strains and the control NEA12 strain

| Strain | # contigs | N50 | Max contig | # bases |
|---|---|---|---|---|
| NEA12 | 143202 | 28621 | 181461 | 32734984 |
| NEA12dh5 | 305031 | 29444 | 191191 | 30994592 |
| NEA12dh17 | 274394 | 37802 | 209957 | 30777017 |
| NEA12dh18 | 282692 | 30717 | 177813 | 30889903 |

Independent de novo sequence assemblies were performed using parameters identical to those used in assembling the genome sequence for the control NEA12 endophyte strain. Differences in sequence assembly statistics may indicate genomic differences between strains. GSS data obtained for the NEA12$^{dh}$ Neotyphodium variant endophyte strains and used in the sequence assemblies reveal fewer bases incorporated into the sequence assembly and produce more sequence contigs. Increased numbers of smaller sequence contigs may be caused by transposon movement/replication.

Figure 83:
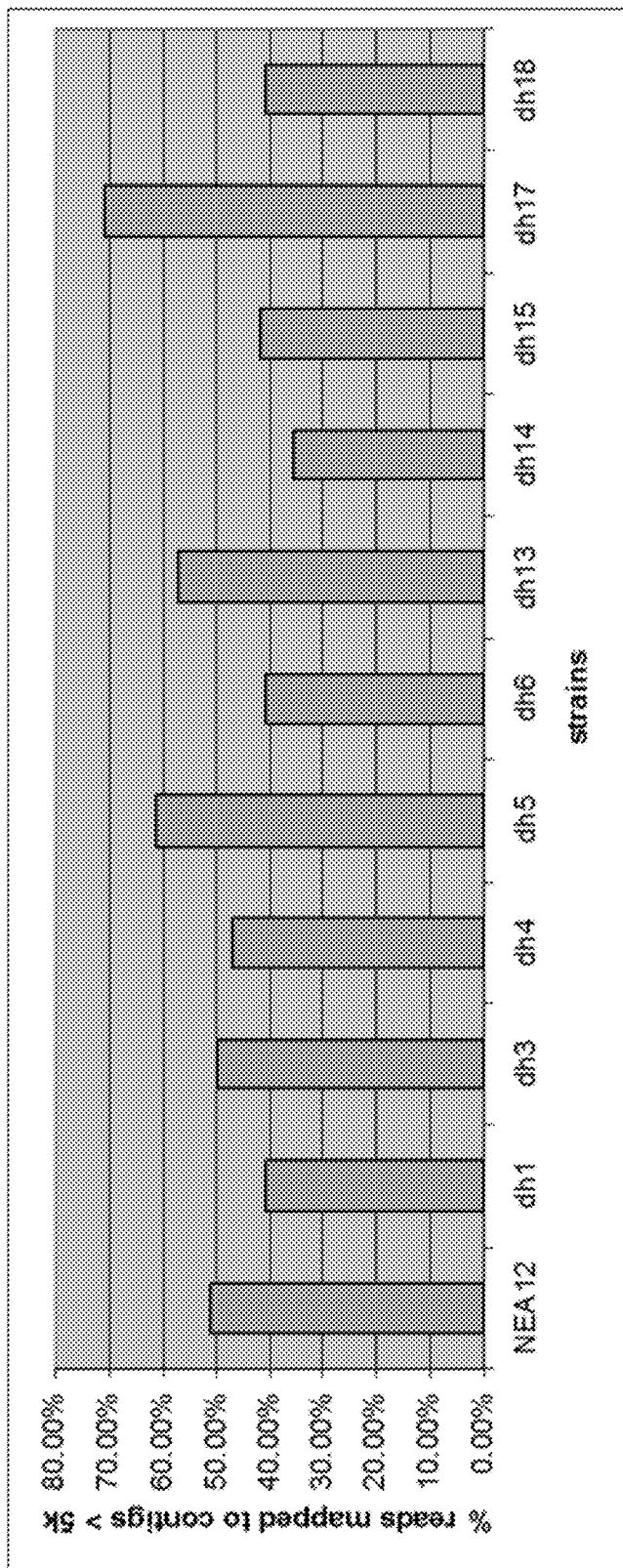
FIG. 83 shows analysis of genome survey sequencing reads mapping to NEA12 genome survey sequence assembly.

Analysis of sequence reads mapping to the NEA12 genome sequence assembly is shown in FIG. 83. While we do not wish to be restricted by theory, if the genomes were the same no difference in the number of sequence reads mapping to the reference genome sequence would be expected. NEA12$^{dh}$ Neotyphodium variant endophyte strains range from 35-70% sequence reads mapping to NEA12 sequence contigs>5 kb in size. There are differences between the genome sequences of the NEA12$^{dh}$ Neotyphodium variant endophyte strains and the control NEA12 strain.

Summary of Results on Generation and Characterisation of Novel Designer Neotyphodium Variant Endophyte Strains Through Colchicine Treatment Based Mutagenesis Sequence read depth changes were analysed in NEA12$^{dh}$ Neotyphodium variant endophyte strains compared with the control NEA12 strain. Whilst no large partial genome sequence duplication events were detected, the occurrence of full genome duplication events in the NEA12$^{dh}$ Neotyphodium variant endophyte strains cannot be excluded based on the GSS sequence analysis.

De novo sequence assemblies were independently performed on GSS data obtained from the NEA12$^{dh}$ Neotyphodium variant endophyte strains. Differences in sequence assembly statistics indicate that genomic changes were caused by the colchicine-treatment in the NEA12$^{dh}$ Neotyphodium variant endophyte strains. The number of sequence reads from NEA12$^{dh}$ Neotyphodium variant endophyte strains mapping to the NEA12 reference genome sequence varies between strains. All GSS data analyses performed on the NEA12$^{dh}$ Neotyphodium variant endophyte strains indicate genomic differences.

In summary, the following novel designer endophytes were generated by colchicine treatment of NEA12 endophytes:
- Four NEA12$^{dh}$ Neotyphodium variant endophyte strains (dh5, dh6, dh13 and dh14) with enhanced bioprotective properties (i.e. antifungal bioactivities);
- One NEA12$^{dh}$ Neotyphodium variant endophyte strain (dh17) with higher in vitro growth rate than control NEA12 strain (i.e. potentially with enhanced stability/host colonization ability);
- Ten NEA12$^{dh}$ Neotyphodium variant endophyte strains (including dh5, dh6, dh13, dh14 and dh17) and control NEA12 strain subjected to genome survey sequencing; and
- Five NEA12$^{dh}$ Neotyphodium variant endophyte strains (including dh5, dh13 and dh17) selected and subjected to isogenic inoculation in planta.

Example 24

In Planta Isogenic Inoculation in Perennial Ryegrass with NEA12$^{dh}$ Neotyphodium Variant Endophyte Strains The following NEA12$^{dh}$ Neotyphodium variant endophyte strains and control NEA12 strain were used for in planta isogenic inoculation in perennial ryegrass:

NEA12

NEA12dh5 showing higher antifungal activity than control NEA12

NEA12dh13 showing higher antifungal activity than control NEA12

NEA12dh4 showing slower in vitro growth rate than control NEA12

NEA12dh15 showing slower in vitro growth rate than control NEA12

NEA12dh17 showing faster in vitro growth rate than control NEA12

TABLE 43

Isogenic inoculation of perennial ryegrass genotypes (IMP04 and TOL03) with NEA12dh Neotyphodium variant endophyte strains. Numbers indicate number of perennial ryegrass plants of the two genotypes subjected to isogenic inoculation with the different NEA12dh *Neotyphodium* variant endophyte strains.

| Plant Genotype | NEA12 dh4 | NEA12 dh5 | NEA12 dh13 | NEA12 dh15 | NEA12 dh17 | NEA12 |
|---|---|---|---|---|---|---|
| IMP04 | 30 | 30 | 30 | 30 | 32 | 30 |
| TOL03 | 25 | 30 | 30 | 20 | 30 | 20 |

Example 25

Generation of Designer N *Lolii* Genotypes by X-Ray Mutagenesis

The generation of designer *Neotyphodium* endophytes genotypes by X-ray mutagenesis offers the opportunity to create novel endophyte variant strains with enhanced properties, such as enhanced stability in grass hosts, broader host compatibility as well as improved toxin profiles e.g. following elimination of the production of the detrimental alkaloid lolitrem B in the highly stable and broadly compatible ST endophyte.

Such an novel designer endophyte would be advantageous over existing commercial endophytes, such as AR1 and AR37, as it would be highly stable and broadly compatible and with optimal toxin profile.

Figure 84:
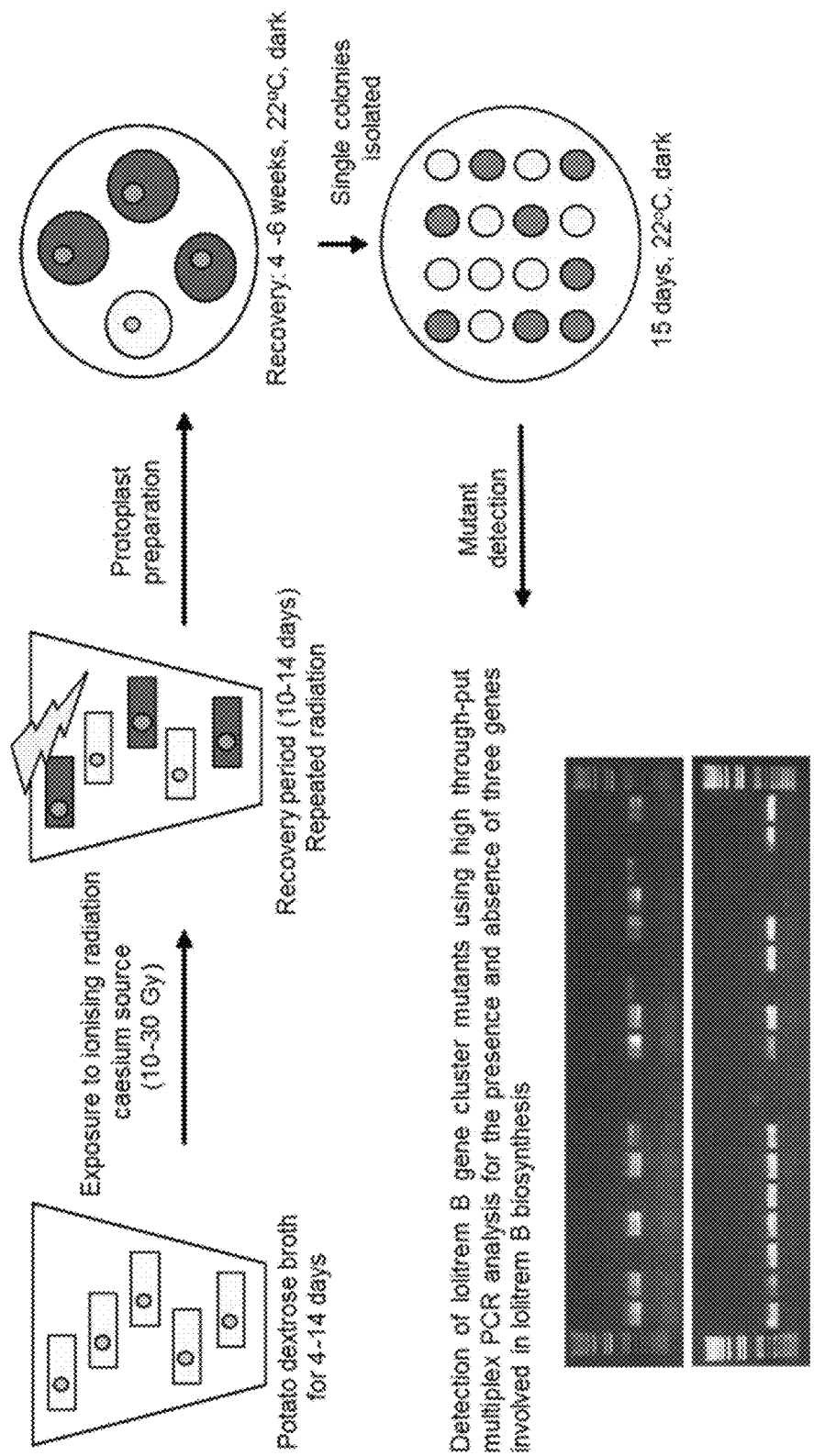
FIG. 84 shows experimental work flow for X-ray mutagenesis.

FIG. 84 shows an experimental work flow for X-ray mutagenesis of endophyte strains.

Figure 85:
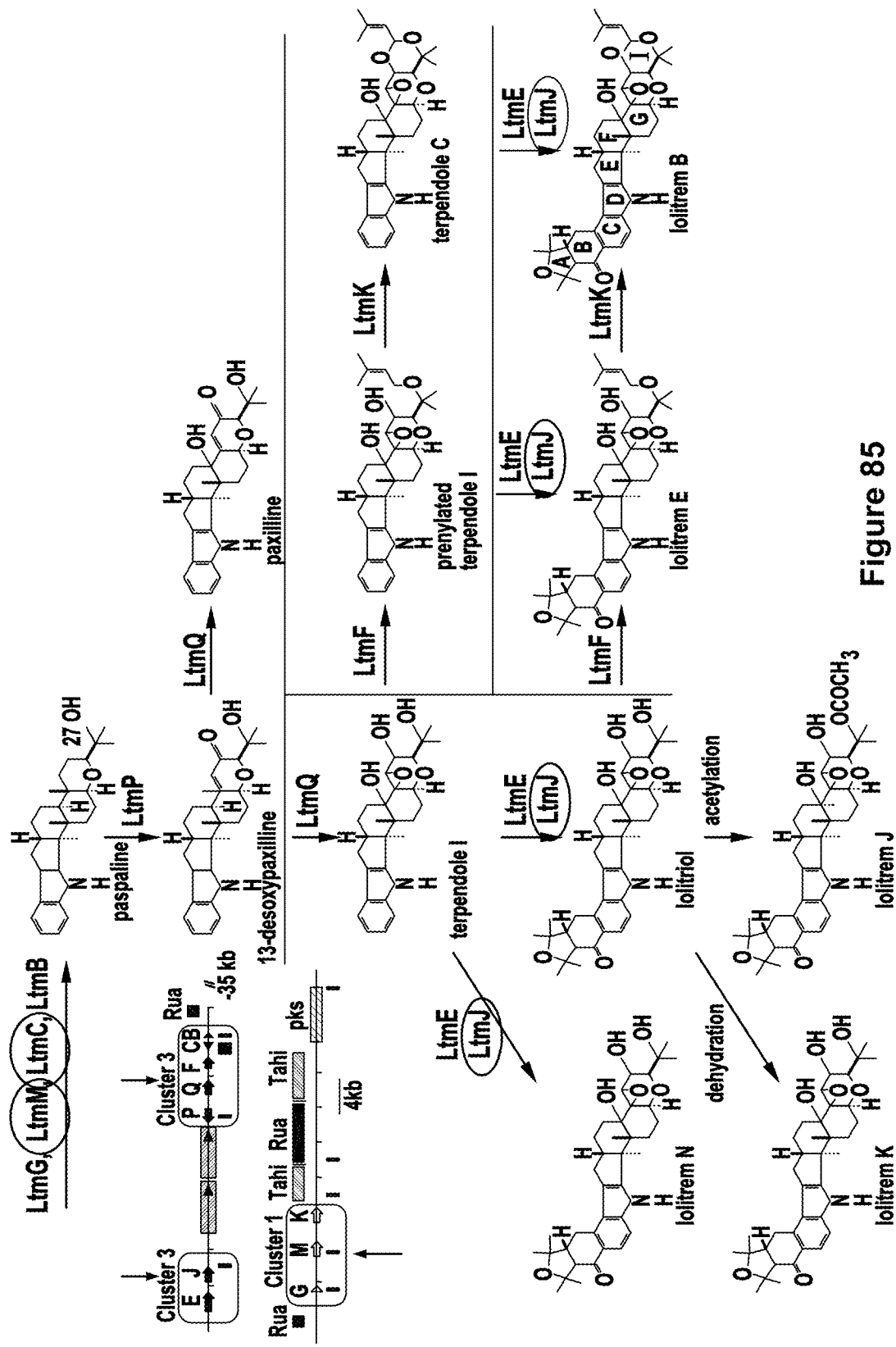
FIG. 85 shows the indole-diterpene biosynthetic pathway of *Neotyphodium* endophytes.

FIG. 85 shows the indole-diterpene biosynthetic pathway. Lolitrem B is the major toxin that causes ryegrass staggers, a disease of grazing animals. Ten genes in 3 gene clusters are required for lolitrem biosynthesis. We focused initial analysis on 3 Ltm genes, one from each gene cluster. Optimised multiplex PCR analysis was designed and implemented.

Example 26

Screening of X-Ray Irradiated *N. lolii* Strains

In a preliminary primary screen >5,000 colonies of X-ray irradiated *N. lolii*—established as an initial resource of novel variation of *N. lolii* endoophytes induced through X-ray mutagenesis and representing a mutagenised *N. lolii* endophyte strain collection—of were screened by multiplex PCR analysis for the presence of targeted Ltm genes leading to a preliminary identification of ~140 putative lolitrem B gene cluster PCR-negative colonies (~2.5% of 5,000 colonies screened). In a secondary screen high quality DNA was extracted (140 liquid cultures) and PCR analysis conducted. This identified 2 putative deletion mutants for one of the lolitrem B genes (ltm J).

TABLE 44

Putative X-ray irradiation-induced ltm gene deletion mutants of *N. lolii* derived from irradiation with 30 Gy dose.

| Dose (Gy) | Colony | ltm J | ltm C | ltm M |
|---|---|---|---|---|
| 30 Gy (1 irradiation) | 139-6 | ■ | ■ | ■ |
| 30 Gy (1 irradiation) | 145-15 | ■ | | |

The colony number represents the unique identifier of the putative X-ray irradiation-induced ltm gene deletion mutant (i.e. 139-6 and 145-15).
Black represents PCR-negative result for respective ltm gene analysis,
white represents PCR-positive result for respective ltm gene analysis.

Example 27

Antifungal Bioassays of Designer X-Ray Irradiated *N. lolii* Variant Strains

There were eight X-ray irradiated *N. lolii* variant strains (i.e. X-ray mutagenesis derived variant strains 1-35, 4-7, 7-22, 7-47, 123-20, 124-6, 139-6, 144-16 and 145-15) and one control *N. lolii* strain (i.e. ST endophyte strain).

Five fungal pathogens (causing a range of fungal diseases and infecting a range of different plant hosts) were included in antifungal bioassays used to analyse the X-ray irradiated *N. lolii* variant strains, as follows:
 *Bipolaris portulacae*
 *Colletotrichum graminicola*
 *Drechslera brizae*
 *Phoma sorghina*
 *Rhizoctonia cerealis*
No significant difference in antifungal activities of X-ray irradiated *N. lolii* variant strains tested was observed compared to the spectrum of antifungal activities observed for the control ST endophyte strain.

Example 28

In Vitro Growth of Designer X-Ray Irradiated *N. lolii* Variant Strains

Figure 86:
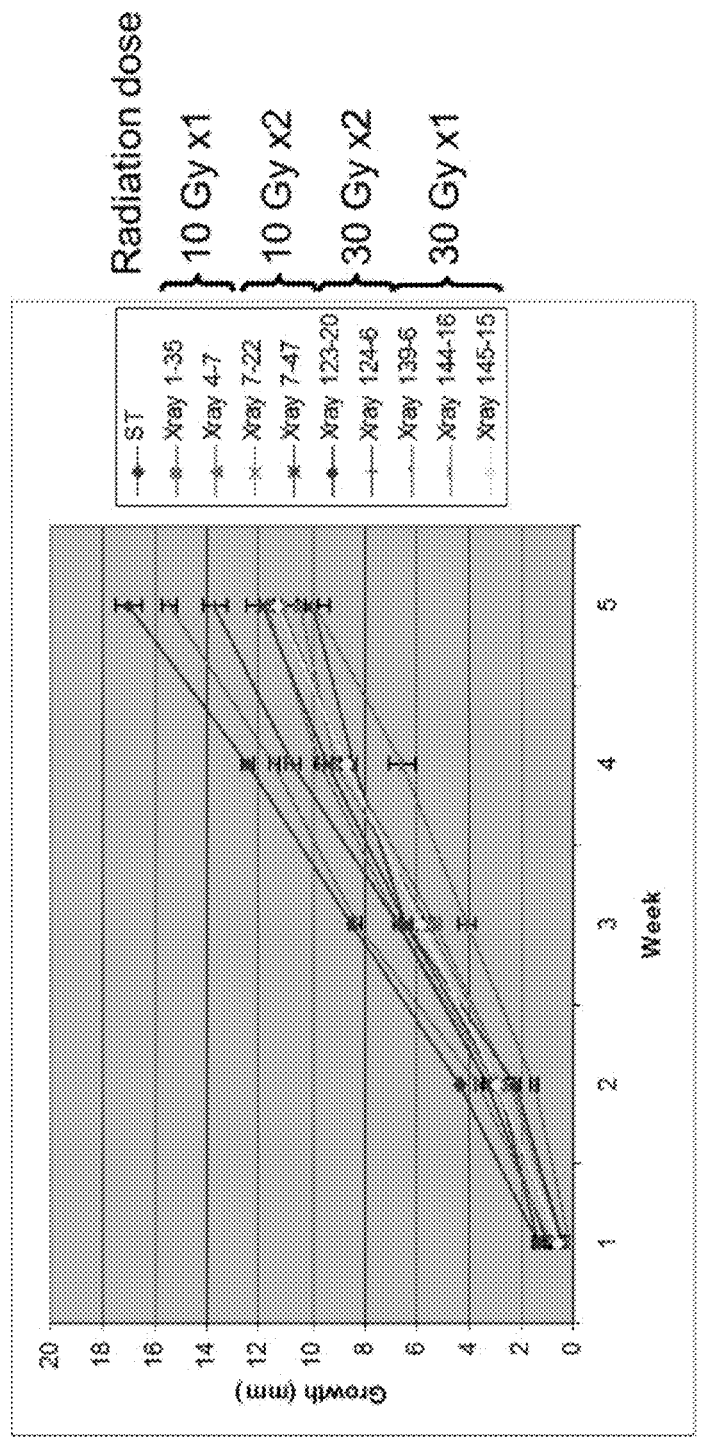
FIG. 86 shows in vitro growth of X-ray irradiated *Neotyphodium* endophyte strains.
Figure 87:
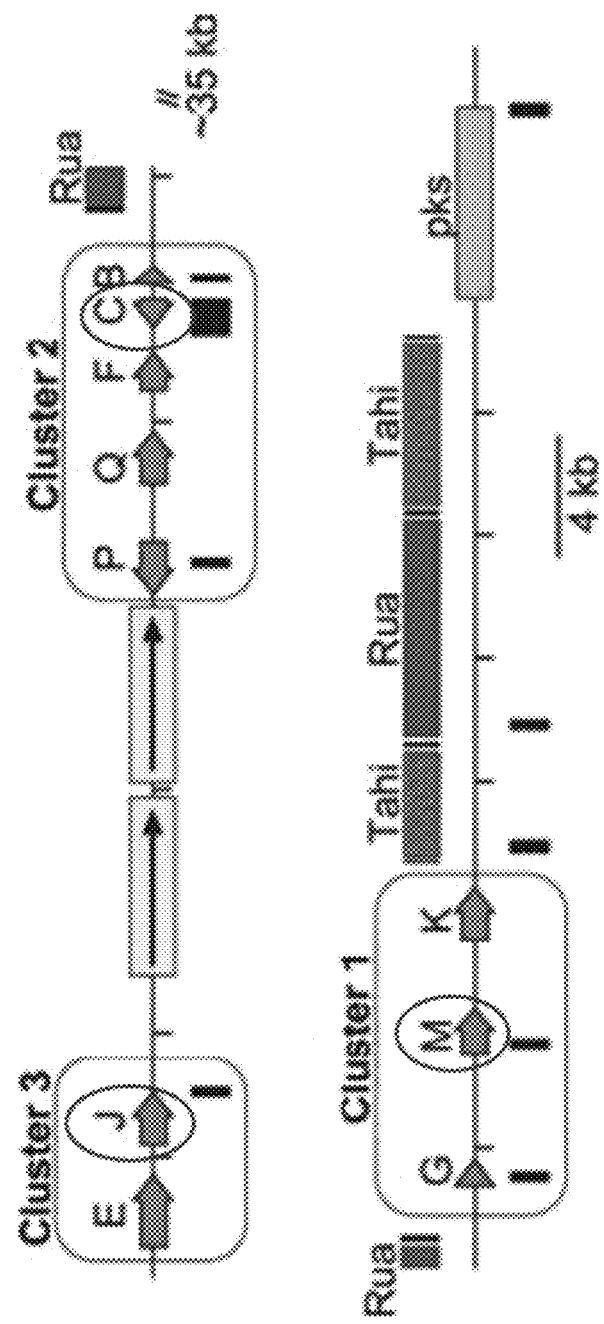
FIG. 87 shows Itm gene clusters of *Neotyphodium* endophytes.
Figure 88:
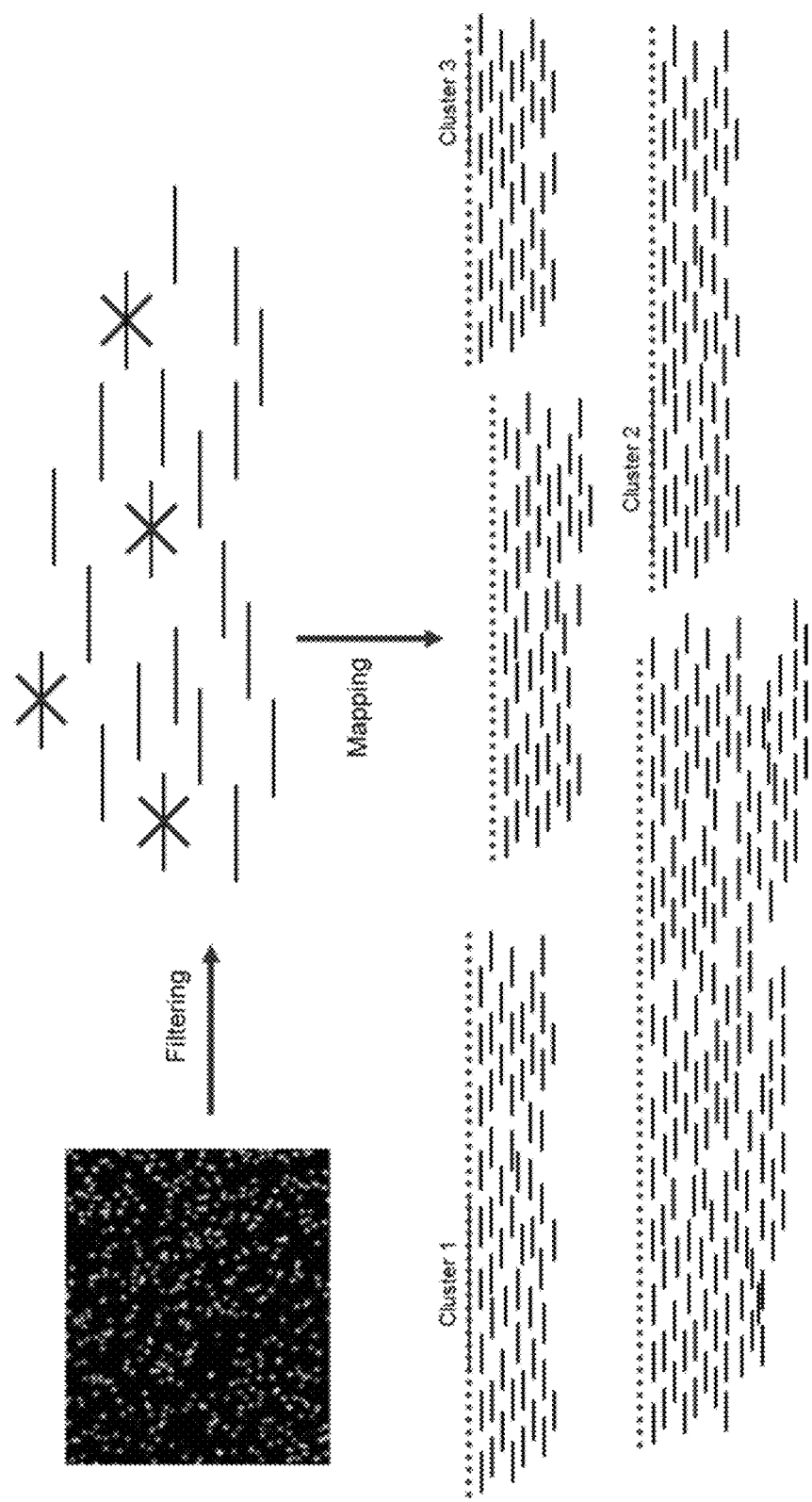
FIG. 88 shows determination of genome sequence variation in X-ray irradiated *Neotyphodium* endophyte strains.
Figure 89:
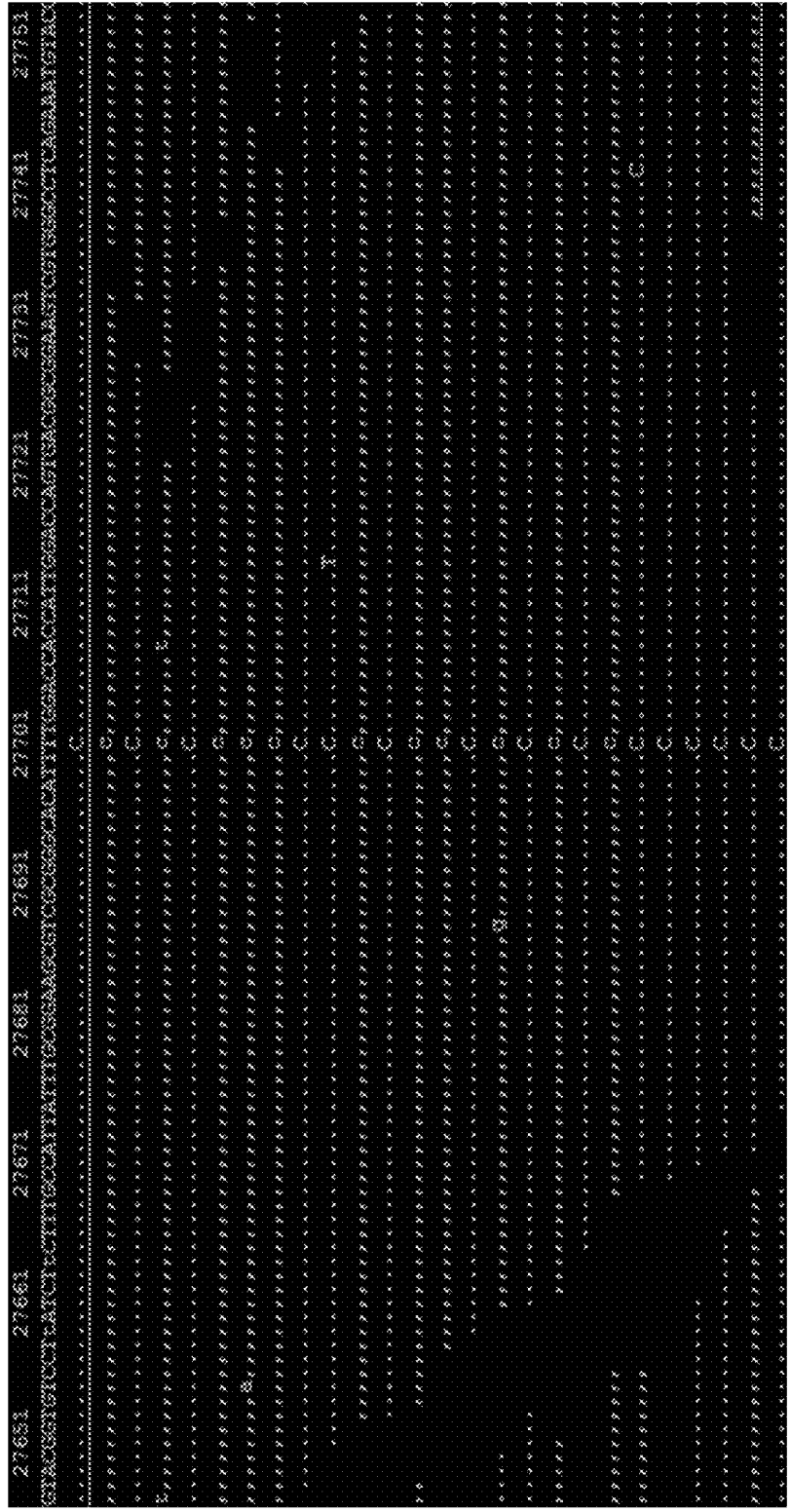
FIG. 89 shows single nucleotide polymorphisms (SNPs) in genome sequences of X-ray irradiated *Neotyphodium* endophyte strains. (SEQ IS NOs: 22-47)
Figure 90:
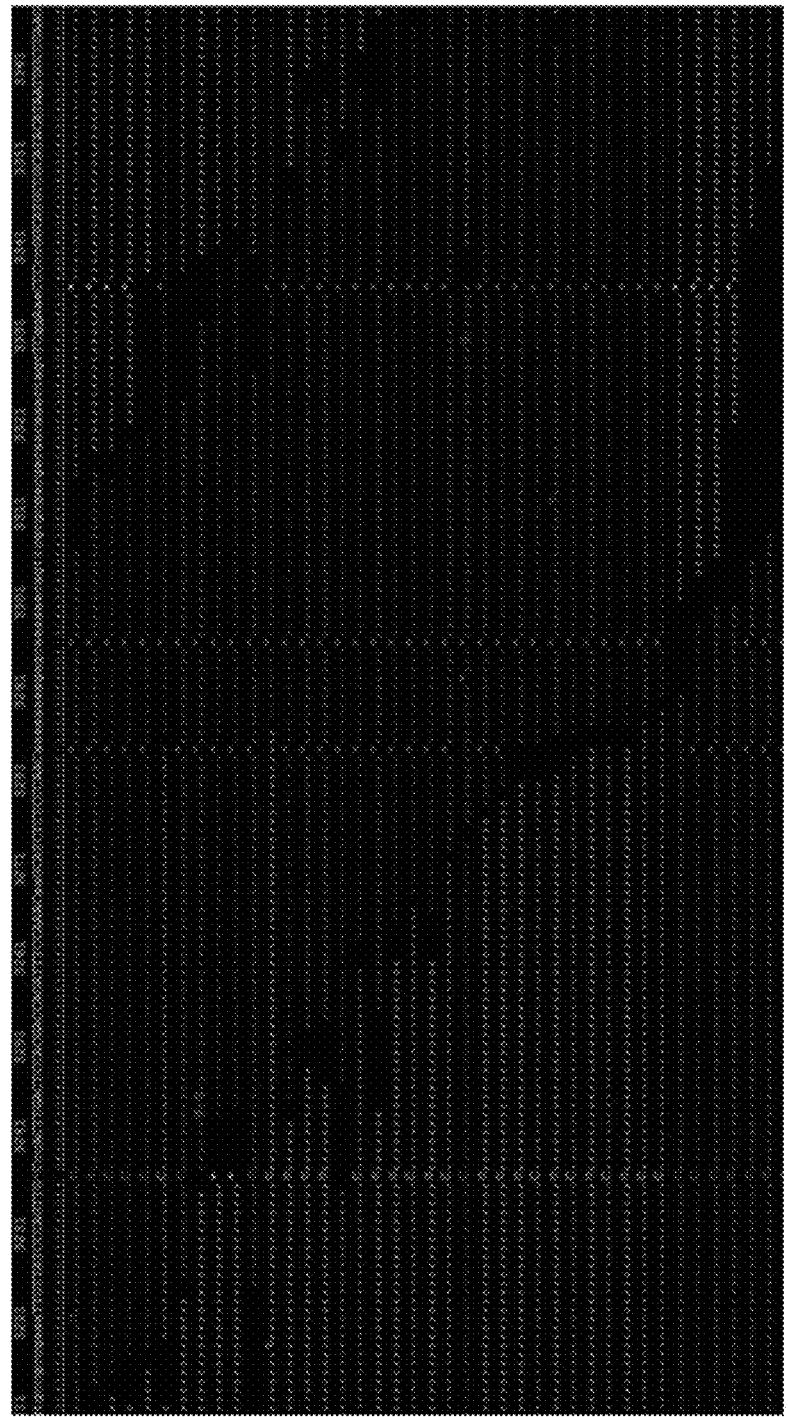
FIG. 90 shows small insertions/deletions (INDELs) in genome sequences of X-ray irradiated *Neotyphodium* endophyte strains. (SEQ IS NOs: 22-47)
Figure 92:
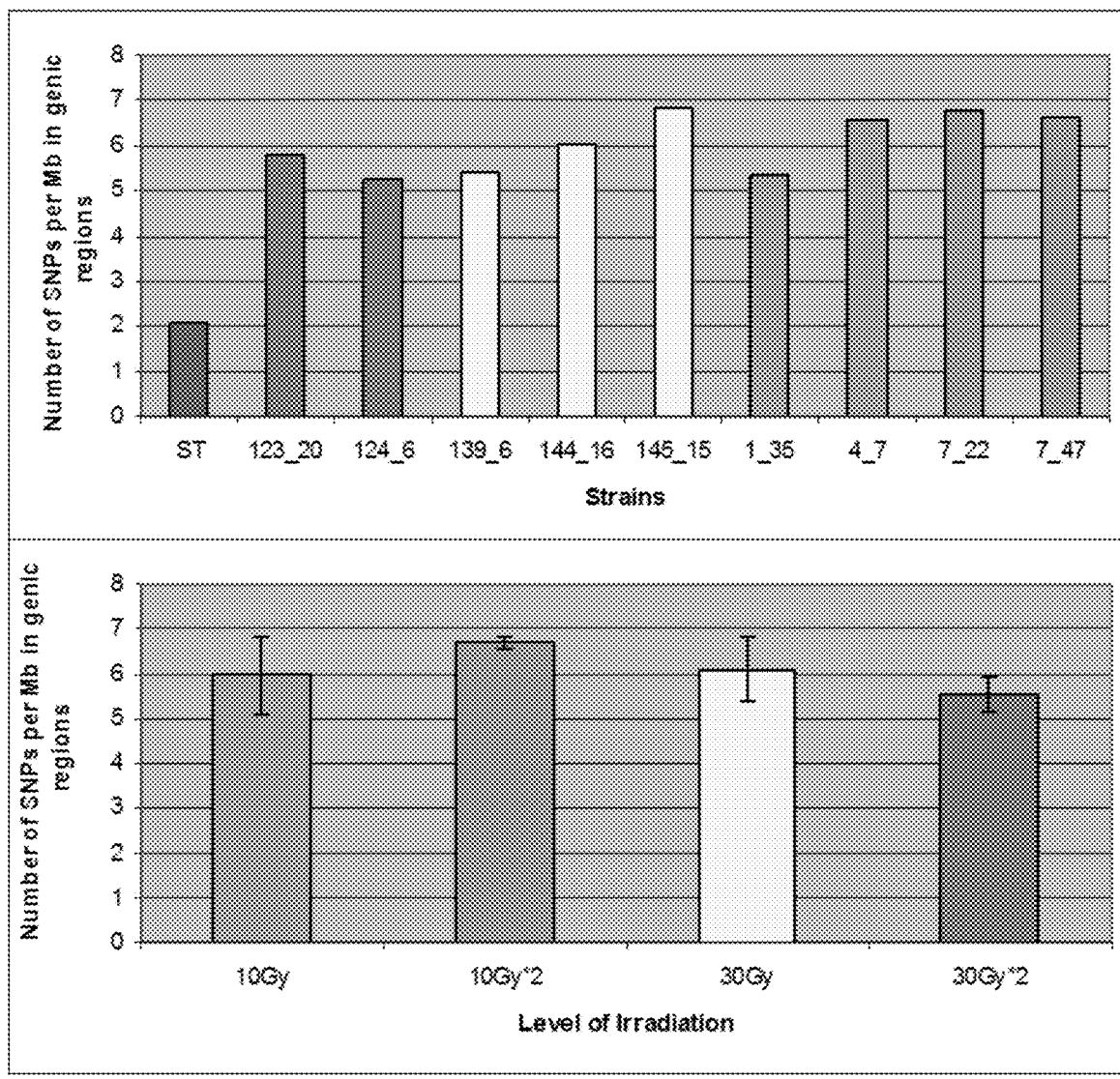
FIG. 92 shows numbers of SNPs in genic regions of genome sequences of X-ray irradiated *Neotyphodium* endophyte strains.
Figure 93:
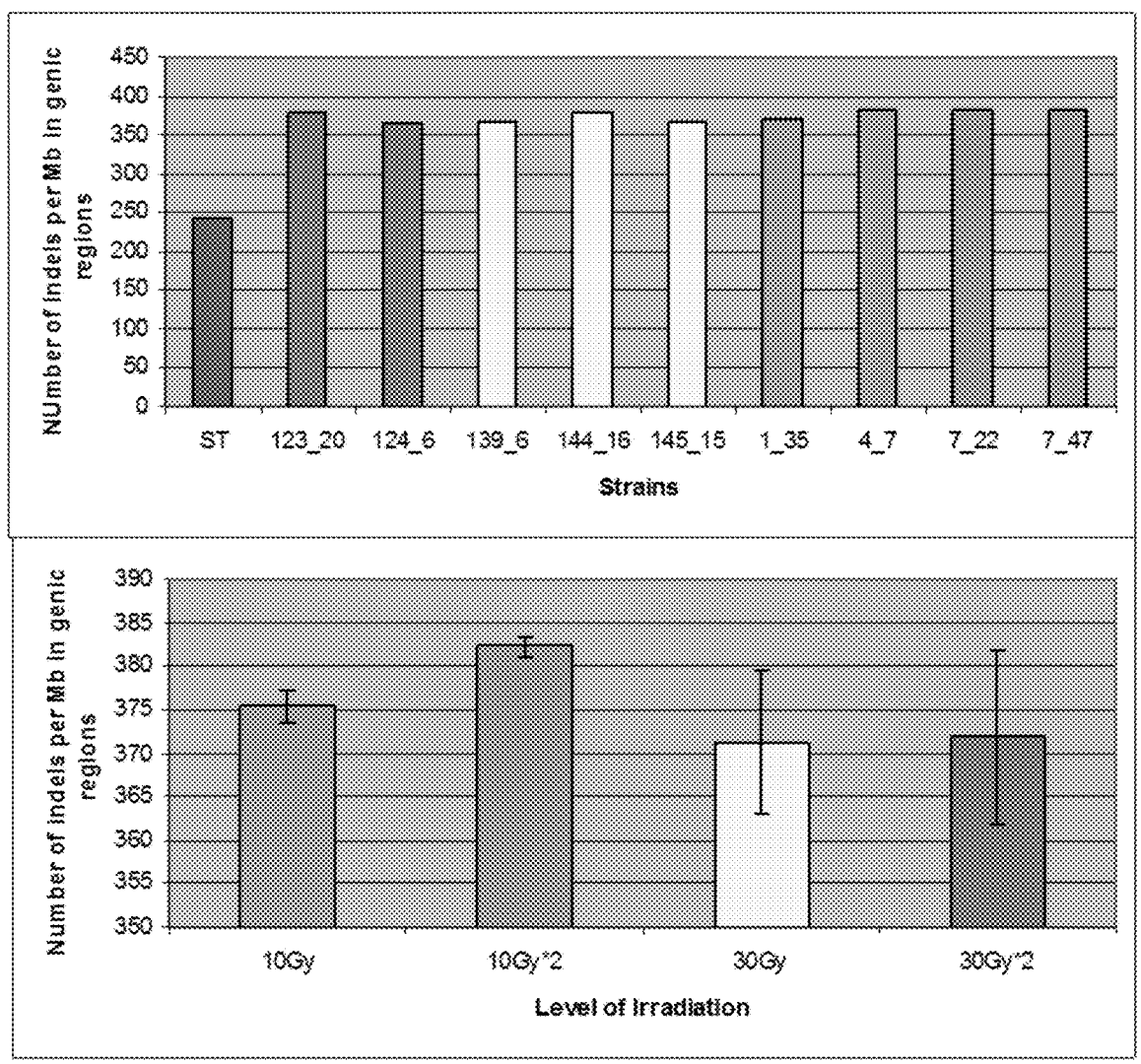
FIG. 93 shows numbers of INDELs in genic regions of genome sequences of X-ray irradiated *Neotyphodium* endophyte strains.
Figure 94:
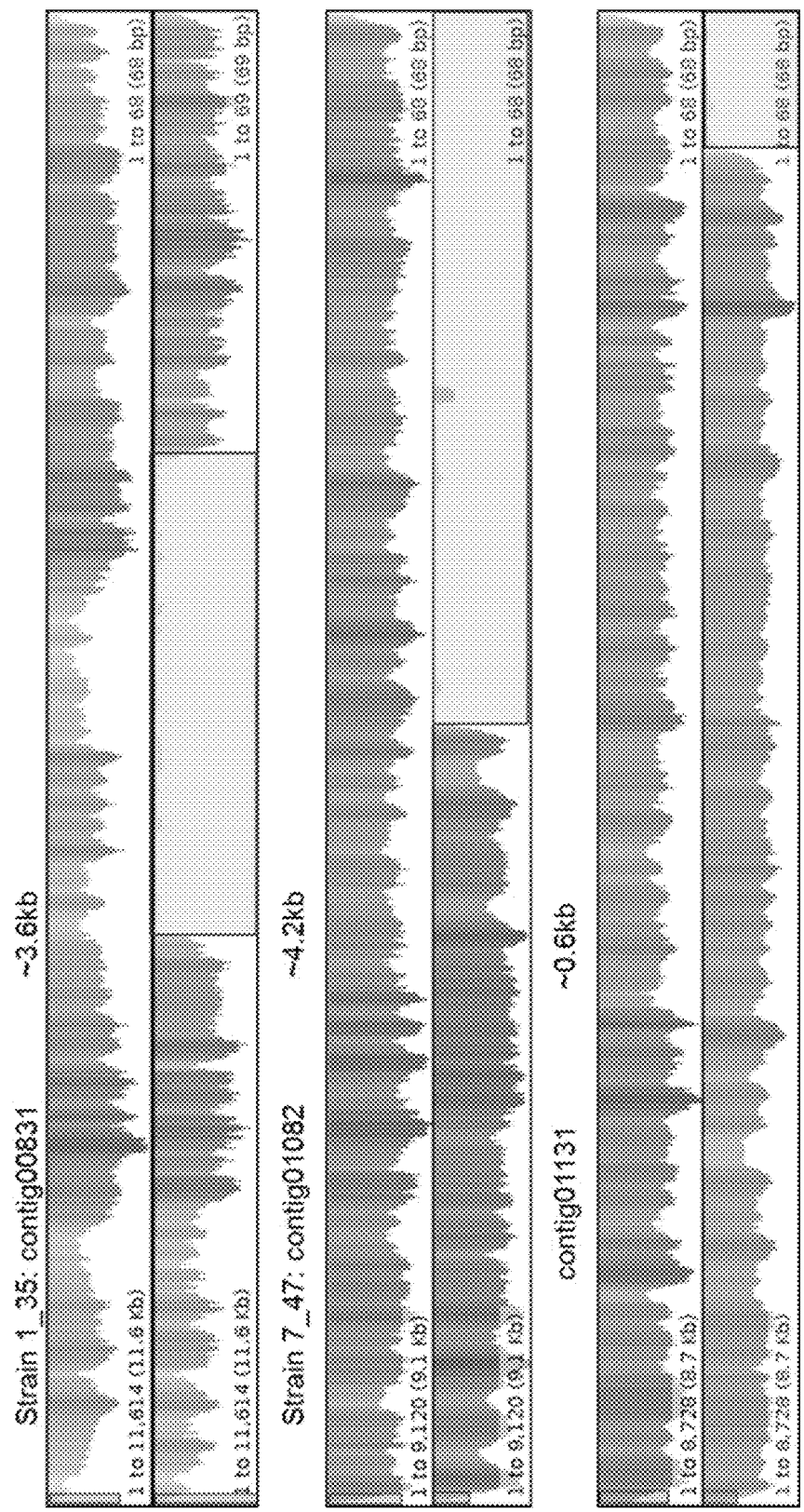
FIG. 94 shows the spectrum of genome sequence changes (deletions) in genome sequences of X-ray irradiated *Neotyphodium* endophyte strains.

Results from the analysis of in vitro growth rate of designer X-ray irradiated *N. lolii* variant strains are shown in FIG. 86, with a statistical analysis of in vitro growth undertaken at week 5 for the X-irradiated *N. lolii* variant strains compared to the control ST strain, revealing significant differences in in vitro growth rates as follows: p<0.05* (for X-irradiated *N. lolii* variant strain 139-6) p<0.01** (for all other mutants)

Example 29

Genome Survey Sequencing of Designer X-Ray Irradiated *N. lolii* Variant Strains Eight X-ray irradiated *N. lolii* ST variant strains and corresponding control ST strain were subjected to genome survey sequencing (GSS), leading to 46-fold to 79-fold genome sequence coverage for the different strains as shown in Table 45.

TABLE 45

Genome sequence coverage obtained in genome survey sequencing for for 8 X-ray irradiated *N. lolii* ST variant strains and corresponding control ST strain

| Strain | Description | Coverage |
|---|---|---|
| ST | ST | 23× |
| 139-6 | ST irradiated | 61× |
| 145-15 | ST irradiated | 52× |
| 144-16 | ST irradiated | 46× |
| 1_35 | ST irradiated | 79× |
| 4_7 | ST irradiated | 46× |
| 7_22 | ST irradiated | 53× |
| 7_47 | ST irradiated | 38× |
| 123-20 | ST irradiated | 54× |
| 124-6 | ST irradiated | 75× |

Example 30

Detecting Genome Sequence Variation in Designer X-Ray Irradiated *N. lolii* Variant Strains Results from the analysis to detect genome sequence variation in X-ray irradiated *N. lolii* variant strains are shown in FIG. 88. Corresponding results on the detection of single nucleotide polymorphisms (SNPs) are shown in FIG. 89 and results on the detection of small insertions/deletions (INDELs) are shown in FIG. 90. Differences in sequence read depth and pair insert size in X-ray irradiated *N. lolii* variant deletion mutant strains are shown in FIG. 91.

Results on sequence analysis for Ltm gene clusters are shown in FIG. 87. No deletions, large or small, were found in the coding or regulatory sequences of Itm gene clusters. No SNPs, insertions or translocations were found in the coding or regulatory sequences of Itm gene clusters.

Example 31

Spectrum of Genome Sequence Changes Detected in the X-Ray Irradiated *N. lolii* Variant Strains FIG. 92 shows numbers of SNPs detected in genic regions of X-ray irradiated *N. lolii* variant deletion mutant strains. There are large differences in the number of SNPs detected in the X-ray irradiated *N. lolii* variant deletion mutant strains and compared to the control ST strain. All X-ray irradiated *N. lolii* variant deletion mutant strains have over double the number of SNPs per Mb across genic regions compared to the control ST strain. X-ray irradiated *N. lolii* variant deletion mutant strains have on average 6 SNPs per Mb, where the control ST strain has 2 SNPs per Mb.

FIG. 93 shows numbers of INDELs in genic regions of X-ray irradiated *N. lolii* variant deletion mutant strains. All X-ray irradiated *N. lolii* variant deletion mutant strains contain more indels in genic regions than the control ST strain. The difference in indel numbers between the X-ray irradiated *N. lolii* variant deletion mutant strains and the control ST strain is on average 134 indels per Mb. When grouped by irradiation treatment (i.e. irradiation dose applied and number of repeat irradiations) there appears to be a peak in number of indels at 10Gy*2 treatment, consistent with the results obtained in the SNP detection analysis.

FIG. 94 shows the spectrum of genome sequence changes in the form of deletions detected in X-ray irradiated *N. lolii* variant deletion mutant strains.

Table 46 shows examples of some of these genome sequence deletions detected in X-ray irradiated *N. lolii* variant deletion mutant strains.

TABLE 46

Deletions detected in genome sequences of X-ray irradiated *N. lolii* variant deletion mutant strains.

| Strain | Radiation Treatment | Deletion |
|---|---|---|
| 123_20 | 30Gy*2 | Contig00915 (268 bp) |
| 124_6 | 30Gy*2 | Partial duplication |
| 139_6 | 30Gy | Partial duplication |
| 144_16 | 30Gy | |
| 145_15 | 30Gy | Partial duplication |
| 1_35 | 10Gy | Contig00831 (3.6 kb) |
| 4_7 | 10Gy | |
| 7_22 | 10Gy*2 | |
| 7_47 | 10Gy*2 | Contig01131 (0.6 kb), contig01082 (4.2 kb), contig02985 (1 kb), contig02725 (83 bp), contig01095 (130 bp) |

Bold indicates deletions confirmed by changes in sequence read coverage.
The remainder are potential transposon deletions.

The X-ray irradiated *N. lolii* variant deletion mutant strain #7_47, which was generated following two X-irradiation treatments at 10 Gy dose (10Gy*2) of *N. lolii* ST endophyte, had the greatest number of large deletions.

Example 32

Annotation of Deleted Sequences in the Genomes of X-Ray Irradiated *N. lolii* Variant Deletion Mutant Strains X-Ray Irradiated *N. lolii* Variant Mutant Strain 1_35:

For the X-ray irradiated *N. lolii* variant mutant strain 1_35 the following deleted sequences in ST454Contig00831 contig with a ~4,400-8,000 bp length was detected, with this genome sequence region containing the following two predicted genes:

ST454contig00831_AUGUSTUS_gene_3318:6018 (847 letters)

1) ref |XP_386347.1| hypothetical protein FG06171.1 [*Gibberella* 660x0.0 gb|EAW12630.1| DUF500 domain protein [*Aspergillus* NRRL 1]; 253×9e-66, and ST454contig00831_AUGUSTUS_gene_3958:4728 (183 letters); and 2) gb|EAW13545.1| 2,3-cyclic-nucleotide 2-phosphodiesterase [*Aspergillus* 32×2.4

X-Ray Irradiated *N. lolii* Variant Mutant Strain 7_47:

For the X-ray irradiated *N. lolii* variant mutant strain 7_47 the following deleted sequences in ST454Contig01082, ST454Contig01131 and ST454Contig02985, with these genome sequence regions containing no predicted genes:

Query=ST454contig01082 length=9120 numreads=287 gb|AAA21442.1| putative pol polyprotein [*Magnaporthe grisea*] 145 1 e-32

Query=ST454contig02985 length=2414 numreads=99 gb|AAA21442.1| putative pol polyprotein [*Magnaporthe grisea*] 92 2e-17

Example 33

Figure 95:
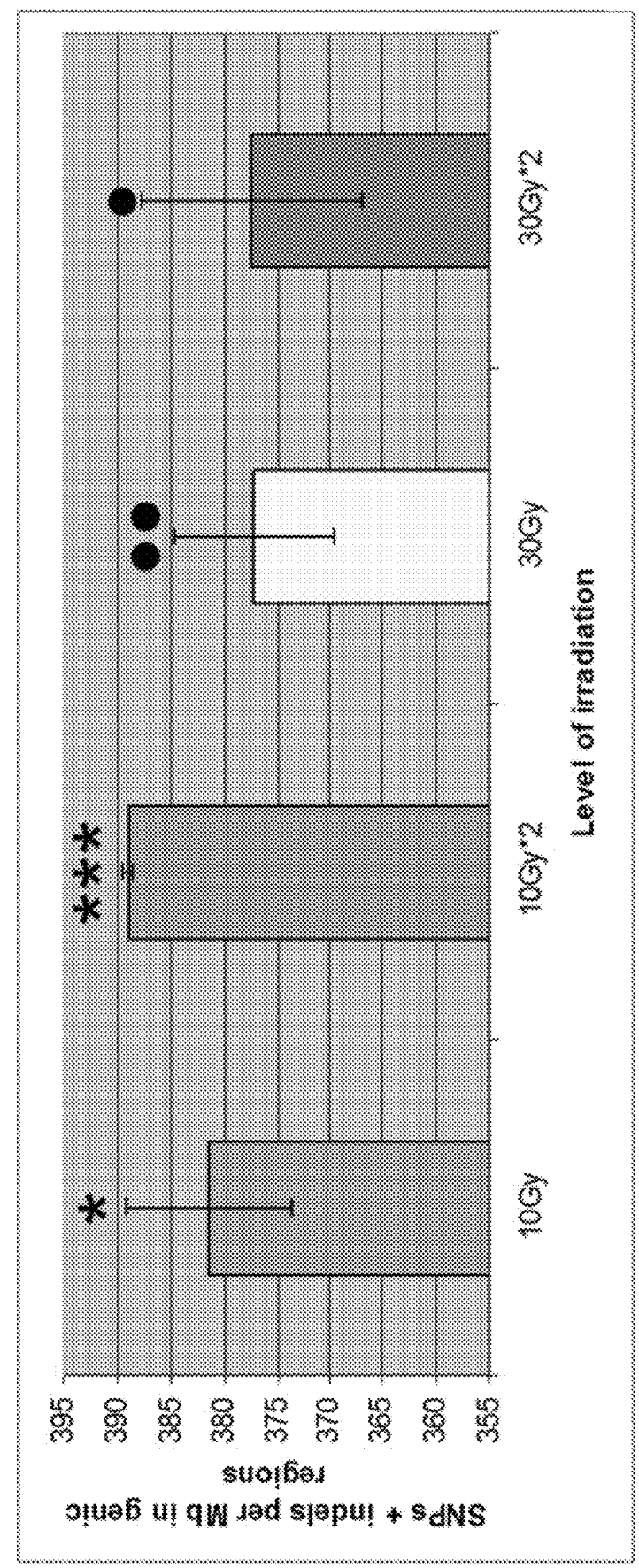
FIG. 95 shows mutagenesis index of X-ray irradiated strains based on number of genome sequence changes observed in genome sequences of X-ray irradiated *Neotyphodium* endophyte strains.

Mutagenesis Index of X-Ray Irradiated *N. lolii* Variant Deletion Mutant Strains FIG. 95 shows SNPs and Indels per Mb in genic regions of X-ray irradiated *N. lolii* variant deletion mutant strains derived from X-ray irradiation of *N. lolii* at different levels of irradiation. Strain 1_35 has a 3.6 kb deletion; Strain 7_47 has 3 deletions (4.2 kb, 1 kb, 0.6 kb in length). Strain 124_6 has a partial duplication. Strains 139_6 and 145_15 have partial duplications.

Given that ST endophyte has approximately 443.5 genes per Mb, using 10Gy*2 treatment, the expected rate of SNP/INDEL occurrence is 0.33 per gene in the genome.

Summary

X-ray irradiated *N. lolii* variant deletion mutant strains were analysed for many types of genome sequence variation i.e. deletions, SNPs, INDELs, inversions and translocations. SNPs, INDELs, deletions and duplications were identified in the genome survey sequences of X-ray irradiated *N. lolii* variant deletion mutant strains. There was an apparent peak in number of SNPs and INDELs in X-ray irradiated *N. lolii* variant deletion mutant strains recovered from administering 10Gy*2 X-ray irradiation treatment to *N. lolii* ST endophyte. The X-ray irradiated *N. lolii* variant deletion mutant strain 7_47 had 3 large deletions. It was demonstrated that this mutagenesis method based on X-ray irradiation can be used to create novel designer *Neotyphodium* endophyte strains, and enabled:

- 5,000 X-ray irradiated *N. lolii* variant endophyte strains derived from X-ray irradiation of ST *N. lolii* endophyte were screened;
- 140 putative X-ray irradiated *N. lolii* variant endophyte mutant strains were identified;
- 9 X-ray irradiated *N. lolii* variant endophyte mutant strains were subjected to antifungal bioassays;
- 9 X-ray X-ray irradiated *N. lolii* variant endophyte mutant strains were subjected to in vitro growth assays;
- 9 X-ray irradiated *N. lolii* variant endophyte mutant strains were subjected to genome survey sequencing;
- 2 X-ray irradiated N. 10111 variant endophyte mutant strains with gene deletions (1_35 and 7_47) were identified; and
- 3 X-ray irradiated N. 10111 variant endophyte mutant strains with gene duplications (124_6, 139_6 and 145_15) were identified.

Example 34

In Planta Isogenic Inoculation in Perennial Ryegrass with X-Ray Irradiated *N. lolii* Variant Endophyte Mutant Strains

TABLE 47

Isogenic inoculation of perennial ryegrass genotypes (IMP04 and TOL03) with X-ray irradiated *N. lolii* variant endophyte mutant strains. Numbers indicate number of perennial ryegrass plants of the two genotypes subjected to isogenic inoculation with the different X-ray irradiated *N. lolii* variant endophyte mutant strains (i.e. ST-IRM 139-6, ST-IRM 145-15, ST-IRM 144-16, ST-IRM 1-35 and ST-IRM 7-47) and control ST endophyte strain.

| Plant Genotype | ST-IRM 139-6 | ST-IRM 145-15 | ST-IRM 144-16 | ST-IRM 1-35 | ST-IRM 7-47 | ST |
|---|---|---|---|---|---|---|
| IMP04 | 30 | 25 | 30 | 30 | 30 | 25 |
| TOL03 | 25 | 0 | 25 | 30 | 30 | 20 |

Example 35

Figure 96:
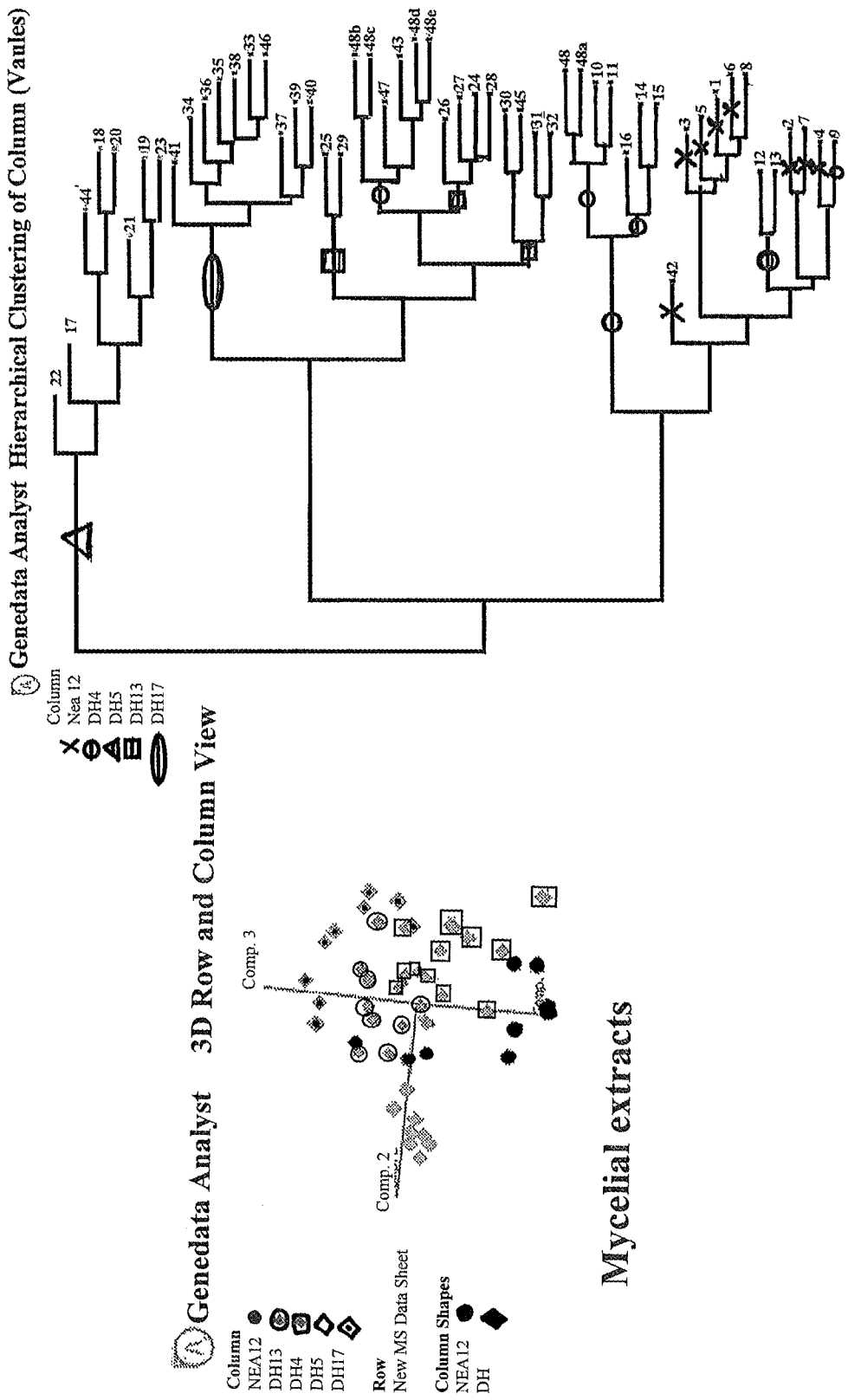
FIG. 96 shows metabolic profiling of NEA12$^{dh}$ *Neotyphodium* endophyte strains.

Metabolic Profiling of Colchicine Treatment-Derived NEA12dh and X-Ray Irradiation-Derived *Neotyphodium* Variant Endophyte Strains Results from metabolic profiling of colchicine treatment derived NEA12dh endophyte variant strains is shown in FIG. 96.

Figure 97:
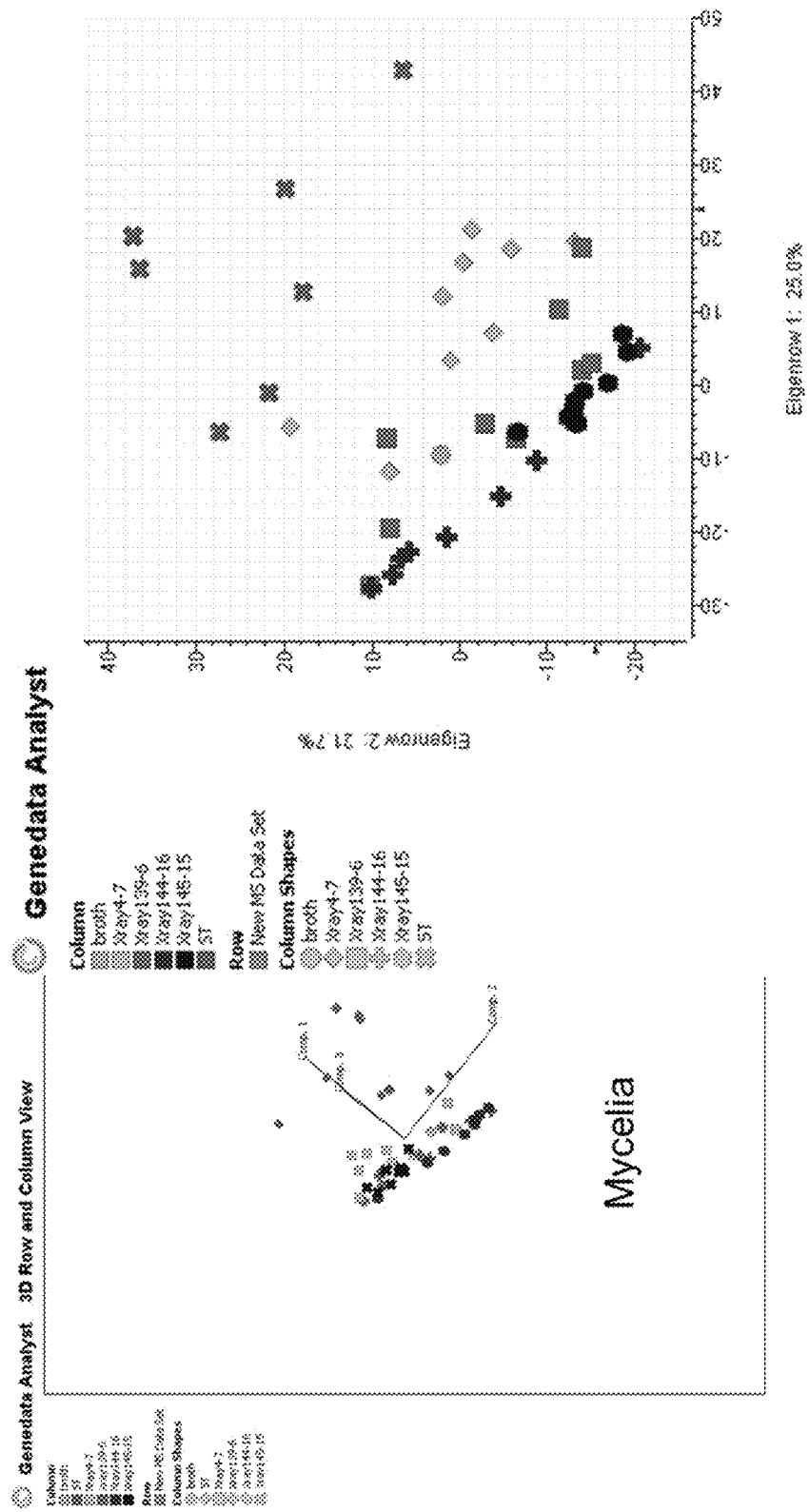
FIG. 97 shows metabolic profiling of X-ray irradiated *Neotyphodium* endophyte strains.

Results from metabolic profiling of X-ray irradiation treatment derived *N. lolii* ST endophyte variant strains is shown in FIG. 97.

The following endophytes were grown on PDB for 3 weeks:

Control *N. lolii* ST endophyte strain

X-ray irradiation treatment derived *N. lolii* ST endophyte variant strain 4-7

X-ray irradiation treatment derived *N. lolii* ST endophyte variant strain 139-6

X-ray irradiation treatment derived *N. lolii* ST endophyte variant strain 144-16

X-ray irradiation treatment derived *N. lolii* ST endophyte variant strain 145-15 and subjected to metabolic profiling using LCMS on corresponding

1. Liquid filtrate
2. Mycelial extract

The X-ray irradiation treatment derived *N. lolii* ST endophyte variant strains could be readily distinguished from control *N. lolii* ST strain using mycelia extracts or filtrates alone.

It will be understood that the invention disclosed and defined in this specification extends to all alternative combinations of two or more of the individual features mentioned or evident from the text or drawings. All of these different combinations constitute various alternative aspects of the invention.

REFERENCES

Bouton, J. H., G. C. M. Latch, N. S. Hill, C. S. Hoveland, M. A. McCann, R. H. Watson, J. A. Parish, L. L. Hawkins and F. N. Thompson (2002) Agronomy Journal 94(3): 567 574.

Latch, G. C. M, Christensen, M. J, Tapper, B. A, Easton, H. S, Hume, D. E, Fletcher, L. R. (2000) U.S. Pat. No. 6,111,170 and references therein.

Li, X and Zhang, Y., (2002) Comparative and Functional Genomics 3: 158-160.

Tapper, B. A, Cooper, B. M, Easton, H. S, Fletcher, L. R, Hume, D. E, Lane, G. A, Latch, G. C. M, Pennell, C. G. L, Popay, A. J, Christensen, M. J. (2004) International Patent Application No. WO 2004/106487 and references therein.

Van Zijll de Jong E, Guthridge K M, Spangenberg G C, Forster J W (2003) Genome 46 (2): 277-290

Young, C. A., Bryant, M. K., Christensen, M. J., Tapper, B. A., Bryan, G. T., Scott, B. (2005) Molecular Genetics and Genomics, 274: 13-39.

The invention claimed is:

1. A grass plant stably infected with a substantially purified or isolated fungal endophyte, said endophyte being non-endogenous to the grass plant and the grass plant producing a desired toxin profile, wherein the stably infected grass plant produces significantly less toxic alkaloids compared with a control plant stably infected with a control endophyte, and/or significantly more alkaloids conferring beneficial properties compared with a control plant stably infected with a control endophyte, wherein said control endophyte is standard toxic endophyte, wherein the grass plant is a member of the genus *Lolium* or the genus *Festuca*, and wherein said endophyte is selected from the group consisting of National Measurement Institute Accession Nos. V10/000001, V10/000002, V10/000003, V10/000004, V10/030284, V10/030285, V12/001413, V12/001414, V12/001415, V12/001416, V12/001417, V12/001418 and V12/001419.

2. The plant according to claim 1, wherein the beneficial alkaloids in the total amount include a beneficial alkaloid selected from the group consisting of peramine, N-formylloline, N-acetylloline and norloline.

3. The plant according to claim 2, wherein toxic alkaloids are produced and include ergovaline.

4. The plant according to claim 3, wherein said endophyte does not produce lolitrem B toxins.

5. The plant according to claim 1, wherein said endophyte is from the genus *Neotyphodium*.

6. The plant according to claim 1, wherein said toxic alkaloids are present in an amount less than 1 µg/g dry weight.

7. The plant according to claim 6, wherein said beneficial alkaloids are present in an amount of between 10 and 50 µg/g dry weight.

8. The plant according to claim 1, wherein said beneficial alkaloids are present in an amount of between 10 and 50 µg/g dry weight.

9. A plant, plant seed or other plant part derived from the plant according to claim 1, and stably infected with the endophyte.

10. A method of producing a modified grass plant comprising stably infecting a host plant with a substantially purified or isolated fungal endophyte, said endophyte being non-endogenous to the grass plant and the grass plant producing a desired toxin profile, wherein the stably infected grass plant produces significantly less toxic alkaloids compared with a control plant stably infected with a control endophyte, and/or significantly more alkaloids conferring beneficial properties compared with control plant stably infected with a a control endophyte, wherein said control endophyte is standard toxic endophyte, wherein the grass plant is a member of the genus *Lolium* or the genus *Festuca*, and wherein said endophyte is selected from the group consisting of National Measurement Institute Accession Nos. V10/000001, V10/000002, V10/000003, V10/000004, V10/030284, V10/030285, V12/001413, V12/001414, V12/001415, V12/001416, V12/001417, V12/001418 and V12/001419.

11. The plant of claim 1, wherein the grass plant is a forage, turf or bioenergy grass.

* * * * *